(12) United States Patent
Haffner et al.

(10) Patent No.: US 10,206,813 B2
(45) Date of Patent: Feb. 19, 2019

(54) IMPLANTS WITH CONTROLLED DRUG DELIVERY FEATURES AND METHODS OF USING SAME

(71) Applicant: Dose Medical Corporation, Laguna Hills, CA (US)

(72) Inventors: David S. Haffner, Mission Viejo, CA (US); Thomas W. Burns, Dana Point, CA (US); Harold A. Heitzmann, Irvine, CA (US); Kenneth M. Curry, Oceanside, CA (US)

(73) Assignee: Dose Medical Corporation, Laguna Hills, CA (US)

( * ) Notice: Subject to any disclaimer, the term of this patent is extended or adjusted under 35 U.S.C. 154(b) by 152 days.

(21) Appl. No.: 14/201,470

(22) Filed: Mar. 7, 2014

(65) Prior Publication Data

US 2014/0303544 A1 Oct. 9, 2014
US 2018/0193189 A9 Jul. 12, 2018

Related U.S. Application Data

(63) Continuation-in-part of application No. 13/321,144, filed as application No. PCT/US2010/035319 on May 18, 2010.

(60) Provisional application No. 61/788,731, filed on Mar. 15, 2013, provisional application No. 61/264,604, filed on Nov. 25, 2009, provisional application No.
(Continued)

(51) Int. Cl.
*A61M 5/00* (2006.01)
*A61F 9/00* (2006.01)
*A61F 9/007* (2006.01)

(52) U.S. Cl.
CPC ........ *A61F 9/0017* (2013.01); *A61F 9/00781* (2013.01); *A61F 2250/0067* (2013.01)

(58) Field of Classification Search
CPC ............ A61F 2250/0067; A61F 9/0017; A61F 9/00781
See application file for complete search history.

(56) References Cited

U.S. PATENT DOCUMENTS 2,031,754 A 2/1936 Bacigalupi
3,416,530 A 12/1968 Ness
(Continued)

FOREIGN PATENT DOCUMENTS

CN 101396335 A 4/2009
EP 0613383 B1 8/1997
(Continued)

OTHER PUBLICATIONS

US 7,524,280, 04/2009, Connors et al. (withdrawn)
(Continued)

*Primary Examiner* — Leslie Deak
(74) *Attorney, Agent, or Firm* — Knobbe, Martens, Olson & Bear, LLP

(57) ABSTRACT

Disclosed herein are drug delivery devices and methods for the treatment of ocular disorders requiring targeted and controlled administration of a drug to an interior portion of the eye for reduction or prevention of symptoms of the disorder. The devices are capable of controlled release of one or more drugs and may also include structures which allow for treatment of increased intraocular pressure by permitting aqueous humor to flow out of the anterior chamber of the eye through the device.

23 Claims, 70 Drawing Sheets

21

Related U.S. Application Data

61/264,615, filed on Nov. 25, 2009, provisional application No. 61/264,594, filed on Nov. 25, 2009, provisional application No. 61/220,527, filed on Jun. 25, 2009, provisional application No. 61/179,332, filed on May 18, 2009.

(56) References Cited

U.S. PATENT DOCUMENTS

| | | |
|---|---|---|
| 3,710,795 A | 1/1973 | Higuchi et al. |
| 3,961,628 A | 6/1976 | Arnold |
| 4,093,708 A | 6/1978 | Zaffaroni et al. |
| 4,113,088 A | 9/1978 | Binkhorst |
| 4,440,769 A | 4/1984 | DeBernardis et al. |
| 4,468,216 A | 8/1984 | Muto |
| 4,521,210 A | 6/1985 | Wong |
| 4,599,353 A | 7/1986 | Bito |
| 4,631,188 A | 12/1986 | Stoy et al. |
| 4,689,386 A | 8/1987 | Chapman et al. |
| 4,713,448 A | 12/1987 | Balazs et al. |
| 4,736,836 A | 4/1988 | Alongi et al. |
| 4,743,248 A | 5/1988 | Bartoo et al. |
| 4,797,413 A | 1/1989 | Baldwin et al. |
| 4,846,793 A | 7/1989 | Leonard et al. |
| 4,853,224 A | 8/1989 | Wong |
| 4,863,457 A | 9/1989 | Lee |
| 4,883,864 A | 11/1989 | Scholz |
| 4,955,881 A | 9/1990 | Eckenhoff |
| 4,997,652 A | 3/1991 | Wong |
| 5,021,410 A | 6/1991 | Burke |
| 5,093,329 A | 3/1992 | Woodward |
| 5,098,443 A | 3/1992 | Parel et al. |
| 5,128,145 A | 7/1992 | Edgren et al. |
| 5,153,192 A | 10/1992 | Dean et al. |
| 5,164,188 A | 11/1992 | Wong |
| 5,177,105 A | 1/1993 | Moll et al. |
| 5,180,721 A | 1/1993 | Burke |
| 5,215,991 A | 1/1993 | Burke |
| 5,238,961 A | 8/1993 | Woodward et al. |
| 5,240,923 A | 8/1993 | Dean et al. |
| 5,248,231 A | 9/1993 | Denham et al. |
| 5,262,437 A | 11/1993 | Chan |
| 5,304,561 A | 4/1994 | Sarfarazi |
| 5,312,842 A | 5/1994 | Chan |
| 5,321,128 A | 6/1994 | Stjernschantz et al. |
| 5,328,933 A | 7/1994 | Chan |
| 5,352,708 A | 10/1994 | Woodward et al. |
| 5,364,374 A | 11/1994 | Morrison et al. |
| 5,378,474 A | 1/1995 | Morella et al. |
| 5,378,475 A | 1/1995 | Smith et al. |
| 5,378,703 A | 1/1995 | Dean et al. |
| 5,443,505 A | 8/1995 | Wong et al. |
| 5,464,450 A | 11/1995 | Buscemi et al. |
| 5,466,233 A | 11/1995 | Weiner et al. |
| 5,502,052 A | 3/1996 | DeSantis |
| 5,516,522 A | 5/1996 | Peyman et al. |
| 5,545,665 A | 8/1996 | Burk |
| 5,547,993 A | 8/1996 | Miki |
| 5,552,434 A | 9/1996 | Garst et al. |
| 5,599,534 A | 2/1997 | Himmelstein et al. |
| 5,629,008 A | 5/1997 | Lee |
| 5,643,321 A | 7/1997 | McDevitt |
| 5,652,014 A | 7/1997 | Galin et al. |
| 5,652,236 A | 7/1997 | Krauss |
| 5,663,205 A | 9/1997 | Ogawa et al. |
| 5,665,114 A | 9/1997 | Weadock et al. |
| 5,670,161 A | 9/1997 | Healy et al. |
| 5,686,425 A | 11/1997 | Lee |
| 5,688,819 A | 11/1997 | Woodward et al. |
| 5,709,854 A | 1/1998 | Griffith-Cima et al. |
| 5,725,493 A | 3/1998 | Avery et al. |
| 5,725,529 A | 3/1998 | Nicholson et al. |
| 5,733,327 A | 3/1998 | Igaki et al. |
| 5,760,161 A | 6/1998 | Goins et al. |
| 5,766,242 A | 6/1998 | Wong et al. |
| 5,767,079 A | 6/1998 | Glaser et al. |
| 5,773,019 A | 6/1998 | Ashton et al. |
| 5,814,620 A | 9/1998 | Robinson et al. |
| 5,824,072 A | 10/1998 | Wong |
| 5,869,079 A | 2/1999 | Wong et al. |
| 5,869,468 A | 2/1999 | Freeman |
| 5,869,697 A | 2/1999 | Bhushan et al. |
| 5,891,084 A | 4/1999 | Lee |
| 5,902,598 A | 5/1999 | Chen et al. |
| 5,925,342 A | 7/1999 | Adorante et al. |
| 5,952,378 A | 9/1999 | Stjerschantz et al. |
| 5,980,928 A | 11/1999 | Terry |
| 5,981,598 A | 11/1999 | Tatton |
| 5,984,913 A | 11/1999 | Kritzinger et al. |
| 6,007,511 A | 12/1999 | Prywes |
| 6,054,485 A | 4/2000 | Schwartz et al. |
| 6,059,812 A | 5/2000 | Clerc et al. |
| 6,060,463 A | 5/2000 | Freeman |
| 6,063,116 A | 5/2000 | Kelleher |
| 6,063,396 A | 5/2000 | Kelleher |
| 6,090,825 A | 7/2000 | Andrews et al. |
| 6,110,912 A | 8/2000 | Kaufman et al. |
| 6,129,761 A | 10/2000 | Hubbell |
| 6,159,458 A | 12/2000 | Bowman et al. |
| 6,177,427 B1 | 1/2001 | Clark et al. |
| 6,184,250 B1 | 2/2001 | Klimko et al. |
| 6,194,415 B1 | 2/2001 | Wheeler et al. |
| 6,201,001 B1 | 3/2001 | Wang et al. |
| 6,217,895 B1 | 4/2001 | Guo et al. |
| 6,228,873 B1 | 5/2001 | Brandt et al. |
| 6,231,600 B1 | 5/2001 | Zhong |
| 6,231,853 B1 | 5/2001 | Hillman et al. |
| 6,251,090 B1 | 6/2001 | Avery et al. |
| 6,268,398 B1 | 7/2001 | Ghosh et al. |
| 6,274,138 B1 | 8/2001 | Bandman et al. |
| 6,299,895 B1 | 10/2001 | Hammang et al. |
| 6,306,120 B1 | 10/2001 | Tan |
| 6,329,369 B1 | 12/2001 | Chow et al. |
| 6,331,313 B1 | 12/2001 | Wong et al. |
| 6,348,042 B1 | 2/2002 | Warren, Jr. |
| 6,369,116 B1 | 4/2002 | Wong et al. |
| 6,375,972 B1 | 4/2002 | Guo et al. |
| 6,378,526 B1 | 4/2002 | Bowman |
| 6,397,849 B1 | 6/2002 | Bowman et al. |
| 6,413,245 B1 | 7/2002 | Yaacobi et al. |
| 6,416,777 B1 | 7/2002 | Yaacobi |
| 6,423,001 B1 | 7/2002 | Abreu |
| 6,436,427 B1 | 8/2002 | Hammang et al. |
| 6,443,893 B1 | 9/2002 | Schnakenberg et al. |
| 6,454,787 B1 | 9/2002 | Maddalo et al. |
| 6,455,062 B1 | 9/2002 | Olejnik et al. |
| 6,455,590 B1 | 9/2002 | Tatton |
| 6,503,231 B1 | 1/2003 | Prausnitz et al. |
| 6,506,411 B2 | 1/2003 | Hunter et al. |
| 6,517,483 B2 | 2/2003 | Park et al. |
| 6,521,658 B1 | 2/2003 | Li et al. |
| 6,524,275 B1 | 2/2003 | Lynch et al. |
| 6,525,046 B1 | 2/2003 | Cirillo et al. |
| 6,525,090 B1 | 2/2003 | Piomelli et al. |
| 6,525,202 B2 | 2/2003 | Hu et al. |
| 6,531,128 B1 | 3/2003 | Wax et al. |
| 6,533,769 B2 | 3/2003 | Homen |
| 6,534,082 B1 | 3/2003 | Epstein |
| 6,534,541 B1 | 3/2003 | Goldblum |
| 6,538,817 B1 | 3/2003 | Farmer et al. |
| 6,544,544 B2 | 4/2003 | Hunter et al. |
| 6,548,078 B2 | 4/2003 | Guo et al. |
| 6,548,081 B2 | 4/2003 | Sadozai et al. |
| 6,551,618 B2 | 4/2003 | Baird et al. |
| 6,555,582 B1 | 4/2003 | Schwartz et al. |
| 6,562,374 B1 | 5/2003 | Han et al. |
| 6,576,219 B2 | 6/2003 | Brandt et al. |
| 6,589,198 B1 | 7/2003 | Soltanpour et al. |
| 6,589,203 B1 | 7/2003 | Mitrev |
| 6,612,311 B2 | 9/2003 | Dailey |
| 6,649,184 B2 | 11/2003 | Hammang et al. |
| 6,656,490 B1 | 12/2003 | Steinemann et al. |
| 6,660,870 B1 | 12/2003 | Ruskinko et al. |
| 6,670,485 B2 | 12/2003 | Burk et al. |

(56) References Cited

U.S. PATENT DOCUMENTS

| | | |
|---|---|---|
| 6,682,500 B2 | 1/2004 | Soltanpour et al. |
| 6,686,340 B2 | 2/2004 | Rath |
| 6,692,759 B1 | 2/2004 | Wong et al. |
| 6,693,093 B2 | 2/2004 | Chowdhary et al. |
| 6,696,415 B2 | 2/2004 | Gendron et al. |
| 6,699,493 B2 | 3/2004 | Wong |
| 6,712,764 B2 | 3/2004 | Jeffries et al. |
| 6,726,666 B2 | 4/2004 | de Juan, Jr. |
| 6,726,918 B1 | 4/2004 | Wong et al. |
| 6,727,354 B2 | 4/2004 | Huang |
| 6,730,056 B1 | 5/2004 | Ghaem et al. |
| 6,745,776 B2 | 6/2004 | Soll |
| 6,758,837 B2 | 7/2004 | Peclat et al. |
| 6,764,698 B1 | 7/2004 | Byun et al. |
| 6,814,966 B1 | 11/2004 | Wax et al. |
| 6,890,300 B2 | 5/2005 | Lloyd et al. |
| 6,926,670 B2 | 8/2005 | Rich et al. |
| 6,939,299 B1 | 9/2005 | Petersen et al. |
| 6,981,958 B1 | 1/2006 | Gharib et al. |
| 6,998,137 B2 | 2/2006 | Shih et al. |
| 7,033,603 B2 | 4/2006 | Nelson et al. |
| 7,041,077 B2 | 5/2006 | Shields |
| 7,048,946 B1 | 5/2006 | Wong et al. |
| 7,083,802 B2 | 8/2006 | Peyman |
| 7,094,225 B2 | 8/2006 | Tu et al. |
| 7,094,226 B2 | 8/2006 | Yaacobi |
| 7,131,945 B2 | 11/2006 | Fink et al. |
| 7,163,543 B2 | 1/2007 | Smedley et al. |
| 7,182,747 B2 | 2/2007 | Kwon |
| 7,195,774 B2 | 3/2007 | Carvalho et al. |
| 7,226,435 B2 | 6/2007 | Darnell |
| 7,252,006 B2 | 8/2007 | Tai et al. |
| 7,261,529 B2 | 8/2007 | Persyn et al. |
| 7,273,475 B2 | 9/2007 | Tu et al. |
| 7,291,125 B2 | 11/2007 | Coroneo |
| 7,402,156 B2 | 7/2008 | Kiehlbauch et al. |
| 7,431,710 B2 | 10/2008 | Tu et al. |
| 7,445,793 B2 | 11/2008 | Niwa et al. |
| 7,458,953 B2 | 12/2008 | Peyman |
| 7,494,487 B2 | 2/2009 | Timm |
| 7,496,174 B2 | 2/2009 | Gertner et al. |
| 7,513,893 B2 | 4/2009 | Soroudi |
| 7,563,255 B2 | 7/2009 | Adamis et al. |
| 7,585,517 B2 | 9/2009 | Cooper et al. |
| 7,592,016 B2 | 9/2009 | Wong et al. |
| 7,638,137 B2 | 11/2009 | Rathjen et al. |
| 7,678,065 B2 | 3/2010 | Haffner et al. |
| 7,678,078 B1 | 3/2010 | Peyman et al. |
| 7,680,244 B2 | 3/2010 | Gertner et al. |
| 7,680,245 B2 | 3/2010 | Gertner |
| 7,697,663 B2 | 4/2010 | Gertner |
| 7,708,711 B2 | 5/2010 | Tu et al. |
| 7,709,049 B2 | 5/2010 | Chappa |
| 7,744,590 B2 | 6/2010 | Eells et al. |
| 7,749,528 B2 | 7/2010 | DeCarvalho et al. |
| 7,753,524 B2 | 7/2010 | Sabel |
| 7,776,024 B2 | 8/2010 | Santini et al. |
| 7,794,751 B2 | 9/2010 | Chudzik et al. |
| 7,811,252 B2 | 10/2010 | Dacquay et al. |
| 7,815,592 B2 | 10/2010 | Coroneo |
| 7,822,175 B2 | 10/2010 | Gertner |
| 7,846,468 B2 | 12/2010 | Wong |
| 7,887,517 B2 | 2/2011 | Santos et al. |
| 7,887,521 B2 | 2/2011 | Dacquey et al. |
| 7,951,155 B2 | 5/2011 | Smedley et al. |
| 7,953,203 B2 | 5/2011 | Gertner et al. |
| 7,958,840 B2 | 6/2011 | Chappa |
| 7,967,772 B2 | 6/2011 | McKenzie et al. |
| 7,978,819 B2 | 7/2011 | Gertner et al. |
| 7,985,415 B2 | 7/2011 | Giroux |
| 7,997,460 B2 | 8/2011 | Pardes et al. |
| 8,012,136 B2 | 9/2011 | Collins, Jr. et al. |
| 8,059,784 B2 | 11/2011 | Gertner |
| 8,060,211 B2 | 11/2011 | Greenberg et al. |
| 8,062,657 B2 | 11/2011 | Edelman et al. |
| 8,071,120 B2 | 12/2011 | Wong |
| 8,073,105 B2 | 12/2011 | Gertner et al. |
| 8,118,768 B2 | 2/2012 | Tu et al. |
| 8,142,364 B2 | 3/2012 | Haffner et al. |
| 8,235,053 B2 | 8/2012 | Sanchez et al. |
| 8,241,656 B2 | 8/2012 | Chudzik et al. |
| 8,273,050 B2 | 9/2012 | Bergheim et al. |
| 8,273,366 B2 | 9/2012 | Chauhan et al. |
| 8,277,830 B2 | 10/2012 | De Juan, Jr. et al. |
| 8,282,593 B2 | 10/2012 | Dacey, Jr. et al. |
| 8,298,578 B2 | 10/2012 | De Juan, Jr. et al. |
| 8,333,726 B2 | 12/2012 | Rapaki et al. |
| 8,337,445 B2 | 12/2012 | Tu et al. |
| 8,343,086 B2 | 1/2013 | Dacey, Jr. et al. |
| 8,348,877 B2 | 1/2013 | Tu et al. |
| 8,366,652 B2 | 2/2013 | Dacey et al. |
| 8,404,269 B2 | 3/2013 | Snyder et al. |
| 8,414,517 B2 | 4/2013 | Dacey, Jr. et al. |
| 8,425,926 B2 | 4/2013 | Qiu et al. |
| 8,425,929 B2 | 4/2013 | Huang et al. |
| 8,440,216 B2 | 5/2013 | Huang et al. |
| 8,444,589 B2 | 5/2013 | Silvestrini |
| 8,452,391 B2 | 5/2013 | Roy |
| 8,454,582 B2 | 6/2013 | Dejuan et al. |
| 8,486,031 B2 | 7/2013 | Bogdan |
| 8,486,052 B2 | 7/2013 | Varner et al. |
| 8,529,492 B2 | 9/2013 | Luke et al. |
| 8,617,094 B2 | 12/2013 | Smedley et al. |
| 8,642,066 B2 | 2/2014 | Abe et al. |
| 8,656,958 B2 | 2/2014 | Unger et al. |
| 8,657,804 B2 | 2/2014 | Horne et al. |
| 8,801,648 B2 | 8/2014 | Bergheim et al. |
| 8,814,820 B2 | 8/2014 | Bergheim et al. |
| 8,882,781 B2 | 11/2014 | Smedley et al. |
| 9,066,782 B2 | 6/2015 | Tu et al. |
| 9,155,654 B2 | 10/2015 | Tu et al. |
| 9,220,632 B2 | 12/2015 | Smedley et al. |
| 9,603,738 B2 | 3/2017 | Haffner et al. |
| 9,636,255 B2 | 5/2017 | Haffner et al. |
| 9,668,915 B2 | 6/2017 | Haffner et al. |
| 9,987,472 B2 | 6/2018 | Tu et al. |
| 2002/0013572 A1 | 1/2002 | Berlin |
| 2002/0037919 A1 | 3/2002 | Hunter |
| 2002/0052640 A1 | 5/2002 | Bigus et al. |
| 2002/0099434 A1 | 7/2002 | Buscemi et al. |
| 2002/0102307 A1 | 8/2002 | Guo et al. |
| 2002/0106395 A1 | 8/2002 | Brubaker |
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2002/0111601 A1 | 8/2002 | Thompson |
| 2002/0111603 A1 | 8/2002 | Cheikh |
| 2002/0127250 A1 | 9/2002 | Guo et al. |
| 2002/0128704 A1 | 9/2002 | Daum et al. |
| 2002/0143284 A1 | 10/2002 | Tu et al. |
| 2002/0160993 A1 | 10/2002 | Egan et al. |
| 2002/0176844 A1 | 11/2002 | Ng et al. |
| 2002/0177599 A1 | 11/2002 | Allerton et al. |
| 2002/0177625 A1 | 11/2002 | O'Donnell et al. |
| 2002/0182185 A1 | 12/2002 | Wong |
| 2002/0183380 A1 | 12/2002 | Hunter |
| 2002/0188282 A1 | 12/2002 | Greenberg |
| 2002/0197298 A1 | 12/2002 | Yaacobi |
| 2003/0003129 A1 | 1/2003 | Yaacobi |
| 2003/0004209 A1 | 1/2003 | Hunter et al. |
| 2003/0010638 A1 | 1/2003 | Hansord et al. |
| 2003/0018044 A1 | 1/2003 | Peyman |
| 2003/0018295 A1 | 1/2003 | Henley et al. |
| 2003/0019833 A1 | 1/2003 | Unger et al. |
| 2003/0021828 A1 | 1/2003 | Guo et al. |
| 2003/0036534 A1 | 2/2003 | Slusher et al. |
| 2003/0040529 A1 | 2/2003 | Yokoyama |
| 2003/0040535 A1 | 2/2003 | Aspnes et al. |
| 2003/0044452 A1 | 3/2003 | Ueno |
| 2003/0060511 A1 | 3/2003 | Ueno |
| 2003/0060873 A1 | 3/2003 | Gertner et al. |
| 2003/0064088 A1 | 4/2003 | Carvalho et al. |
| 2003/0083227 A1 | 5/2003 | Civan et al. |
| 2003/0083646 A1 | 5/2003 | Sirhan et al. |

(56) References Cited

U.S. PATENT DOCUMENTS

| | | |
|---|---|---|
| 2003/0095995 A1 | 5/2003 | Wong et al. |
| 2003/0097117 A1 | 5/2003 | Buono |
| 2003/0108588 A1 | 6/2003 | Chen et al. |
| 2003/0119000 A1 | 6/2003 | Polansky |
| 2003/0139784 A1 | 7/2003 | Morimoto et al. |
| 2003/0143274 A1 | 7/2003 | Viegas et al. |
| 2003/0153626 A1 | 8/2003 | Civan et al. |
| 2003/0175324 A1 | 9/2003 | Robinson et al. |
| 2003/0176854 A1 | 9/2003 | Rodstrom |
| 2003/0185892 A1 | 10/2003 | Bell et al. |
| 2003/0186928 A1 | 10/2003 | Yerxa et al. |
| 2003/0191072 A1 | 10/2003 | Hinton et al. |
| 2003/0191173 A1 | 10/2003 | Garcia et al. |
| 2003/0195438 A1 | 10/2003 | Petillo |
| 2003/0203003 A1 | 10/2003 | Nelson et al. |
| 2003/0208163 A1 | 11/2003 | Yaron et al. |
| 2003/0211071 A1 | 11/2003 | Bologna et al. |
| 2003/0225101 A1 | 12/2003 | Scheman |
| 2003/0236484 A1 | 12/2003 | Lynch et al. |
| 2004/0013702 A1 | 1/2004 | Glover |
| 2004/0018238 A1 | 1/2004 | Shukla |
| 2004/0022853 A1 | 2/2004 | Ashton et al. |
| 2004/0029771 A1 | 2/2004 | Rigdon et al. |
| 2004/0057979 A1 | 3/2004 | Wong et al. |
| 2004/0082660 A1 | 4/2004 | Ueno |
| 2004/0082939 A1 | 4/2004 | Berlin |
| 2004/0092548 A1 | 5/2004 | Embleton et al. |
| 2004/0092911 A1 | 5/2004 | Yaacobi |
| 2004/0111080 A1 | 6/2004 | Harper et al. |
| 2004/0115268 A1 | 6/2004 | Ashton et al. |
| 2004/0121943 A1 | 6/2004 | Hsu et al. |
| 2004/0127843 A1 | 7/2004 | Tu et al. |
| 2004/0131654 A1 | 7/2004 | Yaacobi |
| 2004/0131655 A1 | 7/2004 | Yaacobi |
| 2004/0137059 A1 | 7/2004 | Nivaggioli et al. |
| 2004/0151714 A1 | 8/2004 | Soll |
| 2004/0175377 A1 | 9/2004 | Peters et al. |
| 2004/0175410 A1 | 9/2004 | Ashton et al. |
| 2004/0176341 A1 | 9/2004 | Chou et al. |
| 2004/0176737 A1 | 9/2004 | Henley et al. |
| 2004/0180075 A1 | 9/2004 | Robinson et al. |
| 2004/0186533 A1 | 9/2004 | Greenberg et al. |
| 2004/0186534 A1 | 9/2004 | Shadduck |
| 2004/0191798 A1 | 9/2004 | Sarfarazi et al. |
| 2004/0208909 A1 | 10/2004 | Brubaker et al. |
| 2004/0219181 A1 | 11/2004 | Viscasillas |
| 2004/0220537 A1 | 11/2004 | Embleton et al. |
| 2004/0225014 A1 | 11/2004 | Habe et al. |
| 2004/0225250 A1 | 11/2004 | Yablonski |
| 2004/0249404 A1 | 12/2004 | Haefliger |
| 2004/0254521 A1 | 12/2004 | Simon |
| 2005/0008673 A1 | 1/2005 | Snyder et al. |
| 2005/0009772 A1 | 1/2005 | Caprioli |
| 2005/0014808 A1 | 1/2005 | Yokoyama |
| 2005/0014837 A1 | 1/2005 | Ueno |
| 2005/0042293 A1 | 2/2005 | Jackson et al. |
| 2005/0055075 A1 | 3/2005 | Pinchuk et al. |
| 2005/0064010 A1 | 3/2005 | Cooper et al. |
| 2005/0069893 A1 | 3/2005 | Flammer et al. |
| 2005/0085905 A1 | 4/2005 | Weiner |
| 2005/0107734 A1 | 5/2005 | Coroneo |
| 2005/0112175 A1 | 5/2005 | Yaacobi |
| 2005/0119737 A1 | 6/2005 | Bene et al. |
| 2005/0137538 A1 | 6/2005 | Kunzler et al. |
| 2005/0143817 A1 | 6/2005 | Hunter et al. |
| 2005/0158356 A1 | 7/2005 | Hunter et al. |
| 2005/0159660 A1 | 7/2005 | Montegrande et al. |
| 2005/0163873 A1 | 7/2005 | Ritch |
| 2005/0165368 A1 | 7/2005 | Py et al. |
| 2005/0175708 A1 | 8/2005 | Carrasquillo et al. |
| 2005/0181018 A1 | 8/2005 | Peyman |
| 2005/0186245 A1 | 8/2005 | Hunter et al. |
| 2005/0186279 A1 | 8/2005 | Guo et al. |
| 2005/0208102 A1 | 9/2005 | Schultz |
| 2005/0228054 A1 | 10/2005 | Tatton |
| 2005/0232972 A1 | 10/2005 | Odrich |
| 2005/0244461 A1 | 11/2005 | Nivaggioli et al. |
| 2005/0244464 A1 | 11/2005 | Hughes |
| 2005/0244465 A1 | 11/2005 | Nivaggioli et al. |
| 2005/0244467 A1 | 11/2005 | Nivaggioli et al. |
| 2005/0244470 A1 | 11/2005 | Hughes et al. |
| 2005/0244475 A1 | 11/2005 | Edelman et al. |
| 2005/0244477 A1 | 11/2005 | Hughes et al. |
| 2005/0244500 A1 | 11/2005 | Whitcup et al. |
| 2005/0244506 A1 | 11/2005 | Burke et al. |
| 2005/0249710 A1 | 11/2005 | Wong |
| 2005/0250788 A1 | 11/2005 | Tu et al. |
| 2005/0261184 A1 | 11/2005 | Kaufman et al. |
| 2005/0261641 A1 | 11/2005 | Warchol et al. |
| 2005/0276841 A1 | 12/2005 | Davis et al. |
| 2005/0281861 A1 | 12/2005 | Hughes et al. |
| 2005/0287188 A1 | 12/2005 | Anderson et al. |
| 2006/0009498 A1 | 1/2006 | Whitcup |
| 2006/0020248 A1 | 1/2006 | Prescott |
| 2006/0021623 A1 | 2/2006 | Varner et al. |
| 2006/0024350 A1 | 2/2006 | Miller et al. |
| 2006/0034929 A1 | 2/2006 | Brubaker |
| 2006/0039952 A1 | 2/2006 | Yaacobi |
| 2006/0039979 A1 | 2/2006 | Yamada et al. |
| 2006/0062826 A1 | 3/2006 | Brubaker et al. |
| 2006/0069340 A1 | 3/2006 | Simon |
| 2006/0083772 A1 | 4/2006 | DeWitt et al. |
| 2006/0084952 A1 | 4/2006 | Pallikaris et al. |
| 2006/0089590 A1 | 4/2006 | Powell et al. |
| 2006/0100408 A1 | 5/2006 | Higuchi et al. |
| 2006/0110429 A1 | 5/2006 | Reiff et al. |
| 2006/0122152 A1 | 6/2006 | Peyman |
| 2006/0127438 A1 | 6/2006 | Hunter et al. |
| 2006/0135477 A1 | 6/2006 | Haitjema et al. |
| 2006/0136022 A1 | 6/2006 | Wong, Jr. et al. |
| 2006/0167435 A1 | 7/2006 | Adamis et al. |
| 2006/0200097 A1 | 9/2006 | Humayun et al. |
| 2006/0210604 A1 | 9/2006 | Dadey et al. |
| 2006/0216324 A1 | 9/2006 | Stucke et al. |
| 2006/0216329 A1 | 9/2006 | Peyman |
| 2006/0240073 A1 | 10/2006 | Hsu et al. |
| 2006/0246112 A1 | 11/2006 | Snyder et al. |
| 2006/0246145 A1 | 11/2006 | Chang et al. |
| 2006/0253151 A1 | 11/2006 | Nun |
| 2006/0257450 A1 | 11/2006 | Mudumba et al. |
| 2006/0257451 A1 | 11/2006 | Varner et al. |
| 2006/0258994 A1 | 11/2006 | Avery |
| 2006/0264453 A1 | 11/2006 | Mudumba et al. |
| 2006/0270968 A1 | 11/2006 | Greenberg et al. |
| 2006/0292222 A1 | 12/2006 | Jonasse |
| 2007/0021653 A1 | 1/2007 | Hattenbach et al. |
| 2007/0026037 A1 | 2/2007 | Kloke et al. |
| 2007/0026048 A1 | 2/2007 | Greeberg |
| 2007/0031471 A1 | 2/2007 | Peyman |
| 2007/0031472 A1 | 2/2007 | Huang et al. |
| 2007/0031473 A1 | 2/2007 | Peyman |
| 2007/0032734 A1 | 2/2007 | Najafi et al. |
| 2007/0038174 A1 | 2/2007 | Hopkins |
| 2007/0059336 A1 | 3/2007 | Hughes et al. |
| 2007/0088014 A1 | 4/2007 | Edelman et al. |
| 2007/0092570 A1 | 4/2007 | Missel et al. |
| 2007/0106199 A1 | 5/2007 | Krivoy et al. |
| 2007/0112263 A1 | 5/2007 | Fink et al. |
| 2007/0112318 A1 | 5/2007 | Leahy et al. |
| 2007/0118065 A1 | 5/2007 | Pinchuk et al. |
| 2007/0118066 A1 | 5/2007 | Pinchuk et al. |
| 2007/0123767 A1 | 5/2007 | Montegrande et al. |
| 2007/0129623 A1 | 6/2007 | Fleischman et al. |
| 2007/0161699 A1 | 7/2007 | Epstein et al. |
| 2007/0190111 A1 | 8/2007 | Robinson et al. |
| 2007/0191863 A1 | 8/2007 | De Juan, Jr. et al. |
| 2007/0197957 A1 | 8/2007 | Hunter et al. |
| 2007/0202186 A1 | 8/2007 | Yamamoto et al. |
| 2007/0212395 A1 | 9/2007 | Donello et al. |
| 2007/0212397 A1 | 9/2007 | Roth |
| 2007/0233037 A1 | 10/2007 | Gifford, III et al. |
| 2007/0244442 A1 | 10/2007 | Chowhan |
| 2007/0249984 A1 | 10/2007 | Molteno |
| 2007/0260203 A1 | 11/2007 | Donello et al. |

(56) References Cited

U.S. PATENT DOCUMENTS

| | | |
|---|---|---|
| 2007/0268340 A1 | 11/2007 | Dacquay et al. |
| 2007/0269487 A1 | 11/2007 | de Juan et al. |
| 2007/0270447 A1 | 11/2007 | Hunter et al. |
| 2007/0270744 A1 | 11/2007 | Dacquay et al. |
| 2007/0270748 A1 | 11/2007 | Dacquay et al. |
| 2007/0270768 A1 | 11/2007 | Dacquay et al. |
| 2007/0270777 A1 | 11/2007 | Dacquay et al. |
| 2007/0292476 A1 | 12/2007 | Landis et al. |
| 2007/0292596 A1 | 12/2007 | Chappa et al. |
| 2007/0293820 A1 | 12/2007 | Dacquay et al. |
| 2007/0293872 A1 | 12/2007 | Peyman |
| 2007/0293873 A1 | 12/2007 | Chang |
| 2007/0298073 A1 | 12/2007 | Whitcup et al. |
| 2007/0298074 A1 | 12/2007 | Robinson et al. |
| 2007/0299516 A1 | 12/2007 | Cui et al. |
| 2008/0027304 A1 | 1/2008 | Pardo et al. |
| 2008/0038316 A1 | 2/2008 | Wong et al. |
| 2008/0039769 A1 | 2/2008 | Peyman |
| 2008/0039792 A1 | 2/2008 | Meng et al. |
| 2008/0045911 A1 | 2/2008 | Borgia et al. |
| 2008/0051385 A1 | 2/2008 | Ingerman et al. |
| 2008/0051680 A1 | 2/2008 | Luebcke |
| 2008/0051691 A1 | 2/2008 | Dragoon et al. |
| 2008/0057101 A1 | 3/2008 | Roorda |
| 2008/0057102 A1 | 3/2008 | Roorda |
| 2008/0057103 A1 | 3/2008 | Roorda |
| 2008/0057123 A1 | 3/2008 | Grenier et al. |
| 2008/0058704 A1 | 3/2008 | Hee et al. |
| 2008/0058793 A1 | 3/2008 | Pilla et al. |
| 2008/0063687 A1 | 3/2008 | Chou et al. |
| 2008/0063898 A1 | 3/2008 | Lally et al. |
| 2008/0071252 A1 | 3/2008 | Santini, Jr. et al. |
| 2008/0075718 A1 | 3/2008 | Colson et al. |
| 2008/0075753 A1 | 3/2008 | Chappa |
| 2008/0081064 A1 | 4/2008 | Jelle et al. |
| 2008/0086101 A1 | 4/2008 | Freilich |
| 2008/0089923 A1 | 4/2008 | Burkstrand et al. |
| 2008/0089952 A1 | 4/2008 | Hunter et al. |
| 2008/0095822 A1 | 4/2008 | Maquet et al. |
| 2008/0097379 A1 | 4/2008 | Daquay et al. |
| 2008/0097390 A1 | 4/2008 | Daquay et al. |
| 2008/0107694 A1 | 5/2008 | Trogden et al. |
| 2008/0112923 A1 | 5/2008 | Hughes et al. |
| 2008/0113031 A1 | 5/2008 | Moodley et al. |
| 2008/0114076 A1 | 5/2008 | Asgharian et al. |
| 2008/0125712 A1 | 5/2008 | Dacquay et al. |
| 2008/0131372 A1 | 6/2008 | Huang et al. |
| 2008/0131481 A1 | 6/2008 | Hughes |
| 2008/0131482 A1 | 6/2008 | Hughes |
| 2008/0131484 A1 | 6/2008 | Robinson et al. |
| 2008/0131486 A1 | 6/2008 | Huang et al. |
| 2008/0138382 A1 | 6/2008 | Huang et al. |
| 2008/0138408 A1 | 6/2008 | Venkatesh et al. |
| 2008/0140024 A1 | 6/2008 | Yaacobi |
| 2008/0145405 A1 | 6/2008 | Kunzler et al. |
| 2008/0145406 A1 | 6/2008 | Asgharian et al. |
| 2008/0145514 A1 | 6/2008 | Hunter et al. |
| 2008/0147021 A1 | 6/2008 | Jani |
| 2008/0152694 A1 | 6/2008 | Lobl et al. |
| 2008/0231485 A1 | 6/2008 | Huang et al. |
| 2008/0161741 A1 | 7/2008 | Bene et al. |
| 2008/0161907 A1 | 7/2008 | Chen et al. |
| 2008/0167600 A1 | 7/2008 | Peyman |
| 2008/0172014 A1 | 7/2008 | Whitcup et al. |
| 2008/0177153 A1 | 7/2008 | Bachman et al. |
| 2008/0177220 A1 | 7/2008 | Lindgren et al. |
| 2008/0181928 A1 | 7/2008 | Hokimi-Mehr et al. |
| 2008/0181929 A1 | 7/2008 | Robinson et al. |
| 2008/0183121 A2 | 7/2008 | Smedley et al. |
| 2008/0183123 A1 | 7/2008 | Behar-Cohen et al. |
| 2008/0208334 A1 | 8/2008 | Jinkerson et al. |
| 2008/0208557 A1 | 8/2008 | Katano |
| 2008/0210322 A1 | 9/2008 | Unger et al. |
| 2008/0228127 A1 | 9/2008 | Burns et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0234352 A1 | 9/2008 | Fischer et al. |
| 2008/0234624 A2 | 9/2008 | Bergheim et al. |
| 2008/0236669 A1 | 10/2008 | Unger et al. |
| 2008/0241217 A1 | 10/2008 | Hunter et al. |
| 2008/0241222 A1 | 10/2008 | Whitcup et al. |
| 2008/0241223 A1 | 10/2008 | Nivaggio et al. |
| 2008/0260803 A1 | 10/2008 | Hughes et al. |
| 2008/0277007 A1 | 11/2008 | Unger et al. |
| 2008/0286336 A1 | 11/2008 | Shiah et al. |
| 2008/0286338 A1 | 11/2008 | Rosenthal et al. |
| 2008/0289710 A1 | 11/2008 | Unger et al. |
| 2008/0292679 A1 | 11/2008 | Lyons et al. |
| 2008/0306429 A1 | 12/2008 | Shields et al. |
| 2008/0318843 A1 | 12/2008 | Schultz et al. |
| 2009/0003525 A1 | 1/2009 | Gertner et al. |
| 2009/0036768 A1 | 2/2009 | Seehusen et al. |
| 2009/0036819 A1 | 2/2009 | Tu et al. |
| 2009/0043250 A1 | 2/2009 | Gonnelli |
| 2009/0043321 A1 | 2/2009 | Conston et al. |
| 2009/0047256 A1 | 2/2009 | Bettinger et al. |
| 2009/0060981 A1 | 3/2009 | Chauhan |
| 2009/0069648 A1 | 3/2009 | Irazoqui et al. |
| 2009/0074786 A1 | 3/2009 | Dor et al. |
| 2009/0082321 A1 | 3/2009 | Edelman et al. |
| 2009/0092654 A1 | 4/2009 | de Juan, Jr. et al. |
| 2009/0093780 A1 | 4/2009 | Tuitupou et al. |
| 2009/0118702 A1 | 5/2009 | Lazar |
| 2009/0123515 A1 | 5/2009 | Taylor et al. |
| 2009/0123546 A1 | 5/2009 | Ashton et al. |
| 2009/0142413 A1 | 6/2009 | Allen et al. |
| 2009/0143752 A1 | 6/2009 | Higuchi et al. |
| 2009/0148498 A1 | 6/2009 | Libin et al. |
| 2009/0149947 A1 | 6/2009 | Frohwitter |
| 2009/0151422 A1 | 6/2009 | Unger et al. |
| 2009/0155338 A1 | 6/2009 | Conway et al. |
| 2009/0157087 A1 | 6/2009 | Wei et al. |
| 2009/0162417 A1 | 6/2009 | Eells |
| 2009/0177182 A1 | 7/2009 | Hickingbotham et al. |
| 2009/0196903 A1 | 8/2009 | Kilman |
| 2009/0196906 A1 | 8/2009 | Spada et al. |
| 2009/0209945 A1 | 8/2009 | Lobl et al. |
| 2009/0214619 A1 | 8/2009 | Reiff et al. |
| 2009/0220572 A1 | 9/2009 | Deschatelets et al. |
| 2009/0220573 A1 | 9/2009 | Kaufman |
| 2009/0227933 A1 | 9/2009 | Karageozian |
| 2009/0240215 A1 | 9/2009 | Humayun et al. |
| 2009/0246252 A1 | 10/2009 | Arps et al. |
| 2009/0264861 A1 | 10/2009 | Jain et al. |
| 2009/0270308 A1 | 10/2009 | Libin et al. |
| 2009/0274877 A1 | 11/2009 | Chan et al. |
| 2009/0275924 A1 | 11/2009 | Lattanzio et al. |
| 2009/0280155 A1 | 11/2009 | Chappa et al. |
| 2009/0280158 A1 | 11/2009 | Butuner |
| 2009/0286773 A1 | 11/2009 | Spada et al. |
| 2009/0287274 A1 | 11/2009 | De Rodder |
| 2009/0306585 A1 | 12/2009 | Pang et al. |
| 2009/0306595 A1 | 12/2009 | Shih et al. |
| 2009/0306608 A1 | 12/2009 | Li et al. |
| 2009/0312742 A1 | 12/2009 | Pang et al. |
| 2009/0318449 A1 | 12/2009 | Old et al. |
| 2009/0326432 A1 | 12/2009 | Schmidt et al. |
| 2010/0004581 A1 | 1/2010 | Brigatti et al. |
| 2010/0004639 A1 | 1/2010 | Pang et al. |
| 2010/0015195 A1 | 1/2010 | Jain et al. |
| 2010/0030136 A1 | 2/2010 | Dacquay et al. |
| 2010/0040670 A1 | 2/2010 | Odrich et al. |
| 2010/0056979 A1 | 3/2010 | Smedley et al. |
| 2010/0057003 A1 | 3/2010 | Dos Santos |
| 2010/0068141 A1 | 3/2010 | Kaushal et al. |
| 2010/0069842 A1 | 3/2010 | Dos Santos et al. |
| 2010/0092536 A1 | 4/2010 | Hunter et al. |
| 2010/0100054 A1 | 4/2010 | Cormier et al. |
| 2010/0106073 A1 | 4/2010 | Haffner et al. |
| 2010/0114039 A1 | 5/2010 | Gazzini |
| 2010/0114309 A1 | 5/2010 | Peyman |
| 2010/0119519 A1 | 5/2010 | Peyman |
| 2010/0119580 A1 | 5/2010 | Guo et al. |

(56) References Cited

U.S. PATENT DOCUMENTS

| | | |
|---|---|---|
| 2010/0119694 A1 | 5/2010 | Guo et al. |
| 2010/0124565 A1 | 5/2010 | Spada et al. |
| 2010/0129424 A9 | 5/2010 | Byrne et al. |
| 2010/0137780 A1 | 6/2010 | Singh et al. |
| 2010/0145180 A1 | 6/2010 | Abreu |
| 2010/0152676 A1 | 6/2010 | Clements |
| 2010/0152699 A1 | 6/2010 | Ferrari et al. |
| 2010/0158980 A1 | 6/2010 | Kopczynski et al. |
| 2010/0160870 A1 | 6/2010 | Clements et al. |
| 2010/0173866 A1 | 7/2010 | Hee et al. |
| 2010/0189765 A1 | 7/2010 | Erickson et al. |
| 2010/0189817 A1 | 7/2010 | Kruger et al. |
| 2010/0191103 A1 | 7/2010 | Stamper et al. |
| 2010/0203155 A1 | 8/2010 | Wei et al. |
| 2010/0204311 A1 | 8/2010 | Hayashi et al. |
| 2010/0204699 A1 | 8/2010 | Wei et al. |
| 2010/0211044 A1 | 8/2010 | Dacquay et al. |
| 2010/0222752 A1 | 9/2010 | Collins, Jr. et al. |
| 2010/0225061 A1 | 9/2010 | Bath |
| 2010/0233241 A1 | 9/2010 | Leahy et al. |
| 2010/0234790 A1 | 9/2010 | Tu et al. |
| 2010/0234817 A1 | 9/2010 | Nazzaro et al. |
| 2010/0239635 A1 | 9/2010 | McClain et al. |
| 2010/0239637 A1 | 9/2010 | Ciolino et al. |
| 2010/0241046 A1 | 9/2010 | Pinchuk et al. |
| 2010/0241055 A1 | 9/2010 | Dacey, Jr. et al. |
| 2010/0247606 A1 | 9/2010 | Robinson et al. |
| 2010/0249692 A1 | 9/2010 | Dacey, Jr. et al. |
| 2010/0255061 A1* | 10/2010 | de Juan, Jr. ............ A61F 9/0017 424/427 |
| 2010/0256578 A1 | 10/2010 | Lust et al. |
| 2010/0256597 A1 | 10/2010 | Prausnitz et al. |
| 2010/0261646 A1 | 10/2010 | Lavik et al. |
| 2010/0266664 A1 | 10/2010 | Asgharian et al. |
| 2010/0274224 A1 | 10/2010 | Jain et al. |
| 2010/0274258 A1 | 10/2010 | Silvestrini et al. |
| 2010/0274259 A1 | 10/2010 | Yaron et al. |
| 2010/0278898 A1 | 11/2010 | Hughes et al. |
| 2010/0318034 A1 | 12/2010 | Goncalves |
| 2010/0331796 A1 | 12/2010 | Leahy et al. |
| 2010/0331975 A1 | 12/2010 | Nissan et al. |
| 2011/0022007 A1 | 1/2011 | Li et al. |
| 2011/0053905 A1 | 3/2011 | Guo et al. |
| 2011/0060265 A1 | 3/2011 | Dragoon et al. |
| 2011/0076318 A1 | 3/2011 | Hughes et al. |
| 2011/0091520 A1 | 4/2011 | Huang et al. |
| 2011/0098632 A1 | 4/2011 | Behar-Cohen et al. |
| 2011/0098640 A1 | 4/2011 | Horne et al. |
| 2011/0104155 A1 | 5/2011 | Rekik |
| 2011/0112352 A1 | 5/2011 | Pilla et al. |
| 2011/0112470 A1 | 5/2011 | Lingenfelder et al. |
| 2011/0125090 A1 | 5/2011 | Peyman |
| 2011/0129516 A1 | 6/2011 | Jacob et al. |
| 2011/0129541 A1 | 6/2011 | Chen et al. |
| 2011/0152767 A1 | 6/2011 | Pinedjian |
| 2011/0166500 A1 | 7/2011 | Roy |
| 2011/0172528 A1 | 7/2011 | Gertner |
| 2011/0172587 A1 | 7/2011 | Santini, Jr. et al. |
| 2011/0182966 A1 | 7/2011 | Robinson et al. |
| 2011/0202020 A1 | 8/2011 | Lazar |
| 2011/0207987 A1 | 8/2011 | DiCarlo et al. |
| 2011/0238036 A1 | 9/2011 | Ashton |
| 2011/0238075 A1 | 9/2011 | Clauson et al. |
| 2011/0244010 A1 | 10/2011 | Doshi |
| 2011/0288396 A1 | 11/2011 | Iyengar et al. |
| 2012/0015978 A1 | 1/2012 | Old |
| 2012/0022505 A1 | 1/2012 | Dacquay et al. |
| 2012/0035146 A1 | 2/2012 | Wong et al. |
| 2012/0059349 A1 | 3/2012 | Kuo et al. |
| 2012/0078224 A1 | 3/2012 | Lerner et al. |
| 2012/0078362 A1 | 3/2012 | Haffner et al. |
| 2012/0083765 A1 | 4/2012 | LaBelle |
| 2012/0089072 A1 | 4/2012 | Cunningham, Jr. |
| 2012/0089073 A1 | 4/2012 | Cunningham, Jr. |
| 2012/0089113 A1 | 4/2012 | Ambati et al. |
| 2012/0100187 A1 | 4/2012 | Chappa et al. |
| 2012/0107371 A1 | 5/2012 | Zion et al. |
| 2012/0136322 A1 | 5/2012 | Alster et al. |
| 2012/0157487 A1 | 6/2012 | Yuan et al. |
| 2012/0165380 A1 | 6/2012 | Gil et al. |
| 2012/0165382 A1 | 6/2012 | Carling et al. |
| 2012/0165933 A1 | 6/2012 | Haffner et al. |
| 2012/0177717 A1 | 7/2012 | Abe et al. |
| 2012/0179122 A1 | 7/2012 | Eilat et al. |
| 2012/0190661 A1 | 7/2012 | Trogden et al. |
| 2012/0238994 A1 | 9/2012 | Nazzaro et al. |
| 2012/0245505 A1 | 9/2012 | Robinson et al. |
| 2012/0253300 A1 | 10/2012 | Kaufman |
| 2012/0259195 A1 | 10/2012 | Haffner et al. |
| 2012/0265149 A1 | 10/2012 | Lerner et al. |
| 2012/0277733 A1 | 11/2012 | Pang et al. |
| 2012/0321719 A1 | 12/2012 | McDonnell et al. |
| 2013/0004651 A1 | 1/2013 | Fu-Giles |
| 2013/0012408 A1 | 1/2013 | Kinoshita et al. |
| 2013/0017244 A1 | 1/2013 | Huang et al. |
| 2013/0017262 A1 | 1/2013 | Mullen et al. |
| 2013/0018360 A1 | 1/2013 | Dockendorf et al. |
| 2013/0023838 A1 | 1/2013 | Leahy et al. |
| 2013/0053794 A1 | 2/2013 | Cadden et al. |
| 2013/0060227 A1 | 3/2013 | Singh et al. |
| 2013/0062809 A1 | 3/2013 | Ellis et al. |
| 2013/0071349 A1 | 3/2013 | Robinson et al. |
| 2013/0071462 A1 | 3/2013 | Jarrett et al. |
| 2013/0090534 A1 | 4/2013 | Burns et al. |
| 2013/0090612 A1 | 4/2013 | De Juan, Jr. et al. |
| 2013/0109866 A1 | 5/2013 | Beard et al. |
| 2013/0110125 A1 | 5/2013 | Silvestrini et al. |
| 2013/0115263 A1 | 5/2013 | Hunter et al. |
| 2013/0116523 A1 | 5/2013 | Jung et al. |
| 2013/0142858 A1 | 6/2013 | Kopczynski et al. |
| 2013/0144128 A1 | 6/2013 | De Juan, Jr. et al. |
| 2013/0150770 A1 | 6/2013 | Horvath et al. |
| 2013/0150773 A1 | 6/2013 | Nissan et al. |
| 2013/0150774 A1 | 6/2013 | Field et al. |
| 2013/0156840 A1 | 6/2013 | Basinger et al. |
| 2013/0157963 A1 | 6/2013 | Gore et al. |
| 2013/0158561 A1 | 6/2013 | Bhagat |
| 2013/0172389 A1 | 7/2013 | Ehring et al. |
| 2013/0281454 A1 | 10/2013 | Schiffman et al. |
| 2013/0289467 A1 | 10/2013 | Haffner et al. |
| 2013/0316983 A1 | 11/2013 | Hill |
| 2014/0011750 A1 | 1/2014 | Feinerman et al. |
| 2014/0035184 A1 | 2/2014 | Nivaggioli et al. |
| 2014/0037746 A1 | 2/2014 | Ashton et al. |
| 2014/0039456 A1 | 2/2014 | Lerner |
| 2014/0121209 A1 | 5/2014 | Pujara |
| 2014/0234389 A1 | 8/2014 | Shiah et al. |
| 2014/0294986 A1 | 10/2014 | Liu et al. |
| 2014/0303544 A1 | 10/2014 | Haffner et al. |
| 2014/0336108 A1 | 11/2014 | Guo et al. |
| 2015/0118279 A1 | 4/2015 | Ghebremeskel et al. |
| 2015/0166504 A1 | 6/2015 | Wu et al. |
| 2015/0210689 A1 | 7/2015 | Martos et al. |
| 2015/0253308 A1 | 9/2015 | Hill |
| 2015/0342875 A1 | 12/2015 | Haffner |
| 2016/0045363 A1 | 2/2016 | Haffner et al. |
| 2016/0354245 A1 | 8/2016 | Horvath et al. |
| 2016/0354309 A1 | 12/2016 | Heitzman et al. |
| 2017/0107279 A1 | 4/2017 | Liang et al. |
| 2017/0135857 A1 | 5/2017 | Hafner et al. |
| 2017/0281409 A1 | 10/2017 | Haffner et al. |
| 2018/0021170 A1 | 1/2018 | Haffner et al. |
| 2018/0028361 A1 | 2/2018 | Haffner et al. |
| 2018/0177633 A1 | 6/2018 | Haffner et al. |

FOREIGN PATENT DOCUMENTS

| | | |
|---|---|---|
| EP | 0955045 A1 | 11/1999 |
| EP | 1100462 A2 | 5/2001 |
| EP | 1296645 A2 | 4/2003 |
| EP | 1339438 A2 | 9/2003 |
| EP | 1420716 A1 | 5/2004 |
| EP | 1477187 A1 | 11/2004 |
| EP | 1521573 A1 | 4/2005 |

(56) References Cited

FOREIGN PATENT DOCUMENTS

| | | |
|---|---|---|
| EP | 1534363 A2 | 6/2005 |
| EP | 1550471 A1 | 7/2005 |
| EP | 1621219 A2 | 2/2006 |
| EP | 1637126 A2 | 3/2006 |
| EP | 2902018 | 11/2016 |
| JP | 2003-520077 | 7/2003 |
| WO | WO 94/02081 | 2/1994 |
| WO | WO 95/013765 A1 | 5/1995 |
| WO | WO 96/20742 | 7/1996 |
| WO | WO 97/30710 | 8/1997 |
| WO | WO 1998/030181 A1 | 7/1998 |
| WO | WO 98/35639 A1 | 8/1998 |
| WO | WO 99/26567 A1 | 6/1999 |
| WO | WO 99/56637 | 11/1999 |
| WO | WO 0072788 A1 | 12/2000 |
| WO | WO 01/41685 | 6/2001 |
| WO | WO 2001/080825 A2 | 11/2001 |
| WO | WO 04/066871 | 8/2004 |
| WO | WO 03/061625 | 9/2004 |
| WO | WO 2004/073552 A2 | 9/2004 |
| WO | WO 04/098565 A2 | 11/2004 |
| WO | WO 2005/110362 | 11/2005 |
| WO | WO 05/117780 | 12/2005 |
| WO | WO 06/014434 A2 | 2/2006 |
| WO | WO 07/084582 | 7/2007 |
| WO | WO 2007/087061 A2 | 8/2007 |
| WO | WO 2007/115259 A2 | 10/2007 |
| WO | WO 2008/005873 A2 | 1/2008 |
| WO | WO 2008/060359 A2 | 5/2008 |
| WO | WO 2008/61043 A2 | 5/2008 |
| WO | WO 2008/083118 A1 | 7/2008 |
| WO | WO 2008/157614 A2 | 12/2008 |
| WO | WO 2009/006370 | 1/2009 |
| WO | WO 2009/012406 | 1/2009 |
| WO | WO 2009/035562 | 3/2009 |
| WO | WO 2009/035571 A2 | 3/2009 |
| WO | WO 2009/063222 A2 | 5/2009 |
| WO | WO 2009/097468 A2 | 8/2009 |
| WO | WO 2009/137085 | 11/2009 |
| WO | WO 2009/151543 A1 | 12/2009 |
| WO | WO 2010/006053 A1 | 1/2010 |
| WO | WO 10/065970 | 6/2010 |
| WO | WO 2010/078063 A1 | 7/2010 |
| WO | WO 2010/093945 | 8/2010 |
| WO | WO 10/102078 | 9/2010 |
| WO | WO 2010/135369 | 11/2010 |
| WO | WO 10/141729 | 12/2010 |
| WO | WO 2011/050054 | 4/2011 |
| WO | WO 2011/066479 A1 | 6/2011 |
| WO | WO 2011/127064 A2 | 10/2011 |
| WO | WO 2012/019136 | 2/2012 |
| WO | WO 2012/071476 A2 | 5/2012 |
| WO | WO 13/022801 | 2/2013 |
| WO | WO 13/041967 | 3/2013 |
| WO | WO 2014/150292 | 9/2014 |
| WO | WO 2014/150292 A1 | 9/2014 |
| WO | WO 2015/073571 | 5/2015 |
| WO | WO 2015/175544 | 11/2015 |
| WO | WO 2015/179707 | 11/2015 |
| WO | WO 2015/188152 | 12/2015 |
| WO | WO 2016/042163 A2 | 3/2016 |
| WO | WO 2016/109457 | 7/2016 |
| WO | WO 2017/020001 | 2/2017 |
| WO | WO 2017/023907 | 2/2017 |
| WO | WO 2017/030909 | 2/2017 |
| WO | WO 2017/053885 | 3/2017 |

OTHER PUBLICATIONS

U.S. Appl. No. 13/490,346, filed Jun. 6, 2012, Heitzmann et al.
International Search Report and Written Opinion in PCT/US2014/065283 mailed Feb. 18, 2015.
Bucciarelli, Patrice D., Working Model is Next Step in Team's Long Journey to Commercial Product, Healthfirst, Business First of Louisville, Louisville, Bizjournals.com, Feb. 27, 2004.
Chen, P.-J., Rodger, D.C., Meng, E., Humayun, M.S., Tai, Y.-C., "Implantable Unpowered Parylene MEMS Intraocular Pressure Sensor", Microtechnologies in Medicine and Biology, 2006 International Conference on Publication Date: May 9-12, 2006, 5pp., downloaded from http://ieeezxplore.ieee.org/xpl/freeabs_all.jsp?arnumber=4281361.
Jordan, Jens F., et al., A Novel Approach to Suprachoroidal Drainage for the Surgical Treatment of Intractable Glaucoma, J Glaucoma, vol. 15, No. 3, Jun. 2006, pp. 200-205.
Katuri, Kalyan C., Asrani, Sanjay and Ramasubramanian, Melur K., "Intraocular Pressure Monitoring Sensors", IEEE Sensors Journal, vol. 8, No. 1, Jan. 2008, 8 pp.
Online encyclopedia article "Hyaluronan," section on "Medical Applications" accessed Monday, Sep. 27, 2010. http://en.wikipedia.org/wiki/Hyaluronic_acid.
Rizq, et al.,Intraocular Pressure measurement at the Chroid Surface: A Feasibility Study with Implications for Implantable Microsystems, Br J Ophthalmol 2001; 85:868-871, Jul. 2001.
Walter, et al., Development of a Completely Encapsulated Intraocular Pressure Sensor, Ophthalmic Research 2000; 32:278-284.
International Search Report and Written Opinion in PCT/US2011/061967 dated Jun. 28, 2012.
International Search Report and Written Opinion for PCT/US2014/022858, dated Jun. 25, 2014.
International Preliminary Report on Patentability, PCT/US2014/022858, dated Sep. 15, 2015.
Search Report in European Application No. 10778286.4 dated Dec. 8, 2017.
Emi, Kazayuki, et al., Hydrostatic Pressure of the Suprachoroidal Space, Investigative Ophthalmology & Visual Science, vol. 30, No. 2, Feb. 1989 (pp. 233-239).
Grant, W.M., MD, Further Studies on Facility of Flow Through the Trabecular Meshwork, AMA Archives of Ophthalmology, Oct. 1958, vol. 60, pp. 523-533.
Grunwald, et al., Acute Effects of Sildenafil Citrate (Viagra) on Intraocular Pressure in Open-angle Glaucoma, 132 AM J Opthalmol 872, 874 (2001).
Hoskins, et al., "Aqueous Humor Outflow", Becker-Shaffer's Diagnosis and Therapy of the Glaucomas, 6th Edition, Chapter 4, pp. 41-66, 1989.
Katz, L. Jay, MD, A Call for Innovative Operations for Glaucoma, Arch Ophthalmology, Mar. 2000, vol. 118, pp. 412-413.
Katz, L. Jay, Ciliochoroidal Detachment, 18:3 Ophthalmic Surgery 175, (Mar. 1987).
Pesin, Michael A. J., Sr., et al., Management of late-onset angle-closure glaucoma associated with retinopathy of prematurity. Ophthamology 98(7): 1991 1093-98.
Spiegel, Detlev, et al.: Outflow Facilities Through Decsement's Membrane in Rabbits; Graefe's Arch Clin Exp. Ophthalmology; Jan. 2002, No. 240, pp. 111-113.
Strange, Kevin (edited by), Cellular and Molecular Physiology of Cell Volume Regulation, Library of Congress Cataloging in-Publication Data, CRC Press, Inc., 1994 pp. 312-321.
Swain, Erik, Nanosprings Could Lead to Biomedical Sensing Applications, MDDI (devicelink.com/mddi), Dec. 2003, p. 32.
Taner, Pelin et al., Effects of Vardenafil on Intraocular Pressure and Orbital Hemodynamics Journal of Ocular Pharmacology and Therapeutics, Jun. 1, 2007, 23(3): 275-279.
Tatton, William, Ruth M.E. Chalmers-Redman, Ajay Sud, Steven M. Podos, and Thomas Mittag, Maintaining Mitochondrial Membrane Impermeability: An Opportunity for New Therapy in Glaucoma, Survey of Ophthalmology, vol. 45, Supplement 3, May 2001, pp. S277 through S283.

* cited by examiner

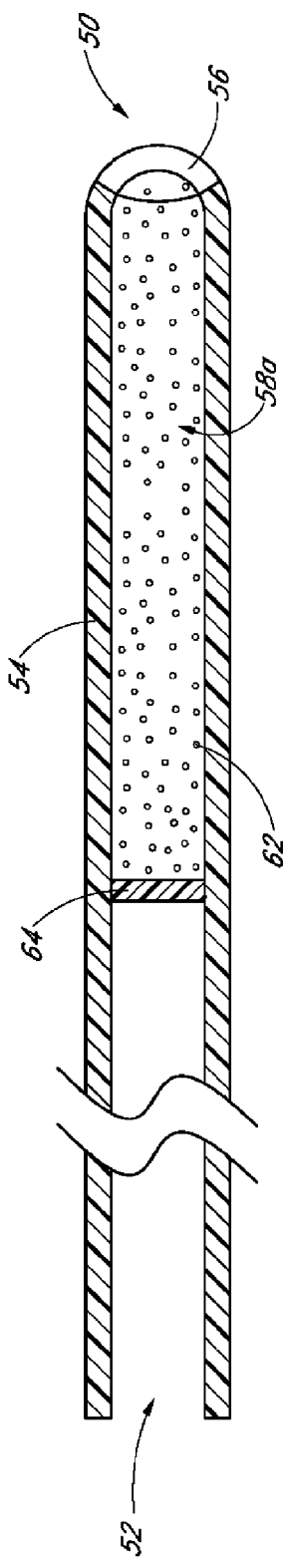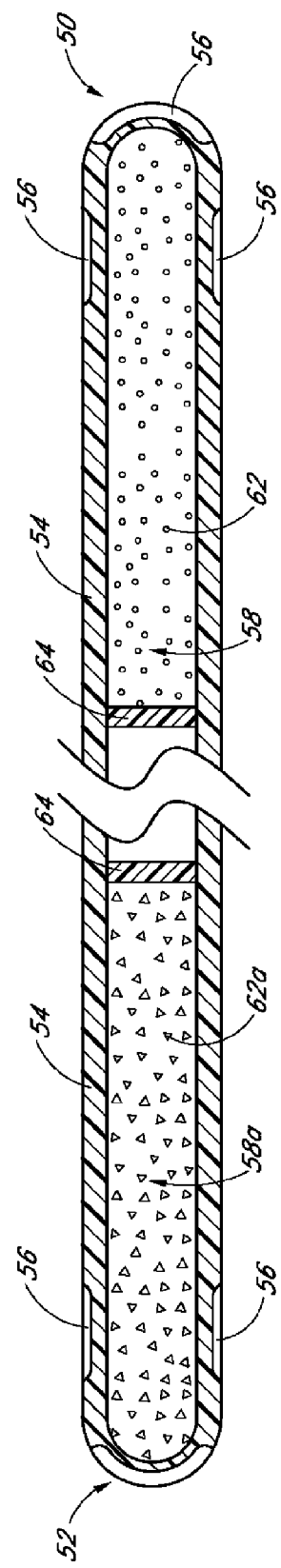

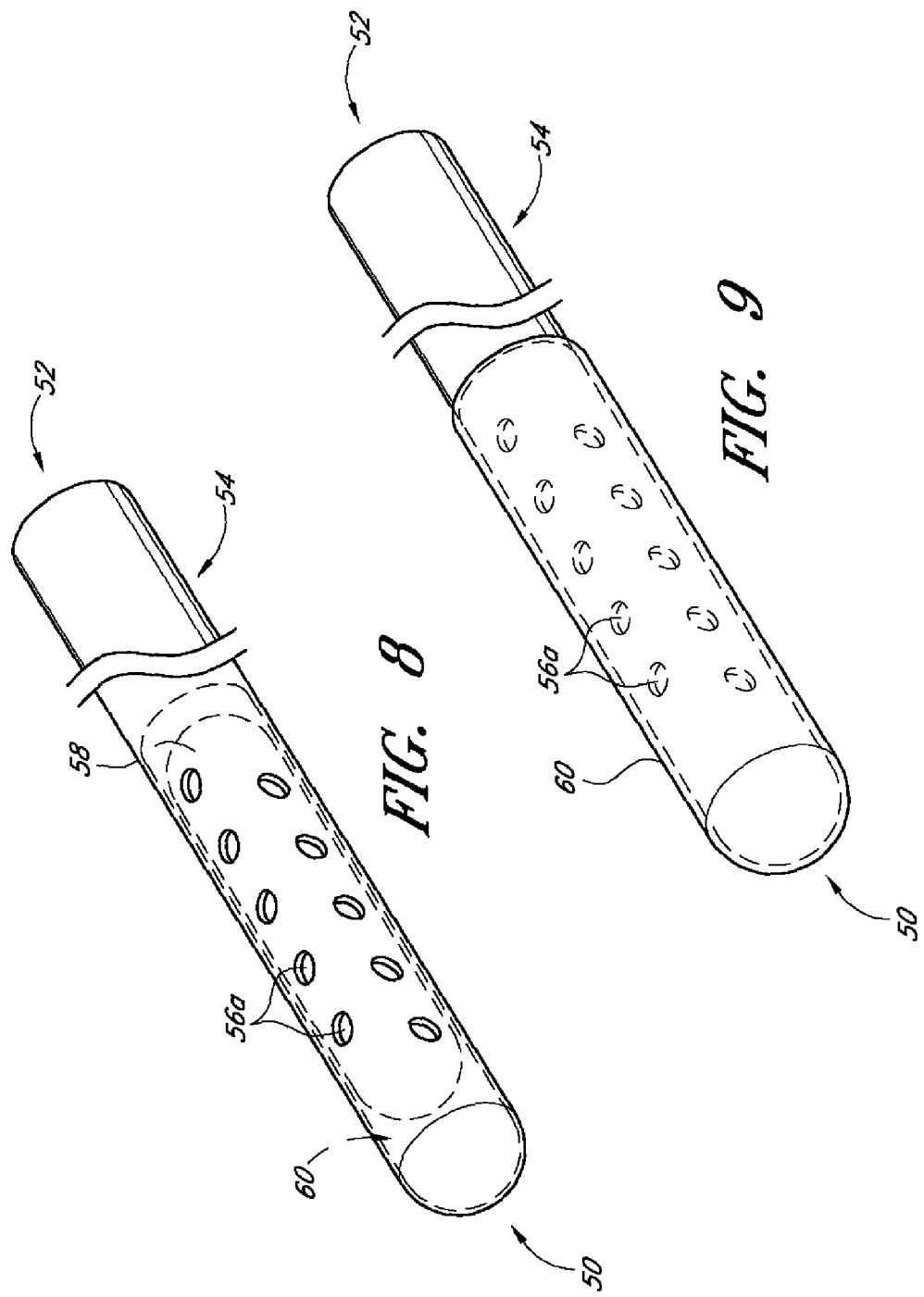

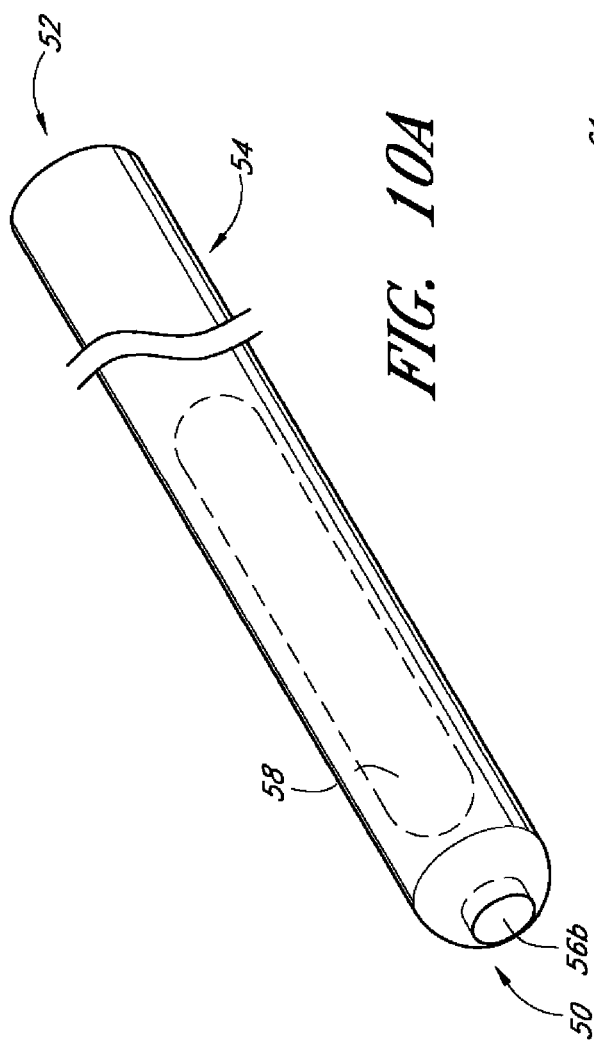
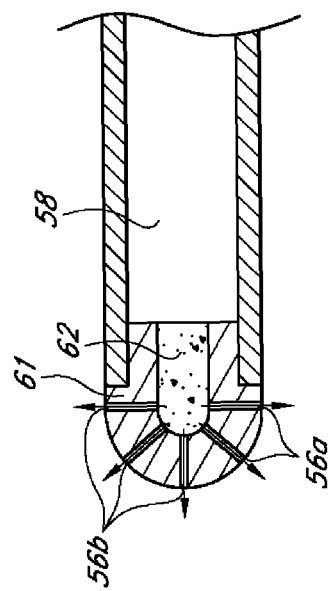
FIG. 10A
FIG. 10B

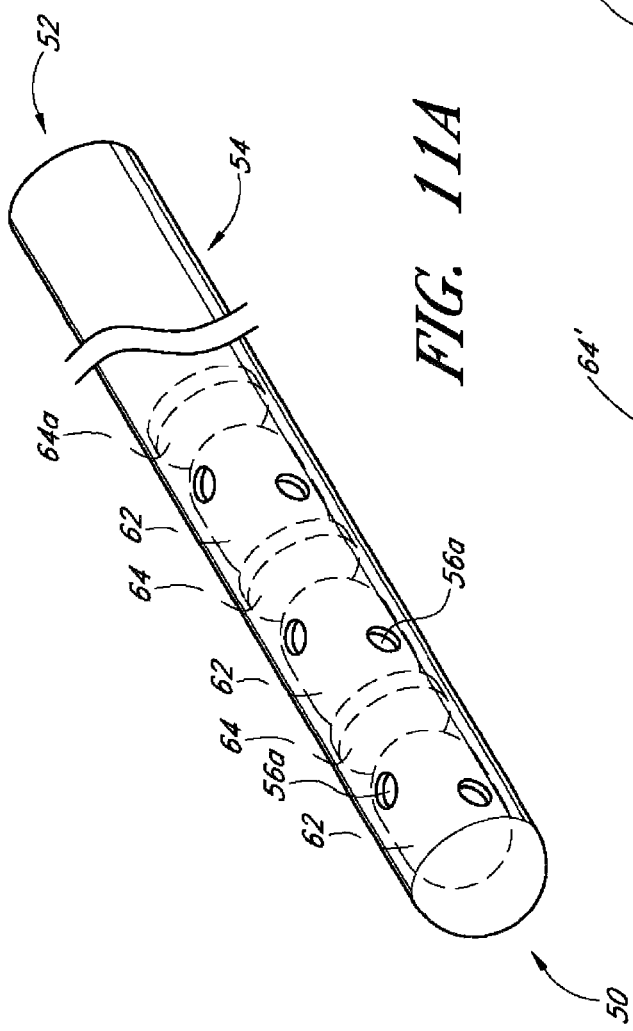
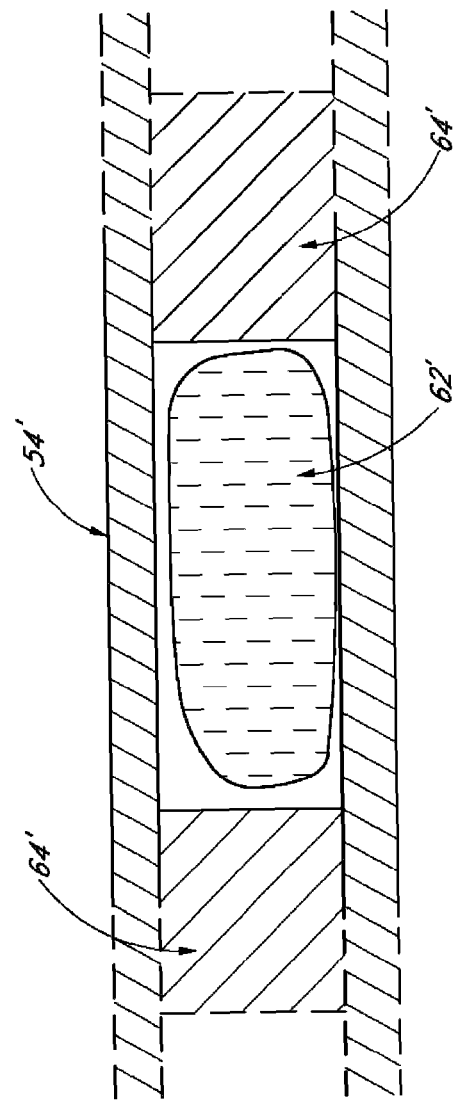

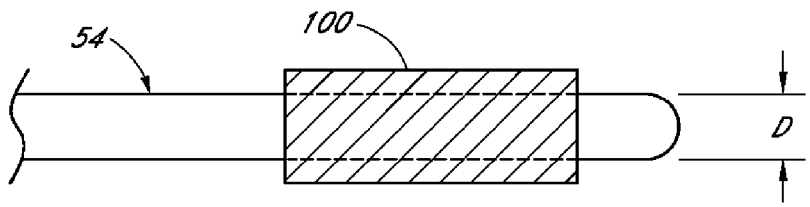
FIG. 19L
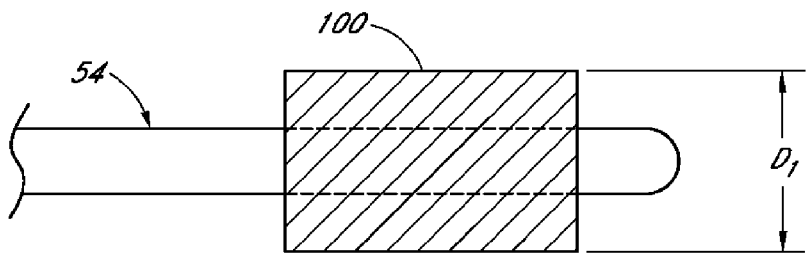
FIG. 19M
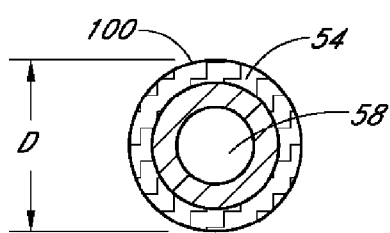 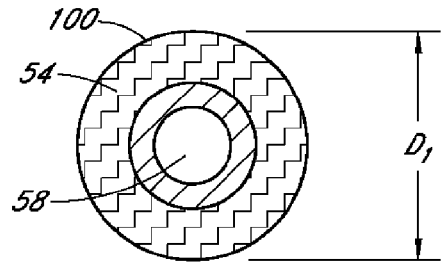
FIG. 19N      FIG. 19O
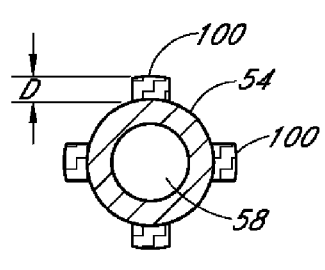 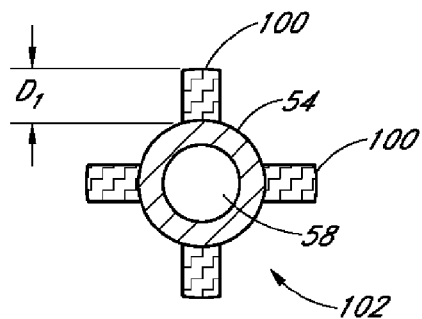
FIG. 19P      FIG. 19Q

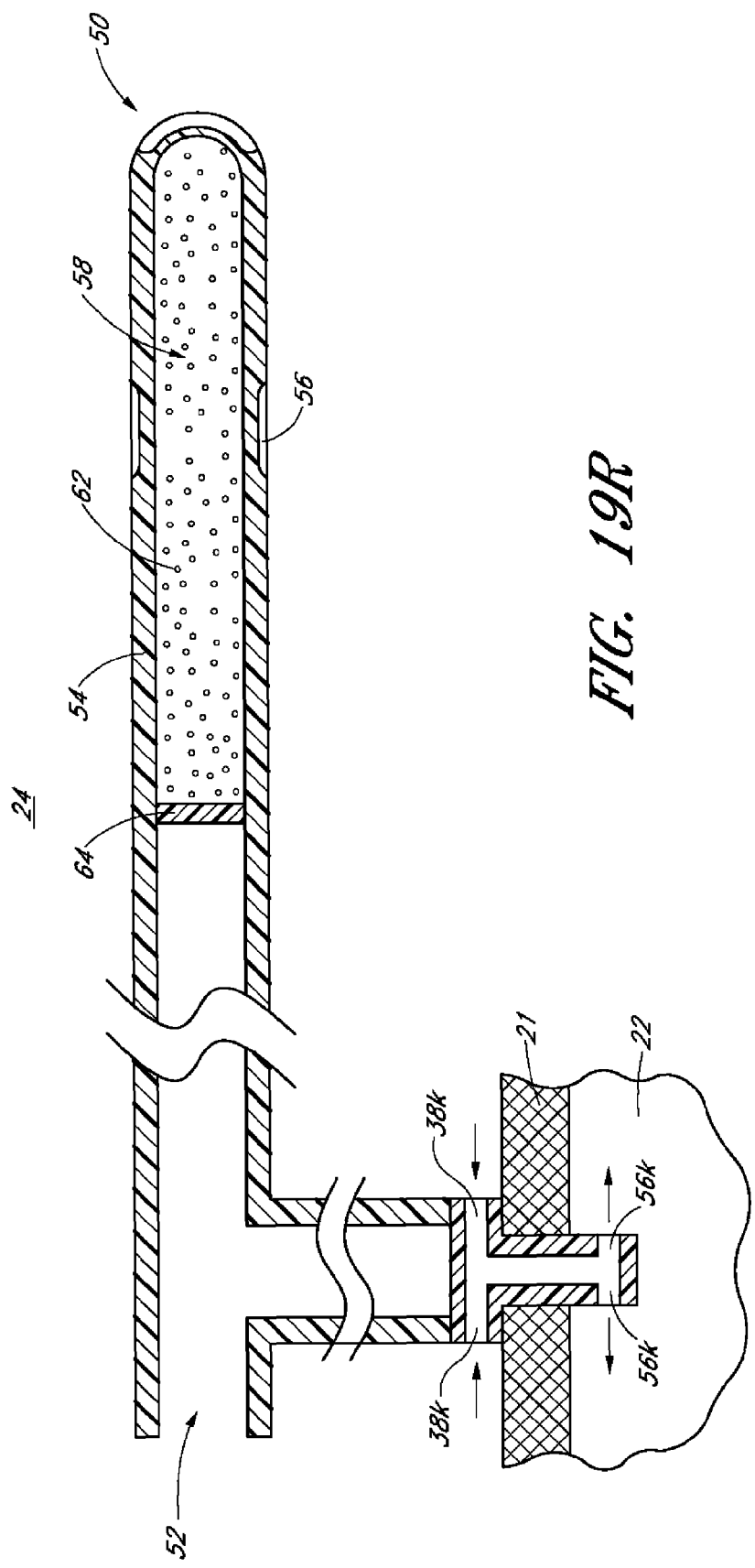

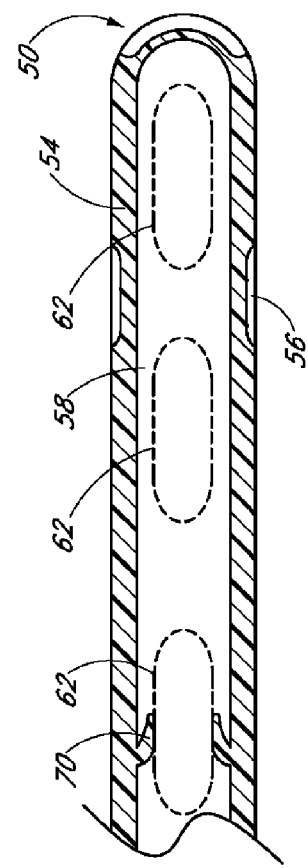
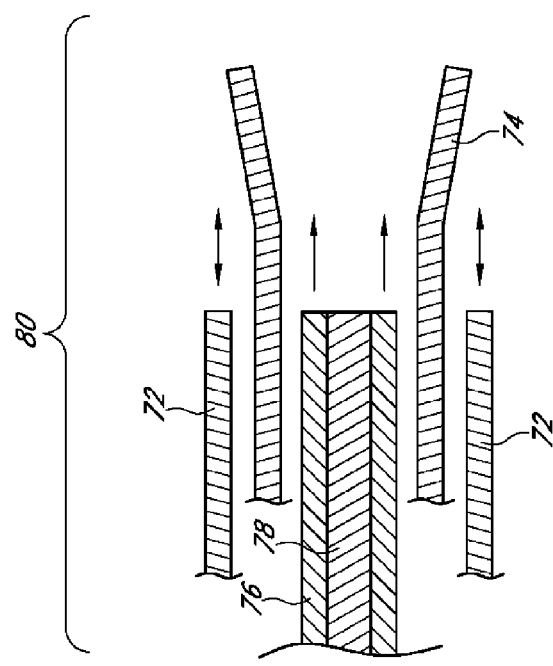
FIG. 20C

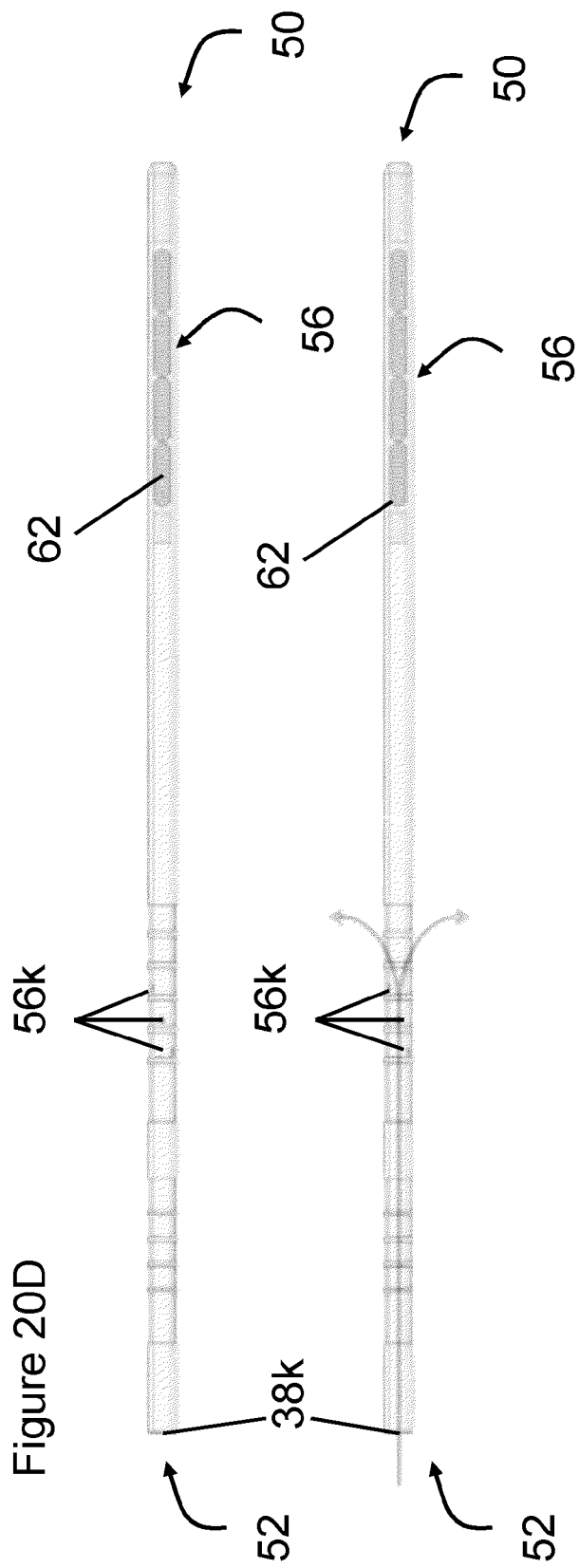

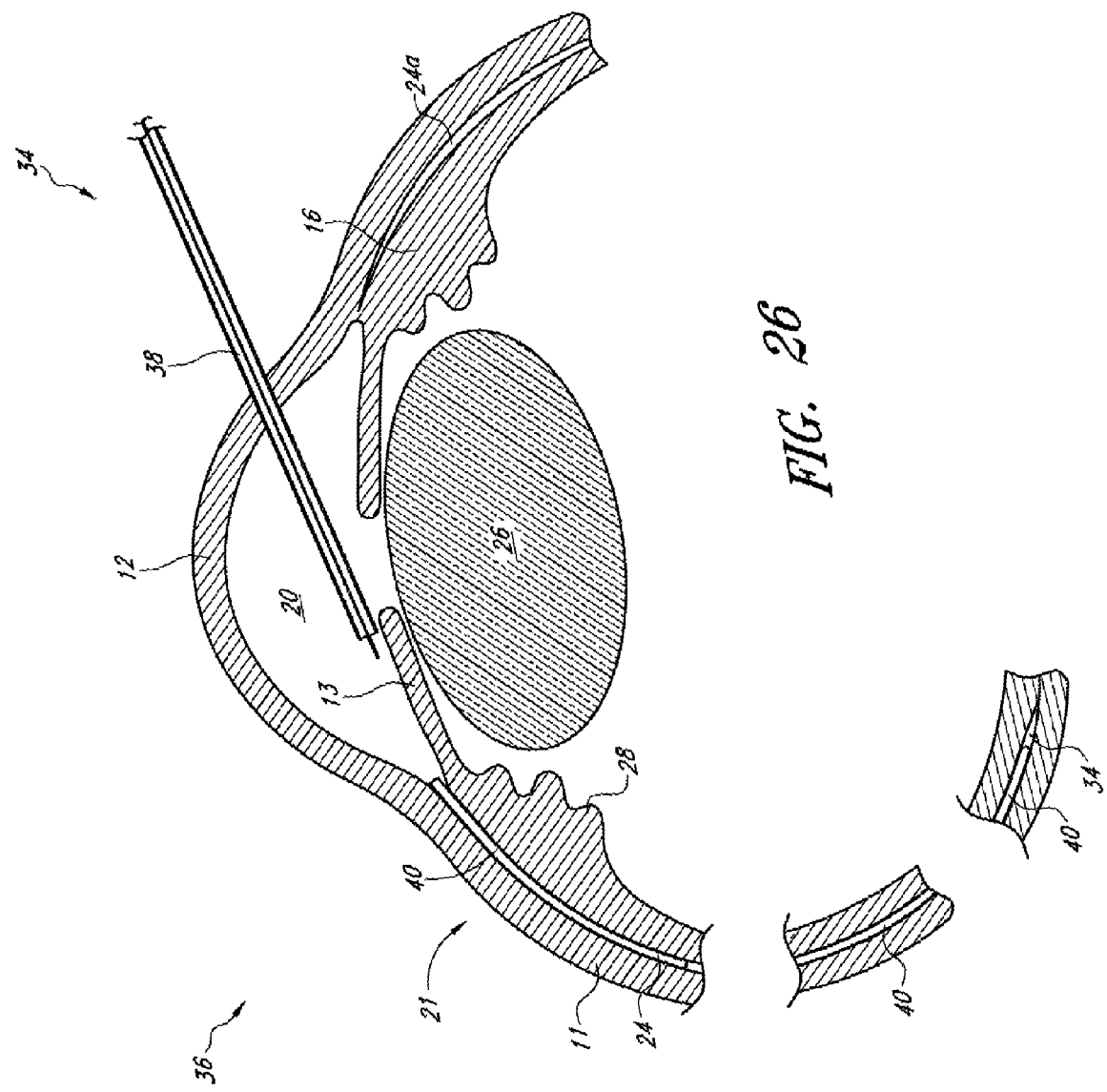

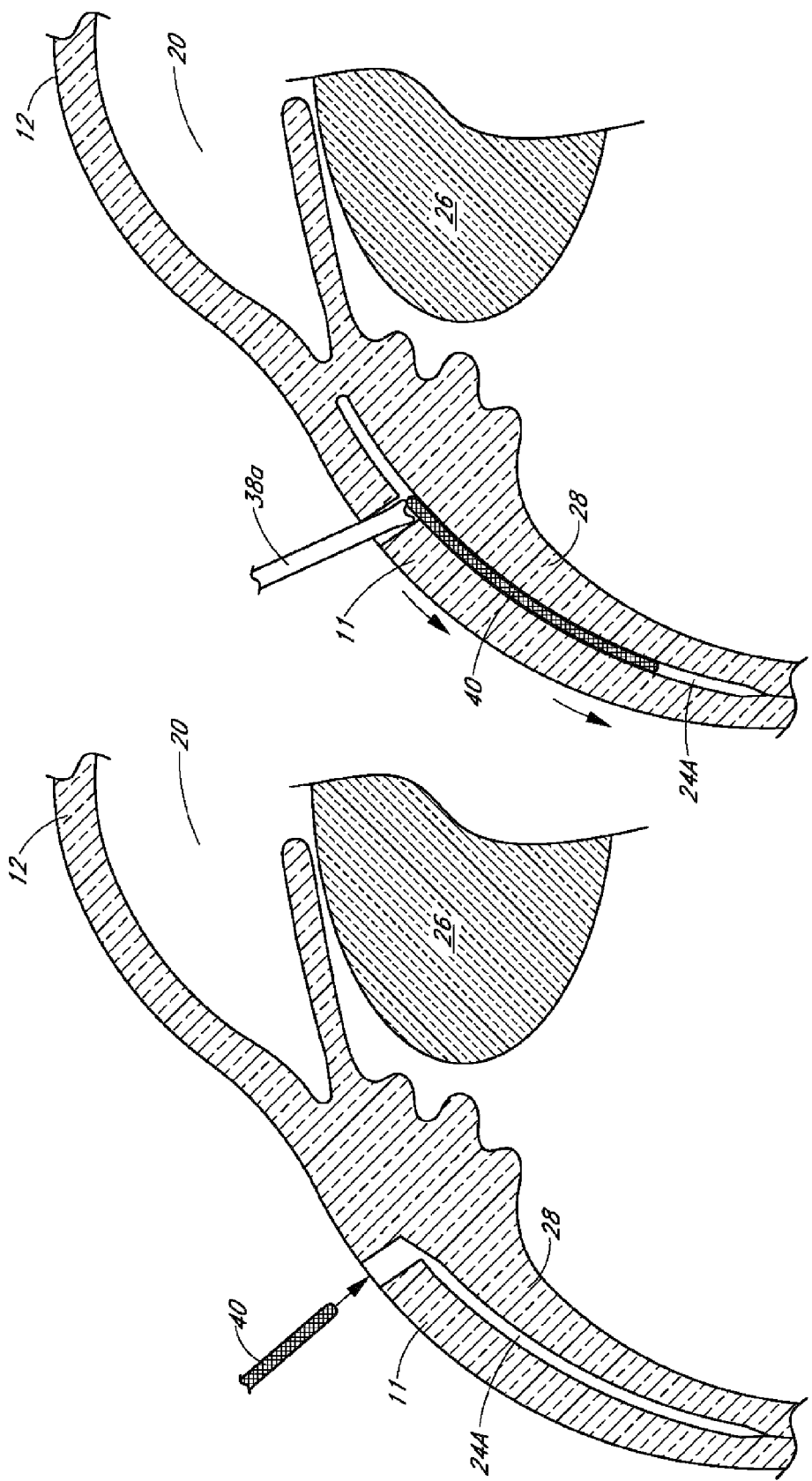

ial Application Ser. No. 61/788,731, filed on Mar. 15, 2013. This application is also a continuation-in-part of co-pending U.S. patent application Ser. No. 13/321,144, filed Nov. 17, 2011, which is the United States National Phase under 25 U.S.C. § 371 of International Application No. PCT/US2010/035319, filed May 18, 2010, which claims the benefit of United States Provisional Application Ser. Nos. 61/179,332, filed May 18, 2009; 61/220,527, filed Jun. 25, 2009; and 61/264,604, 61/264,594, and 61/264,615, each filed Nov. 25, 2009. The contents of the each of the priority applications listed above are incorporated in their entirety by reference herein.

IMPLANTS WITH CONTROLLED DRUG DELIVERY FEATURES AND METHODS OF USING SAME

RELATED CASES

This application claims the benefit of Unites States Provisional Application Ser. No. 61/788,731, filed on Mar. 15, 2013. This application is also a continuation-in-part of co-pending U.S. patent application Ser. No. 13/321,144, filed Nov. 17, 2011, which is the United States National Phase under 25 U.S.C. § 371 of International Application No. PCT/US2010/035319, filed May 18, 2010, which claims the benefit of United States Provisional Application Ser. Nos. 61/179,332, filed May 18, 2009; 61/220,527, filed Jun. 25, 2009; and 61/264,604, 61/264,594, and 61/264,615, each filed Nov. 25, 2009. The contents of the each of the priority applications listed above are incorporated in their entirety by reference herein.

BACKGROUND

Field

This disclosure relates to implantable intraocular drug delivery devices structured to provide targeted and/or controlled release of a drug to a desired intraocular target tissue and methods of using such devices for the treatment of ocular diseases and disorders. In certain embodiments, this disclosure relates to a treatment of increased intraocular pressure wherein aqueous humor is permitted to flow out of an anterior chamber of the eye through a surgically implanted pathway. In certain embodiments, this disclosure also relates particularly to a treatment of ocular diseases with drug delivery devices affixed to the eye, such as to fibrous tissue within the eye.

Description of the Related Art

The mammalian eye is a specialized sensory organ capable of light reception and is able to receive visual images. The retina of the eye consists of photoreceptors that are sensitive to various levels of light, interneurons that relay signals from the photoreceptors to the retinal ganglion cells, which transmit the light-induced signals to the brain. The iris is an intraocular membrane that is involved in controlling the amount of light reaching the retina. The iris consists of two layers (arranged from anterior to posterior), the pigmented fibrovascular tissue known as a stroma and pigmented epithelial cells. The stroma connects a sphincter muscle (sphincter pupillae), which contracts the pupil, and a set of dilator muscles (dilator pupillae) which open it. The pigmented epithelial cells block light from passing through the iris and thereby restrict light passage to the pupil.

Numerous pathologies can compromise or entirely eliminate an individual's ability to perceive visual images, including trauma to the eye, infection, degeneration, vascular irregularities, and inflammatory problems. The central portion of the retina is known as the macula. The macula, which is responsible for central vision, fine visualization and color differentiation, may be affected by age related macular degeneration (wet or dry), diabetic macular edema, idiopathic choroidal neovascularization, or high myopia macular degeneration, among other pathologies.

Other pathologies, such as abnormalities in intraocular pressure, can affect vision as well. Aqueous humor is a transparent liquid that fills at least the region between the cornea, at the front of the eye, and the lens and is responsible for producing a pressure within the ocular cavity. Normal intraocular pressure is maintained by drainage of aqueous humor from the anterior chamber by way of a trabecular meshwork which is located in an anterior chamber angle, lying between the iris and the cornea or by way of the "uveoscleral outflow pathway." The "uveoscleral outflow pathway" is the space or passageway whereby aqueous exits the eye by passing through the ciliary muscle bundles located in the angle of the anterior chamber and into the tissue planes between the choroid and the sclera, which extend posteriorly to the optic nerve. About two percent of people in the United States have glaucoma, which is a group of eye diseases encompassing a broad spectrum of clinical presentations and etiologies but unified by increased intraocular pressure. Glaucoma causes pathological changes in the optic nerve, visible on the optic disk, and it causes corresponding visual field loss, which can result in blindness if untreated. Increased intraocular pressure is the only risk factor associated with glaucoma that can be treated, thus lowering intraocular pressure is the major treatment goal in all glaucomas, and can be achieved by drug therapy, surgical therapy, or combinations thereof.

Many pathologies of the eye progress due to the difficulty in administering therapeutic agents to the eye in sufficient quantities and/or duration necessary to ameliorate symptoms of the pathology. Often, uptake and processing of the active drug component of the therapeutic agent occurs prior to the drug reaching an ocular target site. Due to this metabolism, systemic administration may require undesirably high concentrations of the drug to reach therapeutic levels at an ocular target site. This can not only be impractical or expensive, but may also result in a higher incidence of side effects. Topical administration is potentially limited by limited diffusion across the cornea, or dilution of a topically applied drug by tear-action. Even those drugs that cross the cornea may be unacceptably depleted from the eye by the flow of ocular fluids and transfer into the general circulation. Thus, a means for ocular administration of a therapeutic agent in a controlled and targeted fashion would address the limitations of other delivery routes.

SUMMARY

Several embodiments disclosed herein provide a drug delivery ocular implant comprising an outer shell having a proximal end, a distal end, the outer shell being shaped to define an interior lumen, at least a first active drug positioned within the interior lumen, a cap configured for reversible interaction with the proximal end of the outer shell, a membrane positioned between the cap and the proximal end of the outer shell, and a retention protrusion on the distal end of the outer shell that is configured to anchor the ocular implant at a target tissue site.

In several embodiments, the cap comprises at least one aperture. In several embodiments a plurality of apertures are provided. The overall surface area of the one or more apertures can be selected in a particular embodiment, based on the desired rate of elution of the first active drug from the implant.

In several embodiments, the placement of the cap over the proximal end of the outer shell enables the retention of the membrane between the cap and the proximal end of the outer shell. In some embodiments the cap is a press-fit cap, while other embodiments employ a crimp cap, screw cap or other type of cap. In several embodiments, the membrane is permeable to the at least a first active drug as well as to ocular fluid (and/or the water component of ocular fluid). In several embodiments, the membrane (once the cap is positioned) occludes the at least one aperture, such that elution of the at least a first active drug occurs only through the membrane (e.g., the compression of the membrane by the cap also functions to seal the implant to other routes of unintended drug release). In several embodiments, selected combinations of the membrane and the dimensions (e.g., surface area) of the aperture(s) are tailored to a specifically desired elution rate of the first active agent.

In several embodiments, the implant further comprises a distally-positioned seal limiting fluid communication between the interior lumen and an ocular space in which the implant is positioned to that occurring through the membrane. In several embodiments, such a seal provides an additional degree of control of the rate of drug elution.

In several embodiments, the membrane has a thickness of between about 50 and about 100 microns. In such embodiments, such a thickness results in drug elution from the implant for a period of time ranging from about 12 to about 24 months. In several embodiments, the membrane has a thickness of between about 90 and about 200 microns. In such embodiments, such a thickness results in drug elution from the implant for a period of time ranging from about 24 to about 48 months.

In several embodiments, the outer shell further comprises at least one fluid inflow pathway and one fluid outflow pathway, and wherein the at least one fluid inflow pathway and one fluid outflow pathway are configured to deliver ocular fluid to a physiological outflow pathway. Thus, in several embodiments, the implant is configured not only to provide a pharmaceutical therapy, but also a physical therapy (e.g., drainage). In several embodiments, the physiological outflow pathway is Schlemm's Canal. In several embodiments, the at least one first active drug comprises a prostaglandin, a prostaglandin analog, a prostaglandin inhibitor, and/or combinations thereof. Additionally, in several embodiments, a second agent may optionally be provided. In several embodiments, the second (or third, etc.) agent results in synergistic effects when combined with the first agent. In other embodiments, the second agent reduces one or more side effects associated with the first agent.

Additionally, there is provided, in several embodiments, a drug delivery ocular implant comprising an elongate outer shell having a proximal end, a distal end, the outer shell being shaped to define an interior lumen, at least a first active drug positioned within the interior lumen, at least one fluid flow pathway running from a proximal region of the outer shell to a more distal region of the outer shell, a valve positioned at the distal-most end of the outer shell, wherein the valve is reversibly openable to enable passage of the at least a first active drug from the interior lumen to a target site external to the implant.

In several embodiments the at least one fluid flow pathway is configured to deliver ocular fluid to a physiological outflow pathway (e.g., supplementing the pharmacologic effects of the active agent). In several embodiments, the first active drug comprises a plurality of drug pellets, and the implant comprises at least a second active agent. In several embodiments, the second active agent is housed within a polymer configured to polymerize and become solid or semi-solid at physiological temperature.

In several embodiments, the second active agent is housed within a micelle or vesicular structure configured to release the second active agent at a known rate. In several embodiments, the second active agent is housed within a micelle or vesicular structure configured to release the second active agent at a known rate and wherein the micelle or vesicular structure is admixed with a polymer configured to polymerize and become solid or semi-solid at physiological temperature. Thus, in several such embodiments, delivery of the second agent to the ocular target tissue results in polymerization of the polymer upon exposure to the normal body temperatures of the intraocular environment, thus reducing migration of the second agent away from the target site (thereby improving its therapeutic effects).

In several additional embodiments, there is provided a drug delivery ocular implant comprising an elongate outer shell having a proximal end, a distal end, the outer shell being shaped to define an interior lumen with at least a first active drug positioned within the interior lumen, wherein the outer shell comprises a first thickness and wherein the outer shell comprises one or more regions of drug release In several embodiments, the elongate shell is formed by extrusion. In several embodiments, the elongate shell comprises a biodegradable polymer. In several embodiments, the outer shell is permeable or semi-permeable to the first active drug, thereby allowing at least about 5% of total the elution of the first active drug to occur through the portions of the shell having the first thickness.

In several embodiments, the outer shell comprises polyurethane. In several embodiments, the polyurethane comprises a polysiloxane-containing polyurethane elastomer.

In several embodiments, the regions of drug release are configured to allow a different rate of drug elution as compared to the elution through the outer shell. In several embodiments, the overall rate of elution of the first active drug out of the implant is greater in the distal region of the implant. In several embodiments, there is a greater amount of the first active drug in the distal half of the implant as compared to the proximal half of the implant. In several other embodiments, the overall rate of elution of the first active drug out of the implant is greater in the proximal region of the implant. In several embodiments, there is a greater amount of the first active drug in the proximal half of the implant as compared to the distal half of the implant. In several such embodiments, the implant is thus configured to treat an anterior portion of the eye of a subject, while optionally providing (depending on the embodiment) drainage of ocular fluid to an outflow tract.

In several embodiments, the one or more regions of drug release comprise one or more of regions of reduced thickness shell material, one or more orifices passing through the outer shell, or combinations thereof. In certain embodiments, the one or more regions of drug release comprise orifices and wherein the orifices are positioned along the long axis of the implant shell.

In several embodiments, the implant additionally comprises one or more coatings that alter the rate of the first active agent elution from the implant.

In several embodiments, at least the distal-most about 5 mm to about 10 mm of the interior lumen houses the drug.

In several embodiments, the elution of the first active drug from the implant continues for at least a period of at least one year.

In several embodiments, the first active drug is present as one or more micro-tablets, wherein the micro-tablets have a density of about 0.7 g/cc to about 1.6 g/cc, an aspect ratio of length to diameter of about 2.8 to 3.6, and/or minor axis of about 0.28 to 0.31 mm and a major axis of about 0.8 to 1.1 mm. In several embodiments, the first active drug is present in an amount of at least 70% by weight of a total weight of the one or more micro-tablets. In several embodiments, the micro-tablets have a surface area to volume ratio of about 13 to 17. In several embodiments, the micro-tablets have dimensions allowing passage of the micro-tablets through a conduit having an inner diameter of about 23 to 25 gauge.

In several embodiments, the micro-tablets are formed by utilizing one or more of processes selected from the group consisting of tabletting, lyophilization, granulation (wet or dry), flaking, direct compression, molding, and extrusion. In several embodiments, the micro-tablets are configured to balance osmotic pressure between the interior lumen and the ocular environment external to an implant after implantation. In further embodiments, the micro-tablets are optionally coated with a coating that regulates the release of the first active drug from the micro-tablet. In some embodiments, the coating is a polymeric coating.

In several embodiments, the first active drug is an anti-angiogenesis agent. In several embodiments, the first active drug is selected from the group consisting of angiostatin, anecortave acetate, thrombospondin, VEGF receptor tyrosine kinase inhibitors and anti-vascular endothelial growth factor (anti-VEGF) drugs. In several embodiments, the anti-VEGF drugs are selected from the group consisting of ranibizumab, bevacizumab, pegaptanib, sunitinib and sorafenib. In several embodiments, the first active drug is bevacizumab.

In several embodiments, the first active drug is a beta-adrenergic receptor antagonist. The beta-adrenergic receptor antagonist may be either a selective beta-adrenergic antagonist, or a non-selective beta-adrenergic receptor antagonist. In several embodiments, the selective beta-adrenergic receptor antagonist is selected from the group consisting of betaxolol and levobetaxolol, and combinations thereof. In several embodiments the non-selective beta-adrenergic antagonist is selected from the group consisting of timolol, levobunolol, certeolol, and metipranolol, and combinations thereof. In several embodiments, at least one active drug is used, and in some embodiments that at least one first active drug is timolol.

In several embodiments, the implants as described herein optionally further comprise a lumen configured to transport ocular fluid from a first location in an eye to one or more other locations, thereby reducing intraocular pressure.

There is also provided herein methods for treating an ocular condition or disorder in an intraocular target tissue comprising making an opening in the temporal portion of an eye to access an anterior chamber of the eye, advancing a delivery device associated with a drug delivery ocular implant through the opening and across the anterior chamber of the eye, inserting the drug delivery ocular implant into eye tissue, positioning the implant such that at least one of the one or more regions of drug release are located proximate an intraocular target, and withdrawing the delivery device from the eye, wherein drug elutes from the implant in sufficient quantity to treat an ocular condition or disorder. In some embodiments, a therapeutic effect is achieved for a period of at least one year.

In several embodiments, the intraocular target is in the posterior chamber of the eye. In some embodiments, the intraocular target is selected from the group consisting of the macula, the retina, the optic nerve, the ciliary body, and the intraocular vasculature. In several other embodiments, the intraocular target is in the anterior chamber of the eye.

In several embodiments, inserting the drug delivery ocular implant into eye tissue comprises placing at least a portion of the implant in a portion of the eye selected from the group consisting of uveoscleral outflow pathway, suprachoroidal space, and Schlemm's canal.

There is also provided for a composition for the treatment of an ocular disorder, comprising a therapeutic agent having anti-vascular endothelial growth factor (VEGF) effects, wherein the anti-VEGF agent is formed into at least one micro-tablet. In several embodiments, the anti-VEGF agent is lyophilized prior to formation of the micro-tablets. In some embodiments, the anti-VEGF agent comprises at least 70% by weight of the total weight of each micro-tablet, and in some embodiments, each micro-tablet has a density of about 0.7 g/cc to about 1.6 g/cc. In additional embodiments, each of the micro-tablets has a minor axis of about 0.28 to 0.31 mm and a major axis of about 0.8 to 1.1 mm. In several embodiments, each of the micro-tablets has an aspect ratio of length to diameter of about 2.8 to 3.6.

In addition, there is provided a system for administering a therapeutic agent to an damaged or diseased eye, comprising an ocular implant delivery apparatus comprising a proximal end, a distal end, and a cannula having an inner diameter of about 23 to 25 gauge, an ocular implant comprising an elongate outer shell having a proximal end, a distal end, the outer shell being shaped to define an interior lumen suitable for receiving one or more micro-tablets and comprising at least a first thickness and comprising one or more regions of drug release, and a therapeutic agent formed in at least one micro-tablet, the agent having anti-vascular endothelial growth factor (VEGF) effects. In several embodiments, the anti-VEGF agent is lyophilized prior to formation of the micro-tablets. In some embodiments, the anti-VEGF agent comprises at least 70% by weight of the total weight of each micro-tablet. In some embodiments, each micro-tablet has a density of about 0.7 g/cc to about 1.6 g/cc. In additional embodiments, the micro-tablets have an aspect ratio of length to diameter of about 2.8 to 3.6.

There is additionally provided for herein methods for the intravitreal injection of an agent for the treatment of an ocular disorder, comprising advancing to the surface of the sclera of an eye a delivery apparatus comprising a proximal end, a distal end, and a cannula having an inner diameter of about 23 to 25 gauge and containing one or more micro-tablets comprising a therapeutic agent having anti-vascular endothelial growth factor (VEGF) effects, an activator that functions to expel the contents of the cannula from the apparatus via passage through the proximal end, piercing the scleral surface to create a hole in the sclera, further advancing the delivery apparatus thru the hole such that the proximal end is within the vitreal cavity of the eye, activating the activator to expel the anti-VEGF micro-tablets; and withdrawing the apparatus from the eye, thereby treating the disorder by the delivery of the anti-VEGF micro-tablets.

In several embodiments, the micro-tablets have a minor axis of about 0.28 to 0.31 mm and a major axis of about 0.8 to 1.1 mm. In several embodiments, the micro-tablets have a density of about 0.7 g/cc to about 1.6 g/cc.

In several embodiments, the piercing of the sclera is performed using an apparatus having a sharpened proximal end. In several embodiments, the hole within the sclera is sufficiently small to be self-healing.

In accordance with several embodiments there is provided a drug delivery ocular implant comprising an elongate outer shell having a proximal end, and a distal end, said outer shell being shaped to define an interior lumen, and at least a first drug positioned within said interior lumen. In certain embodiments, the outer shell comprises a substantially uniform first thickness, wherein said outer shell is permeable or semi-permeable to said drug, thereby allowing at least about 5% of the total elution of the drug to occur through the portions of the shell having said first thickness, and wherein said outer shell comprises one or more regions of drug release. In some embodiments, the one or more regions of drug release comprise regions of greater or increased elution or permeability to the drug than the portion of the outer shell having the first thickness. Such regions of increased permeability may comprise one or more of the outer shell having a reduced thickness, one or more orifices, a different material than the remainder of the outer shell and/or other means to provide increased permeability or elution of the drug. In other embodiments, the entirety of the elution of the drug is through the outer shell, the entirety of which or one or more portions of which may be considered to be a region of drug release.

In several embodiments, there is provided a drug delivery ocular implant comprising an elongate outer shell having a proximal end, a distal end, the outer shell being shaped to define an interior lumen, and at least a first drug positioned within the interior lumen. The outer shell preferably has a substantially uniform first thickness that allows about 5 to 15% of the total elution of the drug to occur through the shell having the first thickness. The outer shell may comprise one or more regions of drug release, wherein the regions of drug release are configured to allow different rates of drug elution as compared to each other. In some embodiments, the overall rate of elution of drug out of the implant is optionally differential along the length of the implant.

In some embodiments, there are provided implants having regions of drug release that are configured or have one or more regions that allow a greater rate of drug elution as compared to the elution through other regions of the outer shell. In some embodiments, the regions of greater drug release comprise one or more of regions of reduced thickness shell material, one or more orifices passing through the outer shell, or combinations thereof. In some embodiments, the outer shell optionally comprises silicone and/or may have one or more orifices passing through the outer shell. In such embodiments, the orifices may be positioned along the long axis of the implant shell or elsewhere. In other embodiments, the outer shell optionally comprises siliconized urethane and/or may comprise regions of reduced thickness, and may or may not have any orifices passing through the outer shell.

In several embodiments disclosed herein, there is provided a drug delivery ocular implant comprising an outer shell having a proximal end, a distal end, and being shaped to define an interior lumen, the outer shell having a substantially uniform first thickness and having one or more regions of a second, reduced shell thickness as compared to the first thickness, and a drug positioned within the interior lumen, wherein the thickness of the outer shell is inversely proportional to the rate of drug elution through the shell. In some embodiments, the outer shell of the first thickness is substantially impermeable to the drug. Release of the drug from the interior lumen is controlled at least in part by the permeability of the outer shell to the drug, with regions of reduced shell thickness having a higher rate of release.

Also provided is a drug delivery ocular implant comprising an outer shell having a proximal end, a distal end, and being shaped to define an interior lumen and having one or more partitions located within the interior lumen thereby creating two or more sub-lumens, a drug positioned within each sub-lumen. In some embodiments, at least a portion of the outer shell is substantially impermeable to the drug, and the outer shell also comprises one or more regions that are more permeable to the drug relative to the remainder of the outer shell, and wherein release of the drug from the interior lumen is controlled at least in part by the permeability of the more permeable outer shell regions.

In several embodiments there is also provided a drug delivery ocular implant comprising an outer shell having a proximal end, a distal end, and being shaped to define an interior lumen, a drug positioned within the interior lumen, wherein at least a portion of the outer shell is substantially impermeable to the drug, and the outer shell comprises one or more regions that are more permeable to the drug relative to the remainder of the outer shell.

In several embodiments disclosed herein, there is provided a drug delivery ocular implant comprising an outer shell being shaped to define an interior lumen, a drug positioned within the interior lumen, wherein the outer shell is comprises a permeable material that is capable of conveying both a solvent and the drug through the outer shell, wherein release of the drug from the interior lumen is initiated by the exposure of the outer shell to a suitable solvent, such that the solvent is conveyed through the permeable material to contact the drug, wherein after contact the solvent contacts the drug, the drug is conveyed through the permeable material to the exterior of the outer shell, and wherein the conveyance of the drug is controlled at least in part by the permeability of the permeable material. The outer shell may also include one or more regions of substantially impermeable material.

In several embodiments, there is provided a medical device for the delivery of a therapeutic agent to a patient, comprising an device dimensioned to be positioned at an area of a patient's body, a therapeutic agent positioned on or in at least a portion of the device, and wherein at least a portion of the device provides a physical effect useful toward mitigation of an unwanted side effect of the therapeutic agent.

In several embodiments, there is provided a drug delivery ocular implant comprising an outer shell that has one or more orifices therein, the shell being shaped to define an interior lumen a drug positioned within the interior lumen one or more coatings positioned on the interior surface of the shell, the outer surface of the shell, and/or partially or fully enveloping the drug positioned within the interior lumen. Embodiments may further comprise one or more of the following optional features: the outer shell comprises a material substantially impermeable to ocular fluids, the outer shell is substantially impermeable to the drug, at least one of the coatings at least partially defines the release rate of the drug, and the implant is dimensioned such that the distal end of the implant is positioned in the suprachoroidal space and the proximal end of the implant is positioned fully within the eye.

In several embodiments, there is provided a drug delivery ocular implant comprising an outer shell that is optionally substantially impermeable to ocular fluids and has one or more orifices therein, the shell being shaped to define an interior lumen, a drug positioned within the interior lumen, one or more coatings positioned on the interior surface of the shell, the outer surface of the shell, and/or partially or fully enveloping the drug positioned within the interior lumen, and wherein the implant is dimensioned such that the drug is released to a desired intraocular target post-implantation.

In several embodiments, there is provided a drug delivery ocular implant comprising a flexible material compounded or coated with at least one drug, a flexible tether, wherein the flexible material may be rolled or folded to form a tube shape, wherein the tube shape is dimensioned to be placed within a delivery apparatus, wherein the delivery apparatus deploys the drug delivery ocular implant to an intraocular tissue, wherein the tube shape is released upon withdrawal of the delivery apparatus, thereby allowing the flexible material, which may be in the form of a sheet or disc, to return substantially to its original shape or configuration.

In several embodiments, there is provided a drug delivery ocular implant comprising an outer shell shaped to define an interior lumen or space with one open end, a cap dimensioned to fit within or over the one open end and having one or more orifices therein, and a drug positioned within the interior lumen. One or more coatings are optionally positioned on the interior surface of the cap, the outer surface of the cap, and/or between layers of drug positioned within the interior lumen.

Any embodiments disclosed herein may optionally further comprise a lumen, opening or shunt configured to transport ocular fluid from a first, undesired location, to one or more other locations, thereby reducing intraocular pressure.

The implants provided for herein optionally provide differential elution along the length of the implant and in some such embodiments, have a rate of elution that is greater at the distal portion of the implant as compared more proximal regions of the implant. In other embodiments, the implants have a rate of elution that is greater at the proximal portion of the implant as compared to more distal regions of the implant. Moreover, implants may optionally additionally comprise one or more coatings on the interior and/or exterior of the device and/or on the drug contained therein, that alter the rate of drug elution from the implant, the coatings optionally covering different portions of the implant.

In several embodiments, the distal-most about 5 mm to about 10 mm of the interior lumen houses the drug. In some embodiments, the outer shell has a length between about 10 mm and about 20 mm, an outer diameter between about 150 microns to about 500 microns, and an interior lumen diameter of about 75 microns to about 475 microns.

Some embodiments provided for herein result in elution of drug from the implant with zero-order or pseudo zero-order kinetics.

Also provided for herein are methods for treating or preventing an ocular condition in an intraocular target tissue comprising making an incision in the cornea or limbus of an eye in an advantageous position (e.g., temporal, nasal, superior, inferior, and the like), advancing a delivery device associated with a drug delivery implant according to several of the embodiments disclosed herein through the cornea of the eye and across the anterior chamber of the eye, inserting at least a portion of the drug delivery implant into the suprachoroidal space of the eye, positioning the implant such that the one or more regions of drug release are located sufficiently near the intraocular target to allow substantially all of the drug released from the implant to reach the intraocular target, and withdrawing the delivery device from the eye.

In some embodiments, the intraocular target is the posterior chamber of the eye, the anterior chamber of the eye, both the anterior chamber and posterior of the eye, or the macula, the retina, the optic nerve, the ciliary body, and the intraocular vasculature.

In several embodiments, the drug acts on the intraocular target tissue to generate a therapeutic effect for an extended period. In one embodiment, the drug comprises a steroid. In such embodiments, the implant contains a total load of steroid ranging from about 10 to about 1000 micrograms, steroid is released from the implant at a rate ranging from about 0.05 to about 10 micrograms per day and/or the steroid acts on the diseased or damaged target tissue at a concentration ranging from about 1 to about 100 nanomolar. In some embodiments, the steroid additionally generates side effects associated with accumulation of physiologic fluid, and an optional shunt transports the accumulated fluid from the first location to the remote second location (such as, for example, from the anterior chamber to an existing physiological outflow pathway, such as Schlemm's canal or the uveoscleral pathway). The optional shunt is also used in other embodiments, however, wherein side effects associated with the active drug do not include accumulation of fluid. For example, several embodiments relate to treatment of a region with a therapeutic drug in combination with drainage (even in the absence of therapeutic drug-induced increases in ocular fluid production).

Various embodiments of the implants disclosed herein may comprise one or more of the following optional features: drug being placed near the distal end of the shell, drug being placed near the proximal end of the shell, one or more barriers placed within the interior lumen to limit anterior (or, in some embodiments, posterior) elution of the drug, and/or a barrier that comprises a one-way valve positioned to allow fluid passage through the implant in a proximal to distal direction. In some embodiments having one or more barriers placed within the interior lumen, the one or more barriers facilitate the simultaneous (or sequential) elution of one or more drugs to the anterior and/or posterior chamber for targeted effects.

In some embodiments disclosed herein, there are provided coatings, preferably polymeric coatings, that are biodegradable. In some embodiments, two or more polymeric coatings are positioned on a surface of the outer shell and in some such embodiments, each coating has a unique rate of biodegradation in ocular fluid (including being substantially non-biodegradable), covers a different portion of the shell including covering one or more optional orifices in the shell, and/or permits ocular fluid to contact the drug within the interior lumen by passing through an increasing number of patent orifices in the shell over time that are created by the degradation of the coating material. In some embodiments, the coatings are optionally placed on the outer surface of the shell, positioned between the drug and the interior surface of outer shell, and/or positioned to envelop the drug within the interior lumen. The drug may be in the form of one or more pellets, beads, or tablets, oils, gels, emulsions, and the like.

In several embodiments, biodegradation of the barriers or coatings is triggered by an externally originating stimulus, such as, for example, intraocular injection of a fluid that initiates biodegradation of the barrier, application of heat, ultrasound, and radio frequency, and the like. In some embodiments, the barriers and/or coatings degrade faster than the drug, while in other embodiments, the degradation rate of the drug is faster, or in still other embodiments, in which the rate of degradation is unique for each.

Any of the embodiments disclosed herein optionally further comprise one or more anchor structures, one or more excipients compounded with the drug, one or more orifices or openings in the proximal portion of the device to allow drainage of ocular fluid from the anterior chamber of the eye, and/or one or more wicks passing through any outer shell of the implant.

Several embodiments optionally comprise a retention protrusion configured to anchor the implant to an ocular tissue. Such retention protrusions optionally comprise one or more of ridges, claws, threads, flexible ribs, rivet-like shapes, flexible barbs, barbed tips, expanding material (such as a hydrogel), and biocompatible adhesives. In some embodiments, the expanding material is placed on an exterior surface of the outer shell of the implant and expands after contact with a solvent, such as, for example, intraocular fluid.

Implants provided for herein are optionally anchored (e.g., any mechanism or element that allows an implant to become affixed to, secured to or otherwise attached, either permanently or transiently, to a suitable target intraocular tissue) to a intraocular tissue, such as ciliary muscles, the ciliary tendons, the ciliary fibrous band, the trabecular meshwork, the iris, the iris root, the lens cortex, the lens epithelium, to or within the lens capsule, the sclera, the scleral spur, the choroid, or to or within Schlemm's canal. In certain embodiments comprising an implant anchored within the lens capsule, such an implant is preferably implanted concurrently, or after, removal of the native lens (e.g., by cataract surgery).

In some embodiments, the devices comprise one or more regions that are permeable to a drug or more permeable to a drug than other regions of a device. The increased permeability may be achieved by any means, including, but not limited to: use of thinner or decreased thickness of material that has some degree of permeability to the drug, whereby the decreased thickness increases the rate of diffusion or transport of the drug; orifices or holes wherein the orifices or holes may be of any suitable size or shape to allow egress of drug and/or ingress of ocular fluids; use of a second material that has increased permeability of a drug; use of a coating which enhances transport of a drug from the interior of a device to the exterior; and any combination of the foregoing.

Any of the implant embodiments described herein may also further comprise a lumen or passageway to allow drainage of ocular fluid from first location to a second location, such as, for example, from the anterior chamber of the eye to a physiological outflow pathway.

In any of the embodiments disclosed herein, the drug preferably is released from the implant to act on a diseased or damaged target tissue to generate a therapeutic effect. In some embodiments, the drug additionally generates side effects associated with accumulation of physiologic fluid and in such embodiments the implant may further comprise a stent or passage to transport the accumulated fluid from the first location to the remote second location.

According the disclosure herein, any of the implants described may comprise a shell of metal or polymeric material, which includes homopolymers, polymer blends and copolymers, such as random copolymers and block copolymers. In some embodiments, the polymeric material comprises ethyl vinyl acetate, polyethylene, Elasthane™, silicone, polyurethane, polyethersulfone, and/or polyamide. In other embodiments, the polymeric material comprises poly(carbonate urethane), poly(ether urethane), silicone poly(carbonate urethane), silicone poly(ether urethane), Pur-Sil™ CarboSil™, or Bionate™.

In those embodiments having regions of reduced shell thickness, such regions may be created by any suitable means, including one or more of ablation, stretching, etching, grinding, and molding. The region may be in any pattern on or around the implant, including a spiral pattern, patches, rings and/or bands.

Regions that are characterized by having an increased rate of drug delivery, be it by reduced shell thickness, orifices, permeable material or any other means or combination of means described herein may be present at or in any portion or combination of portions of the device. Preferably the regions are placed so as to direct the drug to tissues in the eye which are the target of treatment by the drug. In some embodiments, such regions (or a single such region) are preferably concentrated towards the distal end of an elongate device so as to target delivery of a drug to tissues in the distal portions of the posterior chamber of the eye. In some embodiments, such regions (or a single such region) are preferably concentrated towards the proximal end of an elongated device so as to target delivery of a drug to tissues in the anterior chamber of the eye.

Implants as described herein may optionally be configured to interact with a recharging device in order to recharge the implant with an additional or supplementary dose of the drug. Such rechargeable implants, optionally comprise a reversible coupling between the proximal end of the implant and a clamping sleeve on the recharging device. In certain embodiments, the clamping sleeve houses flexible clamping grippers that create a secure coupling between the implant and the recharging device. The secure coupling optionally enables the recharging device to enable a flexible pusher or filling tube incorporated into the recharging device to be used to deliver a drug to a lumen of the implant. In several embodiments, the secure coupling between the implant and the recharging device enable a spring loaded flexible pusher tube incorporated into the recharging device to be used to deliver drug to a lumen of the implant. In some embodiments, there is a provided a one-way passage that allows deposition of a drug to the lumen of the implant, but prevents the drug from escaping the lumen through the passage after the removal of the recharging device.

In some embodiments, implants are provided that further comprise at least one partition within the interior lumen, thereby creating at least two sub-lumens. In some embodiments having two or more sub-lumens, each sub-lumen optionally houses a different drug or a different concentration of the same drug as compared to the other sub-lumens, optionally releases a drug to a different portion of the eye. In some embodiments where the implant houses multiple drugs one drug is therapeutically effective against an ocular disorder and another drug ameliorates a side effect of administration of the first drug.

In addition to sub-lumens, several embodiments are provided for in which implants further comprise: distal regions of the shell that are more permeable to the drugs as compared to more proximal regions; proximal regions of the shell that are more permeable to the drugs as compared to more distal regions; have partitions that are positioned perpendicular to a long axis of the outer shell; have partitions that are semi-permeable to a drug positioned within the sub-lumens; wherein drug release from the sub-lumens occurs first from the distal-most sub-lumen and last from the proximal-most sub-lumen; and/or wherein drug release from the sub-lumens occurs first from the proximal-most sub-lumen and last from the distal-most sub-lumen.

In some such embodiments, the partitions are optionally varied in permeability to the drugs within the sub-lumens such that the overall elution profile includes periods of time where drug release is reduced or eliminated.

Any of the embodiments disclosed herein comprising a lumen, pathway or shunt in addition to drug elution in an implant may optionally drain fluid to any existing physiological outflow pathway, including the suprachoroidal space, the trabecular meshwork, or Schlemm's canal, and may optionally target drug delivery to the anterior chamber of the eye, the posterior chamber of the eye, both the anterior chamber and posterior of the eye, and/or specifically target the macula, the retina, the optic nerve, the ciliary body, and/or the intraocular vasculature.

In several such embodiments, the implant comprises a substantially straight, rigid, generally cylindrical shell or body. In several embodiments, the implant, when implanted, extends into the anterior chamber at its proximal end into the suprachoroidal space at its distal end. For example, the body may be of a length no greater than 7 mm, preferably not greater than about 5 mm, and more preferably not greater than about 4 mm and not shorter than about 2 mm. In several embodiments, the body has a tip that narrows toward a distal end of the implant. In additional embodiments, the body comprises a substantially flexible, generally cylindrical shell or body, that may be of length approximately 25 mm, including about 15 to about 18 mm, about 18 to about 21 mm, about 21 to about 23 mm, about 23 to about 25 mm, about 25 mm to about 27 mm, about 27 to about 30 mm, and overlapping ranges thereof.

In several embodiments, at least one opening located in or near the proximal end of the implant communicates with at least one interior lumen. The proximal opening can be located in the proximal end of the implant and can be substantially perpendicular to a longitudinal axis of the implant. In several embodiments, a first active drug is positioned within the interior lumen. When implanted, the drug can elute into the anterior chamber of the eye of a subject via the proximal opening. Control of drug elution into the anterior chamber is achieved, depending on the embodiment, for example, by locating a membrane having a known permeability to the drug over or around the proximal opening. In several embodiments, the membrane is also permeable to aqueous humor or the water component of aqueous humor (e.g., the membrane allows two-way flow, aqueous humor or the water component of aqueous humor into the device, and drug out of the device).

In embodiments comprising a shunt, the interior lumen terminates at one or more openings located in or near the distal end of the implant. In such embodiments, aqueous humor from the anterior chamber drains through the proximal opening, into the implant, and out of the distal opening into the suprachoroidal space to reduce the intraocular pressure of the anterior chamber of the eye.

Any of the embodiments disclosed herein may deliver a drug and/or provide a therapeutic effect for several days, one to two months, at least six months, at least a year, at least two years, at least three years, at least four years, and/or at least five years.

Any of the embodiments disclosed herein may be configured to target a diseased or damaged target tissue that is characterized by a limited ability to swell without loss or impairment of physiological function.

In several embodiments, there is provided a method of treating or preventing an ocular condition comprising: making an incision in the eye, inserting at least a portion of a drug delivery implant according to several embodiments disclosed herein into the suprachoroidal space of the eye, and withdrawing the delivery device from the eye.

In some embodiments, the implants are positioned such that the regions of the implant from which drug is released are located sufficiently near an intraocular target to allow substantially all of the drug released from the implant to reach the intraocular target In several embodiments, the methods disclosed herein optionally comprise one or more of making an incision in the cornea or limbus of the eye in an advantageous position (e.g., temporal, nasal, superior, inferior, and the like), advancing the delivery device through the cornea of the eye and to the site of implantation.

In several embodiments there is provided a method for delivering an ocular implant comprising a stent according to several embodiments disclosed herein that simultaneously treats an ocular condition and limits treatment-associated side-effects, particularly those associated with increased fluid accumulation in the eye and/or increased intraocular pressure. In several embodiments, an ocular implant having shunt works in conjunction with elution of a first drug from the ocular implant to lower intraocular pressure by providing a patent outflow pathway through which aqueous humor can drain.

Other embodiments optionally comprise placing a peripheral iridotomy adjacent to the implanted drug delivery device and optionally maintaining the peripheral iridotomy as patent with a stent.

BRIEF DESCRIPTION OF THE DRAWINGS

These and other features, aspects, and advantages of the present disclosure will now be described with reference to the drawings of embodiments, which embodiments are intended to illustrate and not to limit the disclosure. One of ordinary skill in the art would readily appreciated that the features depicted in the illustrative embodiments are capable of combination in manners that are not explicitly depicted, but are both envisioned and disclosed herein.

FIG. 4 illustrates a drug delivery device in accordance with embodiments disclosed herein.

FIG. 5 illustrates a drug delivery device in accordance with embodiments disclosed herein.

FIG. 8 illustrates the distal portion of a drug delivery implant in accordance with embodiments disclosed herein.

FIG. 9 illustrates the distal portion of another drug delivery implant in accordance with embodiments disclosed herein.

FIGS. 10A-10G illustrate other drug delivery implants in accordance with embodiments disclosed herein.

FIGS. 11A-11B illustrate various embodiments of implants as disclosed herein that house one or more drug-containing pellets within the implant.

FIG. 26 illustrates a schematic cross-section view of an eye with a delivery device implanting an implant that extends from the anterior chamber through the suprachoroidal space and terminates in close proximity to the macula.

FIGS. 27A-27D illustrate a cross-sectional view an eye during the steps of one embodiment of a method for implanting drug delivery devices as disclosed herein.

DETAILED DESCRIPTION

Figure 1:
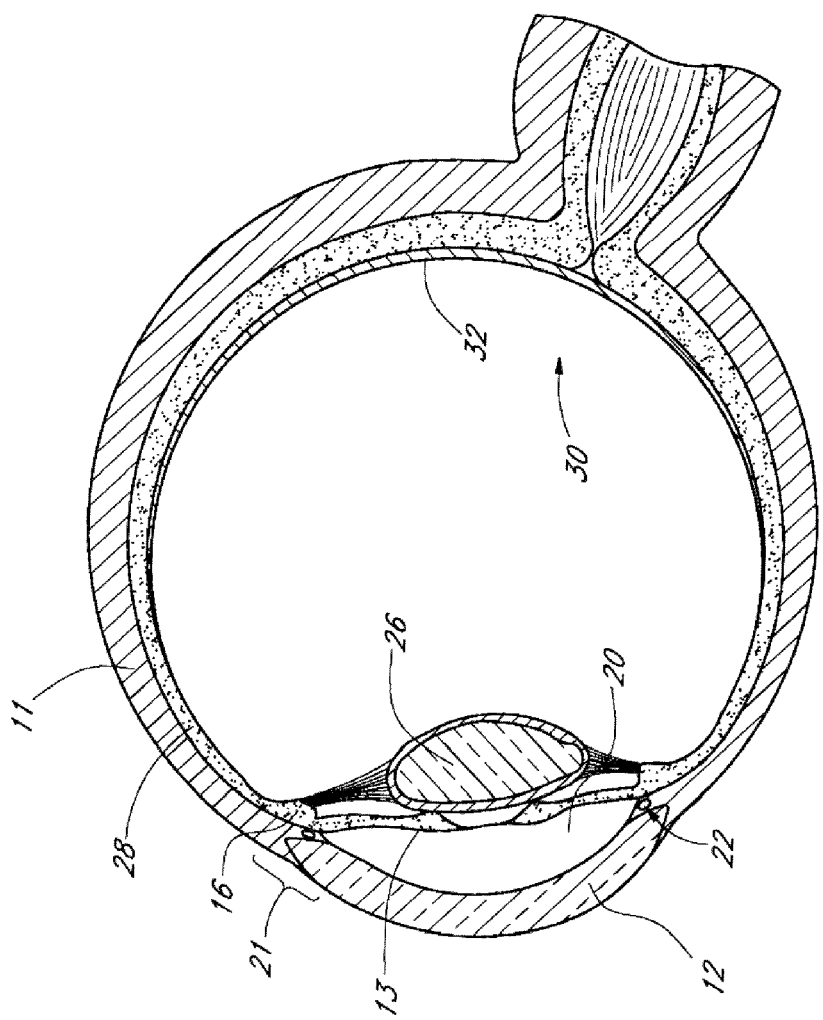
FIG. 1 illustrates a schematic cross sectional view of an eye.

Achieving local ocular administration of a drug may require direct injection or application, but could also include the use of a drug eluting implant, a portion of which, could be positioned in close proximity to the target site of action within the eye or within the chamber of the eye where the target site is located (e.g., anterior chamber, posterior chamber, or both simultaneously). Use of a drug eluting implant could also allow the targeted delivery of a drug to a specific ocular tissue, such as, for example, the macula, the retina, the ciliary body, the optic nerve, or the vascular supply to certain regions of the eye. Use of a drug eluting implant could also provide the opportunity to administer a controlled amount of drug for a desired amount of time, depending on the pathology. For instance, some pathologies may require drugs to be released at a constant rate for just a few days, others may require drug release at a constant rate for up to several months, still others may need periodic or varied release rates over time, and even others may require periods of no release (e.g., a "drug holiday"). Further, implants may serve additional functions once the delivery of the drug is complete. Implants may maintain the patency of a fluid flow passageway within an ocular cavity, they may function as a reservoir for future administration of the same or a different therapeutic agent, or may also function to maintain the patency of a fluid flow pathway or passageway from a first location to a second location, e.g. function as a stent. Conversely, should a drug be required only acutely, an implant may also be made completely biodegradable.

Implants according to the embodiments disclosed herein preferably do not require an osmotic or ionic gradient to release the drug(s), are implanted with a device that minimizes trauma to the healthy tissues of the eye which thereby reduces ocular morbidity, and/or may be used to deliver one or more drugs in a targeted and controlled release fashion to treat multiple ocular pathologies or a single pathology and its symptoms. However, in certain embodiments, an osmotic or ionic gradient is used to initiate, control (in whole or in part), or adjust the release of a drug (or drugs) from an implant. In some embodiments, osmotic pressure is balanced between the interior portion(s) of the implant and the ocular fluid, resulting in no appreciable gradient (either osmotic or ionic). In such embodiments, variable amounts of solute are added to the drug within the device in order to balance the pressures.

As used herein, "drug" refers generally to one or more drugs that may be administered alone, in combination and/or compounded with one or more pharmaceutically acceptable excipients (e.g. binders, disintegrants, fillers, diluents, lubricants, drug release control polymers or other agents, etc.), auxiliary agents or compounds as may be housed within the implants as described herein. The term "drug" is a broad term that may be used interchangeably with "therapeutic agent" and "pharmaceutical" or "pharmacological agent" and includes not only so-called small molecule drugs, but also macromolecular drugs, and biologics, including but not limited to proteins, nucleic acids, antibodies and the like, regardless of whether such drug is natural, synthetic, or recombinant. Drug may refer to the drug alone or in combination with the excipients described above. "Drug" may also refer to an active drug itself or a prodrug or salt of an active drug.

As used herein, "patient" shall be given its ordinary meaning and shall also refer to mammals generally. The term "mammal", in turn, includes, but is not limited to, humans, dogs, cats, rabbits, rodents, swine, ovine, and primates, among others. Additionally, throughout the specification ranges of values are given along with lists of values for a particular parameter. In these instances, it should be noted that such disclosure includes not only the values listed, but also ranges of values that include whole and fractional values between any two of the listed values.

In several embodiments, a biocompatible drug delivery ocular implant is provided that comprises an outer shell that is shaped to define at least one interior lumen that houses a drug for release into an ocular space. The outer shell is polymeric in some embodiments, and in certain embodiments is substantially uniform in thickness, with the exception of areas of reduced thickness, through which the drug more readily passes from the interior lumen to the target tissue. In other words, a region of drug release may be created by virtue of the reduced thickness. In several other embodiments the shell of the implant comprises one or more regions of increased drug permeability (e.g., based on the differential characteristics of portions of the shell such as materials, orifices, etc.), thereby creating defined regions from which the drug is preferentially released. In other embodiments, if the material of the outer shell is substantially permeable to a drug, the entire outer shell can be a region of drug release. In yet another embodiment, portions of the outer shell that surround where the drug is placed in the interior lumen or void of the device may be considered a region of drug release. For example, if the drug is loaded toward the distal end or in the distal portion of the device (e.g. the distal half or distal ⅔ of the device), the distal portion of the device will be a region of drug release as the drug will likely elute preferentially through those portions of the outer shell that are proximate to the drug. Therefore, as used herein, the term "region of drug release" shall be given its ordinary meaning and shall include the embodiments disclosed in this paragraph, including a region of drug permeability or increased drug permeability based on the characteristics of a material and/or the thickness of the material, one or more orifices or other passageways through the implant (also as described below), regions of the device proximate to the drug and/or any of these features in conjunction with one or more added layers of material that are used to control release of the drug from the implant. Depending on the context, these terms and phrases may be used interchangeably or explicitly throughout the present disclosure.

In some embodiments, the outer shell comprises one or more orifices to allow ocular fluid to contact the drug within the lumen (or lumens) of the implant and result in drug release. In some embodiments, as discussed in more detail below, a layer or layers of a permeable or semi-permeable material is used to cover the implant (wholly or partially) and the orifice(s) (wholly or partially), thereby allowing control of the rate of drug release from the implant. Additionally, in some embodiments, combinations of one or more orifices, a layer or layers covering the one or more orifices, and areas of reduced thicknesses are used to tailor the rate of drug release from the implant.

In still other embodiments, combinations of materials may be used to construct the implant (e.g., polymeric portions of outer shell bonded or otherwise connected, coupled, or attached to outer shell comprising a different material).

In still other embodiments, the drug to be delivered is not contained within an outer shell. In several embodiments, the drug is formulated as a compressed pellet (or other form) that is exposed to the environment in which the implant is deployed. For example, a compressed pellet of drug is coupled to an implant body which is then inserted into an ocular space (see e.g., FIG. 19T). In some embodiments, the implant body comprises a fluid flow pathway. In some embodiments, the implant optionally comprises a retention feature. In some embodiments, the drug is encapsulated, coated, or otherwise covered with a biodegradable coating, such that the timing of initial release of the drug is controlled by the rate of biodegradation of the coating. In some embodiments, such implants are advantageous because they allow a variable amount of drug to be introduced (e.g., not constrained by dimensions of an implant shell) depending on the type and duration of therapy to be administered. In some embodiments having a shunt feature the shunt feature works in conjunction with the drug to treat one or more symptoms of the disease or condition affecting the patient. For example, in some embodiments, the shunt removes fluid from the anterior chamber while the drug simultaneously reduces the production of ocular fluid. In other embodiments, as discussed herein, the shunt counteracts one or more side effects of administration of a particular drug (e.g., the shunt drains ocular fluid that was produced by the actions of the drug).

In some embodiments, biocompatible drug delivery implants comprise a flexible sheet or disc flexibly optionally associated with (e.g., tethered to) a retention protrusion (e.g., an anchoring element, gripper, claw, or other mechanism to permanently or transiently affix the sheet or disc to an intraocular tissue). In certain of such embodiments, the therapeutic agent is compounded with the sheet or disc and/or coated onto the sheet or disc. In some embodiments, the flexible sheet or disc implants are dimensioned such that they may be rolled or folded to be positioned within the lumen of a delivery instrument, for example a small diameter hollow needle.

Following implantation at the desired site within the eye, drug is released from the implant in a targeted and controlled fashion, based on the design of the various aspects of the implant, preferably for an extended period of time. The implant and associated methods disclosed herein may be used in the treatment of pathologies requiring drug administration to the posterior chamber of the eye, the anterior chamber of the eye, or to specific tissues within the eye, such as the macula, the ciliary body or other ocular target tissues.

FIG. 1 illustrates the anatomy of an eye, which includes the sclera 11, which joins the cornea 12 at the limbus 21, the iris 13 and the anterior chamber 20 between the iris 13 and the cornea 12. The eye also includes the lens 26 disposed behind the iris 13, the ciliary body 16 and Schlemm's canal 22. The eye also includes a uveoscleral outflow pathway, which functions to remove a portion of fluid from the anterior chamber, and a suprachoroidal space positioned between the choroid 28 and the sclera 11. The eye also includes the posterior region 30 of the eye which includes the macula 32.

General

In some embodiments functioning as a drug delivery device alone, the implant is configured to deliver one or more drugs to anterior region of the eye in a controlled fashion while in other embodiments the implant is configured to deliver one or more drugs to the posterior region of the eye in a controlled fashion. In still other embodiments, the implant is configured to simultaneously deliver drugs to both the anterior and posterior region of the eye in a controlled fashion. In yet other embodiments, the configuration of the implant is such that drug is released in a targeted fashion to a particular intraocular tissue, for example, the macula or the ciliary body. In certain embodiments, the implant delivers drug to the ciliary processes and/or the posterior chamber. In certain other embodiments, the implant delivers drug to one or more of the ciliary muscles and/or tendons (or the fibrous band). In some embodiments, implants deliver drug to one or more of Schlemm's canal, the trabecular meshwork, the episcleral veins, the lens cortex, the lens epithelium, the lens capsule, the sclera, the scleral spur, the choroid, the suprachoroidal space, retinal arteries and veins, the optic disc, the central retinal vein, the optic nerve, the macula, the fovea, and/or the retina. In still other embodiments, the delivery of drug from the implant is directed to an ocular chamber generally. It will be appreciated that each of the embodiments described herein may target one or more of these regions, and may also optionally be combined with a shunt feature (described below).

In several embodiments, the implant comprises an outer shell. In some embodiments, the outer shell is tubular and/or elongate, while in other embodiments, other shapes (e.g., round, oval, cylindrical, etc.) are used. In certain embodiments, the outer shell is not biodegradable, while in others, the shell is optionally biodegradable. In several embodiments, the shell is formed to have at least a first interior lumen. In certain embodiments, the first interior lumen is positioned at or near the distal end of the device. In other embodiments, a lumen may run the entire length of the outer shell. In some embodiments, the lumen is subdivided. In certain embodiments, the first interior lumen is positioned at or near the proximal end of the device. In those embodiments additionally functioning as a shunt, the shell may have one or more additional lumens within the portion of the device functioning as a shunt.

In several embodiments, the drug (or drugs) is positioned within the interior lumen (or lumens) of the implant shell. In several embodiments, the drug is preferentially positioned within the more distal portion of the lumen. In some embodiments, the distal-most 15 mm of the implant lumen (or lumens) house the drug (or drugs) to be released. In some embodiments, the distal-most 10 mm, including 1, 2, 3, 4, 5, 6, 7, 8, and 9 mm of the interior lumen(s) house the drug to be released. In several embodiments, the drug is preferentially positioned within the more proximal portion of the lumen.

In some embodiments, the drug diffuses through the shell and into the intraocular environment. In several embodiments, the outer shell material is permeable or semi-permeable to the drug (or drugs) positioned within the interior lumen, and therefore, at least some portion of the total elution of the drug occurs through the shell itself, in addition to that occurring through any regions of increased permeability, reduced thickness, orifices etc. In some embodiments, about 1% to about 50% of the elution of the drug occurs through the shell itself. In some embodiments, about 10% to about 40%, or about 20% to about 30% of the elution of the drug occurs through the shell itself. In some embodiments, about 5% to about 15%, about 10% to about 25%, about 15% to about 30%, about 20% to about 35%, about 25% to about 40%, about 30% to about 45%, or about 35% to about 50% of the elution of the drug occurs through the shell itself. In certain embodiments, about 1% to 15%, including, 2, 3, 4, 5, 6, 7, 8, 9, 10, 11, 12, 13, and 14% of the total elution of the drug (or drugs) occurs through the shell. The term "permeable" and related terms (e.g. "impermeable" or "semi permeable") are used herein to refer to a material being permeable to some degree (or not permeable) to one or more drugs or therapeutic agents and/or ocular fluids. The term "impermeable" does not necessarily mean that there is no elution or transmission of a drug through a material, instead such elution or other transmission is negligible or very slight, e.g. less than about 3% of the total amount, including less than about 2% and less than about 1%.

In some embodiments, the implant shell has one or more regions of increased drug permeability through which the drug is released to the target ocular tissue in a controlled fashion.

In some embodiments, the drug or drugs are positioned within the interior lumen or lumens of an implant wherein the implant shell comprises one or more orifices to allow ocular fluid to contact the agent or agents and result in drug release. In some embodiments, the implant comprises a polymeric coating on the exterior surface of a shell. In other embodiments, the implant comprises a polymeric coating on the interior surface of a shell. In still other embodiments, polymeric coatings are on both the interior and exterior surfaces. In yet other embodiments, the polymeric coatings are biodegradable. Some embodiments comprise a non-polymeric coating (e.g. heparin) in place of, or in addition to the polymeric coatings. Additionally, in some embodiments, combinations of one or more orifices, a layer or layers covering the one or more orifices, and areas of reduced thicknesses are used to tailor the rate of drug release from the implant.

In some embodiments, the interior lumen containing the drug(s) are separated from the proximal portion of the implant by way of an proximal barrier within the interior lumen that prevents elution of the drug to the anterior portion of the eye. In some embodiments, the interior lumen(s) containing the drug(s) are separated from the proximal portion of the implant by way of a one way valve within the interior lumen that prevents elution of the drug to the anterior portion of the eye, but allows ocular fluid from the anterior portion of the eye to reach the interior lumen(s) containing the drug(s).

In some embodiments, the implant further comprises a proximal portion structured for recharging/refilling the implant with the same, or an additional therapeutic drug, multiple drugs, or adjuvant compound, or compounds.

In some embodiments comprising a shunt, the shunt portion, following implantation at an implantation site, drains fluid from an ocular chamber into a physiologic outflow space to reduce intraocular pressure. In some embodiments, the implant is dimensioned such that when either the proximal or distal end of the implant is at an implantation site near a tissue targeted for drug delivery, the outflow ports of the implant will drain ocular fluid to a remote region and/or a physiological outflow pathway.

For example, in some embodiments, the implant is dimensioned such that, following implantation, the distal end of the implant is located sufficiently close to the macula that the drug delivered by the implant reaches the macula. In some embodiments incorporating a shunt feature, the implant is dimensioned such that when the distal end of the implant is positioned sufficiently near the macula, the proximal end of the implant extends into the anterior chamber of the eye. In those embodiments, outflow ports in the implant, described in more detail below, are positioned such that the aqueous humor will be drained into the uveoscleral outflow pathway or other physiological outflow pathway.

In still other embodiments, combination drug delivery-shunt implants may be positioned in any physiological location that necessitates simultaneous drug delivery and transport of fluid from a first physiologic site to a second site (which may be physiologic or external to a patient). In some embodiments, the shunt feature works in conjunction with the drug delivery function to potentiate the therapeutic effects of the delivered agent. In other embodiments, the therapeutic effects of the delivered agent may be associated with unwanted side effects, such as fluid accumulation or swelling. In some embodiments, the shunt feature functions ameliorate the side effects of the delivered agent. It shall be appreciated that the dimensions and features of the implants disclosed herein may be tailored to attain targeted and/or controlled delivery to various regions of the eye while still allowing communication with a physiological outflow pathway.

For example, in some embodiments, the implant is dimensioned such that following implantation the distal end of the implant is located in the suprachoroidal space and the proximal end of the implant is located in the anterior chamber of the eye. In several embodiments, the drug eluted from the implant elutes from the proximal end of the implant into the anterior chamber. In some embodiments incorporating a shunt feature, one or more outflow ports in the implant are positioned such that aqueous humor will drain into the uveoscleral pathway. In several embodiments, aqueous humor will drain from the anterior chamber to the suprachoroidal space.

The delivery instruments, described in more detail below, may be used to facilitate delivery and/or implantation of the drug delivery implant to the desired location of the eye. The delivery instrument may be used to place the implant into a desired position, such as the inferior portion of the iris, the suprachoroidal space near the macula, in a position extending from the anterior chamber to the suprachoroidal space, or other intraocular region, by application of a continual implantation force, by tapping the implant into place using a distal portion of the delivery instrument, or by a combination of these methods. The design of the delivery instruments may take into account, for example, the angle of implantation and the location of the implant relative to an incision. For example, in some embodiments, the delivery instrument may have a fixed geometry, be shape-set, or actuated. In some embodiments, the delivery instrument may have adjunctive or ancillary functions, such as for example, injection of dye and/or viscoelastic fluid, dissection, or use as a guidewire. As used herein, the term "incision" shall be given its ordinary meaning and may also refer to a cut, opening, slit, notch, puncture or the like.

In certain embodiments the drug delivery implant may contain one or more drugs which may or may not be compounded with a bioerodible polymer or a bioerodible polymer and at least one additional agent. In still other embodiments, the drug delivery implant is used to sequentially deliver multiple drugs. Additionally, certain embodiments are constructed using different outer shell materials, and/or materials of varied permeability to generate a tailored drug elution profile. Certain embodiments are constructed using different numbers, dimensions and/or locations of orifices in the implant shell to generate a tailored drug elution profile. Certain embodiments are constructed using different polymer coatings and different coating locations on the implant to generate a tailored drug elution profile. Some embodiments elute drug at a constant rate, others yield a zero-order release profile. Yet other embodiments yield variable elution profiles. Still other embodiments are designed to stop elution completely or nearly completely for a predetermined period of time (e.g., a "drug holiday") and later resume elution at the same or a different elution rate or elution concentration. Some such embodiments elute the same therapeutic agent before and after the drug holiday while other embodiments elute different therapeutic agents before and after the drug holiday.

Drug Deliver Implants

The present disclosure relates to ophthalmic drug delivery implants which, following implantation at an implantation site, provide controlled release of one or more drugs to a desired target region within the eye, the controlled release being for an extended, period of time. Various embodiments of the implants are shown in FIGS. 2-20 and will be referred to herein.

Figure 2:
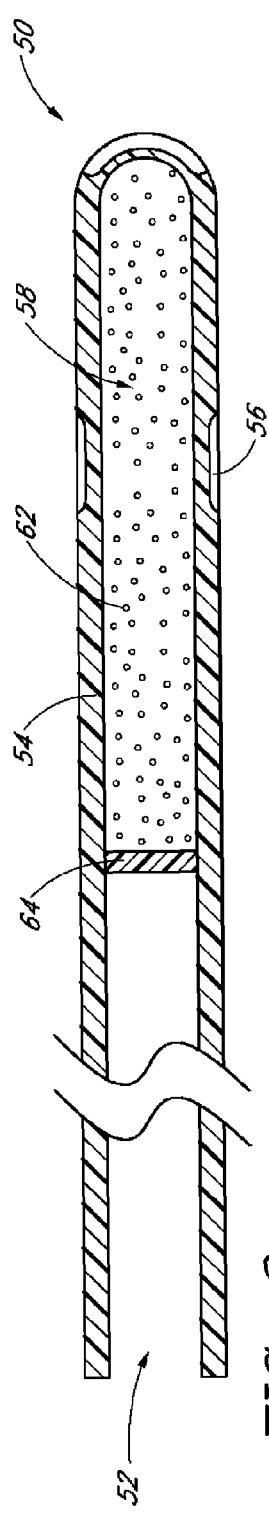
FIG. 2 illustrates a drug delivery device in accordance with embodiments disclosed herein.

FIG. 2 depicts a cross sectional schematic of one embodiment of an implant in accordance with the description herein. The implant comprises an outer shell 54 made of one or more biocompatible materials. The outer shell of the implant is manufactured by extrusion, drawing, injection molding, sintering, micro machining, laser machining, and/or electrical discharge machining, or any combination thereof. Other suitable manufacturing and assembly methods known in the art may also be used. In several embodiments, the outer shell is tubular in shape, and comprises at least one interior lumen 58. In some embodiments the interior lumen is defined by the outer shell and a partition 64. In some embodiments, the partition is impermeable, while in other embodiments the partition is permeable or semi-permeable. In some embodiments, the partition allows for the recharging of the implant with a new dose of drug(s). In some other embodiments, other shell shapes are used, yet still produce at least one interior lumen. In several embodiments the outer shell of the implant 54 is manufactured such that the implant has a distal portion 50 and a proximal portion 52. In several embodiments, the thickness of the outer shell 54 is substantially uniform. In other embodiments the thickness varies in certain regions of the shell. Depending on the desired site of implantation within the eye, thicker regions of the outer shell 54 are positioned where needed to maintain the structural integrity of the implant.

In some embodiments, the implant is made of a flexible material. In other embodiments, a portion of the implant is made from flexible material while another portion of the implant is made from rigid material. In some embodiments, the implant comprises one or more flexures (e.g., hinges). In some embodiments, the drug delivery implant is pre-flexed, yet flexible enough to be contained within the straight lumen of a delivery device.

In other embodiments, at least a portion of the implant (e.g., an internal spine or an anchor) is made of a material capable of shape memory. A material capable of shape memory may be compressed and, upon release, may expand axially or radially, or both axially and radially, to assume a particular shape. In some embodiments, at least a portion of the implant has a preformed shape. In other embodiments, at least a portion of the implant is made of a superelastic material. In some embodiments, at least a portion of the implant is made up of nitinol. In other embodiments, at least a portion of the implant is made of a deformable material.

In several embodiments the majority of the surface of the outer shell of the implant is substantially impermeable to ocular fluids. In several embodiments, the majority of the surface of the outer shell of the implant is also substantially impermeable to the drug 62 housed within the interior lumen of the implant (discussed below). In other embodiments, the outer shell is semi-permeable to drug and/or ocular fluid and certain regions of the implant are made less or more permeable by way of coatings or layers or impermeable (or less permeable) material placed within or on the outer shell.

In several embodiments, the outer shell also has one or more regions of drug release 56. In some embodiments the regions of drug release are of reduced thickness compared to the adjacent and surrounding thickness of the outer shell. In some embodiments, the regions of reduced thickness are formed by one or more of ablation, stretching, etching, grinding, molding and other similar techniques that remove material from the outer shell. In other embodiments the regions of drug release are of a different thickness (e.g., some embodiments are thinner and other embodiments are thicker) as compared to the surrounding outer shell, but are manufactured with an increased permeability to one or more of the drug 62 and ocular fluid. In still other embodiments, the outer shell is uniform or substantially uniform in thickness but constructed with materials that vary in permeability to ocular fluid and drugs within the lumen. As such, these embodiments have defined regions of drug release from the implant.

Figure 3A:
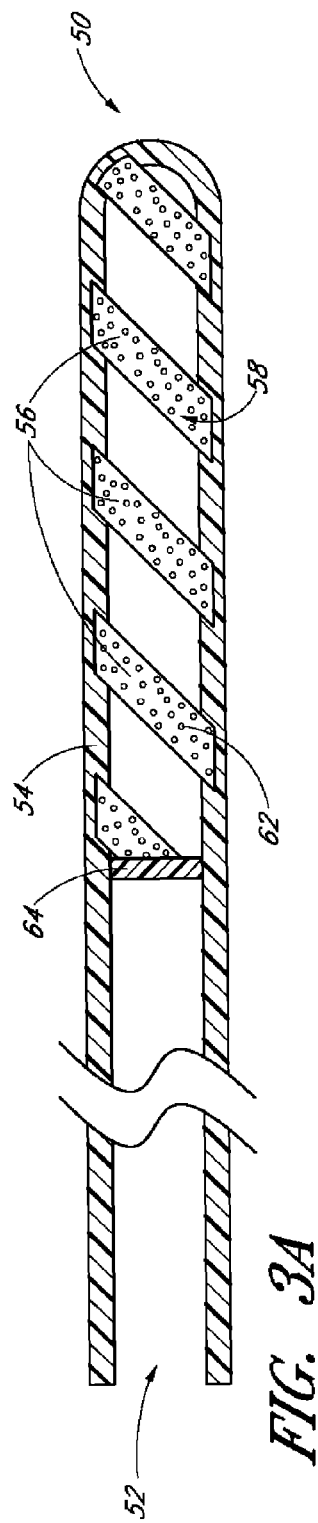
FIGS. 3A and 3B illustrate drug delivery devices in accordance with embodiments disclosed herein.
Figure 3B:
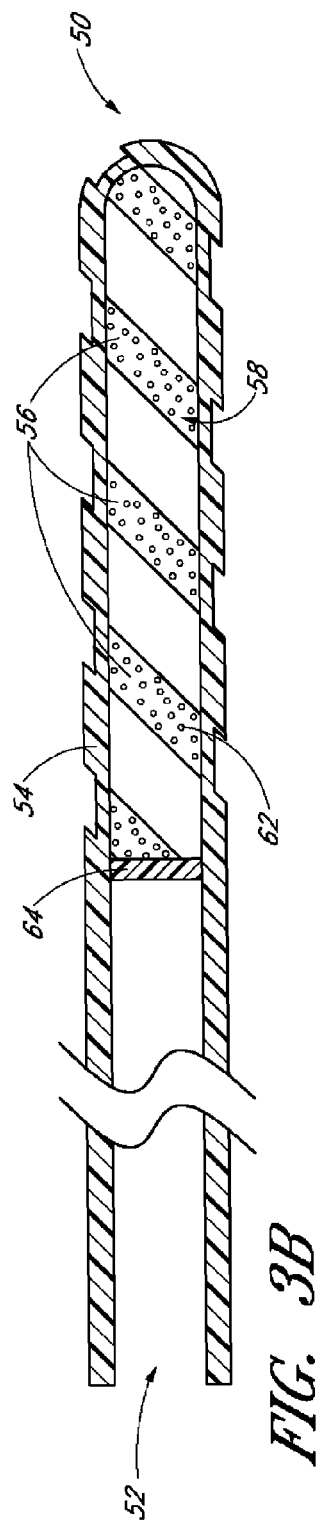

The regions of drug release may be of any shape needed to accomplish sufficient delivery of the drug to a particular target tissue of the eye. For example, in FIG. 2, the regions 56 are depicted as defined areas of thinner material. FIG. 3A depicts the regions of drug release used in other embodiments, namely a spiral shape of reduced thickness 56. In some embodiments, the spiral is located substantially at the distal end of the implant, while in other embodiments, the spiral may run the length of the interior lumen. In still other embodiments, the spiral region of drug release is located on the proximal portion of the implant. In some embodiments, the spiral is on the interior of the implant shell (i.e., the shell is rifled; see FIG. 3A). In other embodiments, spiral is on the exterior of the shell (see FIG. 3B). In other embodiments, the region of drug release is shaped as circumferential bands around the implant shell.

FIG. 4 depicts another embodiment, wherein a region of drug release is located at the distal-most portion of the implant. Certain such embodiments are used when more posterior regions of the eye are to be treated. Alternatively, or in conjunction with the embodiment of FIG. 4, the proximal portion of the implant may also have a region of drug release at or near the proximal-most portion. In other embodiments, the regions of drug release are uniformly or substantially uniformly distributed along the distal and/or proximal portions of the implant. In some embodiments, the regions of drug release are located at or near the distal end of the implant or, in alternative embodiments at or near the proximal end of the implant (or in still additional embodiments, at or near both the proximal and distal ends). In certain embodiments, the implants (based on the regions of drug release (based on thickness/permeability, orifices, layers etc.) are strategically placed to create a differential pattern of drug elution from the implant, depending on the target tissue to be treated after implantation. In some embodiments, the regions of drug release are configured to preferentially elute drug from the distal end of the implant. In some such embodiments, the regions of drug release are strategically located at or near a target tissue in the more posterior region of the eye after the implantation procedure is complete. In some embodiments, the regions of drug release are configured to preferentially elute drug from the proximal end of the implant. In some such embodiments, the regions of drug release are strategically located at or near a target tissue in the anterior chamber of the eye after the implantation procedure is complete. As discussed in more detail below, in several embodiments, the regions of drug release comprises one (or more) orifices that allow communication between an interior lumen of the implant and the environment in which the implant is implanted. It shall also be appreciated from the disclosure herein that, in certain embodiments, combinations of regions of drug release (as described above) may be combined with one or more orifices and/or coatings (below) in order to tailor the drug release profile.

The implant in some embodiments includes a distal portion located at the distal end of the implant. In some embodiments, the distal portion is sufficiently sharp to pierce eye tissue near the scleral spur of the eye. The distal portion can be sufficiently blunt so as not to substantially penetrate scleral tissue of the eye. In some embodiments, the implant has a generally sharpened forward end and is self-trephinating, i.e., self-penetrating, so as to pass through tissue without pre-forming an incision, hole, or aperture. The sharpened forward end can be, for example, conical or tapered. The taper angle of the sharpened end is, for example, about 30°±15° in some embodiments. In some embodiments, the radius of the tip of the distal end is about 70 microns to about 200 microns. In embodiments comprising a shunt, discussed further herein, an outlet opening is formed at the distal end of the shunt and the distal portion gradually increases in cross-sectional size in the proximal direction, preferably at a generally constant taper or radius, or in a parabolic manner.

In some embodiments, the body of the implant includes at least one surface irregularity. The surface irregularity can comprise, for example, a ridge, groove, relief, hole, or annular groove. The surface discontinuities or irregularities can also comprise barbs or other projections, which can extend from the outer surface of the implant to inhibit migration of the implant from its implanted position. In some embodiments, the projections comprise external ribbing to resist displacement of the implant. The surface irregularity in some embodiments interacts with the tissue of the interior wall of the sclera and/or with the tissue of the ciliary attachment tissue. In some embodiments, the implant is anchored by mechanical interlock between tissue and an irregular surface and/or by friction fit. In several embodiments, as discussed in more detail herein, the surface irregularities function to prevent growth of host tissue into or onto the implant (e.g., fibrotic growth) that could, depending on the embodiment, reduce the efficiency of drug elution.

In some embodiments, the implant incorporates fixation features, such as flexible radial (i.e., outwardly-extending) extensions. The extensions may be separate pieces attached to the implant, may be formed integrally with the implant, or may be formed by slitting the implant wall and thermally forming or mechanically deforming the extensions radially outward. If the extensions are separate pieces, they may be comprised of flexible material, such as nitinol or polyimide. The extensions may be located at the proximal or distal ends of the implant, or both, to prevent extrusion of the implant from its intended location. In several embodiments, the extensions are longitudinally spaced along the implant. Spacing between the extensions may be regular or irregular. The flexibility of the fixation features will facilitate entry through the corneal incision, and also through the ciliary muscle attachment tissue.

In some embodiments, the implant has a cap or tip at one or both ends. A distal end cap can include a tissue-piercing end. In some embodiments the cap has a conically shaped tip. In other embodiments, the cap can have a tapered angle tip. The tip can be sufficiently sharp to pierce eye tissue near the scleral spur of the eye. The tip can also be sufficiently blunt so as not to substantially penetrate scleral tissue of the eye. In some embodiments, the conically shaped tip facilitates delivery of the shunt to the desired location. In embodiments comprising a shunt, the distal end cap has one or more outlet openings to allow fluid flow. Each of the one or more outlet openings can communicate with at least one of the one or more lumens.

In some embodiments, the implant has a proximal end cap. For example, an O-ring cap with a region of drug release (as discussed more fully herein and with reference to FIGS. 18K and 18M) can be located over the proximal end of the implant to allow for drug elution into the anterior chamber of the eye. In other embodiments, a cramp cap comprising a region of drug release (as discussed more fully herein and with reference to FIGS. 18L and 18N) is located over the proximal end of the implant. Regions of the crimp cap can be compressible such that the cap can be securely placed on, and sealed to, the body of the implant. In some embodiments, the cap comprises one or more orifices or layers in place of, or in addition to, regions of drug release based on thickness and/or permeability of the cap material.

In some embodiments, a coating is placed within the cap to cover an orifice therein. The coating may comprise a membrane or layer of semi-permeable polymer. In some embodiments, the coating has a defined thickness, and thus a defined and known permeability to various drugs and ocular fluid. In some embodiments, the coating is placed in other locations, including on the exterior of the cap, within the orifice, or combinations thereof.

In some embodiments, the implant has an outer diameter that will permit the implant to fit within a 23-gauge needle during implantation. The implant can also have a diameter that is designed for insertion with larger needles. For example, the implant can also be delivered with 18-, 19-, or 20-gauge needles. In other embodiments, smaller gauge applicators, such as 23-gauge or smaller, are used. In some embodiments, the implant has a substantially constant cross-sectional shape through most of its length. Alternatively, the implant can have portions of reduced or enlarged cross-sectional size (e.g., diameter) along its length. In some embodiments, the distal end of the implace has a tapered portion, or a portion having a continually decreasing radial dimension with respect to the lumen axis along the length of the axis. The tapered portio preferably in some embodiments terminates with a smaller radial dimension at the distal end. During implantation, the tapered portion can operate to form, dilate, and/or increase the size of an incision or puncture created in the tissue. The tapered portion may have a diameter of about 30-gauge to about 23-gauge, and preferably about 25-gauge.

In several embodiments, lumens are present in both the proximal and distal portions of the implant (see FIG. 5; 58a and 58, respectively). In such embodiments both the proximal 52 and the distal portion 50 of the implant have one or more regions of drug release. In some such embodiments the proximal and distal portions of the implant house two different drugs 62a (proximal) and 62 (distal) in the lumens. See FIG. 5. In other embodiments, the proximal and distal portion of the implant may house the same drugs, or the same drug at different concentrations or combined with alternate excipients. It will be appreciated that the placement of the regions of drug release, whether within the proximal portion, distal portion, or both portions of the implant, are useful to specifically target certain intraocular tissues. For example, placement of the region of drug release at the distal most portion of the implant, is useful, in some embodiments, for specifically targeting drug release to particular intraocular regions, such as the macula. In other embodiments, the regions of drug release are placed to specifically release drug to other target tissues, such as the ciliary body, the retina, the vasculature of the eye, or any of the ocular targets discussed above or known in the art. In some embodiments, the specific targeting of tissue by way of specific placement of the region of drug release reduces the amount of drug needed to achieve a therapeutic effect. In some embodiments, the specific targeting of tissue by way of specific placement of the region of drug release reduces non-specific side effects of an eluted drug. In some embodiments, the specific targeting of tissue by way of specific placement of the region of drug release increases the overall potential duration of drug delivery from the implant.

Figure 6A:
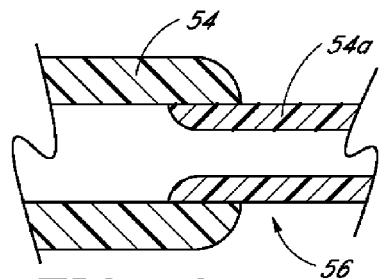
FIGS. 6A-6I illustrate various aspects of a drug delivery device in accordance with embodiments disclosed herein.

Regardless of their shape and location(s) on the outer shell of the in implant, the regions of drug release are of a defined and known area. The defined area assists in calculating the rate of drug elution from the implant (described below). The regions of drug release are formed in several embodiments by reducing the thickness of the outer shell in certain defined areas and/or controlling the permeability of a certain region of the outer shell. FIGS. 6A-I represent certain embodiments of the region of drug release. FIGS. 6A and B depict overlapping regions of a thicker 54 and thinner 54a portion of the outer shell material with the resulting formation of an effectively thinner region of material, the region of drug release 56. FIGS. 6C and 6D depict joinder of thicker 54 with thinner 54a portions of the outer shell material. The resulting thinner region of material is the region of drug release 56. It will be appreciated that the joining of the thicker and thinner regions may be accomplished by, for example, butt-welding, gluing or otherwise adhering with a biocompatible adhesive, casting the shell as a single unit with varying thickness, heat welding, heat fusing, fusing by compression, or fusing the regions by a combination of heat and pressure. Other suitable joining methods known in the art may also be used.

Figure 6E:
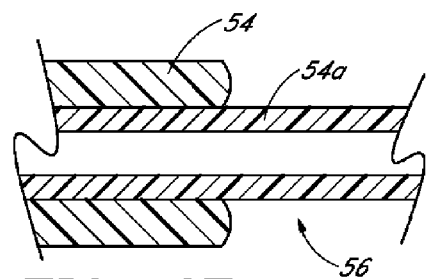
Figure 6B:
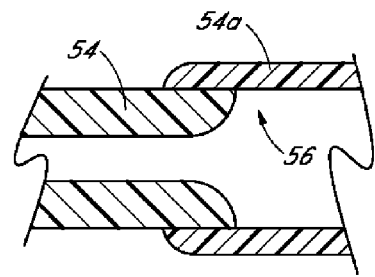

FIG. 6E depicts a thicker sleeve of outer shell material overlapping at least in part with a thinner shell material. The thinner, non-overlapped area, 56, is the region of drug release. It will be appreciated that the degree of overlap of the material is controllable such that the region of non-overlapped shell is of a desired area for a desired elution profile.

Figure 6F:
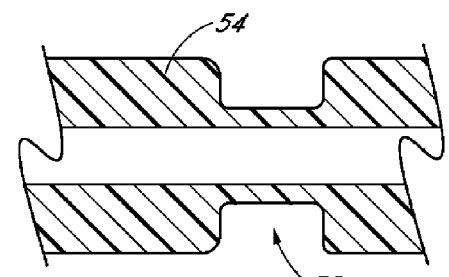
Figure 6C:
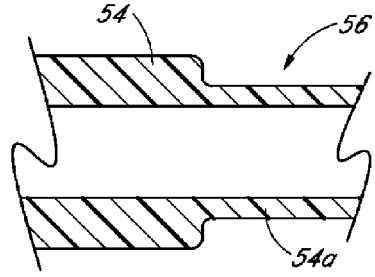

FIG. 6F illustrates an outer shell material with a thin area 56 formed by one or more of ablation, stretching, etching, grinding, molding and other similar techniques that remove material from the outer shell.

Figure 6G:
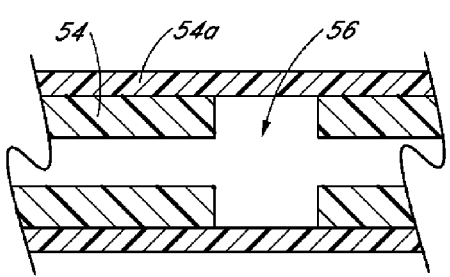
Figure 6D:
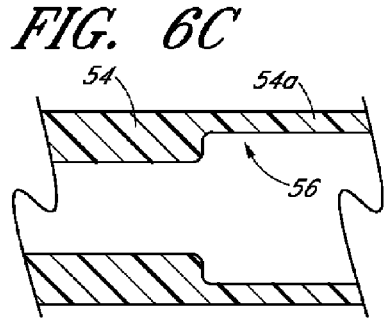

FIG. 6G depicts a "tube within a tube" design, wherein a tube with a first thickness 54 is encased in a second tube with a second thickness 54a. The first tube has one or more breaks or gaps in the shell, such that the overlaid thinner shell 54a covers the break or gap, thereby forming the region of drug release. In the embodiment shown in FIG. 6G, and in certain other embodiments, the break or gap in the shell with a first thickness 54, does not communicate directly with the external environment.

Figure 6H:
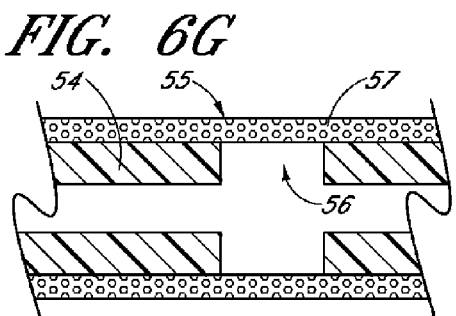

FIG. 6H depicts an embodiment wherein the region of drug release is bordered both by the outer shell 54 and by a substantially impermeable matrix material 55 having a communicating particulate matter 57 dispersed within the impermeable matrix. In several embodiments, the communicating particulate matter is compounded with the impermeable matrix material during implant manufacturing. The implant may then be contacted with a solvent, which is subsequently carried through the communicating particulate matter and reaches the drug housed within the lumen of the implant. Preferred solvents include water, saline, or ocular fluid, or biocompatible solvents that would not affect the structure or permeability characteristics of the impermeable matrix.

As the drug in the lumen is dissolved into the solvent, it travels through the communicating particulate matter from the lumen of the implant to the ocular target tissue. In some embodiments, the implant is exposed to a solvent prior to implantation in the eye, such that drug is ready for immediate release during or soon after implantation. In other embodiments, the implant is exposed only to ocular fluid, such that there is a short period of no drug release from the implant while the ocular fluid moves through the communicating particulate matter into the lumen of the implant.

In some such embodiments, the communicating particulate matter comprises hydrogel particles, for example, polyacrylamide, cross-linked polymers, poly2-hydroxyethyl-methacrylate (HEMA) polyethylene oxide, polyAMPS and polyvinylpyrrolidone, or naturally derived hydrogels such as agarose, methylcellulose, hyaluronan. Other hydrogels known in the art may also be used. In some embodiments, the impermeable material is silicone. In other embodiments, the impermeable material may be Teflon®, flexible graphite, silicone rubber, silicone rubber with fiberglass reinforcement, Neoprene®, fiberglass, cloth inserted rubber, vinyl, nitrile, butyl, natural gum rubber, urethane, carbon fiber, fluoroelastomer, and or other such impermeable or substantially impermeable materials known in the art. In this and other embodiments disclosed herein, terms like "substantially impermeable" or "impermeable" should be interpreted as relating to a material's relative impermeability with regard to the drug of interest. This is because the permeability of a material to a particular drug depends upon characteristics of the material (e.g. crystallinity, hydrophilicity, hydrophobicity, water content, porosity) and also to characteristics of the drug.

Figure 6I:
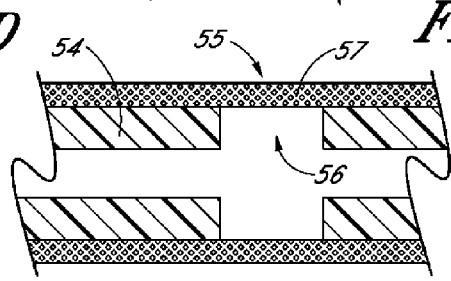

FIG. 6I depicts another embodiment wherein the region of drug release is bordered both by the outer shell 54 and by an impermeable matrix material 55, such as silicone having a communicating particulate matter 57 dispersed within the impermeable matrix. In other embodiments, the impermeable material may be Teflon®, flexible graphite, polydimethylsiloxane and other silicone elastomers, Neoprene®, fiberglass, cloth inserted rubber, vinyl, nitrile, butyl, natural gum rubber, urethane, carbon fiber, fluoroelastomer, and or other such impermeable or substantially impermeable materials known in the art. In several embodiments, the communicating particulate matter is compounded with the impermeable matrix material during implant manufacturing. The resultant matrix is impermeable until placed in a solvent that causes the communicating particulate matter to dissolve. In several embodiments, the communicating particles are salt crystals (for example, sodium bicarbonate crystals or sodium chloride crystals). In other embodiments, other soluble and biocompatible materials may be used as the communicating particulate matter. Preferred communicating particulate matter is soluble in a solvent such as water, saline, ocular fluid, or another biocompatible solvent that would not affect the structure or permeability characteristics of the impermeable matrix. It will be appreciated that certain embodiments, the impermeable matrix material compounded with a communicating particulate matter has sufficient structural integrity to form the outer shell of the implant (i.e., no additional shell material is necessary).

In certain embodiments, the communicating particles are extracted with a solvent prior to implantation. The extraction of the communicating particles thus creates a communicating passageway within the impermeable material. Pores (or other passages) in the impermeable material allow ocular fluid to pass into the particles, which communicate the fluid into the lumen of implant. Likewise, the particles communicate the drug out of the lumen of the implant and into the target ocular tissue.

In contrast to a traditional pore or orifice (described in more detail below), embodiments such as those depicted in FIGS. 6H and 6I communicate drug from the lumen of the implant to the ocular tissue through the communicating particles or through the resultant vacancy in the impermeable matrix after dissolution of the particle. These embodiments therefore create an indirect passage from the lumen of the implant to the eye (i.e. a circuitous route or tortuous path of passage). Thus, purposeful design of the particulate material, its rate of communication of fluids or rate of dissolution in solvent, allows further control of the rate and kinetics of drug release.

Figure 7:
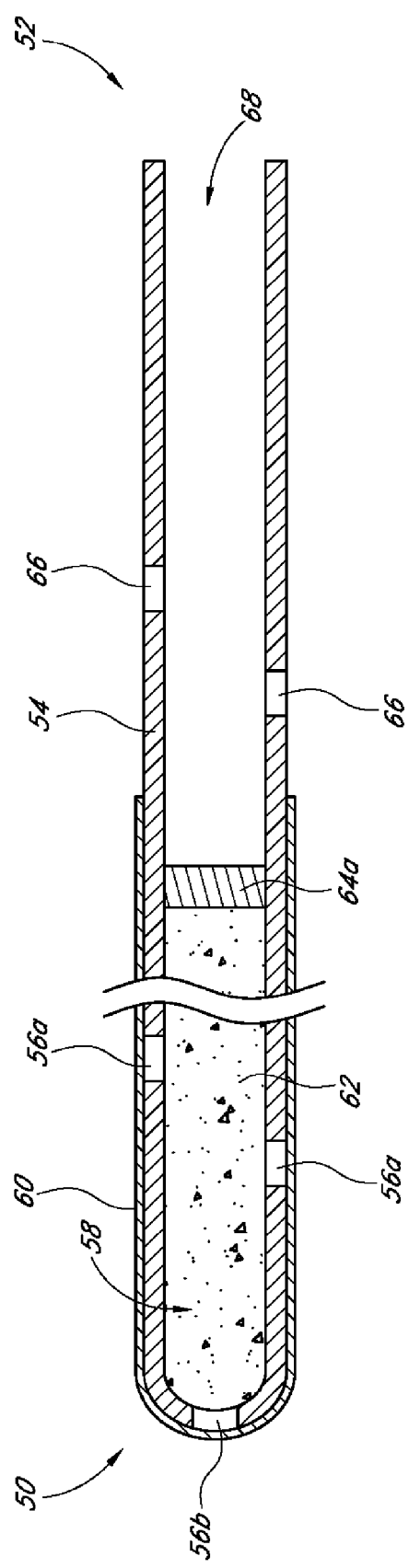
FIG. 7 illustrates a cross sectional view of drug delivery implant in accordance with embodiments disclosed herein.

In several embodiments, the region of drug release comprises one or more orifices. It shall be appreciated that certain embodiments utilize regions of drug release that are not orifices, either alone or in combination with one or more orifices in order to achieve a controlled and targeted drug release profile that is appropriate for the envisioned therapy. FIG. 7 shows a cross sectional schematic of one embodiment of an implant in accordance with the description herein. As discussed above, the implant comprises a distal portion 50, a proximal portion 52, an outer shell 54 made of one or more biocompatible materials, and one or more orifices that pass through the shell 56a. In some embodiments the outer shell of the implant is substantially impermeable to ocular fluids. In several embodiments, the implant houses a drug 62 within the interior lumen 58 of the implant.

As discussed in more detail below, in some embodiments, the drug comprises a therapeutically effective drug against a particular ocular pathology as well as any additional compounds needed to prepare the therapeutic agent in a form with which the drug is compatible. In some embodiments the therapeutic agent is in the form of a drug-containing pellet. Some embodiments of therapeutic agent comprise a drug compounded with a polymer formulation. In certain embodiments, the polymer formulation comprises a poly (lactic-co-glycolic acid) or PLGA co-polymer or other biodegradable or bioerodible polymer. While the drug is represented as being placed within the lumen 58 in FIG. 7, it has been omitted from several other Figures, so as to allow clarity of other features of those embodiments. It should be understood, however, that all embodiments herein optionally include one or more drugs.

In several embodiments, the implant further comprises a coating 60 which may be positioned in various locations in or on the implant as described below. In some embodiments, the coating 60 is a polymeric coating. FIG. 8 depicts an implant wherein the coating 60 is positioned inside the implant, but enveloping the therapeutic agent housed within the lumen, while FIG. 9 depicts the coating 60 on the exterior of the shell 54. Some other embodiments may comprise implants with non-polymeric coatings in place of, or in addition to a polymeric coating. The coating is optionally biodegradable. Some other embodiments may comprise an implant made entirely of a biodegradable material, such that the entire implant is degraded over time. In some embodiments, the coating is placed over the entire implant (e.g., enveloping the implant) while in other embodiments only a portion of the implant is covered. In some embodiments, the coating is on the exterior surface of the implant. In some embodiments, the coating is placed on the luminal wall within the implant. Similarly, in some embodiments in which the coating is positioned inside the implant, the coating covers the entire inner surface of the lumen, while in other embodiments, only a portion of the inner surface is covered. It shall be appreciated that, in addition to the regions of drug release described above, implants according to several embodiments, disclosed herein combine regions of drug release with one or more coatings in order to control drug release characteristics.

In several embodiments, one or more orifices 56a traversing the thickness of the outer shell 54 provide communication passages between the environment outside the implant and the interior lumen 58 of the implant (FIGS. 7-9). The one or more orifices are created through the implant shell by way of drilling through the various shells of a particular implant or any other technique known in the art. The orifices may be of any shape, such as spherical, cubical, ellipsoid, and the like. The number, location, size, and shape of the orifices created in a given implant determine the ratio of orifice to implant surface area. This ratio may be varied depending on the desired release profile of the drug to be delivered by a particular embodiment of the implant, as described below. In some embodiments, the orifice to implant surface area ratio is greater than about 1:100. In some embodiments, the orifice to implant surface area ratio ranges from about 1:10 to about 1:50, from about 1:30 to about 1:90, from about 1:20 to about 1:70, from about 1:30 to about 1:60, from about 1:40 to about 1:50. In some embodiments, the orifice to implant surface area ratio ranges from about 1:60 top about 1:100, including about 1:70, 1:80 and 1:90.

In other embodiments, the outer shell may contain one or more orifice(s) 56b in the distal tip of the implant, as shown in FIGS. 10A and 10B. In other embodiments, the outer shell contains one or more orifice(s) in the proximal tip of the implant, such as for example drug elution and/or fluid influx (e.g., for dissolution of drug housed within the implant and/or for shunting of fluid to a fluid outflow pathway). The shape and size of the orifice(s) can be selected based on the desired elution profile. Still other embodiments comprise a combination of a distal orifice and multiple orifices placed more proximally on the outer shell. Additional embodiments comprise combinations of distal orifices, proximal orifices on the outer shell and/or regions of drug release as described above (and optionally one or more coatings). Additional embodiments have a closed distal end. In such embodiments the regions of drug release (based on thickness/permeability of the shell, orifices, coatings, placement of the drug, etc.) are arranged along the long axis of the implant. Such a configuration is advantageous in order to reduce the amount of tissue damage caused by the advancing distal end that occurs during the several embodiments of the implantation procedures disclosed herein.

In some embodiments, the distal orifice comprises a biodegradable or bioerodible plug 61 with a plurality of orifice(s) 56b that maintain drug elution from the implant, should one or more orifices become plugged with tissue during the insertion/implantation. In other embodiments, the orifice(s) can comprise permeable or semi-permeable membranes, porous films or sheets, or the like. In some such embodiments, the permeable or semi-permeable membranes, films, or sheets may lie outside the shell and cover the orifices, inside the shell to cover the orifices or both. The permeability of the material will partially define the release rate of the drug from the implant, which is described in further detail below. Such membranes, sheets, or films are useful in those embodiments having elongated orifices in the outer shell. Arrows in FIG. 10B depict flow of drug out of the implant.

Figure 10C:
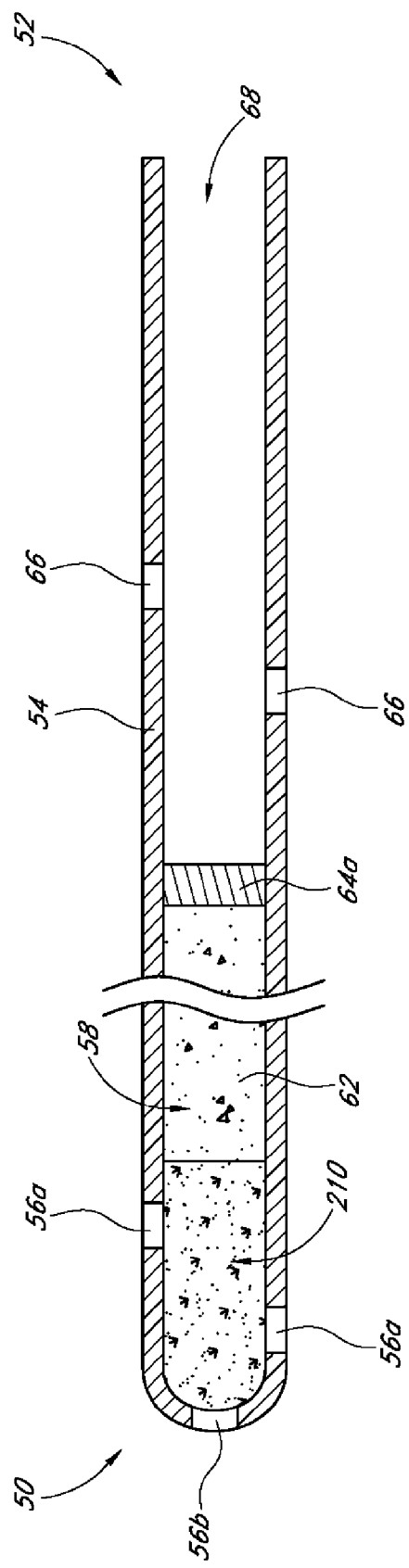
Figure 10D:
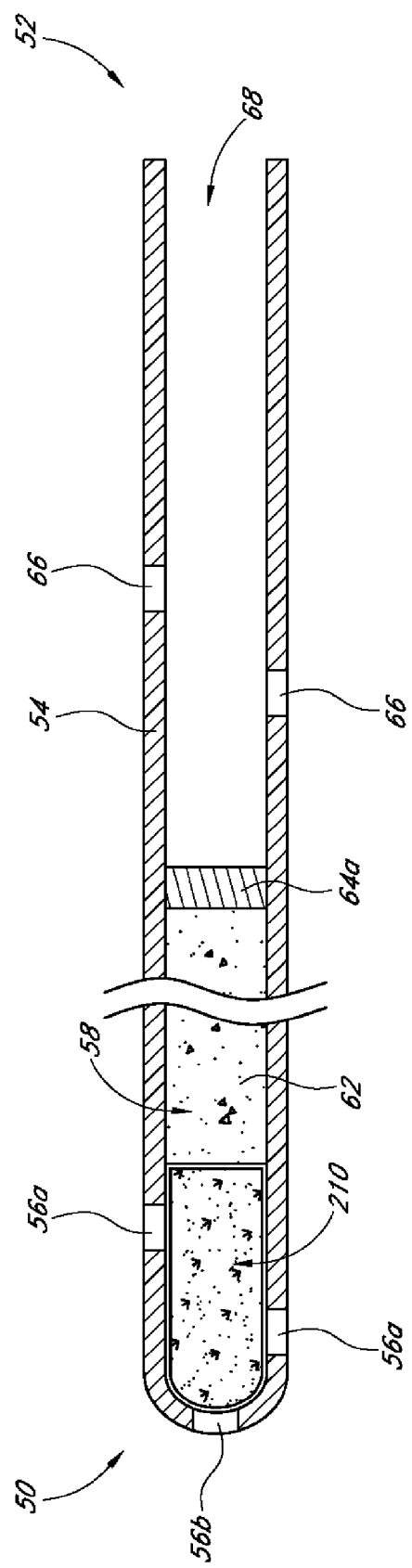
Figure 10E:
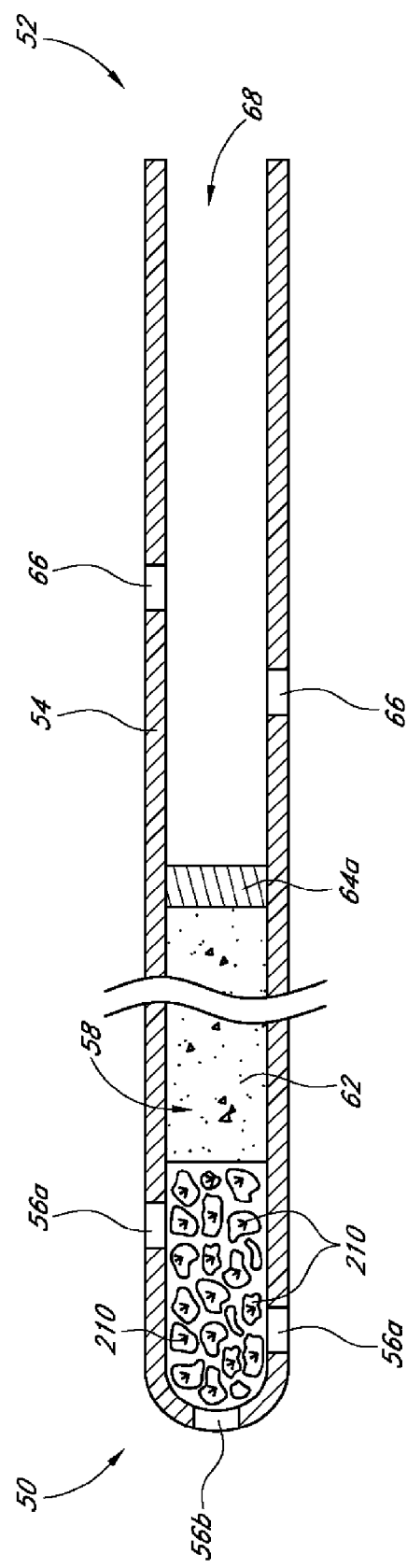
Figure 10F:
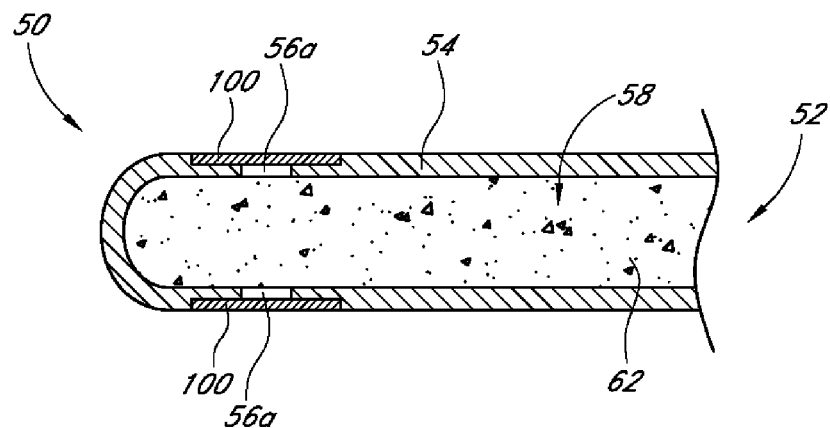
Figure 10G:
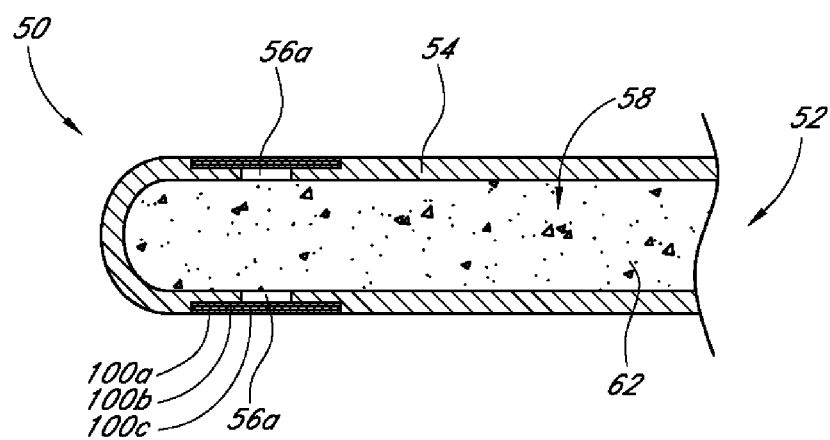

In several embodiments, an additional structure or structures within the interior of the lumen partially controls the elution of the drug from the implant. In some embodiments, a proximal barrier 64a is positioned proximally relative to the drug 62 (FIGS. 7 and 10C). An optional shunt feature may also be included which comprises outflow apertures 66 in communication with a proximal inflow lumen 68 located in the proximal region 52 of the implant. In addition to the layer or layers of permeable or semi-permeable material may be used to envelope the drug discussed above, FIG. 10C depicts an internal plug 210 that is be located between the drug 62 and the various orifices 56a and 56b in certain embodiments. In such embodiments, the internal plug need not completely surround the drug. In some embodiments, the material of the internal plug 210 differs from that of the shell 54, while in some embodiments the material of the internal plug 210 is the same material as that of the shell 54. Suitable materials for the internal plug include, but are not limited to, agarose or hydrogels such as polyacrylamide, polymethyl methacrylate, or HEMA (hydroxyethyl methacrylate). In additional any material disclosed herein for use in the shell or other portion of the implant may be suitable for the internal plug, in certain embodiments.

In such embodiments where the material is the same, the physical characteristics of the material used to construct 210 are optionally different than that of the shell 54. For example, the size, density, porosity, or permeability of the material of 210 may differ from that of the shell 54. In some embodiments, the internal plug is formed in place (i.e. within the interior lumen of the implant), for example by polymerization, molding, or solidification in situ of a dispensed liquid, powder, or gel. In other embodiments, the internal plug is preformed external to the shell placed within the shell prior to implantation. In such embodiments, tailored implants are constructed in that the selection of a pre-formed internal plug may be optimized based on a particular drug, patient, implant, or disease to be treated. In several embodiments, the internal plug is biodegradable or bioerodible, while in some other embodiments, the internal plug is durable (e.g., not biodegradable or bioerodible).

In several embodiments, the internal plug may be closely fit or bonded to the inner wall of shell. In such embodiments, the internal plug is preferably permeable to the drug, thereby allowing passage of the drug through the plug, through the orifices and to the target tissue. In some embodiments, the internal plug is also permeable to body fluids, such that fluids from outside the implant may reach the drug. The overall release rate of drug from the device in this case may be controlled by the physical characteristics of several aspects of the implant components, including, but not limited to, the area and volume of the orifices, the surface area of any regions of drug release, the size and position of the internal plug with respect to both the drug and the orifices and/or regions of drug release, and the permeability of the internal plug to the drug and bodily fluids. In addition, in several embodiments, the internal plug increases path length between the drug and the orifices and/or regions of drug release, thereby providing an additional point of control for the release rate of drug.

In several other embodiments, the internal plug 210 may be more loosely fit into the interior lumen of the shell which may allow flow or transport of the drug around the plug. See FIG. 10D. In still other embodiments, the internal plug may comprise two or more pieces or fragments. See FIG. 10E. In such embodiments with a looser fitting or fragmented plug, the drug may elute from the implant by passing through the gap between the internal plug and the interior wall of shell. The drug may also elute from the implant by passing through the gaps between pieces or fragments of the internal plug. The drug may also elute from the implant by passing through the permeable inner plug. Similarly, bodily fluids may pass from the external portion of the implant into the implant and reach the drug by any of these, or other, pathways. It shall be appreciated that elution of the drug can occur as a result of a combination of any of these routes of passage or permeability.

In several embodiments, the orifices 56a are covered (wholly or partially) with one or more elution membranes 100 that provide a barrier to the release of drug 62 from the interior lumen 58 of the implant shell 54. See FIG. 10F. In several embodiments, the elution membrane is permeable to the therapeutic agent, to bodily fluids or to both. In some embodiments the membrane is elastomeric and comprises silicone. In other embodiments, the membrane is fully or partially coated with a biodegradable or bioerodible material, allowing for control of the inception of entry of bodily fluid, or egress of therapeutic agent from the implant. In certain embodiments, the membrane is impregnated with additional agents that are advantageous, for example an anti-fibrotic agent, a vasodilator, an anti-thrombotic agent, or a permeability control agent. In addition, in certain embodiments, the membrane comprises one or more layers 100*a*, 100*b*, and 100*c* in FIG. 10G, for example, allowing a specific permeability to be developed.

Similar to the internal plug and regions of drug release described above, the characteristics of the elution membrane at least partially define the release rate of the therapeutic agent from the implant. Thus, the overall release rate of drug from the implant may be controlled by the physical characteristics of the implant, including, but not limited to, the area and volume of the orifices, the surface area of any regions of drug release, the size and position of any internal plug with respect to both the drug and the orifices and/or regions of drug release, and the permeability of any layers overlaying any orifices or regions of drug release to the drug and bodily fluids.

In some embodiments, multiple pellets 62 of single or multiple drug(s) are placed end to end within the interior lumen of the implant (FIG. 11A). In some such embodiments, the orifices 56*a* (or regions of drug release) are positioned at a more distal location on the implant shell. In other such embodiments, the orifices 56*a* (or regions of drug release) are positioned at a more proximal location on the implant shell, depending on the ocular tissue being targeted. In some other embodiments a partition 64 is employed to seal therapeutic agents from one another when contained within the same implant inner lumen. In some embodiments, the partition 64 bioerodes at a specified rate. In some embodiments, the partition 64 is incorporated into the drug pellet and creates a seal against the inner dimension of the shell of the implant 54 in order to prevent drug elution in an unwanted direction. In certain embodiments further comprising a shunt, a partition may be positioned distal to the shunt outlet holes, which are described in more detail below.

In certain alternative embodiments, the orifices or regions of drug release may be positioned along a portion of or substantially the entire length of the outer shell that surrounds the interior lumen and one or more partitions may separate the drugs to be delivered.

An additional non-limiting additional embodiment of a drug pellet-containing implant is shown in FIG. 11B (in cross section). In certain embodiments, the pellets are micro-pellets 62' (e.g., micro-tablets) with characteristics described more fully below. In some embodiments, such one or more such micro-pellets are housed within a polymer tube having walls 54' of a desired thickness. In some embodiments, the polymer tube is extruded and optionally has a circular cross-section. In other embodiments, other shapes (e.g., oval, rectangular, octagonal etc.) are formed. In some embodiments, the polymer is a biodegradable polymer, such as those discussed more fully below. Regardless of the material or the shape, several embodiments of the implant are dimensioned for implantation into the eye of a subject (e.g., sized to pass through a 21 gauge, 23 gauge, 25 gauge, 27 gauge, or smaller needle).

Within that context, the dimensions of several embodiments of such a device may be varied in order to provide a desired release time for the therapeutic agent in the micropellets. For example, the wall thickness of a polymer tube can be adjusted to alter the permeability of the polymer tube to the therapeutic agent. Moreover, in the case of biodegradable polymers, the wall thickness can also be altered in order to control the overall rate of degradation of the device. In combination with other variables more fully described herein, e.g., the polymer chemistry and the molecular weight of the polymers used, elution of the therapeutic agent from the implant is highly controllable.

As shown generally in FIG. 11B, the micro-pellet 62' can be housed within a compartment defined by endpieces or partitions 64'. In some embodiments, the endpieces 64' defining each lumen or compartment are thermoformed from the same material as tubing 54'. In other embodiments, they may be formed of sections of polymer filaments. In still other embodiments, the endpieces are formed within the interior of the tube by injecting or otherwise applying small volumes of thermosetting polymers, adhesives, polymer solutions in volatile solvents, and the like. Alternatively, endpieces may be machined from hard polymers, metals or other materials, and positioned and retained within the tube using solvent or adhesive bonding. In those embodiments wherein the endpieces are polymers, some embodiments employ biodegradable polymers, which may be designed to degrade before, at the time of, or after the micro-pelleted therapeutic agent is released. Moreover, polymeric endpieces may comprise the same polymer as the extruded polymeric tube 54', or may be a different polymer.

While shown in FIG. 11B as dimensioned to hold one micro-tablet of therapeutic agent 62', it shall be appreciated that, in some embodiments, the lumen 58' may be dimensioned to hold a plurality of micro-tablets comprising the same or differing therapeutic agents. Advantageously, such embodiments employed an extruded shell and one or more micro-pellets allow the release of the therapeutic agents from the implant, in a controlled fashion, without the therapeutic agent being exposed to the elevated temperatures that are often required for extrusion. Rather, the shell may first be extruded and then loaded with micro-pellets once temperatures are normalized.

As discussed in more detail herein, each tablet comprises a therapeutic agent (also referred to herein as an active pharmaceutical ingredient (API)) optionally combined with one or more excipients. Excipients may include, among others, freely water soluble small molecules (e.g., salts) in order to create an osmotic pressure gradient across the wall of tubing 54'. In some embodiments, such a gradient increases stress on the wall, and decreases the time to release drug.

The in vivo environment into which several embodiments of the implants disclosed herein are positions may be comprised of a water-based solution (such as aqueous humor or blood plasma) or gel (such as vitreous humor). Water from the surrounding in vivo environment may, in some embodiments, diffuse through semipermeable or fenestrated stent walls into the drug reservoir (e.g., one or more of the interior lumens, depending on the embodiment). Water collecting within the drug-containing interior lumen then begins dissolving a small amount of the tablet or drug-excipient powder. The dissolution process continues until a solution is formed within the lumen that is in osmotic equilibrium with the in vivo environment.

In additional embodiments, osmotic agents such as saccharides or salts are added to the drug to facilitate ingress of water and formation of the isosmotic solution. With relatively insoluble drugs, for example corticosteroids, the isosmotic solution may become saturated with respect to the drug in certain embodiments. In certain such embodiments, saturation can be maintained until the drug supply is almost exhausted. In several embodiments, maintaining a saturated condition is particularly advantageous because the elution rate will tend to be essentially constant, according to Fick's Law.

Implants such as those depicted generally in FIG. 11B may be implanted singularly (e.g., a single implant) or optionally as a plurality of multiple devices. In some embodiments, the plurality of implants may be joined together (e.g., end to end) to form a single, larger implant. As discussed above, and in greater detail below, such implants may be generated having different drug release times, for example, by varying the time or -degradation properties of extruded tubing 54'. Implantation of a plurality of varied devices having different release times, a desired overall drug release profile can be obtained based on the serial (or concurrent) release of drug from the plurality of implants a given time period. For example, release times can be designed such that a first period of drug release occurs, and is then followed by a drug "holiday" prior a second period of drug release.

Several embodiments of the implant may also comprise a shunt in addition to functioning as a drug delivery device. The term "shunt" as used herein is a broad term, and is to be given its ordinary and customary meaning to a person of ordinary skill in the art (and it is not to be limited to a special or customized meaning), and refers without limitation to the portion of the implant defining one or more fluid passages for transport of fluid from a first, often undesired location, to one or more other locations. In some embodiments, the shunt can be configured to provide a fluid flow path for draining aqueous humor from the anterior chamber of an eye to an outflow pathway to reduce intraocular pressure, such as is depicted generally in FIG. 12A. In other embodiments the shunt can be configured to provide a fluid flow path for draining aqueous humor to an outflow pathway. Still other embodiments can be configured to drain ocular fluid or interstitial fluid from the area in and around the eye to a remote location. Yet other combination drug delivery-shunt implants may be configured to drain physiological fluid from a first physiologic site to a second site (which may be physiologic or external to a patient). In still additional embodiments, the shunt additionally (or alternatively) functions to provide a bulk fluid environment to facilitate the dilution and/or elution of the drug.

The shunt portion of the implant can have an inflow portion 68 and one or more outflow portions 66. As described above, the outflow portion may be disposed at or near the proximal end 52 of the implant. While not illustrated, in some embodiments a shunt outflow portion may be disposed at or near the distal end of the implant with the inflow portion residing a different location (or locations) on the implant. In some embodiments, when the implant is deployed, the inflow portion may be sized and configured to reside in the anterior chamber of the eye and the outflow portion may be sized and configured to reside in the supraciliary or suprachoroidal space. In some embodiments, the outflow portion may be sized and configured to reside in the supraciliary region of the uveoscleral outflow pathway, the suprachoroidal space, other part of the eye, or within other physiological spaces amenable to fluid deposition.

In some embodiments, at least one lumen extends through the shunt portion of the implant. In some embodiments, there is at least one lumen that operates to conduct the fluid through the shunt portion of the implant. In certain embodiments, each lumen extends from an inflow end to an outflow end along a lumen axis. In some embodiments the lumen extends substantially through the longitudinal center of the shunt. In other embodiments, the lumen can be offset from the longitudinal center of the shunt.

In implants additionally comprising a shunt in the proximal portion of the device, the first (most proximal) outflow orifice on the implant is positioned between 1 and 10 mm from the anterior chamber of the subject. In some embodiments additionally comprising a shunt in the proximal portion of the device, the first (most proximal) outflow orifice on the implant is positioned preferably between 2 and 5 mm from the anterior chamber of the subject. Additional outflow orifices may be positioned in more distal locations, up to or beyond the point where the interior lumen housing the drug or therapeutic agent begins.

In some embodiments comprising a shunt, a shunt inflow portion preferably is disposed at or near a proximal end of the implant and a shunt outflow portion preferably is disposed at or near a distal end of the shunt. When implanted, in several embodiments, the shunt inflow portion is sized and configured to reside in the anterior chamber of the eye and the shunt outflow portion is sized and configured to reside in the uveoscleral outflow pathway. In some embodiments, the shunt outflow portion is sized and configured to reside in the supraciliary region of the iveoscleral outflow pathway or in the suprachoroidal space. Multiple outflow points may be used in a single device, depending on the embodiment.

In some embodiments, the flow path through the implant is configured to regulate the flow rate to reduce the likelihood of hypotony in the eye. In some embodiments, the intraocular pressure is maintained at about 8 mm Hg. In other embodiments, the intraocular pressure is maintained at pressures less than about 8 mm Hg, for example the intraocular pressure may be maintained between about 6 mm Hg and about 8 mm Hg. In other embodiments, the intraocular pressure is maintained at pressures greater than about 8 mm Hg. For example, the intraocular pressure may be maintained between about 8 mm Hg and about 18 mm Hg, and more preferably between 8 mm Hg and 16 mm Hg, and most preferably not greater than 12 mm Hg. In some embodiments, the flow rate can be limited to about 2.5 µL/min or less. In some embodiments, the flow rate can be limited to between about 1.9 µL/min and about 3.1 µL/min.

For example, the Hagen-Poisseuille equation suggests that a 4 mm-long shunt at a flow rate of 2.5 µL/min should have an inner diameter of 52 micrometers to create a pressure gradient of 5 mm Hg above the pressure in the suprachoroidal space.

Figure 12A:
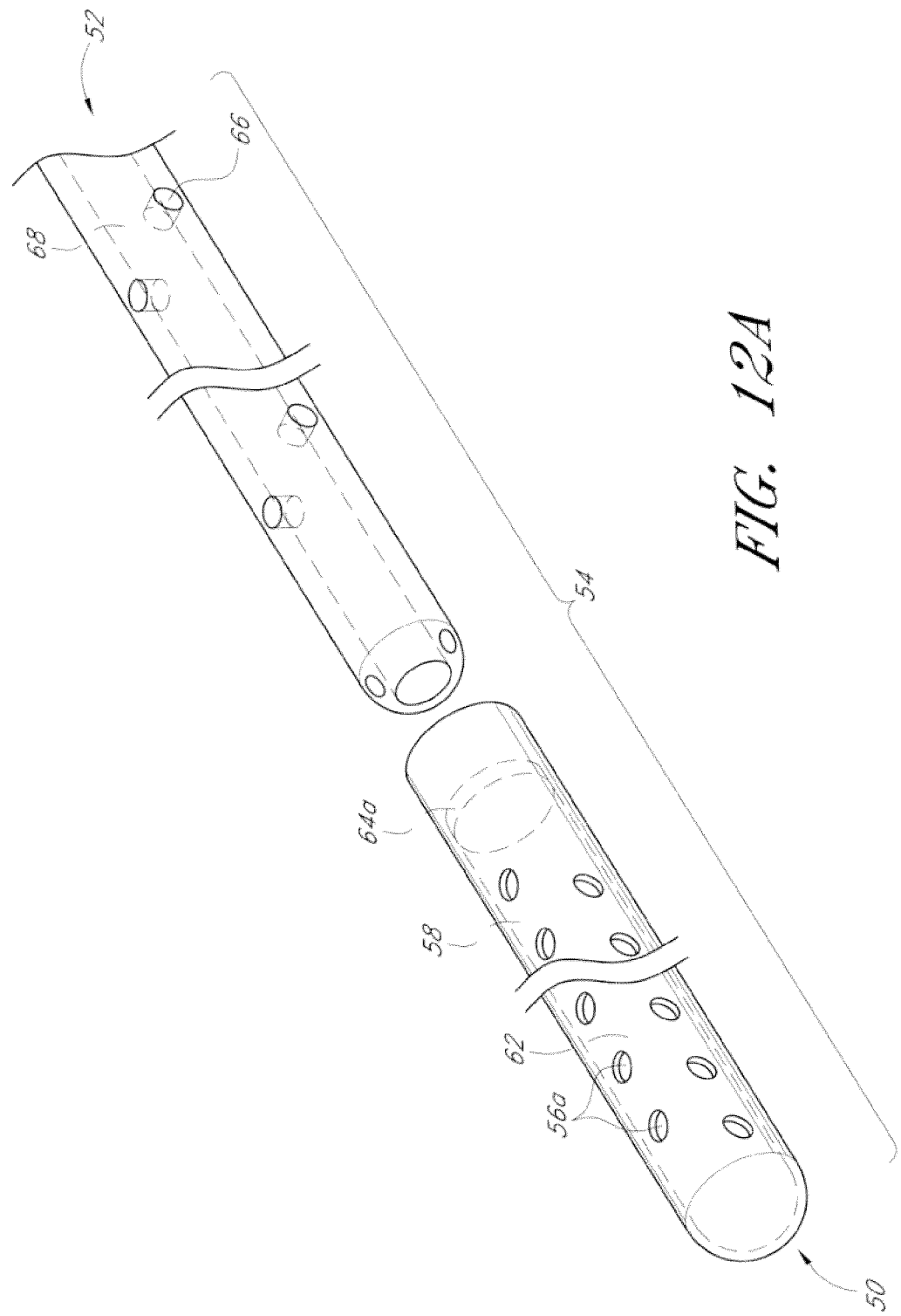
FIG. 12A illustrates another drug delivery implant incorporating a shunt in accordance with embodiments disclosed herein.
Figure 12C:
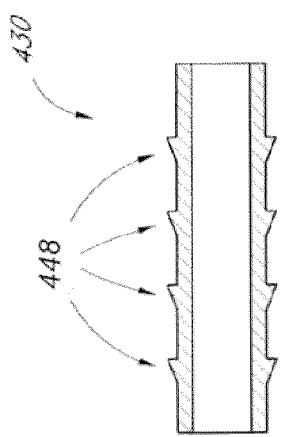
FIG. 12C illustrates a cross-sectional view of an embodiment of retention features disposed on a drug delivery implant in accordance with embodiments disclosed herein.
Figure 12B:
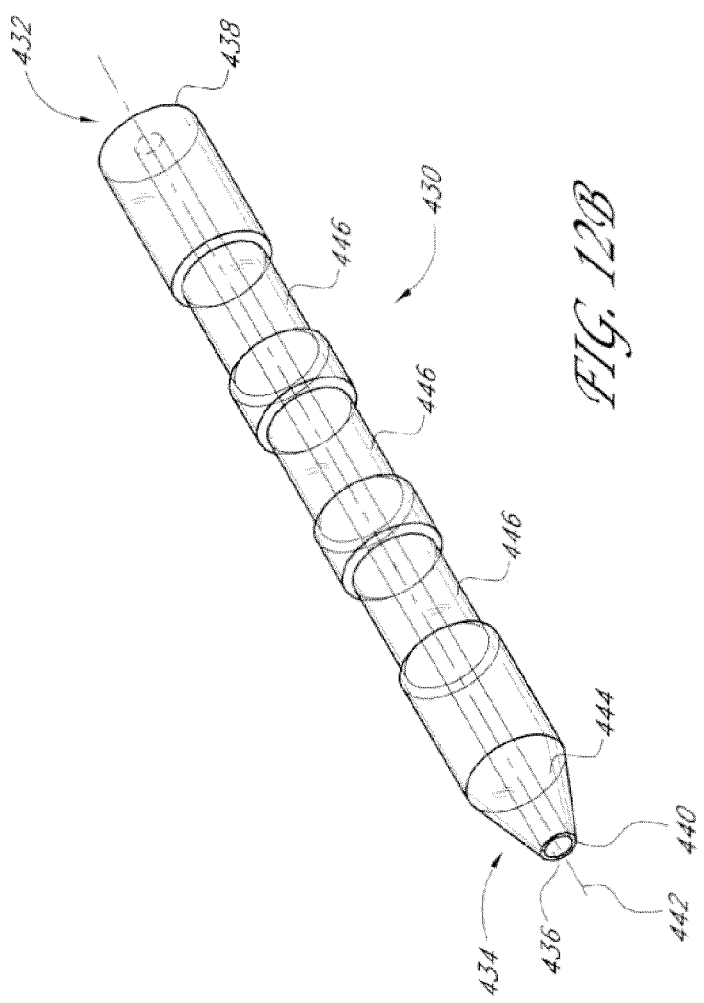
FIG. 12B illustrates a further drug delivery implant incorporating a shunt in accordance with embodiments disclosed herein.

FIG. 12B illustrates another embodiment of a drug eluting implant 430 comprising a shunt that is operable to drain fluid from the anterior chamber to the uveoscleral outflow pathway (e.g., the suprachoroidal space). The drug eluting implant 430 can comprise at least one interior lumen 436 extending therethrough, wherein at least a first active drug can be placed. The interior lumen 436 of the implant 430 can communicate with an inflow portion 432 and an outflow portion 434. When implanted, the inflow portion 432 is sized and configured to reside in the anterior chamber of the eye and the outflow portion 434 is sized and configured to reside in the uveoscleral outflow pathway. The first active drug can elute from the inflow portion 432 into the anterior chamber to treat a target ocular tissue. As the first active drug elutes from the interior lumen 436 into the anterior chamber, fluid can be conducted through the interior lumen 436 if the implant.

The implant 430 preferably has an outer diameter that will permit the implant 430 to fit within a 21-gauge or 23-gauge needle or hollow instrument during implantation; however, larger or smaller gauge instruments may also be used. The implant 430 can also have a diameter that is designed for delivery with larger needles. For example, the implant 430 can also be delivered with 18-, 19- or 20-gauge needles. The implant 430 can have a constant diameter through most of its length. In some embodiments, the implant 430 comprises retention features 446 that operate to mechanically lock or anchor the implant 430 in place when implanted. In some embodiments, the retention features 446 comprise portions of reduced diameter, e.g., annular grooves, between the proximal end 438 and the distal end 440. In some embodiments, the retention features 446 comprise barbs or other projections, which extend from the outer surface of the implant 430, to inhibit migration of the implant 430 from its implanted position, as described above.

As shown in FIG. 12C, for example, some embodiments of an implant 430 have a plurality of annular ribs 448 formed on an exterior surface of the implant 430. The annular ribs 448 can be spaced longitudinally along the implant 430 between the proximal end 438 and the distal end 440. Spacing between the annular ribs 448 can be regular or irregular.

The outflow portion 434 of the implant 430 preferably is disposed at or near the distal end 440 of the implant 430. In the embodiment illustrated in FIG. 12B, the outflow portion 434 has a tapered portion 444; however, it may also have other shapes (e.g. semi-sphere, a paraboloid, a hyperboloid) with a continually decreasing radial dimension with respect to the lumen axis 442 along the length of the axis 442. The tapered portion 444 preferably terminates with a smaller radial dimension at the outflow end 440. During implantation, the tapered portion 444 can operate to form, dilate, and/or increase the size of, an incision or puncture created in the tissue. For example, the distal end 440 can operate as a trocar to puncture or create an incision in the tissue. Following advancement of the distal end 440 of the implant 430, the tapered portion 444 can be advanced through the puncture or incision. The tapered portion 444 will operate to stretch or expand the tissue around the puncture or incision to accommodate the increasing size of the tapered portion 444 as it is advanced through the tissue.

The tapered portion 444 can also facilitate proper location of the implant 430 into the supraciliary or suprachoroidal spaces. For example, the implant 430 is preferably advanced through the tissue within the anterior chamber angle during implantation. This tissue typically is fibrous or porous, which is relatively easy to pierce or cut with a surgical device, such as the tip of the implant 430. The implant 430 can be advanced through this tissue and abut against the sclera once the implant 430 extends into the uveoscleral outflow pathway. As the implant 430 abuts against the sclera, the tapered portion 444 preferably provides a generally rounded edge or surface that facilitates sliding of the implant 430 within the suprachoroidal space along the interior wall of the sclera. For example, as the implant 430 is advanced into the uveoscleral outflow pathway and against the sclera, the implant 430 will likely be oriented at an angle with respect to the interior wall of the sclera. As the tip of the implant 430 engages the sclera, the tip preferably has a radius that will permit the implant 430 to slide along the sclera instead of piercing or substantially penetrating the sclera. As the implant 430 slides along the sclera, the tapered portion 444 will provide an edge against which the implant 430 can abut against the sclera and reduce the likelihood that the implant 430 will pierce the sclera.

Once the implant 430 is implanted in position with the inflow portion 432 residing in the anterior chamber and the outflow portion 434 residing in the uveoscleral outflow pathway, the first active drug can elute from the lumen 436 of the implant 430 into the anterior chamber and aqueous humor can flow from the anterior chamber to the uveoscleral outflow pathway through the lumen 436 of the implant 430. The flow of fluid is preferably restricted by the size of the lumen 436, which produces a capillary effect that limits the fluid flow for given pressures. The capillary effect of the lumen allows the shunt to restrict flow and provides a valveless regulation of fluid flow. The flow of fluid through the implant 430 is preferably configured to be restricted to a flow rate that will reduce the likelihood of hypotony in the eye. For example, in some embodiments, the flow rate can be limited to about 2.5 μL/min or less. In some embodiments the flow rate can be limited to between about 1.9 μL/min and about 3.1 μL/min. In other applications, a plurality of implants 430 can be used in a single eye to elute at least a first drug into the anterior chamber and to conduct fluid from the anterior chamber to the uveoscleral outflow pathway. In such applications, the cumulative flow rate through the implants preferably is within the range of about 1.9 μL/min to about 3.1 μL/min, although the flow rate for each of the implants can be significantly less than about 2.5 μL/min. For example, if an application called for implantation of five implants, then each implant 430 can be configured to have a flow rate of about 0.5 μL/min.

While the lumen 436 is depicted in FIG. 4 as extending substantially through the longitudinal center of the implant 430, in some embodiments, the lumen can be offset from the longitudinal center of the shunt. For example, while FIG. 4 depicts the implant 430 as having a tapered portion 444 that terminates substantially where the tapered portion 444 meets the lumen 436, the lumen 436 can be offset from the center of the implant 430 such that lumen 436 opens along one of the sides of the tapered portion 444. Accordingly, the tapered portion 444 can terminate at a location offset from the lumen axis 442 and can extend beyond the point at which the interior lumen 436 and the exterior tapered portion 444 meet. Additionally, the lumen 436 can vary in direction along its length.

In some embodiments, the implant comprises one or more lumens or sub-lumens, as described further herein. In some embodiments, at least a first active drug is placed in at least one sub-lumen. The sub-lumen can have a closed distal end or can have an outlet located in or near the distal end to allow fluid to flow from the anterior chamber to the uveoscleral outflow pathway. In some embodiments, at least one sub-lumen does not contain any active drugs and is configured exclusively to allow fluid to drain from the anterior chamber to the uveoscleral outflow pathway.

The implant 430 preferably comprises any of the materials described herein. The implant 430 can be fabricated through conventional micro machining techniques or through procedures commonly used for fabricating optical fibers. For example, in some embodiments, the implant 430 is drawn with a bore, or lumen, extending therethrough. In some embodiments, the tapered portion 444 at the outflow portion 434 can be constructed by shearing off an end tubular body. This can create a tapered portion 444 that can be used to puncture or incise the tissue during implantation and dilate the puncture or incision during advancement of the implant 430. Other materials can be used for the implant 430 of FIG. 4, and other methods of manufacturing the implant 430 can also be used. For example, the implant 430 can be constructed of metals or plastics, and the implants can be machined with a bore that is drilled as described above.

The implant 430 of FIG. 4 represents an implant having a construction that provides for the opportunity to vary the size of the implant 430 or the lumen 436. The implant 430 also need not have a unitary configuration; that is, be formed of the same piece of material. For example, a proximal portion of the implant can be formed of glass drawn to have at least one small diameter lumen. A distal portion of the implant can be a cap formed of a different material. The cap can include a tissue-piercing end and one or more outlet openings. Each of the one or more outlet openings communicates with at least one of the one or more lumens in the proximal portion. In one preferred mode, the cap has a conically shaped tip with a plurality of outlet openings disposed proximal of the tip's distal end.

In some embodiments, the implant has a proximal end cap. For example, an O-ring cap with a region of drug release (as discussed more fully herein and with reference to FIGS. 18K and 18M) can be located over the proximal end of the implant to allow for drug elution into the anterior chamber of the eye. In other embodiments, a crimp cap comprising a region of drug release (as discussed more fully herein and with reference to FIGS. 18L and 18N) is located over the proximal end of the implant. Regions of the crimp cap can be compressible such that the cap can be securely placed on, and sealed to, the body of the implant. The regions of drug release are further permeable to aqueous humor to allow for drainage of aqueous humor from the anterior chamber and through the lumen of the implant. In some embodiments, the cap comprises one or more orifices or layers in place of, or in addition to, regions of drug release based on thickness and/or permeability of the cap material. The one or more orifices or layers can be permeable to aqueous humor to allow for drainage from the anterior chamber. In some embodiments, a coating is placed within the cap to cover an orifice therein. The coating may comprise a membrane or layer of semi-permeable polymer. In some embodiments, the coating has a defined thickness, and thus a defined and known permeability to various drugs and ocular fluid. In some embodiments, the coating is placed in other locations, including on the exterior of the cap, within the orifice, or combinations thereof.

In some embodiments, the implant is formed with one or more dividers positioned longitudinally within the outer shell, creating multiple additional sub-lumens within the interior lumen of the shell. The divider(s) can be of any shape (e.g. rectangular, cylindrical) or size that fits within the implant so as to form two or more sub-lumens, and may be made of the same material or a different material than the outer shell, including one or more polymers, copolymers, metal, or combinations thereof. In one embodiment, a divider is made from a biodegradable or bioerodible material. The multiple sub-lumens may be in any configuration with respect to one another. In some embodiments, a single divider may used to form two sub-lumens within the implant shell. See e.g., FIG. 13A. In some embodiments, the two sub-lumens are of equal dimension. In other embodiments the divider may be used to create sub-lumens that are of non-equivalent dimensions. In still other embodiments, multiple dividers may be used to create two or more sub-lumens within the interior of the shell. In some embodiments the lumens may be of equal dimension. See, e.g. FIG. 13B. Alternatively, the dividers may be positioned such that the sub-lumens are not of equivalent dimension.

In some embodiments, one or more of the sub-lumens formed by the dividers may traverse the entire length of the implant. In some embodiments, one or more of the sub-lumens may be defined of blocked off by a transversely, or diagonally placed divider or partition. The blocked off sub-lumens may be formed with any dimensions as required to accommodate a particular dose or concentration of drug.

In some embodiments comprising a shunt, one or more lumens extend through the shunt to form at least a portion of the flow path. Preferably, there is at least one lumen that operates to conduct the fluid through the shunt. Each lumen preferably extends from an inflow end to an outflow end along a lumen axis. In some embodiments the lumen extends substantially through the longitudinal center of the shunt. In other embodiments, the lumen can be offset from the longitudinal center of the shunt.

Figure 13C:
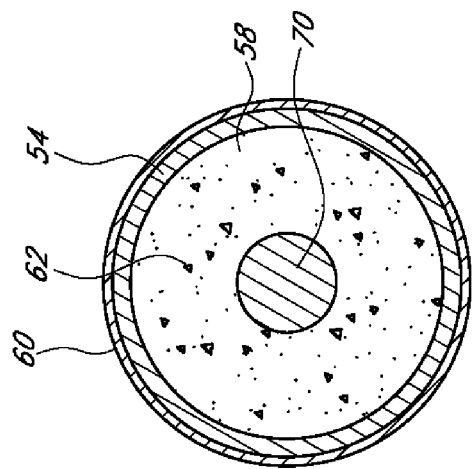
FIGS. 13A-13C illustrate drug delivery implants in accordance with embodiments disclosed herein.
Figure 13A:
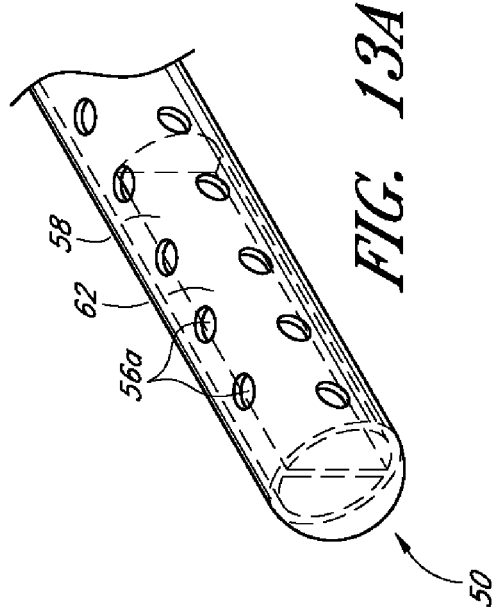
Figure 13B:
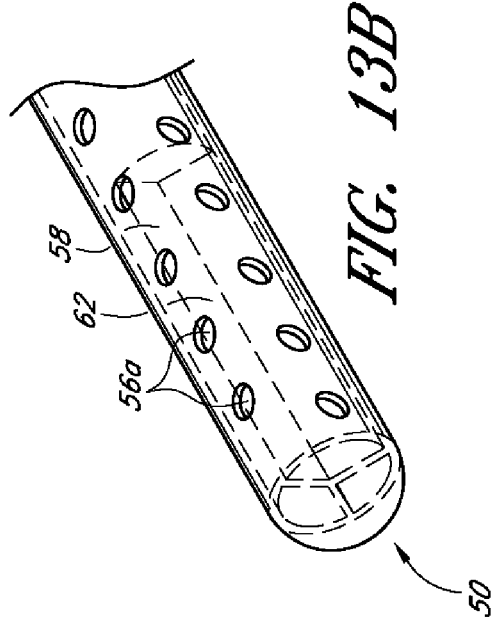

In other embodiments, the implant is formed as a combination of one or more tubular shell structures 54 that are substantially impermeable to ocular fluids that are nested within one another to form a "tube within a tube" design, as shown in FIG. 13C. In alternative embodiments, a cylindrical divider is used to partition the interior of the implant into nested "tubes." In such embodiments, a coating 60, which can optionally be polymer based, can be located in or on the tubular implant. In such embodiments, at least a first interior lumen 58 is formed as well as an ocular fluid flow lumen 70. In some embodiments, the ocular fluid flow lumen 70 is centrally located. In other embodiments, it may be biased to be located more closely to the implant shell. In still other embodiments, additional shell structures are added to create additional lumens within the implant. Drugs 62 may be positioned within one or more of said created lumens. Orifices or regions of drug release may be placed as necessary to allow ocular fluid to contact the therapeutic agent. In certain embodiments the coating is placed on the outer surface of the outer shell. In certain embodiments, two or more biodegradable coatings are used on a single implant, with each coating covering a separate or overlapping portion of the implant. In those embodiments employing biodegradable coatings, each coating optionally has a unique rate of biodegradation in ocular fluid.

Figure 14:
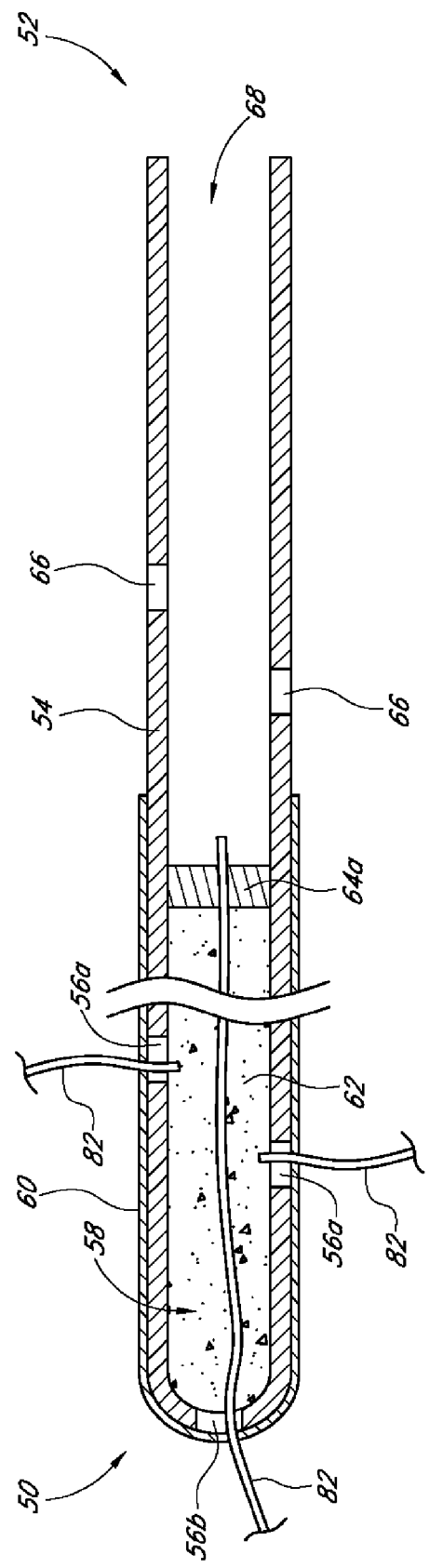
FIG. 14 illustrates a drug delivery implant in accordance with embodiments disclosed herein.

In some embodiments, a wick 82 is included in the implant (FIG. 14). The wick may take any form that assists in transporting ocular fluid from the external side of the device to an interior lumen more rapidly than would be achieved through the orifices of regions of drug release alone. While FIG. 14 depicts a wick passing through an orifice, it shall be appreciated that an implant having only regions of drug release are also capable of employing a wick. In such embodiments a wick may be positioned to pass through the outer shell during the manufacture of the implant such that an orifice is not created. In some embodiments, a fiber is positioned in an orifice or through the outer shell such a portion of the wick lies adjacent to the drug within the lumen of the implant. In other embodiments, the drug is formed around the wick, so that ocular fluid is delivered directly to an interior portion of the agent. In still other embodiments, one or more wicks are used as described above, thus allowing dissolution of the agent from the exterior and interior portions of the pellet or mass of drug.

Figure 15:
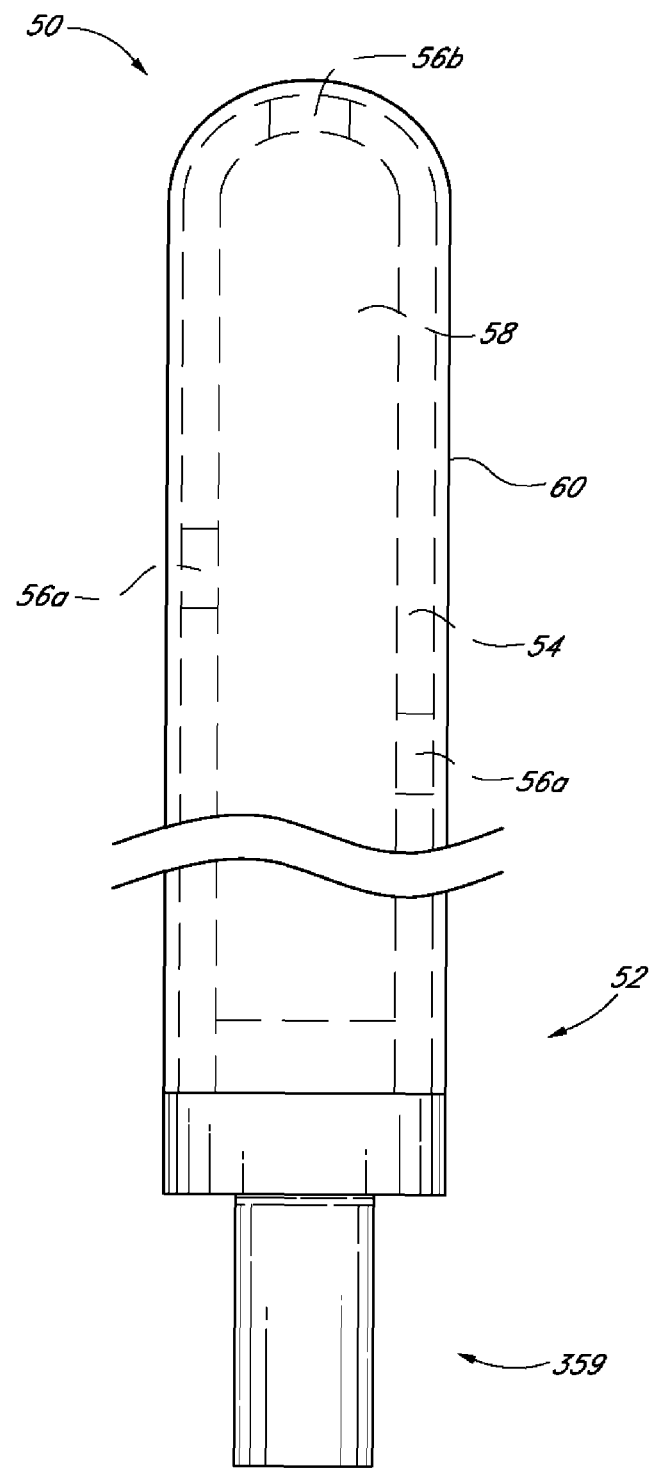
FIG. 15 illustrates an illustrative embodiment of a drug delivery implant and retention protrusion.
Figure 16:
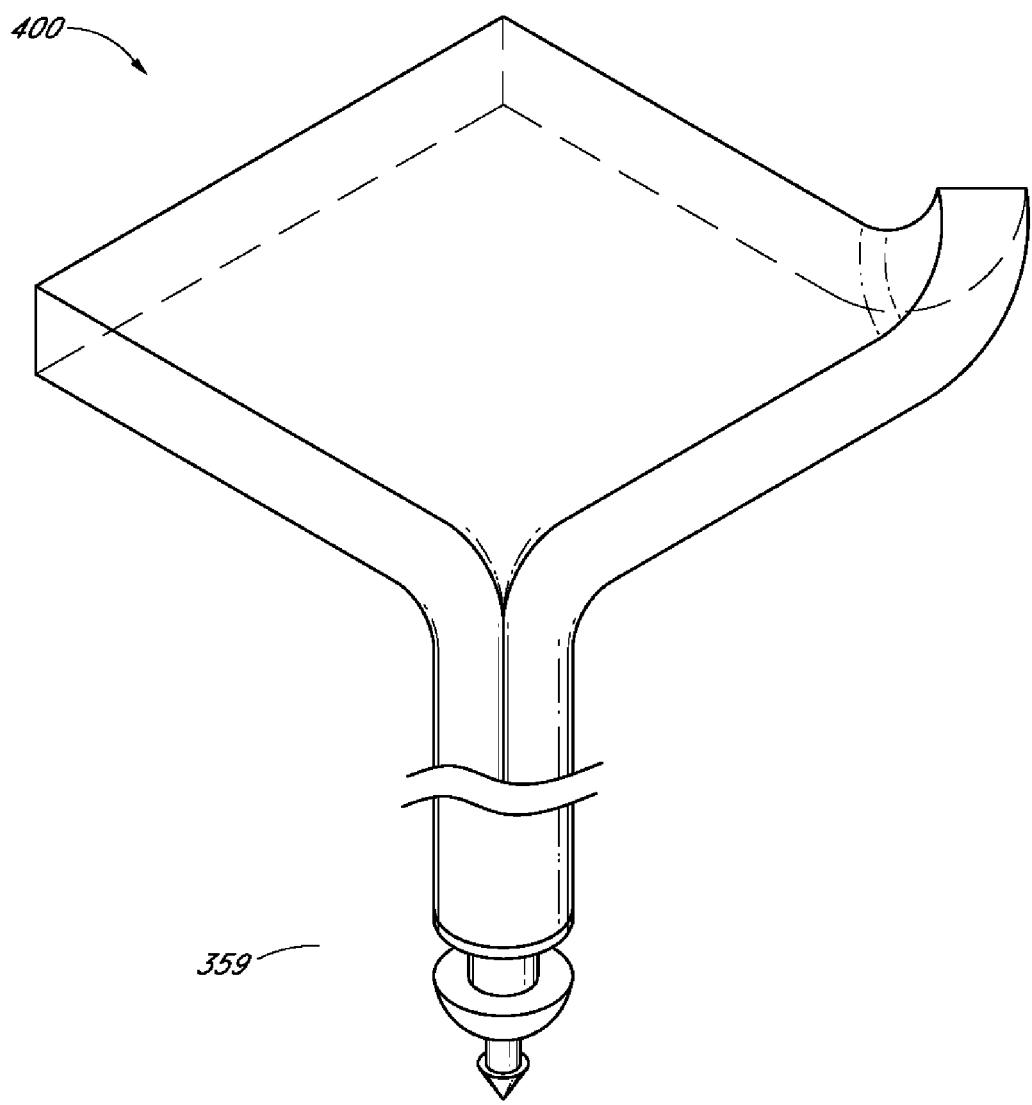
FIG. 16 illustrates an embodiment of a drug delivery implant in accordance with embodiments disclosed herein.
Figure 17:
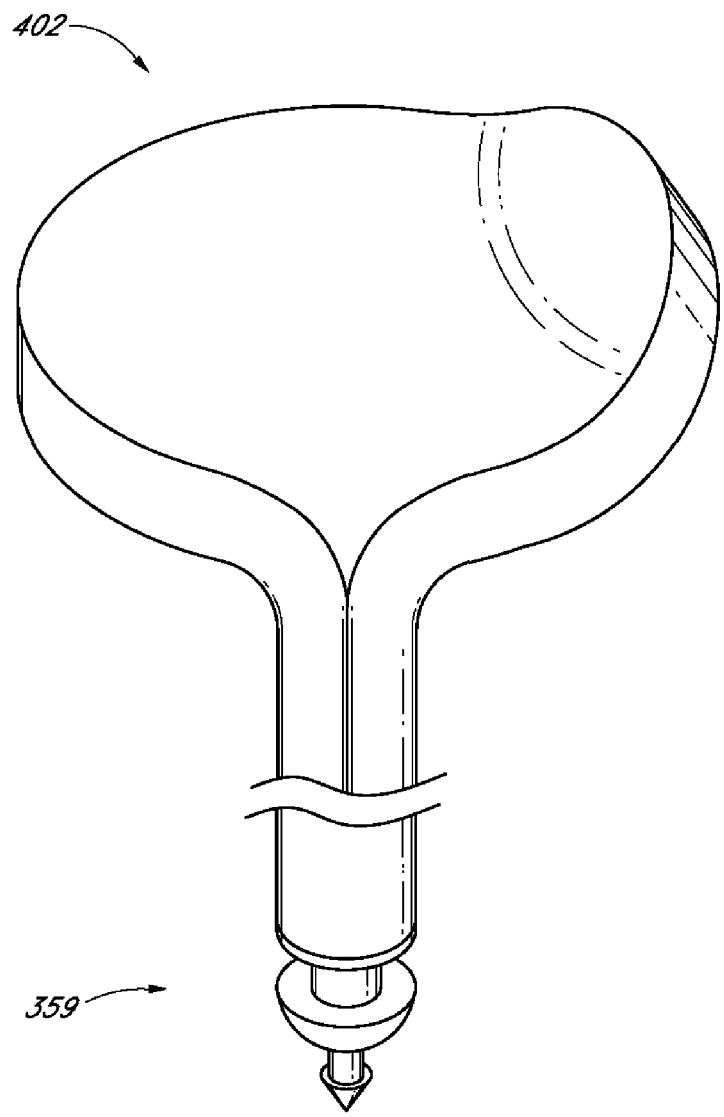
FIG. 17 illustrates another embodiment of a drug delivery implant in accordance with embodiments disclosed herein.

FIG. 15 shows a cross sectional schematic of one embodiment of an implant in accordance with the description herein and further comprising a retention protrusion 359 for anchoring the implant to ocular tissue. While depicted in FIG. 15, and other Figures, as having the distal portion being the implant end and the proximal portion being the retention protrusion 359 end, in some embodiments, depending on the site and orientation of implantation, the distal portion and proximal portion may be reversed relative to the orientation in FIG. 15. Additionally, while the illustrated implant depicts the presence of orifices that pass through the outer shell, it shall be appreciated that embodiments of the implants comprising regions of drug release based on thickness and/or permeability of the shell material can also be used in conjunction with a retention feature. Moreover, implants comprising combinations of one or more orifices, one or more layers of permeable and/or semi-permeable material, and one or more areas of drug release based on thickness and/or permeability of the shell material are used in several embodiments.

In several embodiments, implants comprise a sheet 400 and a retention protrusion 359. See FIG. 16. In some embodiments, the sheet is not joined to a retention protrusion. The sheet can be made of any biocompatible material, including but not limited to, polymers, fibers, or composite materials. In some embodiments, the sheet is compounded with one or more therapeutic agent(s). In some embodiments, the sheet is coated with a material that is compounded with one or more therapeutic agents. In other embodiments, a sheet compounded with a first therapeutic agent is coated with a material compounded with a second therapeutic agent, a different concentration of the first therapeutic agent, or an auxiliary agent. In some embodiments the sheet is biodegradable, while in others it is not. In other embodiments, a disc 402 (FIG. 17) is used in place of a sheet. In several embodiments, the sheet or disc is flexible.

For delivery of some embodiments of the sheet or disc implants, the sheets or discs are dimensioned such that they can be rolled, folded, or otherwise packaged within a delivery instrument. In some embodiments, the entire implant is flexible. In some embodiments, the implant is pre-curved or pre-bent, yet still flexible enough to be placed within a non-curved lumen of a delivery apparatus. In some embodiments the flexible sheets or discs have thicknesses ranging from about 0.01 mm to about 1.0 mm. Preferably, the delivery instrument has a sufficiently small cross section such that the insertion site self seals without suturing upon withdrawal of the instrument from the eye, for example an outer dimension preferably no greater than about 18 gauge and is not smaller than about 27 or 30 gauge. In such embodiments, the rolled or folded sheets or discs can return to substantially their original dimensions after attachment to the ocular tissue and withdrawal of the delivery instrument. In certain embodiments, thicknesses of about 25 to 250 microns, including about 50 to 200 microns, about 100 to 150 microns, about 25 to 100 microns, and about 100 to 250 microns are used.

The implant is dimensioned, in some embodiments, to be affixed (e.g., tethered) to the iris and float within the aqueous of the anterior chamber. In this context, the term "float" is not meant to refer to buoyancy of the implant, but rather that the sheet surface of the implant is movable within ocular fluid of the anterior chamber to the extent allowed by the retention protrusion. In certain embodiments, such implants are not tethered to an intraocular tissue and are free floating within the eye. In certain embodiments, the implant can be adhesively fixed to the iris with a biocompatible adhesive. In some embodiments, a biocompatible adhesive may be pre-activated, while in others, contact with ocular fluid may activate the adhesive. Still other embodiments may involve activation of the adhesive by an external stimulus, after placement of the implant, but prior to withdrawal of the delivery apparatus. Examples of external stimuli include, but are not limited to heat, ultrasound, and radio frequency, or laser energy. In certain embodiments, affixation of the implant to the iris is preferable due to the large surface area of the iris. In other embodiments, the implant is flexible with respect to a retention protrusion affixed to the iris, but is not free floating. Embodiments as disclosed herein are affixed to the iris in a manner that allows normal light passage through the pupil.

Figure 18A:
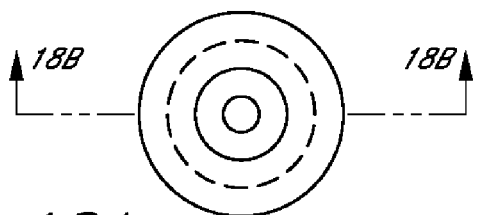
FIGS. 18A-18U illustrate various drug delivery devices in accordance with embodiments disclosed herein.
Figure 18B:
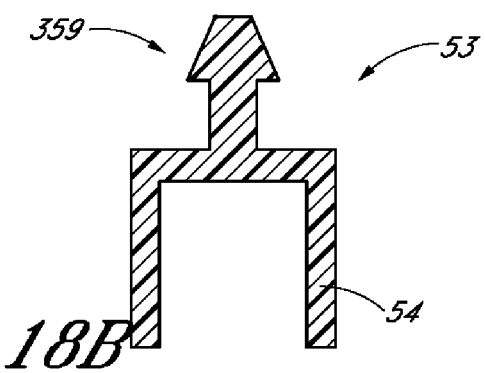
Figure 18C:
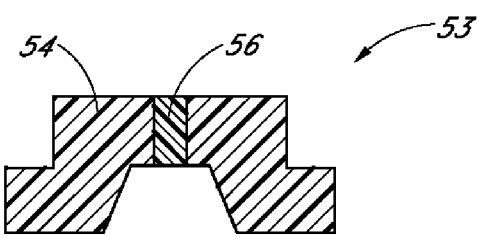
Figure 18D:
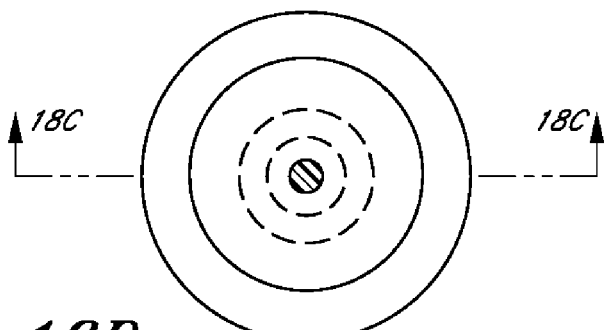
Figure 18E:
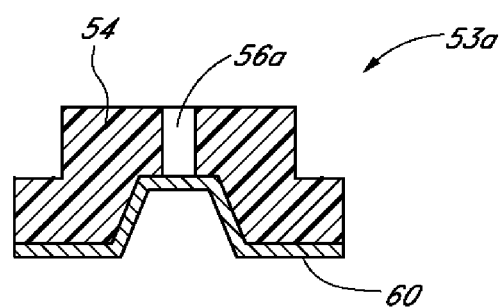
Figure 18F:
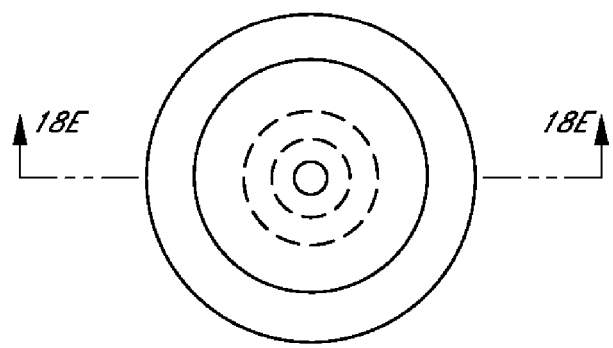
Figure 18G:
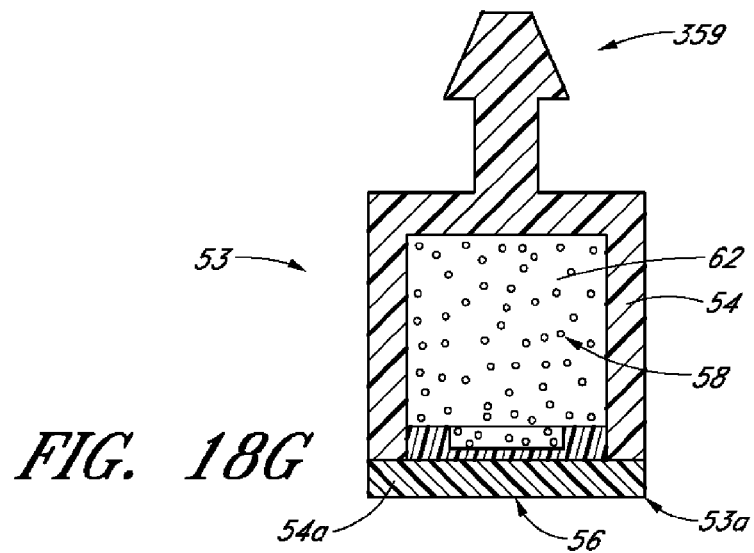
Figure 18H:
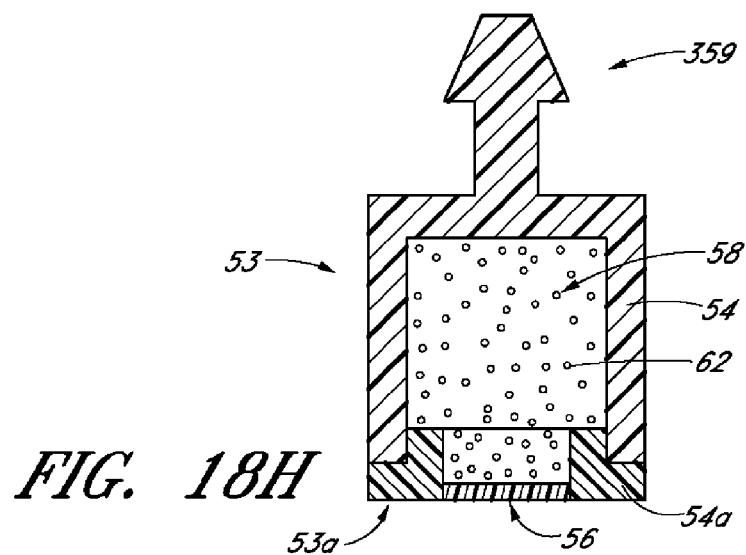
Figure 18I:
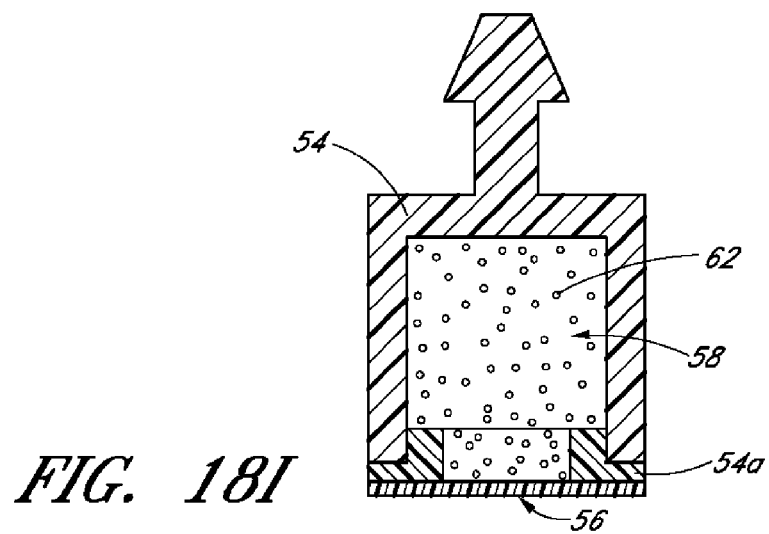
Figure 18J:
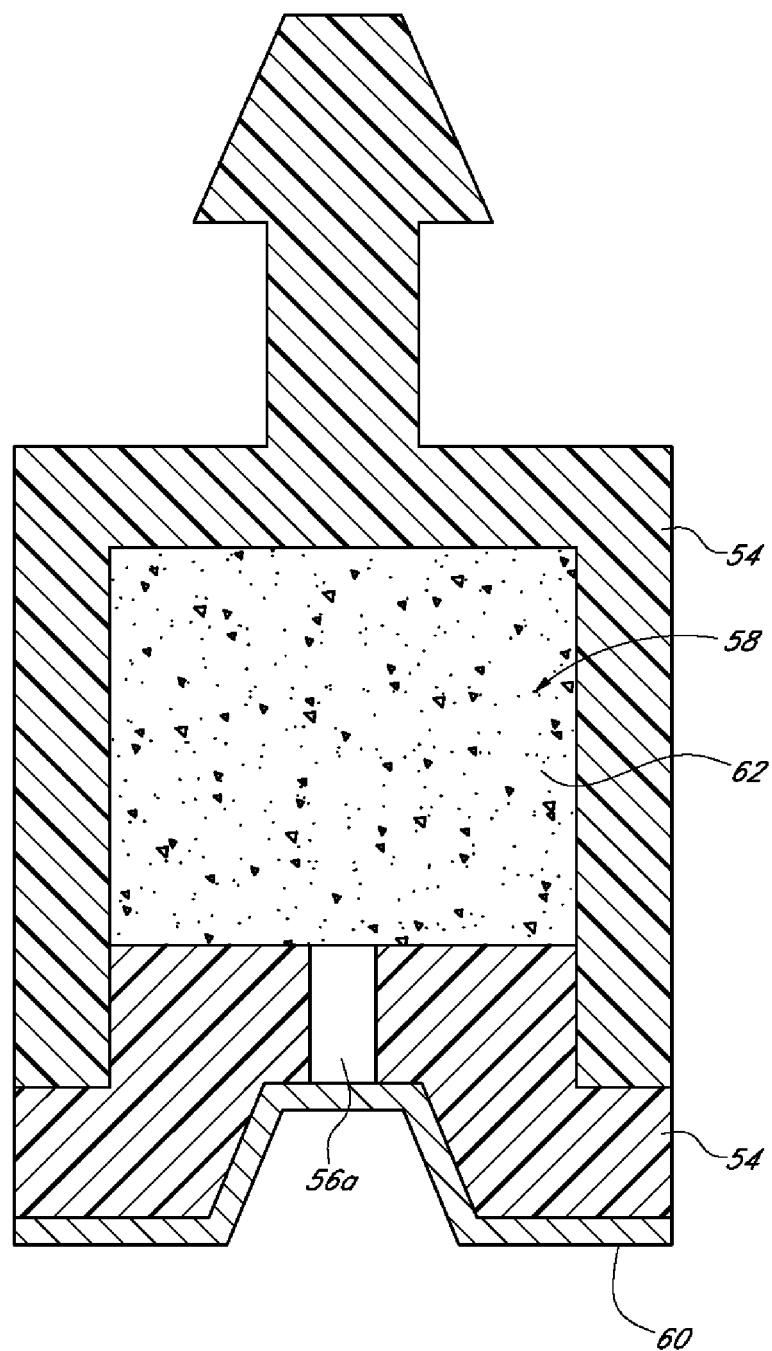

As discussed above, several embodiments disclosed herein employ multiple materials of varying permeability to control the rate of drug release from an implant. FIGS. 18A-18Q depict additional implant embodiments employing materials with varied permeability to control the rate of drug release from the implant. FIG. 18A shows a top view of the implant body 53 depicted in FIG. 18B. The implant body 53 comprises the outer shell 54 and retention protrusion 359. While not explicitly illustrated, it shall be appreciated that in several embodiments, implants comprising a body and a cap are also constructed without a retentions protrusion. FIG. 18C depicts an implant cap 53a, which, in some embodiments, is made of the same material as the outer shell 54. In other embodiments, the cap 53 is made of a different material from the outer shell. A region of drug release 56 is formed in the cap through the use of a material with permeability different from that of the shell 54. It shall also be appreciated that implants comprising a body and a cap (and optionally a retention protrusion) may be constructed with orifices through the body or the cap, may be constructed with layers or coatings of permeable or semi-permeable material covering all or a portion of any orifices, and may also be constructed with combinations of the above and regions of drug release based on thickness and/or permeability of the shell material. See 18E-18F.

FIGS. 18G-18J depict assembled implants according to several embodiments disclosed herein. The implant body 53 is joined with the implant cap 53a, thereby creating a lumen 58 which is filled with a drug 62. In some embodiments, the material of the implant body 54 differs from that of the cap 54a. Thus, the assembly of a cap and body of differing materials creates a region of drug release 56.

Figure 18K:
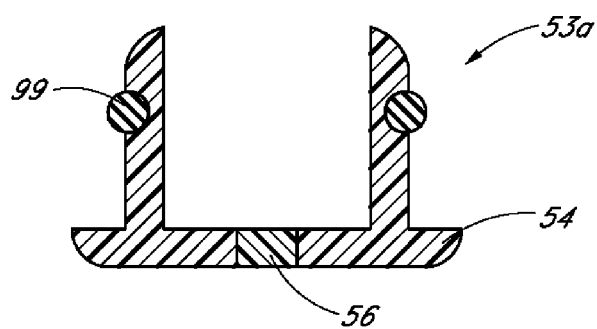
Figure 18L:
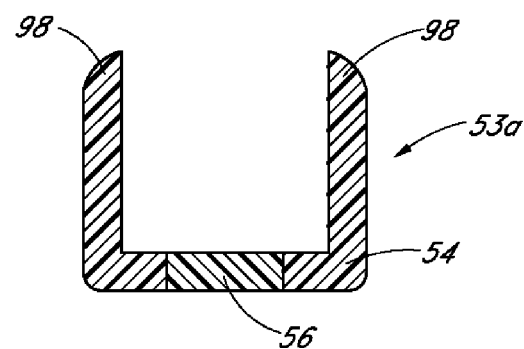
Figure 18M:
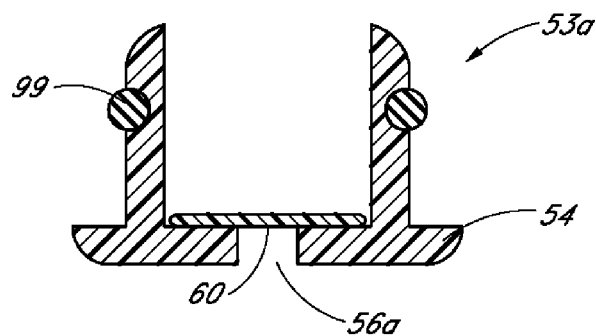
Figure 18N:
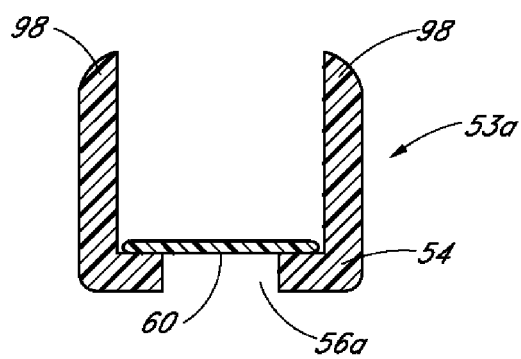
Figure 180:
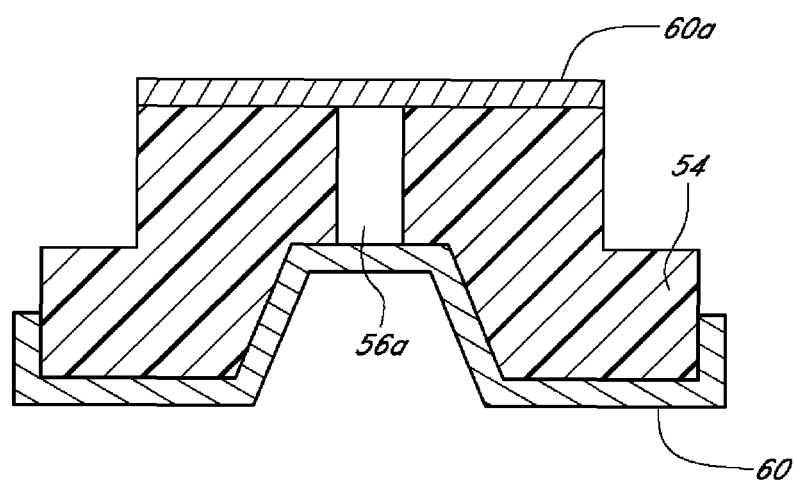

Additional non-limiting embodiments of caps are shown in FIGS. 18K and 18L. In FIG. 18K, an O-ring cap 53a with a region of drug release 56 is shown in cross-section. In other embodiments there may be one or more regions of drug release in the cap. An o-ring 99 (or other sealing mechanism) is placed around the cap such that a fluid impermeable seal is made between the cap and the body of the implant when assembled. In FIG. 18L, a crimp cap is shown. The outer shell of the cap comprises regions that are compressible 98 such that the cap is securely placed on, and sealed to, the body of the implant. As discussed above, certain embodiments employ orifices and layers in place of, or in addition to regions of drug release based on thickness and/or permeability of the shell material. FIG. 18M depicts an O-ring cap 53a shown in cross-section. A coating 60 is placed within the outer shell 54 of the cap and covering an orifice 56a. In other embodiments there may be one or more orifices in the cap. In some embodiments, the coating 60 comprises a membrane or layer of semi-permeable polymer. In some embodiments, the coating 60 has a defined thickness, and thus a defined and known permeability to various drugs and ocular fluid. In FIG. 18N, a crimp cap comprising an orifice and a coating is shown. While the coatings are shown positioned within the caps, it shall be appreciated that other locations are used in some embodiments, including on the exterior of the cap, within the orifice, or combinations thereof (See FIG. 18O).

Figure 18P:
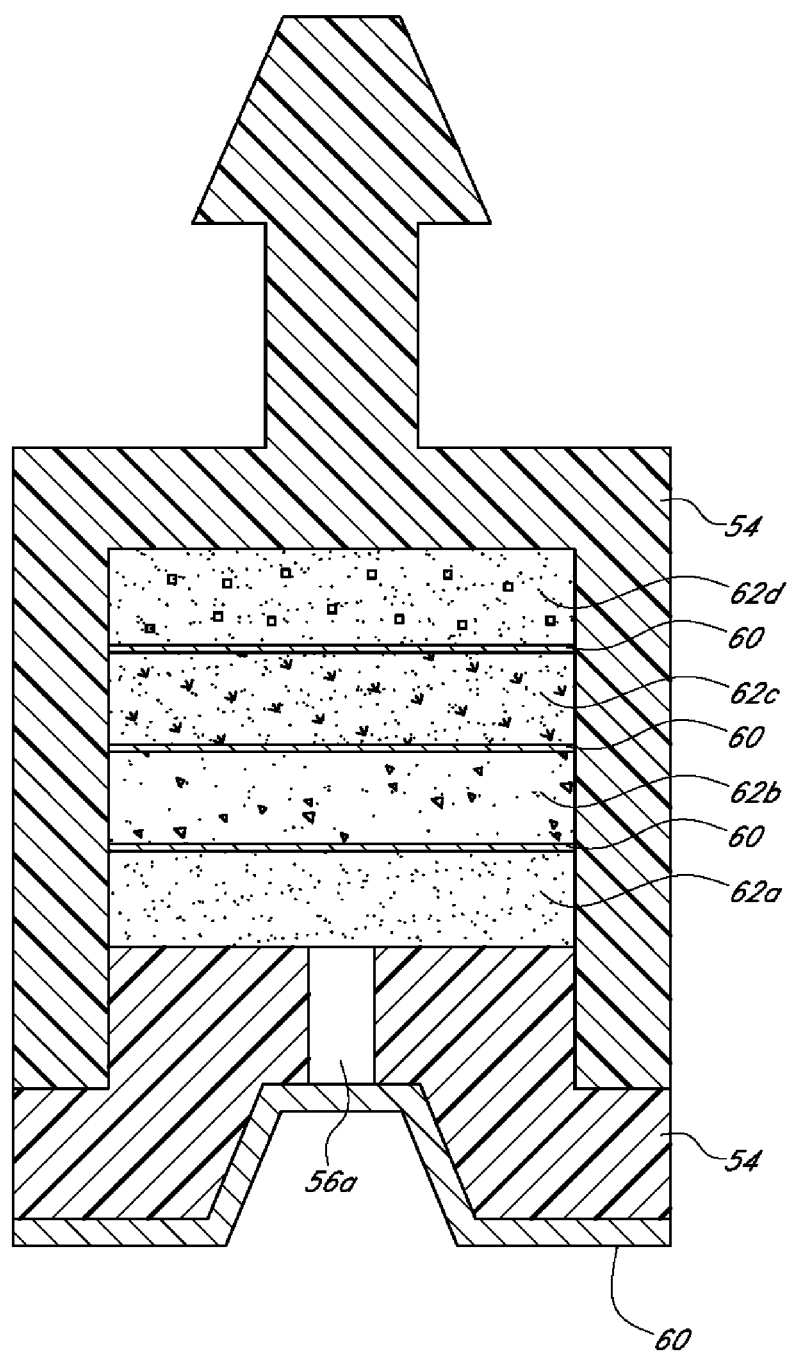
Figure 18Q:
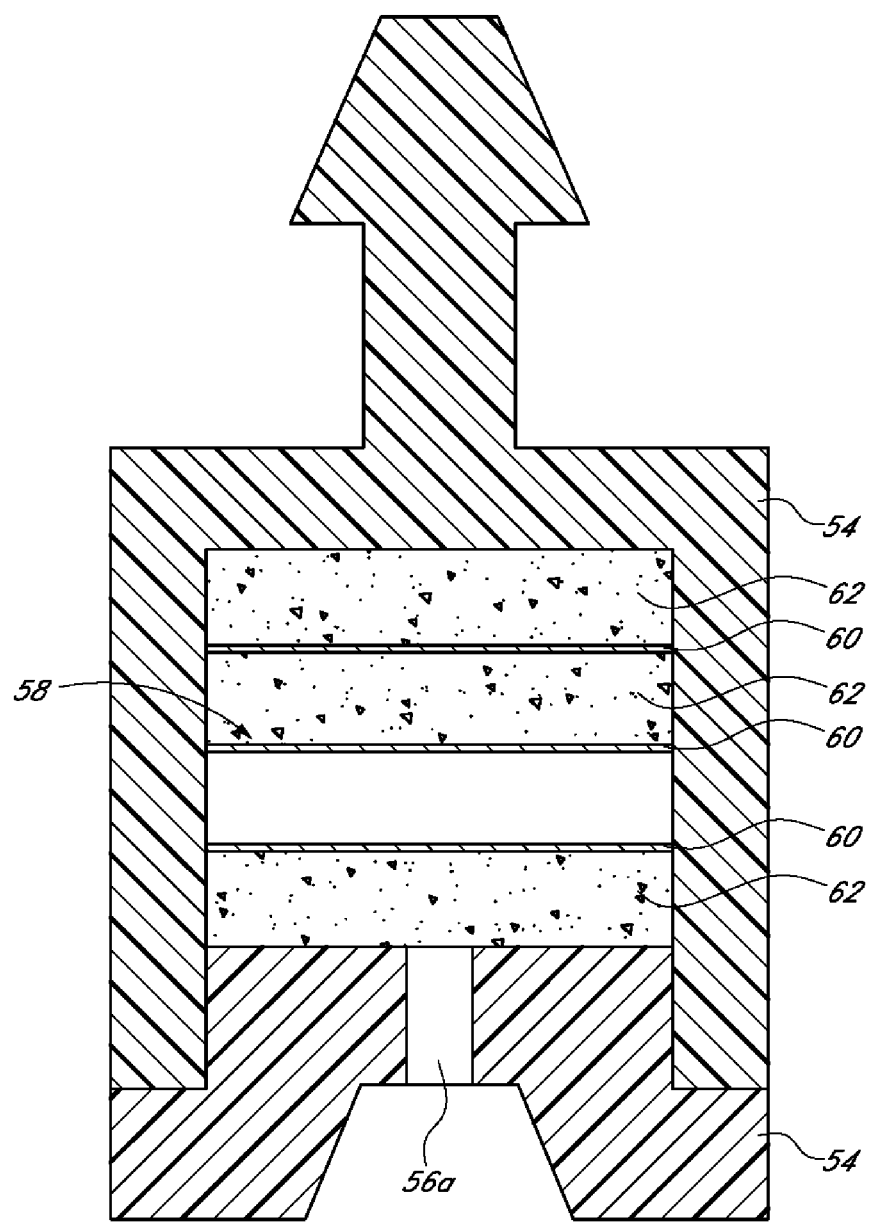

Additionally, as shown in FIGS. 18P and 18Q, in certain embodiments, coatings are employed within the drug material such that layers are formed. Coatings can separate different drugs 62a, 62b, 62c, 62d within the lumen (FIG. 18P). In certain embodiments, coatings are used to separate different concentration of the same drug (FIG. 18Q). It shall be appreciated that such internal layers are also useful in embodiments comprising regions of drug release (either alone or in combination with other drug release elements disclosed herein, e.g., orifices). In certain embodiments, the layers create a particularly desired drug elution profile. For example, use of slow-eroding layers is used to create periods of reduced drug release or drug "holidays." Alternatively, layers may be formulated to create zero order (or other kinetic profiles) as discussed in more detail below.

In each of the embodiments depicted in the Figures, as well as other embodiments, the coatings or outer layers of shell material may be formed by spraying, dipping, or added by some other equivalent means known in the art. Thus, in some embodiments, the permeability of the region of drug release or layer(s) covering an orifice (and hence the elution rate) will be at least partially defined by the materials used in manufacturing the implant, the coatings (if any) on the implant, and the effective thickness of implant outer shell.

Figure 18R:
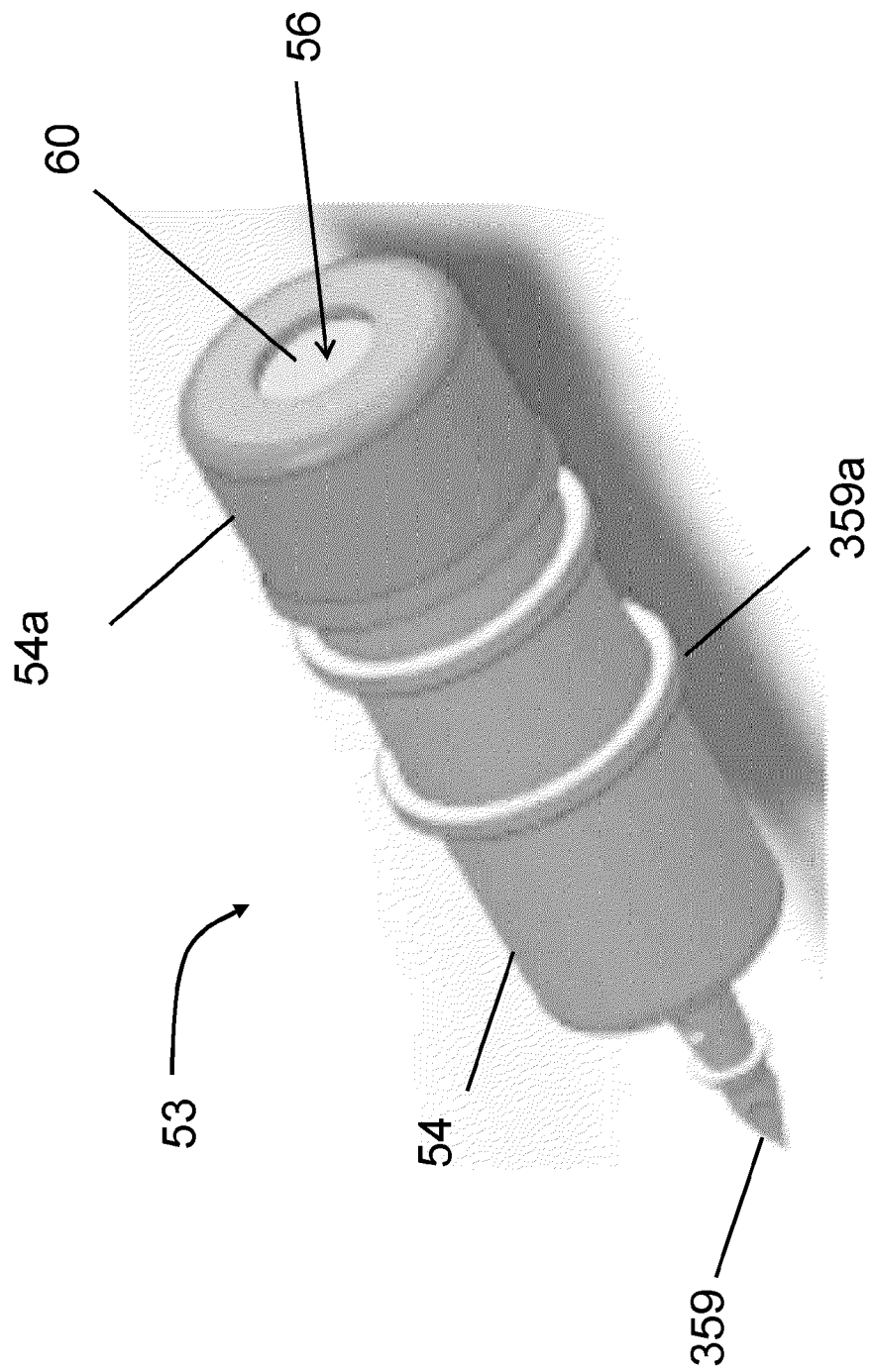

Additionally, in several embodiments, one or more portions of the implant are manufactured separately, then combined for a final implant that is ready for insertion to a target site (e.g., an assembled cap and implant shell). As shown, for example, in FIG. 18R, the implant 53, in several embodiments, comprises an implant shell 54, a separate cap 54a (which is shown for clarity in a different shade, but is optionally constructed of the same or of different material as compared to the implant shell). Any of the various cap configurations can be used with any of the implant shells (adjusting, of course, for dimensions that allow interaction between the components). As shown in FIG. 18R, the cap 54a comprises a central aperture, thereby creating a region of drug release 56. In several embodiments, the assembly of certain such embodiments exploit the elastic or semi-elastic characteristics of the membrane 60 through which the drug (or drugs) housed within the implant will elute. Advantageously, in several embodiments, the elastic properties of the membrane 60 allow the cap of an implant to be press fit onto the implant shell, and then retained by the pressure provided against the cap by the elastic rebound of the membrane (e.g., a "self-lock" feature). Thus, the membrane 60, in several embodiments, not only serves to define the release rate of the drug (or drugs), it also functions as a gasket to seal the interior portions of the implant from the outer environment, thus limiting the fluid communication between interior and exterior portions to that occurring through the membrane 60. As discussed in more detail below with respect to the possible materials from which the outer shell is constructed, the membrane 60 is (depending on the embodiment) constructed of similar materials, or combinations thereof. For example, the membrane 60, in one embodiment, comprises ethyelene vinyl acetate, while in another embodiment, the membrane comprises silicone or other partially or semi-permeable materials material, homopolymers, polymer blends and copolymers, such as random copolymers and block copolymers, polyethylene, polyurethane, polyethersulfone, polyamide, poly(carbonate urethane), poly(ether urethane), silicone poly(carbonate urethane), silicone poly (ether urethane), PurSil™, Elasthane™, CarboSil™ and/or Bionate™. The selection of the membrane material and its dimensions (e.g., its thickness) are derived, at least in part, by the therapeutic agent of choice.

Figure 18S:
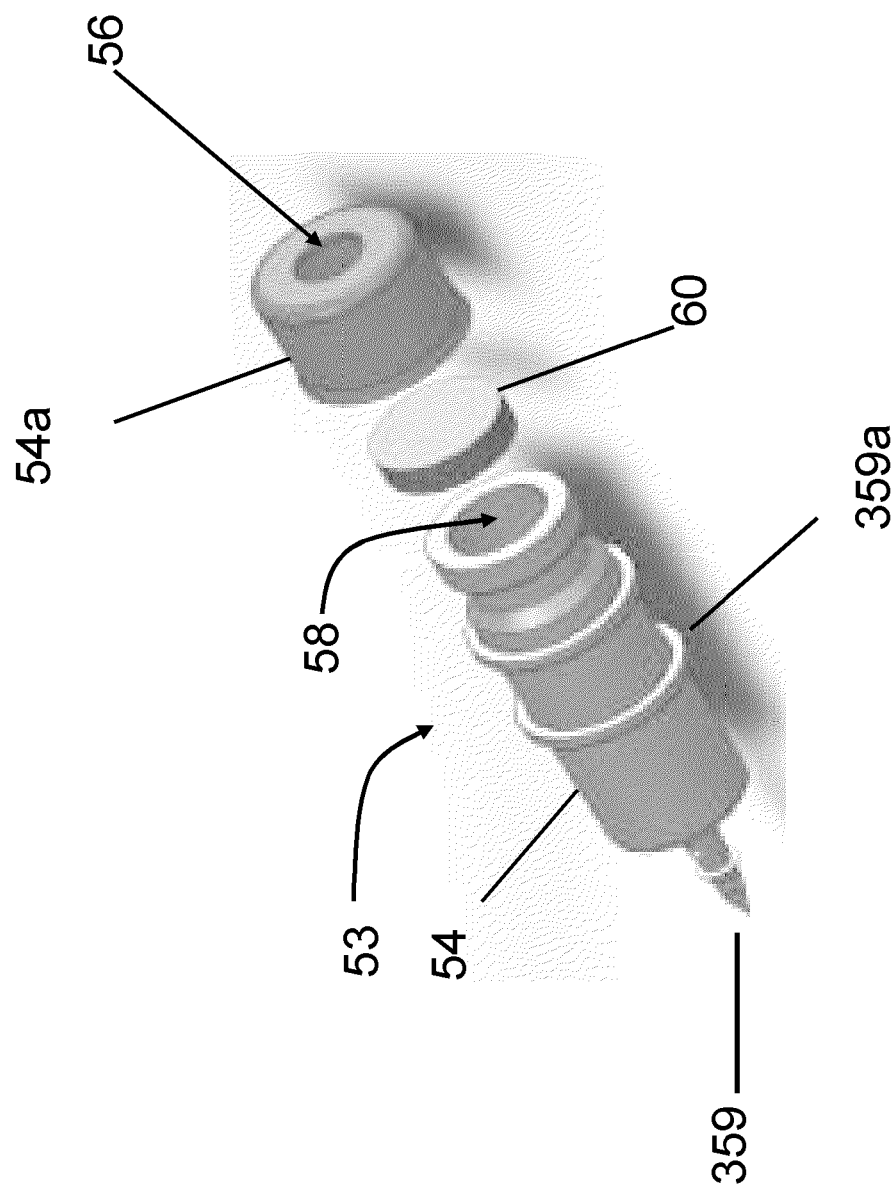

FIG. 18S depicts an exploded view of one embodiment of the implants disclosed herein. The implant 53 comprises, for example, a retention protraction 459 at one end in order to anchor the implant into a target tissue. The implant comprises at least one internal lumen 58 to house a therapeutic agent (or agents). As discussed above, the implant further comprises a cap 54a and an membrane 60, which when assembled together create a region of drug release 56 that is tailored (based on the membrane) to a particular therapeutic drug (or drugs) of interest.

In various embodiments, the thickness of the membrane 60 (taken in conjunction with the particular therapeutic agent or agents of choice) ranges from about 30 to about 200 µm in thickness, including about 30 to about 200 µm, about 50 to about 200 µm, about 70 to about 200 µm, about 90 to about 200 µm, about 30 to about 100 µm, about 30 to about 115 µm, about 50 to about 125 µm, about 63 to about 125 µm, about 84 to about 110 µm, about 57 to about 119 µm, and overlapping ranges thereof. In several embodiments, the thickness of the membrane 60 also defines, at least in part, the elution rate of the drug (or drugs) of interest.

As discussed herein, the elution rate of the drug is controlled, depending on the embodiment, to allow drug release over a desired time frame. For example, in several embodiments, the duration drug release, depending on the embodiment, ranges from several months to several years, e.g., about 6 to about 12 months, about 12 to about 18 months, about 18 to about 24 months, about 24 to about 30 months, about 30 to about 36 months, etc.

Figure 18T:
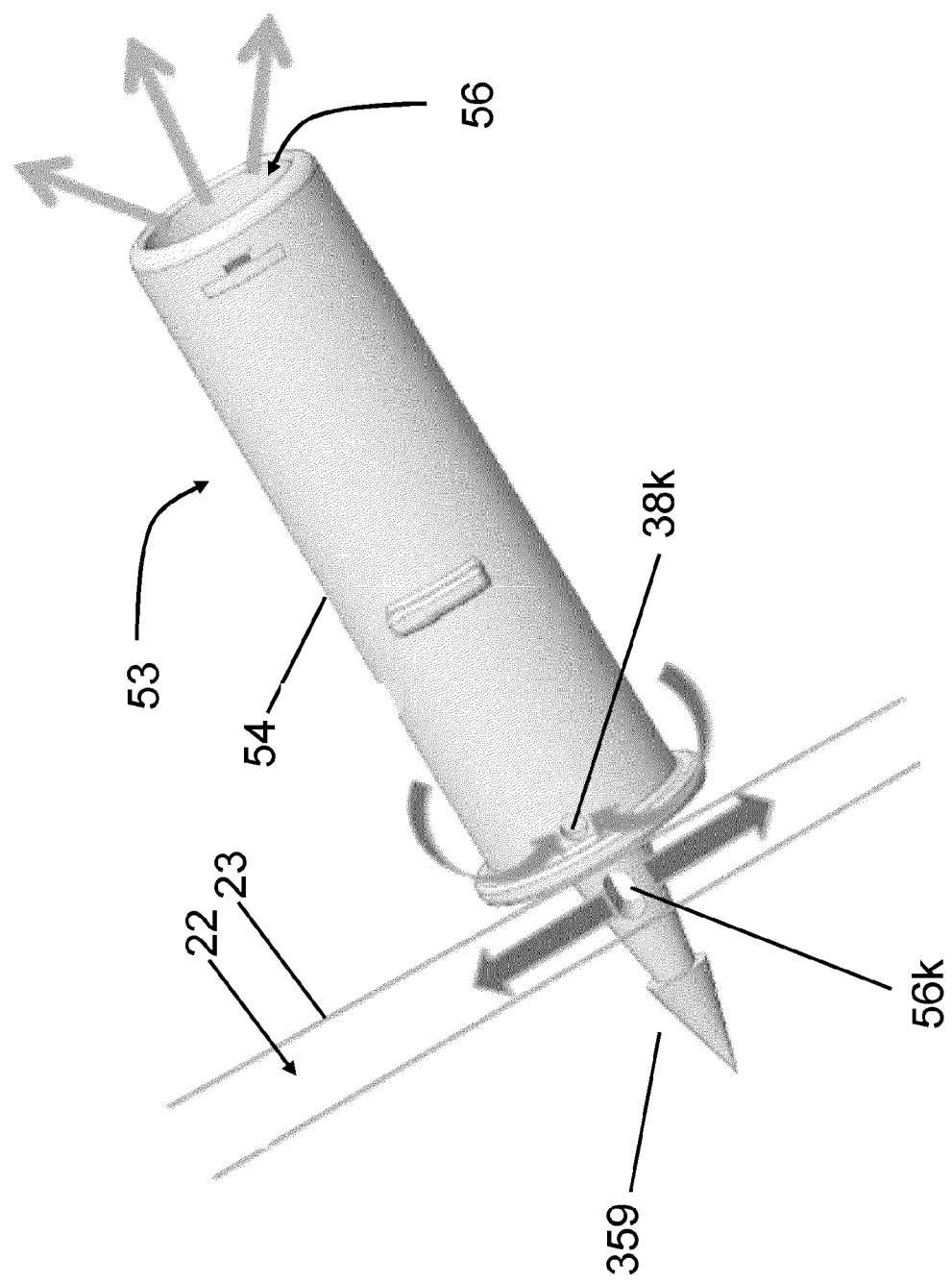

FIG. 18T depicts another embodiment in which the implant 53 further comprises at least one inflow pathway 38k and at least one fluid outflow pathway 56k. Other fluid inflow/outflow configurations are described in detail elsewhere here (e.g., see FIGS. 19R-19Y). As shown in FIG. 18T, a retention protrusion 359 anchors the implant in the ocular tissue such that the implant rests at or near the trabecular meshwork 23 and the fluid outflow pathway 56k allows ocular fluid to be directed through the implant (via fluid inflow pathway 38k) and to a physiological outflow space, shown here as Schlemm's canal 22. Similar to those embodiments described above, there is a region of drug release 56 which allows drug elution to a target tissue(s) of interest). It shall be appreciated that any of the various fluid inflow/outflow configurations can readily be adapted for use with any of the variety of implant bodies disclosed herein. Likewise, any of the retention protrusions are ready configurable for use with any of the implant shells, depending on the target tissue, the drug to be delivered, the desired drug delivery duration, and the like. For example, while the implant shown in FIG. 18T is depicted as having a spike-like or barb-like retention protrusion, the implant can also be configured with, for example, a threaded region as depicted in FIG. 19C.

Figure 18U:
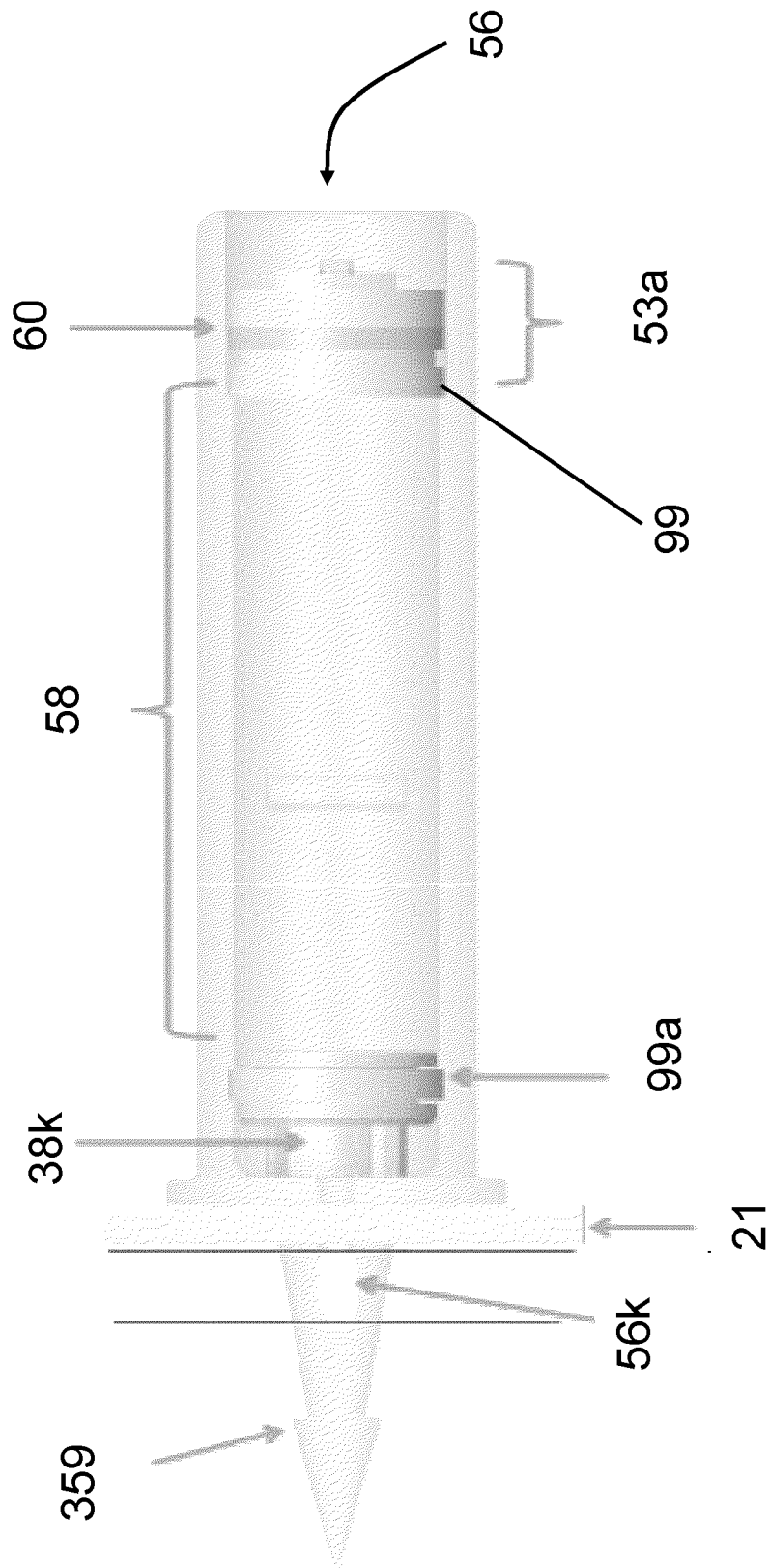

FIG. 18U depicts a cross sectional view of one embodiment of an implant having fluid inflow 38K and fluid outflow pathways 56k. As shown, the implant comprises a lumen 58 for containing drug to be delivered to a target tissue via elution through a membrane 60 and out of the implant via the region of drug release 56. One embodiment of a cap structure 53a is shown, into which the membrane 60 is integrated. To ensure that ocular fluid passes into the implant to dissolve drug (and drug flows out of the implant) only through the membrane 60 (which ensures controlled release) the cap 53 comprises a seal 99. Similarly, to prevent intrusion of ocular fluid into the implant from the portion adjacent to the inflow pathway 38k, and additional lower seal 99a is placed distal to the drug containing lumen 58.

During manufacture of the implants of certain embodiments, one or more interior lumen 58 is formed within the outer shell of the implant. In some embodiments, an interior lumen is localized within the proximal portion of the implant, while in other embodiments, an interior lumen runs the entire length or any intermediate length of the implant. Some embodiments consist of a single interior lumen, while others comprise two or more interior lumens. In some embodiments, one or more of the internal lumens may communicate with an ocular chamber or region, e.g., the anterior chamber. In some embodiments, implants are dimensioned to communicate with more than one ocular chamber or region. In some embodiments, both the proximal and the distal end of the implant are positioned within a single ocular chamber or region, while in other embodiments, the ends of the implant are positioned in different ocular chambers or regions.

A drug 62 is housed within the interior lumen 58 of the implant. The drug 62 comprises a therapeutically effective agent against a particular ocular pathology as well as any additional compounds needed to prepare the drug in a form with which the drug is compatible. In some embodiments, one or more of the internal lumens may contain a different drug or concentration of drug, which may be delivered simultaneously (combination therapy) or separately. In some preferred embodiments, an interior lumen is sized in proportion to a desired amount of drug to be positioned within the implant. The ultimate dimensions of an interior lumen of a given embodiment are dictated by the type, amount, and desired release profile of the drug or drugs to be delivered and the composition of the drug(s).

In some embodiments, the drug is in the form of a drug-containing pellet, while in other embodiments, the drug is a liquid, a slurry, micro-pellets (e.g., micro-tablets) or powder. In certain such embodiments, the form of the drug allows the implant to be flexible. In some embodiments the drug is compounded with a polymer formulation. In some embodiments, the drug positioned in the lumen is pure drug. In certain embodiments, the polymer formulation comprises a poly (lactic-co-glycolic acid) or PLGA co-polymer or other biodegradable or bioerodible polymer. In still other embodiments, the interior lumen contains only drug.

In some embodiments, multiple pellets 62 of single or multiple drug(s) are placed within an interior lumen of the implant. In some embodiments an impermeable partition 64 is used to seal drug(s) within the lumen, such that the sole route of exit from the implant is through the region of drug release. In some embodiments, the impermeable partition 64 may bioerode at a specified rate. In some embodiments, the impermeable partition 64 is incorporated into the drug pellet and creates a seal against the inner dimension of the shell of the implant 54. In other embodiments, more than one impermeable partition is used within a lumen, thereby creating sub-lumens, which may contain different drugs, the same drug at a different concentration, or the same or another drug compounded with different excipients etc. In such embodiments, sequential drug release or release of two agents that are inert within the implant and active when co-mingled outside their respective sub-lumens may be achieved.

In some embodiments, the therapeutic agent is formulated as micro-pellets or micro-tablets. Additionally, in some embodiments, micro-tablets allow a greater amount of the therapeutic agent to be used in an implant. This is because, in some embodiments, tabletting achieves a greater density in a pellet than can be achieved by packing a device. Greater amounts of drug in a given volume may also be achieved by decreasing the amount of excipient used as a percentage by weight of the whole tablet, which has been found by the inventors to be possible when creating tablets of a very small size while retaining the integrity of the tablet. In some embodiments, the percentage of active therapeutic (by weight) is about 70% or higher. As discussed herein, the therapeutic agent can be combined with excipients or binders that are known in the art. In some embodiments, the percentage of therapeutic agent ranges from about 70% to about 95%, from about 75 to 85%, from about 75 to 90%, from about 70 to 75%, from about 75% to about 80% from about 80% to about 85%, from about 85% to about 90%, from about 90% to about 95%, from about 95% to about 99%, from about 99% to about 99.9%, and overlapping ranges thereof. In some embodiments, the percentage of therapeutic agent ranges from about 80% to about 85%, including 81, 82, 83, and 84% by weight.

In several embodiments, micro-tablets provide an advantage with respect to the amount of an agent that can be packed, tamped, or otherwise placed into an implant disclosed herein. The resultant implant comprising micro-tablets, in some embodiments, thus comprises therapeutic agent at a higher density than can be achieved with non-micro-tablet forms. For example, in some embodiments, the density of the micro-pellet form of an agent within an implant ranges from about 0.7 g/cc to about 1.6 g/cc. In some embodiments, the density used in an implant ranges from about 0.7 g/cc to about 0.9 g/cc, from about 0.9 g/cc to about 1.1 g/cc, from about 1.1 g/cc to about 1.3 g/cc, from about 1.1 g/cc to about 1.5 g/cc, from about 1.3 g/cc to about 1.5 g/cc, from about 1.5 g/cc to about 1.6 g/cc, and overlapping ranges thereof. In some embodiments, densities of therapeutic agent that are greater than 1.6 g/cc are used.

As described herein, some embodiments of the devices disclosed herein are rechargeable, and as such, the size of micro-tablets is advantageous. In some embodiments, the loading and/or recharging of a device is accomplished with a syringe/needle, through which the therapeutic agent is delivered. In some embodiments, micro-tablets are delivered through a needle of about 23 gauge to about 32 gauge, including 23-25 gauge, 25 to 27 gauge, 27-29 gauge, 29-30 gauge, 30-32 gauge, and overlapping ranges thereof. In some embodiments, the needle is 23, 25, 27, 30, or 32 gauge. In some embodiments, the micro-tablets may be introduced into the eye directly, such as into the vitreous cavity, using a syringe or cannula.

In one embodiment, micro-tablets with the above properties, or any combination thereof, are made using known techniques in the art including tableting, lyophilization, granulation (wet or dry), flaking, direct compression, molding, extrusion, and the like. Moreover, as discussed below, alterations in the above-discussed characteristics can be used to tailor the release profile of the micro-tableted therapeutic agent from an implant.

In several embodiments, lyophilization of a therapeutic agent is used prior to the micro-pelleting process. In some embodiments, lyophilization improves the stability of the therapeutic agent once incorporated into a micro-tablet. In some embodiments, lyophilization allows for a greater concentration of therapeutic to be obtained prior to micro-pelleting, thereby enhancing the ability to achieve the high percentages of active therapeutic agents that are desirable in some embodiments. For example, many commercially available therapeutic agents useful to treat ocular diseases are developed as first-line agents for other diseases. As such, their original formulation may not be suitable or ideal for micro-pelleting or for administration to an ocular target via an ocular implant such as those disclosed herein. For example, several anti-VEGF compounds are supplied as sterile liquid in single use vials meant to be administered intravenously (e.g., bevacizumab). As a result, such a liquid formulation is less preferred for formation of micro-pellets as compared to a solid, though a liquid therapeutic agent may optionally be used in some embodiments. To achieve micro-pelleting at high percentages of therapeutic agent, such liquid formulations may be frozen (e.g., stored at temperatures between −20 and −80 C for 16 to 24 hours or longer) and then subject to lyophilization until dry. Alternatively, air spraying, crystallization, or other means may optionally be used to dry the therapeutic agent.

Once dry, the lyophilized (or otherwise dried) therapeutic agent is optionally tested for purity. In some embodiments, solvents may be added to a liquid (or solid) formulation in order to dissolve and remove (via evaporation) non-therapeutic components (e.g., excipients or inert binding agents). In some embodiments, a therapeutic agent is purified by conventional methods (e.g., antibody-based chromatography, HPLC, etc.) prior to lyophilization. In such embodiments, lyophilization often functions to increase the concentration of the therapeutic agent in the recovered purified sample.

In some embodiments, the dried therapeutic agent (which, for efficiency purposes is optionally dried in bulk) is ground, sieved, macerated, freeze-fractured, or subdivided into known quantities by other means, and then micro-pelleted.

After lyophilization and or subdivision, the therapeutic agent is fed into a micro-pelleting process. In some embodiments, standard techniques (e.g., compression, extrusion, molding, or other means) are used. However, in several embodiments employing high percentages of active therapeutic agent, more specialized techniques are used.

In several embodiments, the therapeutic agent is a protein, and in such embodiments, drying and/or tabletization should be completed under conditions (e.g., temperature, acid/base, etc.) that do not adversely affect the biological activity of the therapeutic agent. To assist in maintenance of biological activity of micro-pelleted therapeutic agents, in some embodiments, protein therapeutics are formulated with a stabilizing agent (e.g., mannitol, trehalose, starch, or other poly-hydroxy polymer) to maintain the structure (and therefore activity) of the therapeutic protein.

Figure 19A:
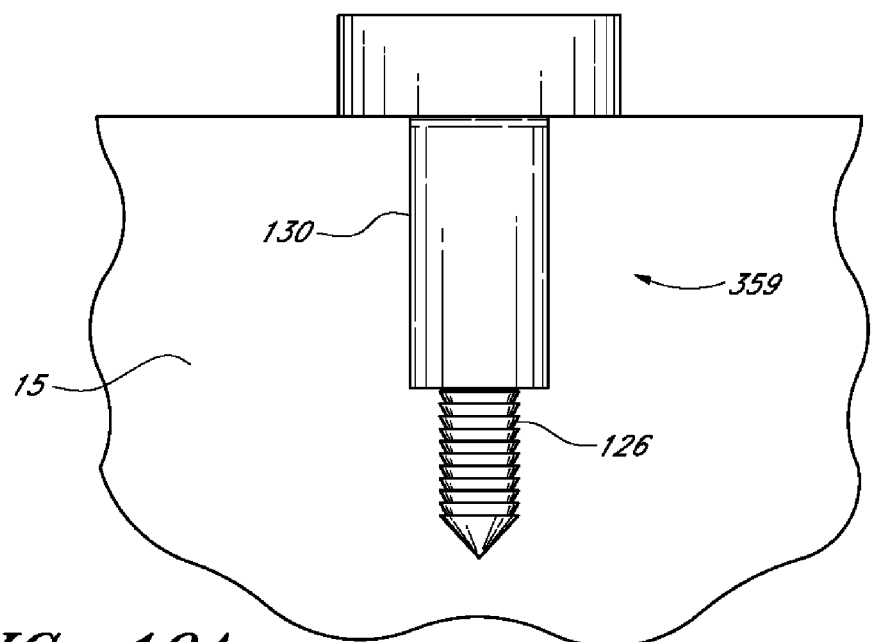
FIGS. 19A-19Y illustrate various anchor elements used in several embodiments disclosed herein.
Figure 19B:
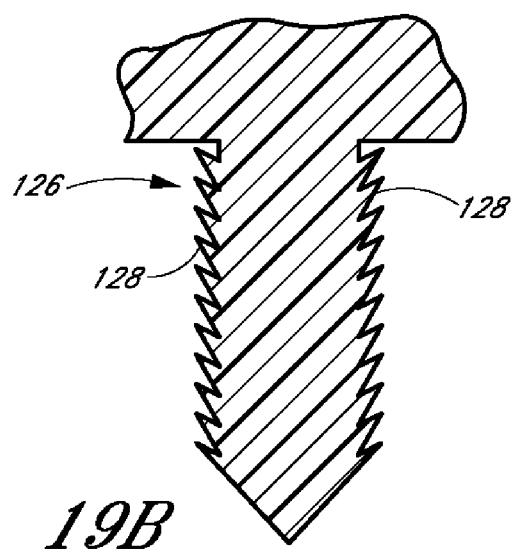
Figure 19C:
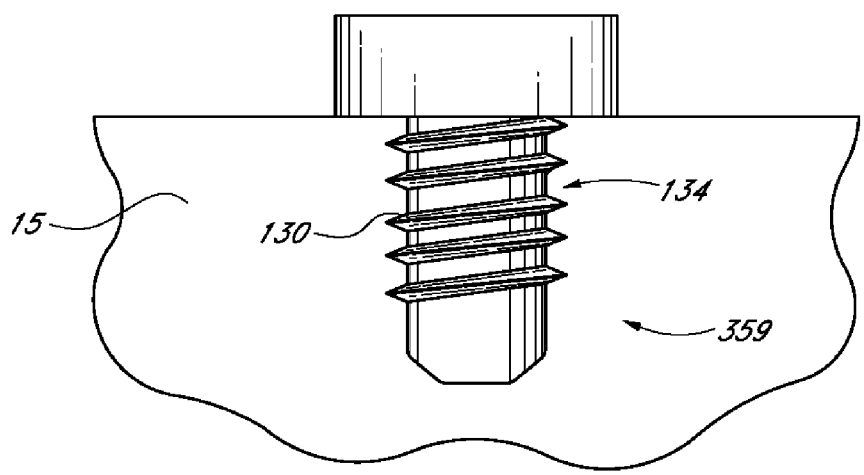
Figure 19D:
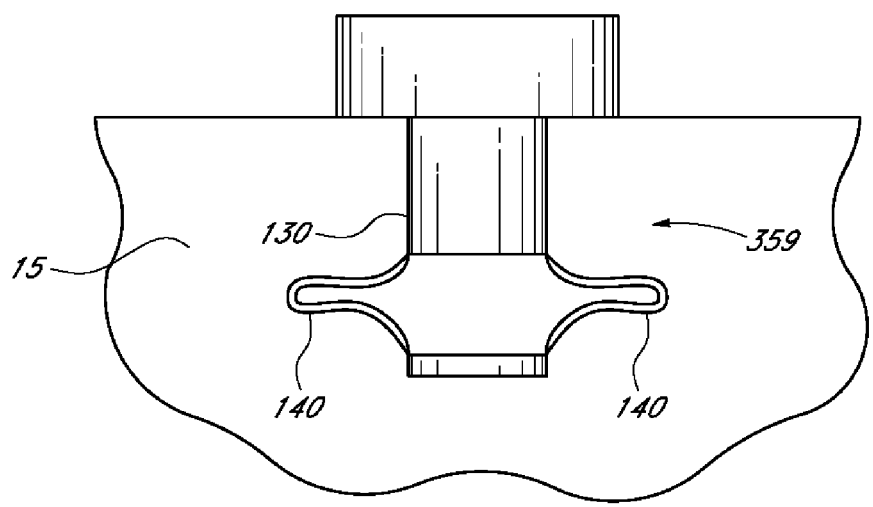
Figure 19E:
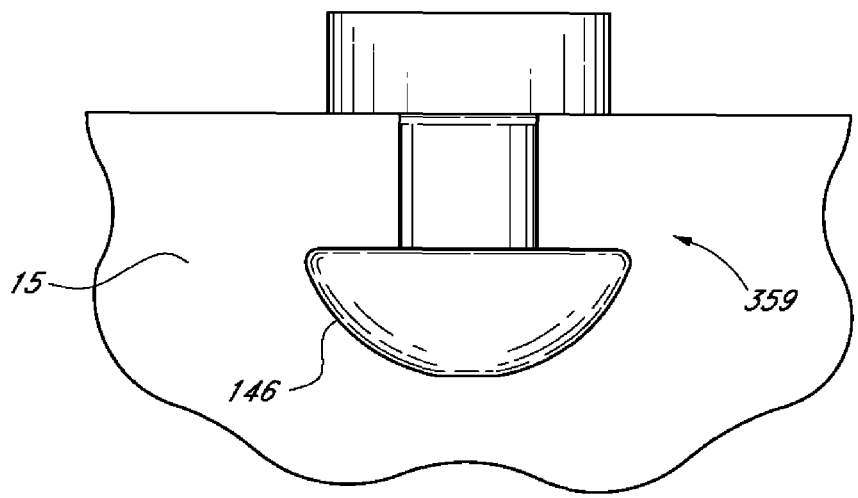
Figure 19F:
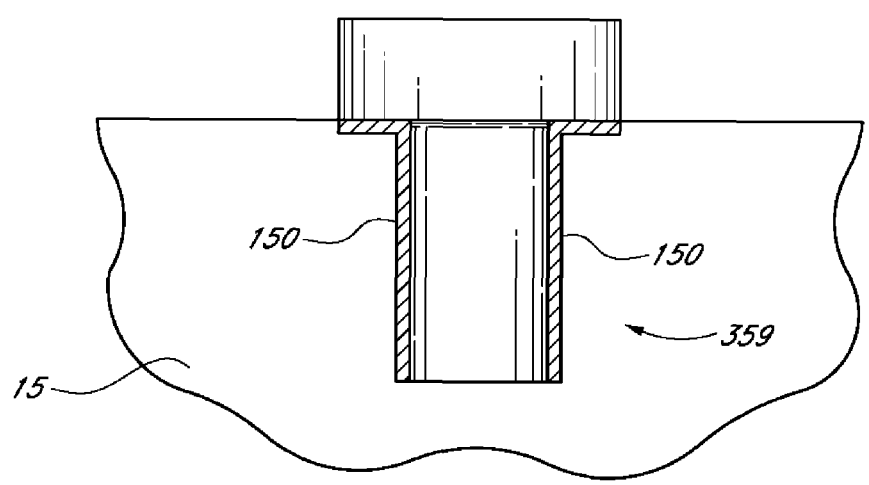
Figure 19G:
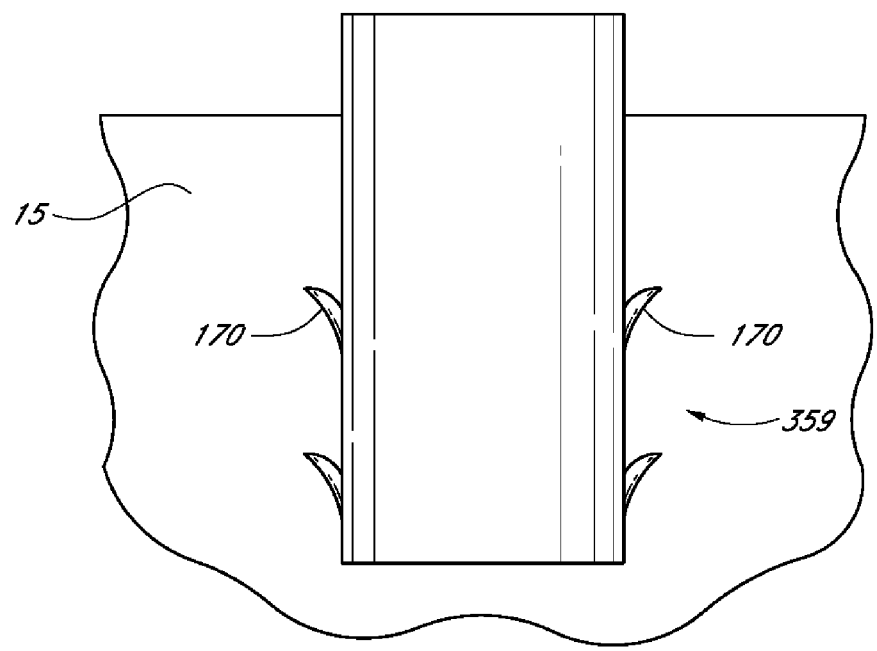
Figure 19H:
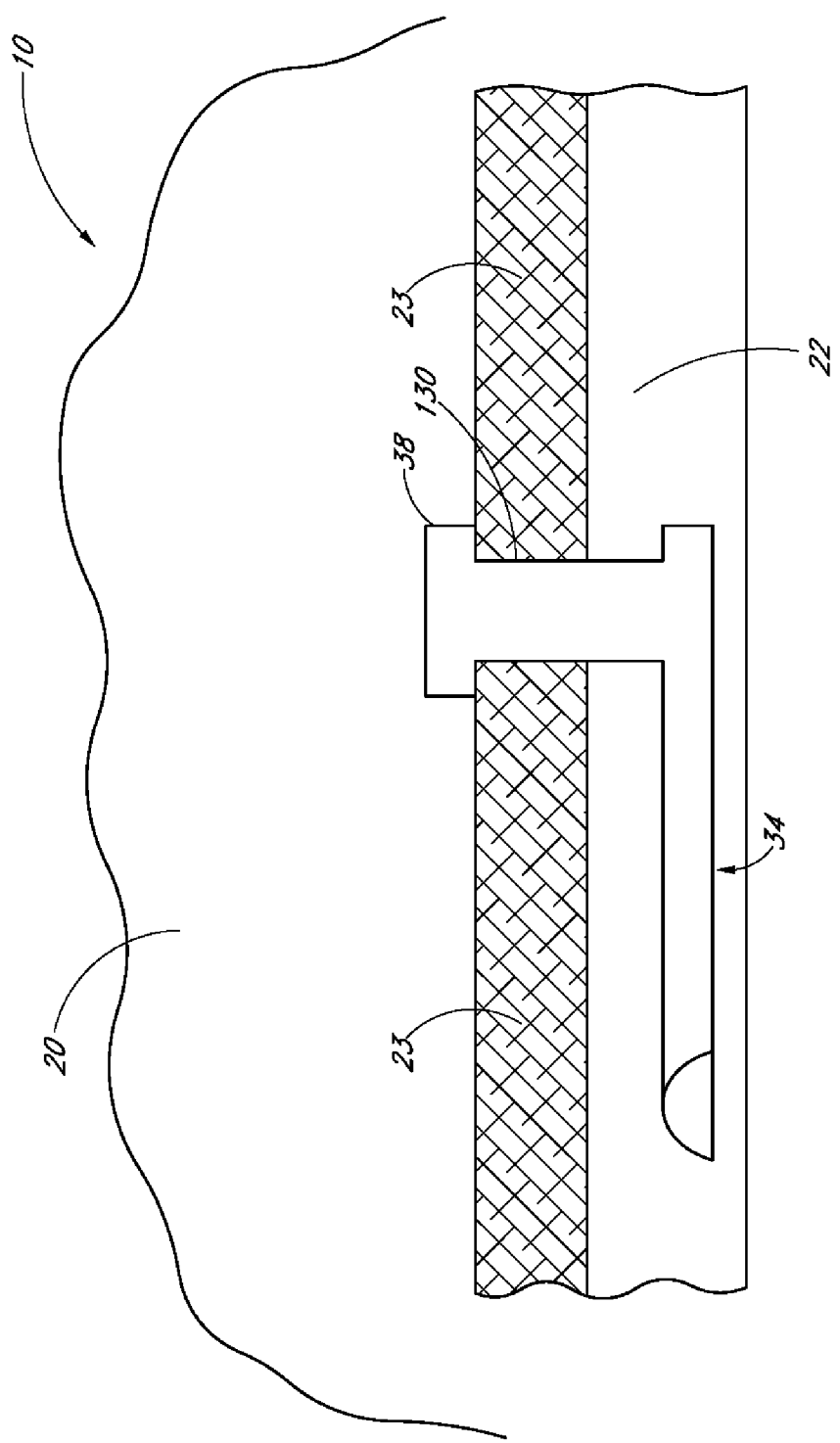
Figure 19I:
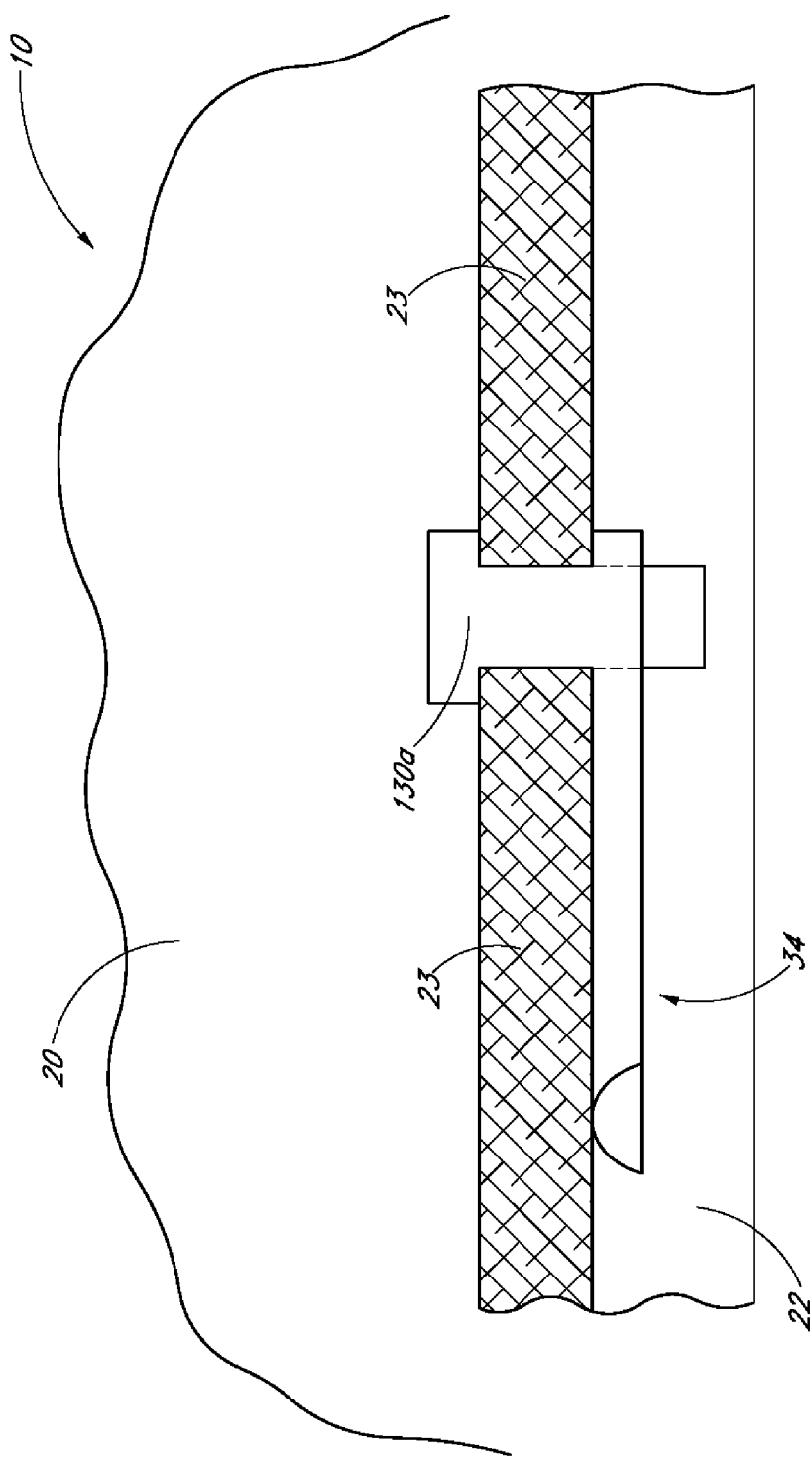
Figure 19J:
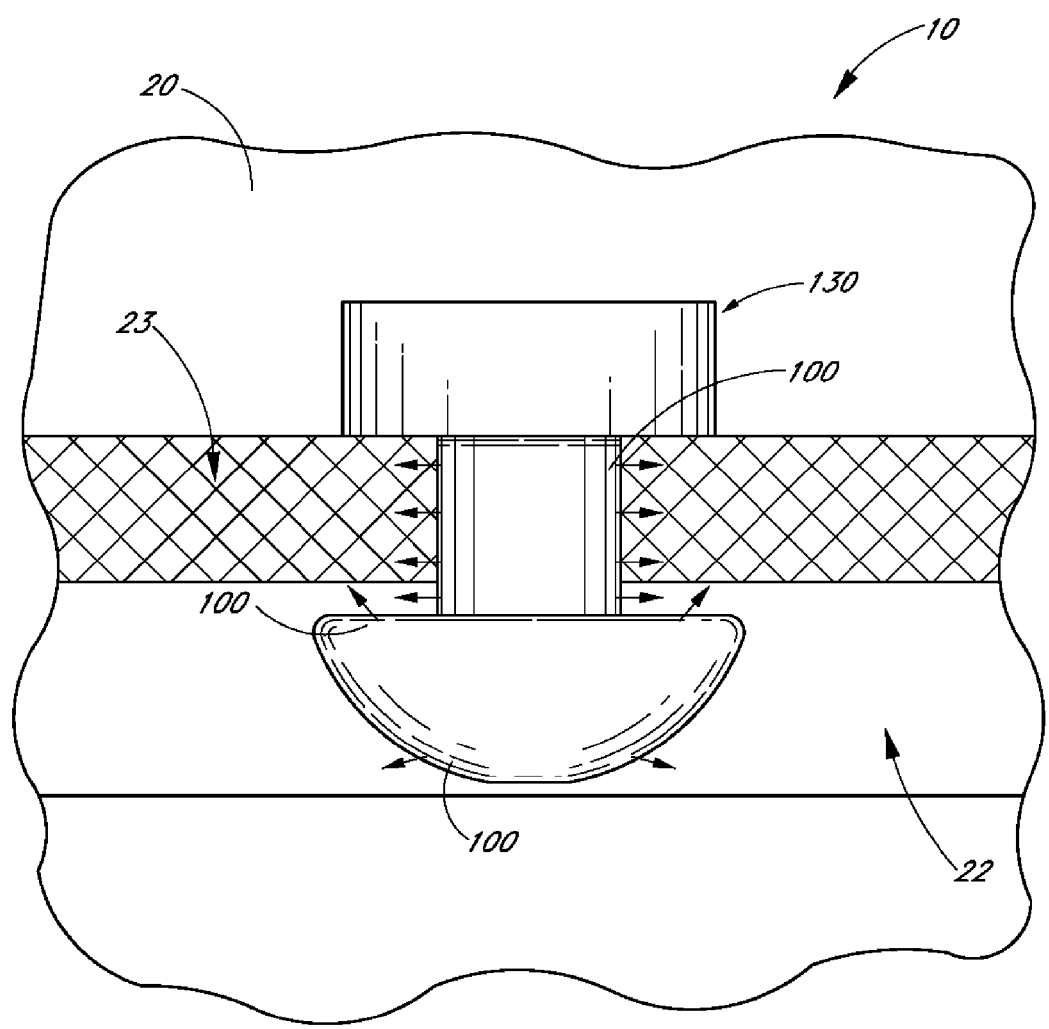
Figure 19K:
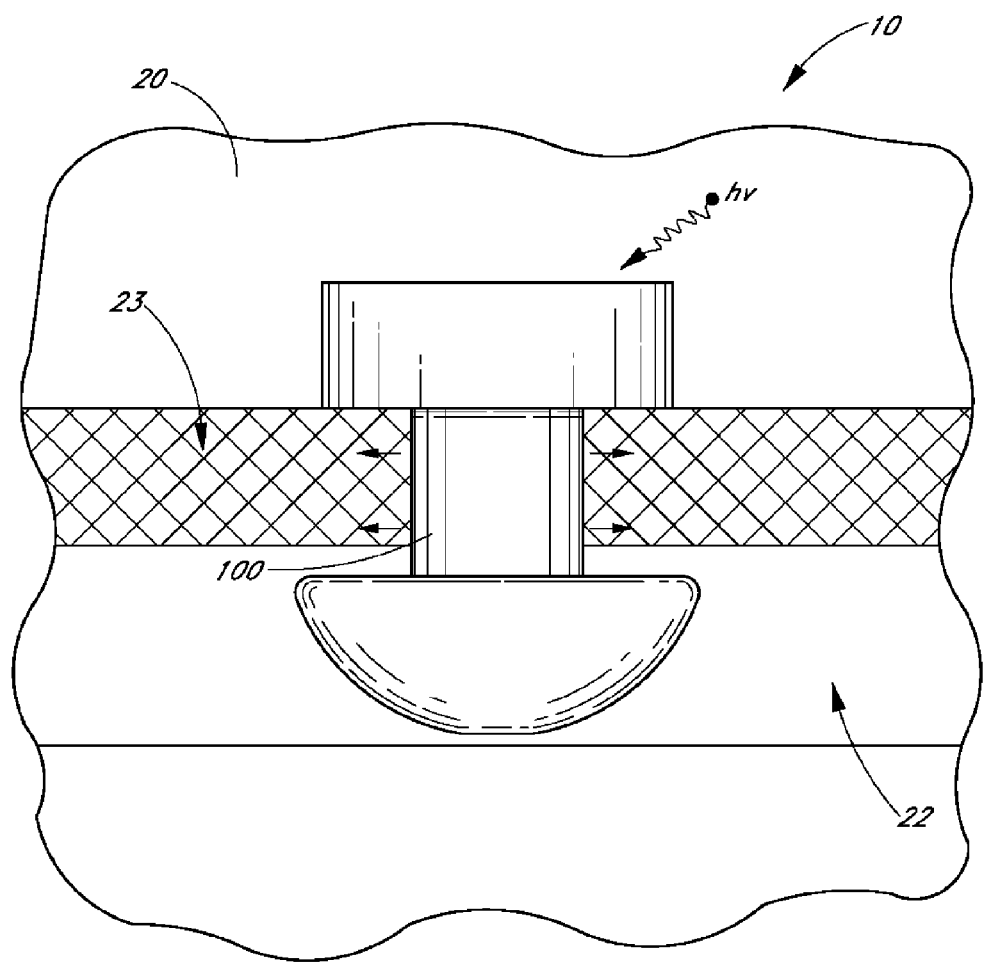
Figure 19S:
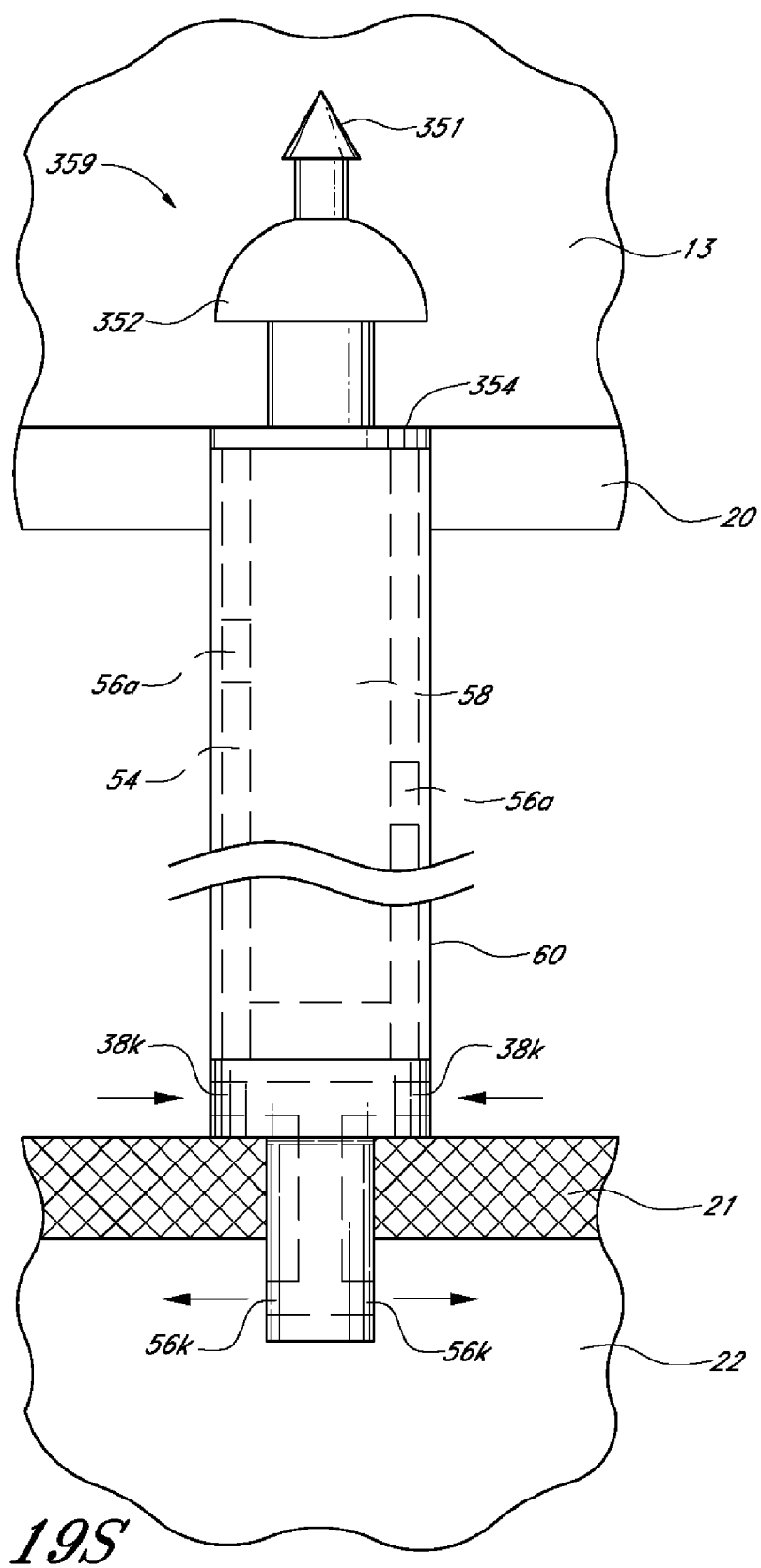
Figure 19T:
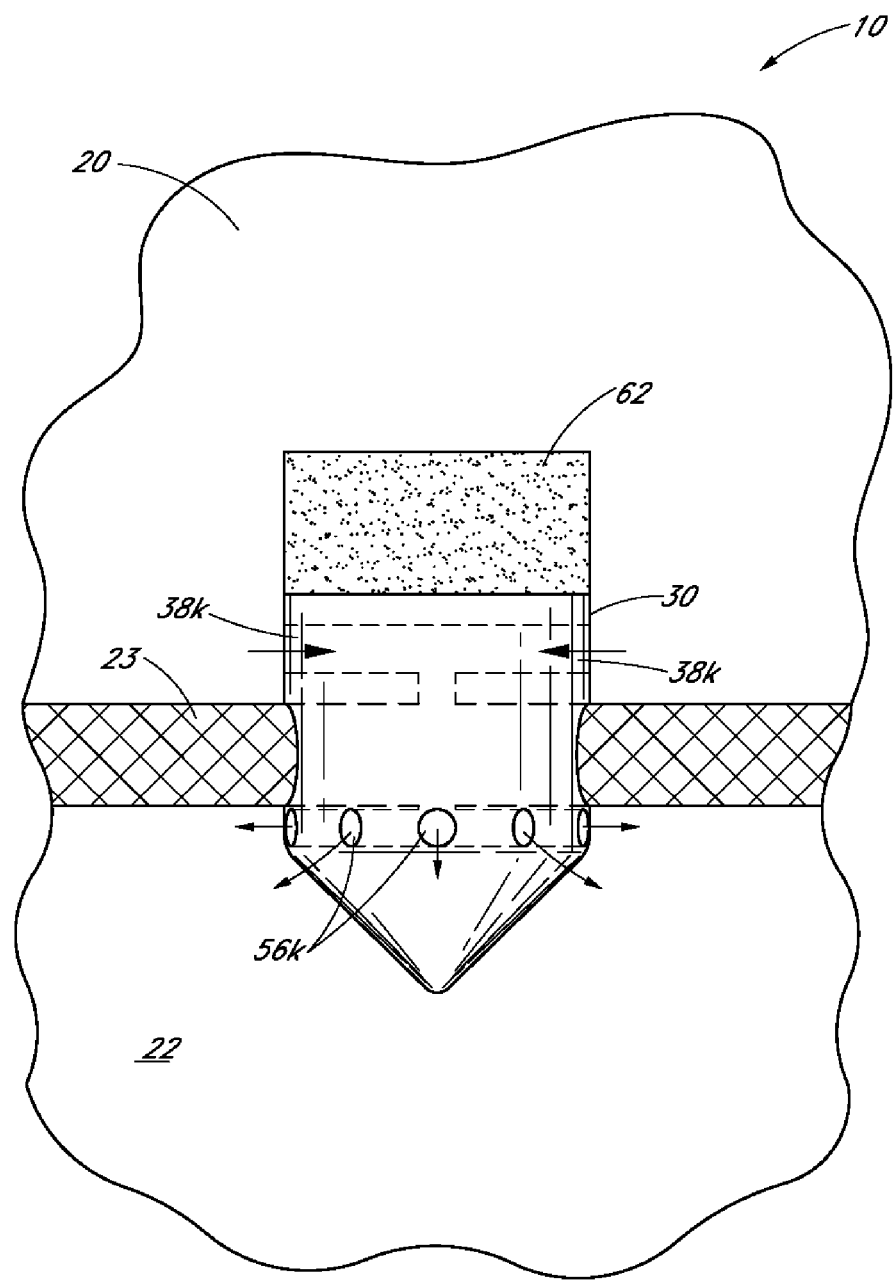
Figure 19U:
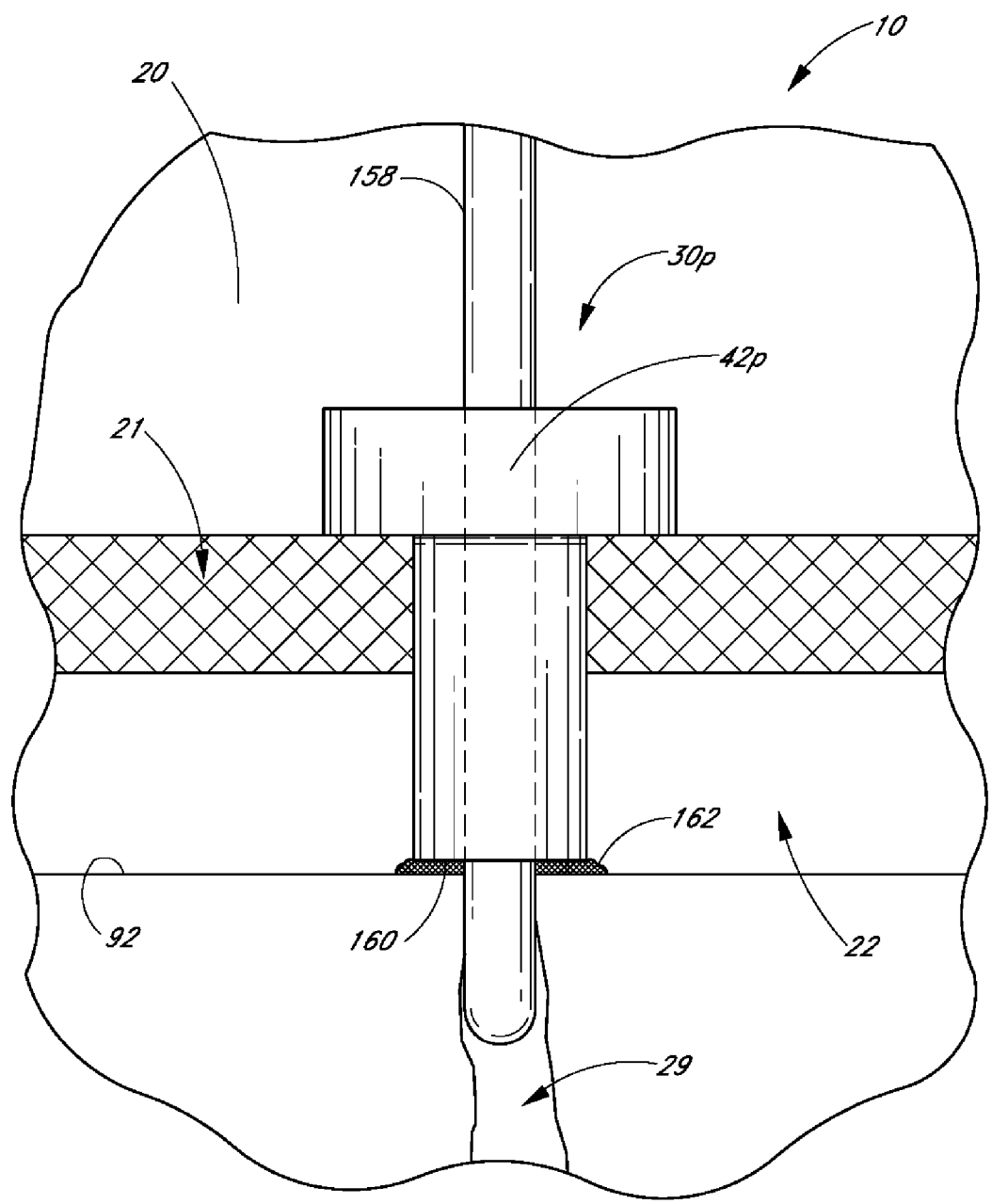
Figure 19V:
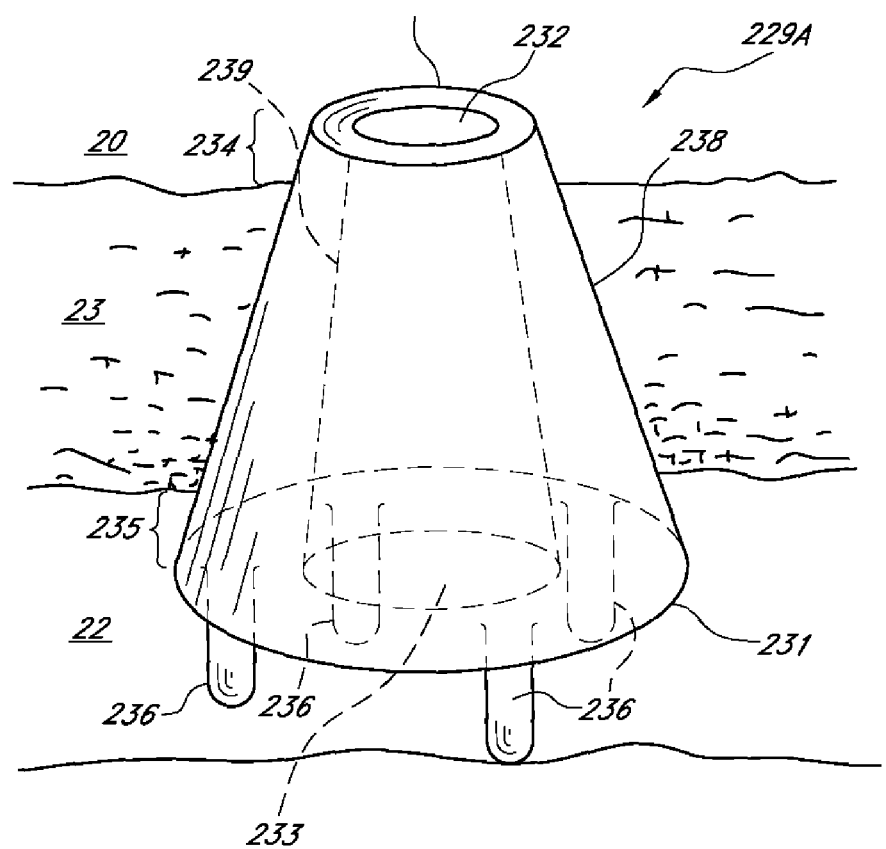
Figure 19W:
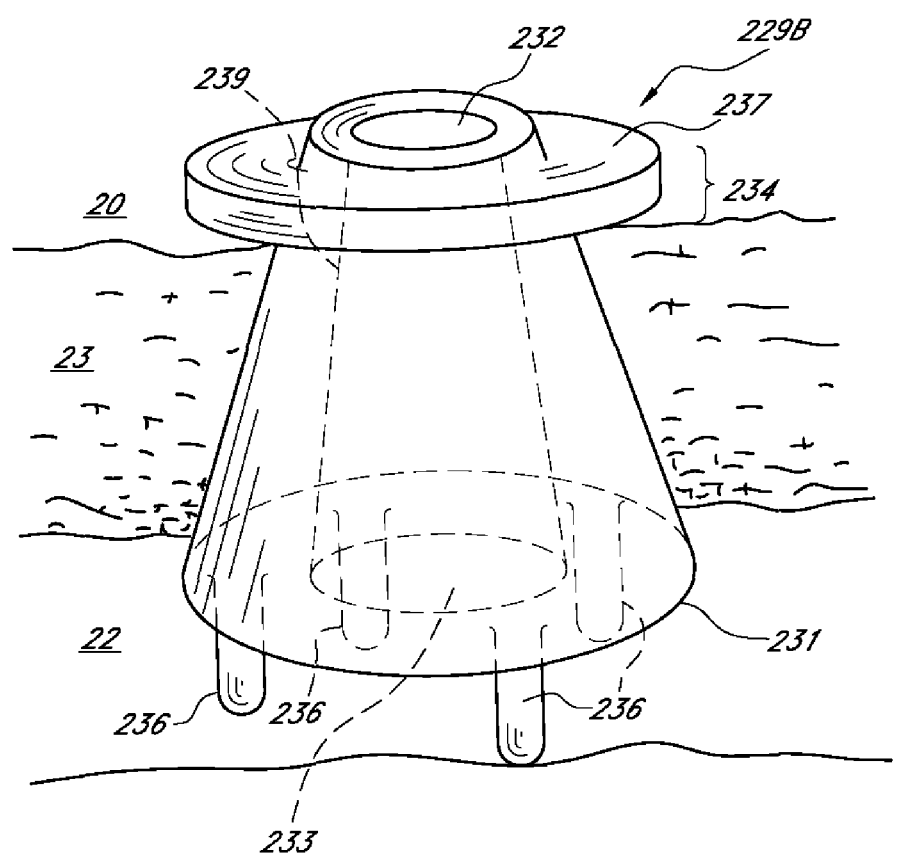

FIGS. 19A-19W illustrate embodiments of drug various embodiments of retention protrusions. As used herein, retention protrusion is to be given its ordinary meaning and may also refer to any mechanism or anchor element that allows an implant to become affixed, anchored, or otherwise attached, either permanently or transiently, to a suitable target intraocular tissue (represented generally as 15 in FIGS. 19A-19G). For example, a portion of an implant that comprises a biocompatible adhesive may be considered a retention protrusion, as may barbs, barbs with holes, screw-like elements, knurled elements, and the like. In some embodiments, implants are sutured to a target tissue. For example, in some embodiments, implants are sutured to the iris, preferably the inferior portion. It should be understood that any retention means may be used with any illustrated (and/or described) implant (even if not explicitly illustrated or described as such). In some embodiments, implants as described herein are wedged or trapped (permanently or transiently) based on their shape and/or size in a particular desirable ocular space. For example, in some embodiments, an implant (e.g., a suprachoroidal stent) is wedged within an ocular space (e.g., the suprachoroidal space) based on the outer dimensions of the implant providing a sufficient amount of friction against the ocular tissue to hold the implant in place.

Intraocular targets for anchoring of implants include, but are not limited to the fibrous tissues of the eye. In some embodiments, implants are anchored to the ciliary muscles and/or tendons (or the fibrous band). In some embodiments, implants are anchored into Schlemm's canal, the trabecular meshwork, the episcleral veins, the iris, the iris root, the lens cortex, the lens epithelium, the lens capsule, the sclera, the scleral spur, the choroid, the suprachoroidal space, the anterior chamber wall, or disposed within the anterior chamber angle. As used herein, the term "suprachoroidal space" shall be given its ordinary meaning and it will be appreciated that other potential ocular spaces exist in various regions of the eye that may be encompassed by the term "suprachoroidal space." For example, the suprachoroidal space located in the anterior region of the eye is also known as the supraciliary space, and thus, in certain contexts herein, use of "suprachoroidal space" shall be meant to encompass the supraciliary space.

The retention protrusions may be formulated of the same biocompatible material as the outer shell. In some embodiments the biodegradable retention protrusions are used. In alternate embodiments, one or more of the retention protrusions may be formed of a different material than the outer shell. Different types of retention protrusions may also be included in a single device.

In some embodiments, see for example FIG. 19A, the retention protrusion 359 may comprise a ridged pin 126 comprising a ridge 128 or series of ridges formed on the surface of a base portion 130. Such ridges may be formed in any direction on the surface of the implant including, but not limited to, biased from the long axis of the implant, spiraling around the implant, or encircling the implant (see, e.g. FIG. 19B). Likewise, the ridges may be distinct or contiguous with one another. Other anchoring elements may also be used, such as raised bumps; cylinders; deep threads 134, as shown in FIG. 19C; ribs 140, as shown in FIG. 19D; a rivet shaped base portion 146, as shown in FIG. 19E; biocompatible adhesive 150 encircling the retention element 359 where it passes through an ocular tissue, as shown in FIG. 19F; or barbs 170, as shown in FIG. 19G. In some embodiments, the retention protrusion is positioned within a preexisting intraocular cavity or space, shown generally as 20. For example, as depicted in FIG. 19H, an elongated blade 34 resides within Schlemm's canal 22 and is attached to a base portion 130 that traverses the trabecular meshwork 21. In other embodiments, as depicted in FIG. 19I, based on the dimensions of intraocular spaces, which are well-known in the art, a shorter base 130a is used and attached to the elongated blade 34 residing within Schlemm's canal 22.

In certain embodiments, an expandable material 100 is used in conjunction with or in place of a physical retention protrusion. For example, in FIG. 19J, the base 130 is covered, in particular areas, with an expandable material 100. Upon contact with an appropriate solvent, which includes ocular fluid, the material expands (as depicted by the arrows), thus exerting pressure on the surrounding tissue, for example the trabecular meshwork 21 and base of Schlemm's canal 22 in FIG. 19J.

In some embodiments, an external stimulus is used to induce the expansion of the expandable material 100. As depicted in FIG. 19K, the base 130 is covered, in particular areas, with an expandable material 100. Upon stimulation by an external stimuli hv, the material expands (as depicted by the arrows), thus exerting pressure on the surrounding tissue, for example the trabecular meshwork 21 and base of Schlemm's canal 22 in FIG. 19K. Suitable external stimuli include, but are not limited to, light energy, electromagnetic energy, heat, ultrasound, radio frequency, or laser energy.

In several other embodiments, the expandable material 100, is coated or layered on the outer shell 54, which expands in response to contact with a solvent. See FIGS. 19L-19Q. In some embodiments, once the implant is fully positioned within the desired intraocular space, contact with bodily fluid causes the expandable material to swell, solidify or gel, or otherwise expand. (Compare dimension D to $D_1$ in FIGS. 19L-19Q). As a result, the expanded material exerts pressure on the surrounding ocular tissue, which secures in the implant in position.

In some embodiments, the expanding material fills any voids between the implant shell and the surrounding intraocular tissue. In some such embodiments, the expanded material seals one portion of the implant off fills or otherwise seals the volume around the implant outer shell such that fluid is prevented from flowing around the implant, and must flow through the implant.

In other embodiments, such as those schematically depicted in FIGS. 19P and 19Q, the expandable material 100 is positioned on selected areas of the implant shell 54, such that the expanded material exerts pressure on the surrounding ocular tissue, but also maintains the patency of a natural ocular fluid passageway by the creation of zones of fluid flow 102 around the implant shell and expandable material. In still other embodiments, the expandable material can be positioned within the lumen of the implant, such that the expansion of the material assists or causes the lumen to be maintained in a patent state.

The expandable material can be positioned on the implant by dipping, molding, coating, spraying, or other suitable process known in the art.

In some embodiments, the expandable material is a hydrogel or similar material. Hydrogel is a three-dimensional network of cross-linked, hydrophilic polymer chains. The hydrophilicity of the polymer chains causes the hydrogel to swell in the presence of sufficient quantities of fluid. In other embodiments, the expandable material is foam, collagen, or any other similar biocompatible material that swells, solidifies or gels, or otherwise expands. In some embodiments, the expandable material begins to expand immediately on contact with an appropriate solvent. In other embodiments, expansion occurs after passage of a short period of time, such that the implant can be fully positioned in the desired target site prior to expansion of the material. Preferred solvents that induce expansion include water, saline, ocular fluid, aqueous humor, or another biocompatible solvents that would not affect the structure or permeability characteristics of the outer shell.

The expansion of the expandable material is varied in several embodiments. In some embodiments, as described above, the material is positioned on the outer shell of implant such that the expanded material exerts pressure on the surrounding ocular tissue, thereby securing the implant in position. In other embodiments, the expandable material may be placed adjacent to, surrounding, or under another anchoring element (such as those described above), such that the expansion of the expandable material causes the anchoring element to move from a first, retracted state to a second, expanded state wherein the anchoring element anchors the implant against an ocular structure in the expanded state. In some embodiments, the expandable material is designed to expand only in two dimensions, while in other embodiments, the material expands in three dimensions.

Although FIGS. 19L and 19M depict the expandable material as rectangular in cross-section, it will be appreciated that the cross-sectional shape can vary and may include circular, oval, irregular, and other shapes in certain embodiments. The relative expansion (change from dimension D to $D_1$) of the material is also controlled in several embodiments. In certain embodiments the D to $D_1$ change is greater than in other embodiments, while in some embodiments, a smaller D to $D_1$ change is realized upon expansion of the material.

FIGS. 19P and 19Q show side views of an implant having expandable anchoring elements 100 comprising projections extending radially outward from the body of the implant. In some such embodiments, the anchoring elements are individually connected to the implant body, while in other embodiments, they are interconnected by a sheath region that mounts over the implant body.

In selected embodiments, the implant and/or the retention protrusion additionally includes a shunt feature. The term "shunt" as used herein is a broad term, and is to be given its ordinary and customary meaning to a person of ordinary skill in the art (and it is not to be limited to a special or customized meaning), and refers without limitation to the portion of the implant defining one or more fluid passages for transport of fluid from a first, often undesired location, to one or more other locations. The term "stent" may also be used to refer to a shunt. In some embodiments, the shunt can be configured to provide a fluid flow path for draining aqueous humor from the anterior chamber of an eye to an outflow pathway to reduce intraocular pressure, for example, as in FIGS. 19R-19T. In still other embodiments, the shunt feature of the implant may be positioned in any physiological location that necessitates simultaneous drug delivery and transport of fluid from a first physiologic site to a second site (which may be physiologic or external to a patient).

The shunt portion of the implant can have an inflow portion 38$k$ and one or more outflow portions 56$k$. In some embodiments, the inflow and outflow portions are positioned at various locations on the implant depending on the physiological space in which they are to be located. As shown in FIG. 19R, the outflow portion may be disposed at or near the proximal end 52 of the implant. When the implant is deployed, the inflow portion may be sized and configured to reside in the anterior chamber of the eye and the outflow portion may be sized and configured to reside within the trabecular meshwork 23 or Schlemm's canal 22. In other embodiments, the outflow portion may be sized and configured to reside in the supraciliary region of the uveoscleral outflow pathway, the suprachoroidal space, other part of the eye, or within other physiological spaces amenable to fluid deposition.

At least one lumen can extend through the shunt portion of the implant. In some embodiments, there is at least one lumen that operates to conduct the fluid through the shunt portion of the implant. In certain embodiments, each lumen extends from an inflow end to an outflow end along a lumen axis. In some embodiments the lumen extends substantially through the longitudinal center of the shunt. In other embodiments, the lumen can be offset from the longitudinal center of the shunt.

As discussed above, in some embodiments, a compressed pellet of drug not coated by an outer shell 62 is attached or otherwise coupled to an implant comprising a shunt and a retention feature. As depicted in FIG. 19T, the shunt portion of the implant comprises one or more inflow portions 38$k$ and one or more outflow portions 56$k$. In some embodiments, the inflow portions are positioned in a physiological space that is distinct from the outflow portions. In some embodiments, such a positioning allows for fluid transport from a first location to a second location. For example, in some embodiments, when deployed intraocularly, the inflow portions are located in the anterior chamber and the outflow portions are located in Schlemm's canal 22. In this manner, ocular fluid that accumulates in the anterior chamber is drained from the anterior chamber into Schlemm's canal, thereby reducing fluid pressure in the anterior chamber. In other embodiments, the outflow portion may be sized and configured to reside in the supraciliary region of the uveoscleral outflow pathway, the suprachoroidal space, other part of the eye, or within other physiological spaces amenable to fluid deposition.

Additional embodiments comprising a shunt may be used to drain ocular fluid from a first location to different location. As depicted in FIG. 19U, a shunt 30p directs aqueous from the anterior chamber 20 directly into a collector channel 29 which empties into aqueous veins. The shunt 30p has a distal end 160 that rests against the back wall of Schlemm's canal. A removable alignment pin 158 is utilized to align the shunt lumen 42p with the collector channel 29. In use, the pin 158 extends through the implant lumen and the shunt lumen 42p and protrudes through the base 160 and extends into the collector channel 29 to center and/or align the shunt 30p over the collector channel 29. The shunt 30p is then pressed firmly against the back wall 92 of Schlemm's canal 22. A permanent bio-glue 162 is used between the shunt base and the back wall 92 of Schlemm's canal 22 to seat and securely hold the shunt 30p in place. Once positioned, the pin 158 is withdrawn from the shunt and implant lumens 42p to allow the aqueous to flow from the anterior chamber 20 through the implant, through the shunt, and into the collector duct 29. The collector ducts are nominally 20 to 100 micrometers in diameter and are visualized with a suitable microscopy method (such as ultrasound biomicroscopy (UBM)) or laser imaging to provide guidance for placement of the shunt 30p. In another embodiment, the pin 158 is biodegradable in ocular fluid, such that it need not be manually removed from the implant.

In some embodiments, the shunt 30p is inserted through a previously made incision in the trabecular meshwork 23. In other embodiments, the shunt 30p may be formed with blade configuration to provide self-trephining capability. In these cases, the incision through the trabecular meshwork 23 is made by the self-trephining shunt device which has a blade at its base or proximate to the base.

As shown in FIG. 19V, a shunt extending between an anterior chamber 20 of an eye, through the trabecular meshwork 23, and into Schlemm's canal 22 of an eye can be configured to be axisymmetric with respect to the flow of aqueous therethrough. For example, as shown in FIG. 19V, the shunt 229A comprises an inlet end 230 configured to be disposed in the anterior chamber 20 and associated with a drug delivery implant in accordance with embodiments disclosed herein. For clarity of the shunt feature, the implant is not shown. The second end 231 of the shunt 229A is configured to be disposed in Schlemm's canal 22. At least one lumen 239 extends through the shunt 229A between the inlet and outlet ends 230, 232. The lumen 239 defines an opening 232 at the inlet end 230 as well as an outlet 233 at the outlet end 231.

In the illustrated embodiment, an exterior surface 238 of the shunt 229A is cone-shaped. Thus, a circumference of the exterior surface 238 adjacent to the inlet end 230 is smaller than the circumference of the outer surface 238 at the outlet end 231.

With the shunt 229A extending through the trabecular meshwork 23, the tissue of the trabecular meshwork 23 provides additional anchoring force for retaining the shunt 229A with its inlet end 230 in the anterior chamber and its outlet end 231 in Schlemm's canal. For example, the trabecular meshwork 23 would naturally tend to close an aperture occupied by the shunt 229A. As such, the trabecular meshwork 23 would tend to squeeze the shunt 229A. Because the exterior surface 238 is conical, the squeezing force applied by the trabecular meshwork 23 would tend to draw the shunt 229A towards Schlemm's canal 22. In the illustrated embodiment, the shunt 229A is sized such that a portion 234 of the shunt 229 adjacent to the inlet end 230 remains in the anterior chamber 20 while a portion 235 of the shunt 229 adjacent to the outlet end 231 remains in Schlemm's canal 22.

In the illustrated embodiment, the outer surface 238 of the shunt 229A is smooth. Alternatively, the outer surface 238 can have other contours such as, for example, but without limitation curved or stepped. In one embodiment, the outer surface 238 can be curved in a concave manner so as to produce a trumpet-like shape. Alternatively, the outer surface 238 can be convex.

In certain embodiments, the shunt 229A preferably includes one or plurality of posts or legs 236 configured to maintain a space between the outlet opening 233 and a wall of Schlemm's canal 22. As such, the legs 236 prevent a wall of Schlemm's canal from completely closing off the outlet opening 233 of the shunt 229A. In the illustrated embodiment, the legs 236 are coupled to the distal-most surface of the shunt 229A and are substantially parallel to an implant axis extending through the shunt 229A and between the anterior chamber 20 and Schlemm's canal 22.

This arrangement of the legs 236 and the outlet 233 imparts an axisymmetric flow characteristic to the shunt 229A. For example, aqueous can flow from the outlet 233 in any direction. Thus, the shunt 229A can be implanted into Schlemm's canal at any angular position relative to its implant axis. Thus, it is not necessary to determine the angular orientation of the shunt 229A prior to implantation, nor is it necessary to preserve a particular orientation during an implantation procedure.

FIG. 19W illustrates a modification of the shunt 229A, identified generally by the reference numeral 229B. In this embodiment, the shunt 229B includes a flange 237 extending radially from the portion 234. Preferably, the flange 237 is configured to retain the first portion 234 within the anterior chamber 20. It is to be recognized that although generally, aqueous will flow from the anterior chamber 20 towards Schlemm's canal 22, the shunt 229A, 229B or any of the above-described shunts as well as other shunts described below, can provide for omni-directional flow of aqueous.

Figure 19X:
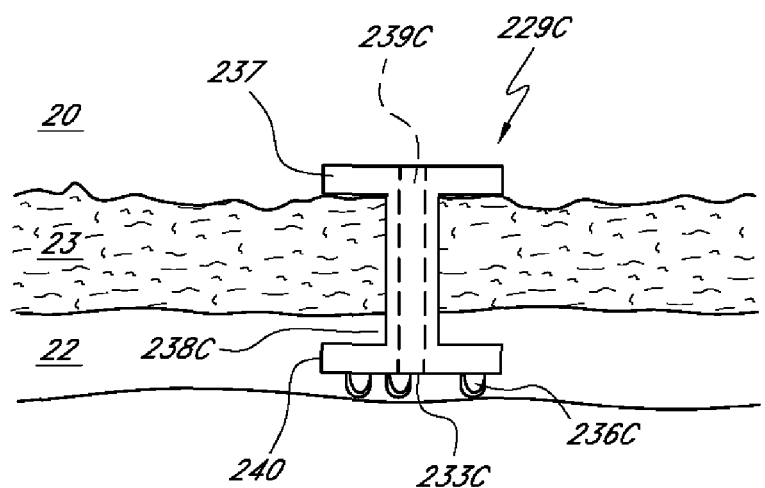

FIG. 19X illustrates another modification of the shunt 229A, identified generally by the reference numeral 229C. In this embodiment, the outer surface 238C is not conical. Rather, the outer surface 238C is cylindrical. The shunt 229C includes a flange 240 that can be the same size and shape as the flange 237. The legs 236C extend from the flange 240.

Constructed as such, the natural tendency of the tissue of the trabecular meshwork 21 to close the hole in which the shunt 229C is disposed, aids in anchoring the shunt 229C in place. Additionally, the legs 236C aid in preventing the walls of Schlemm's canal from completely closing the outlet 233C of the lumen 239C.

Figure 19Y:
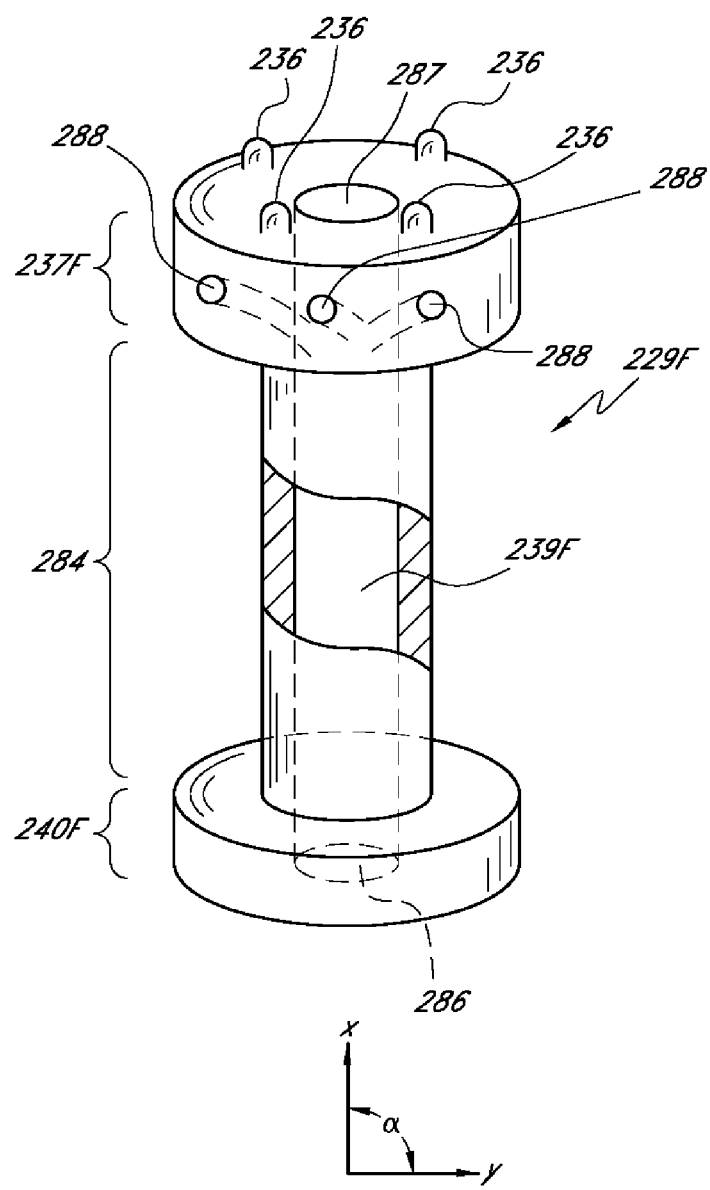

With reference to FIG. 19Y, another embodiment of an axisymmetric trabecular shunting device is illustrated therein and identified generally by the reference numeral 229F.

The shunt 229F comprises an inlet (proximal) section having a first flange 240F, an outlet (distal) section having a second flange 237F and a middle section 284 connecting the inlet section and the outlet section. A lumen 239F of the device 229F is configured to transport aqueous, liquid, or therapeutic agents between the inlet section and the outlet section.

The inlet section of the shunt 229F has at least one inlet opening 286 and the outlet section comprises at least one outlet opening 287. In some embodiments, the inlet opening 286 is directly associated with the proximal end of an implant, such that ocular fluid flowing through a lumen of the implant passes into the lumen 239F of the shunt. In other embodiments, the shunt is joined or associated with an implant in a manner where the inlet opening 286 receives ocular fluid directly from an ocular cavity, without having first passed through the implant. In still other embodiments, the shunt carries fluid from both sources (e.g., from the eye and from the implant lumen).

A further advantage of such embodiments is provided where the outlet section 237F includes at least one opening 287, 288 suitably located for discharging substantially axisymmetrically the aqueous, liquid or therapeutic agents, wherein the opening 287, 288 is in fluid communication with the lumen 285 of the device 281. In the illustrated embodiment, the openings 288 extend radially from the lumen 285 and open at the outwardly facing surface around the periphery of the outlet flange 237F.

It should be understood that all such anchoring elements and retention protrusions may also be made flexible. It should also be understood that other suitable shapes can be used and that this list is not limiting. It should further be understood the devices may be flexible, even though several of the devices as illustrated in the Figures may not appear to be flexible. In those embodiments involving a rechargeable device, the retention protrusions not only serve to anchor the implant, but provide resistance to movement to allow the implant to have greater positional stability within the eye during recharging.

For the sake of clarity, only a small number of the possible embodiments of the implant have been shown with the various retention projections. It should be understood that any implant embodiment may be readily combined with any of the retention projections disclosed herein, and vice versa.

It will further be appreciated that, while several embodiments described above are shown, in some cases as being anchored within or to particular intraocular tissues, that each embodiment may be readily adapted to be anchored or deployed into or onto any of the target intraocular tissues disclosed herein or to other ocular tissues known in the art.

Additionally, while embodiments described both above and below include discussion of retention projections, it will be appreciated that several embodiments of the implants disclosed herein need not include a specific retention projection. Such embodiments are used to deliver drug to ocular targets which do not require a specific anchor point, and implants may simply be deployed to a desired intraocular space. Such targets include the vitreous humor, the ciliary muscle, ciliary tendons, the ciliary fibrous band, Schlemm's canal, the trabecular meshwork, the episcleral veins, the anterior chamber and the anterior chamber angle, the lens cortex, lens epithelium, and lens capsule, the ciliary processes, the posterior chamber, the choroid, and the suprachoroidal space. For example, in some embodiments, an implant according to several embodiments described herein is injected (via needle or other penetrating delivery device) through the sclera at a particular anatomical site (e.g., the pars plana) into the vitreous humor. Such embodiments need not be constructed with a retention protrusion, thus it will be appreciated that in certain embodiments, the use of a retention protrusion is optional for a particular target tissue.

Some embodiments disclosed herein are dimensioned to be wholly contained within the eye of the subject, the dimensions of which can be obtained on a subject to subject basis by standard ophthalmologic techniques. Upon completion of the implantation procedure, in several embodiments, the proximal end of the device may be positioned in or near the anterior chamber of the eye. The distal end of the implant may be positioned anywhere within the suprachoroidal space. In some embodiments, the distal end of the implant is near the limbus. In other embodiments, the distal end of the implant is positioned near the macula in the posterior region of the eye. In other embodiments, the proximal end of the device may be positioned in or near other regions of the eye. In some such embodiments, the distal end of the device may also be positioned in or near other regions of the eye. As used herein, the term "near" is used at times to as synonymous with "at," while other uses contextually indicate a distance sufficiently adjacent to allow a drug to diffuse from the implant to the target tissue. In still other embodiments, implants are dimensioned to span a distance between a first non-ocular physiologic space and a second non-ocular physiologic space.

In one embodiment, the drug delivery implant is positioned in the suprachoroidal space by advancement through the ciliary attachment tissue, which lies to the posterior of the scleral spur. The ciliary attachment tissue is typically fibrous or porous, and relatively easy to pierce, cut, or separate from the scleral spur with the delivery instruments disclosed herein, or other surgical devices. In such embodiments, the implant is advanced through this tissue and lies adjacent to or abuts the sclera once the implant extends into the uveoscleral outflow pathway. The implant is advanced within the uveoscleral outflow pathway along the interior wall of the sclera until the desired implantation site within the posterior portion of the uveoscleral outflow pathway is reached.

In some embodiments the total length of the implant is between 2 and 30 mm in length. In some embodiments, the implant length is between 2 and 25 mm, between 6 and 25 mm, between 8 and 25 mm, between 10 and 30 mm, between 15 and 25 mm or between 15 and 18 mm. In some embodiments the length of the implant is about 8, 9, 10, 11, 12, 13, 14, 15, 16, 17, 18, 19, 20, 21, 22, 23, 24, or 25 mm. So that that the delivery device containing an implant can be inserted and advanced through the cornea to the iris and produce only a self-sealing puncture in the cornea, in some embodiments, the outer diameter of the implants are between about 100 and 600 microns. In some embodiments, the implant diameter is between about 150-500 microns, between about 125-550 microns, or about 175-475 microns. In some embodiments the diameter of the implant is about 100, 125, 150, 160, 170, 180, 190, 200, 225, 250, 275, 300, 325, 350, 375, 400, 425, 450, 460, 470, 475, 480, 490, or 500 microns. In some embodiments, the inner diameter of the implant is from about between 50-500 microns. In some embodiments, the inner diameter is between about 100-450 microns, 150-500 microns, or 75-475 microns. In some embodiments, the inner diameter is about 80, 90, 100, 110, 125, 150, 175, 200, 225, 250, 275, 300, 325, 350, 375, 400, 410, 420, 425, 430, 440, or 450 microns. In some embodiments, including but not limited to those in which the device is disc or wafer-shaped, the thickness is from about 25 to 250 microns, including about 50 to 200 microns, about 100 to 150 microns, about 25 to 100 microns, and about 100 to 250 microns.

In further embodiments, any or all of the interior lumens formed during the manufacture of the implants may be coated with a layer of hydrophilic material, thereby increasing the rate of contact of ocular fluid with the therapeutic agent or agents positioned within the lumen. In one embodiment, the hydrophilic material is permeable to ocular fluid and/or the drug. Conversely, any or all of the interior lumens may be coated with a layer of hydrophobic material, to coordinately reduce the contact of ocular fluid with the therapeutic agent or agents positioned within the lumen. In one embodiment, the hydrophobic material is permeable to ocular fluid and/or the drug.

Figure 20A:
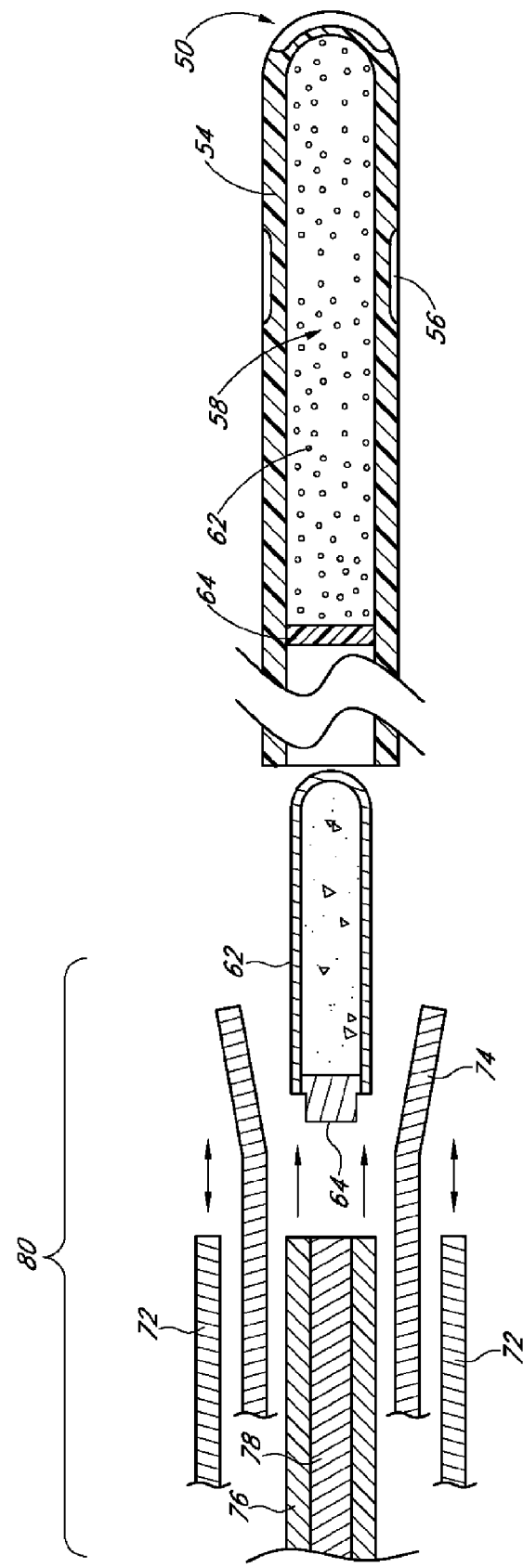
FIGS. 20A-20C illustrate a rechargeable drug delivery device in accordance with embodiments disclosed herein.
Figure 20B:
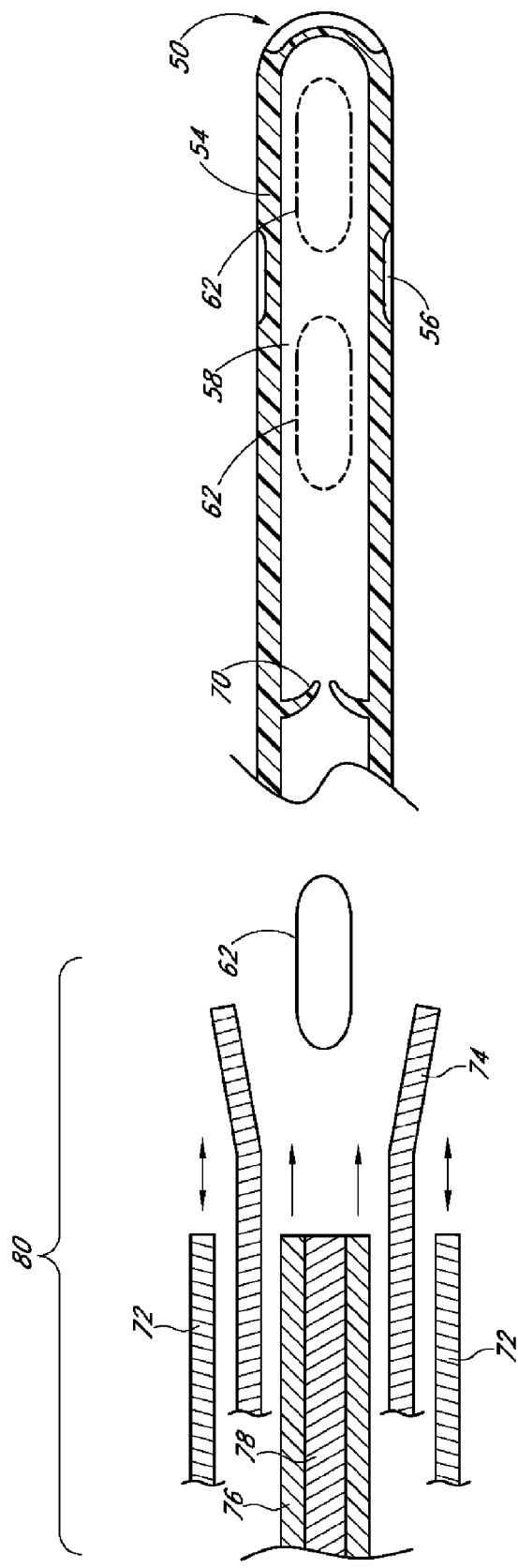

Selected embodiments of the drug delivery implants described herein allow for recharging of the implant, i.e. refilling the implant with additional (same or different) therapeutic agent. In the embodiments shown in FIGS. 20A-20C, the proximal end 52 of the implant is open and interacts with a recharging device 80. The recharging device 80 comprises a clamping sleeve 72 that houses flexible clamping grippers 74 that interacts with the proximal end 52 of the implant. A flexible pusher tube 76 that may be spring loaded contains a small internal recess 78 that holds the new therapeutic agent 62 for delivery to the implant lumen 58. In FIG. 20A, a new dose of agent, coated in a shell and capped with proximal barrier is inserted into the lumen of the implant. FIGS. 20B and 20C depict recharging the implant with multiple drug pellets. In such embodiments, a one-way passage 70 allows the insertion of a recharging device carrying a drug pellet into the lumen of the implant, but upon removal of the recharging device, the passage closes to prevent the drug from escaping the lumen. In addition to providing the ability to renew dose of drug in the implant, recharging an implant with multiple pellets may provide one or more other benefits. In some embodiments, the pellets are sized to allow an increased surface area of drug that is exposed to ocular fluids (as compared to an implant packed with a solid drug core). As the exposure to ocular fluid is one variable in the overall elution rate of a drug, in such embodiments, the size of the pellets may be adjusted as needed to provide a particular desired release rate. Moreover, in certain embodiments, the size of the multiple pellets is adjusted to provide a greater rate or capacity for fluid to flow through the lumen of the implant, even when a full drug load is present. Furthermore, one or more of the multiple pellets, in certain embodiments, is coated in order to regulate the dissolution or elution of the drug. It shall be appreciated that, as discussed for coatings in relation to the implant itself, the pellets may be coated with coatings of various thickness, compositions, with or without apertures, etc., in order to control the rate of drug release from the pellet itself. In some embodiments, coated pellets are used in a non-coated device, while in other embodiments, combinations of coated and uncoated pellets are used with coated devices. For example, if an ocular condition is known to require drug therapy in addition to removal/diversion of ocular fluid, the pellets can be sized to deliver a sufficient quantity of drug to provide a therapeutic effect and simultaneously allow ocular fluid to flow through the lumen of the implant from a first location to a second location. Additionally, the presence of multiple pellets, or a plurality of particles, as opposed to a single solid core of drug, allows, in certain embodiments, the implant to be flexible. In such embodiments, the shape of the pellets may be designed to provide space around the periphery of the pellets such that the implant is able to articulate as needed to fit within or adjacent to a desired physiological space without inhibition of this articulation from pellet to pellet contact. It shall be appreciated that in such embodiments, the pellets may contact one another to some degree, still allowing for a high degree of efficiency in packing the implant with drug. It shall also be appreciated that in certain embodiments where flexibility of the implant is unnecessary or undesirable, the pellets may be shaped to contact one another more fully, thereby supplementing the rigidity of an implant.

As schematically shown in FIGS. 20D and 20E, elongate implants can comprise a plurality of the features disclosed herein. For example, FIG. 20D depicts an elongate implant with a proximal 52 and distal end 50, containing a plurality of pellets of therapeutic agent 62. As discussed in more detail herein, the therapeutic agent, depending on the embodiment, may be in a variety of forms, such as pellets, micropellets, vesicles, micelles, or other membrane-like bound structures, oils, emulsions, gels, slurries, etc. The implant comprises a region of drug release 56. Moreover, the embodiments depicted in FIGS. 20D and 20E comprise fluid inflow 38$k$ and outflow 56$k$ pathways, thus allowing the combination of delivery of a therapeutic agent as well as directing fluid to an ocular fluid outflow pathway (e.g., Schlemm's canal).

Figure 20F:
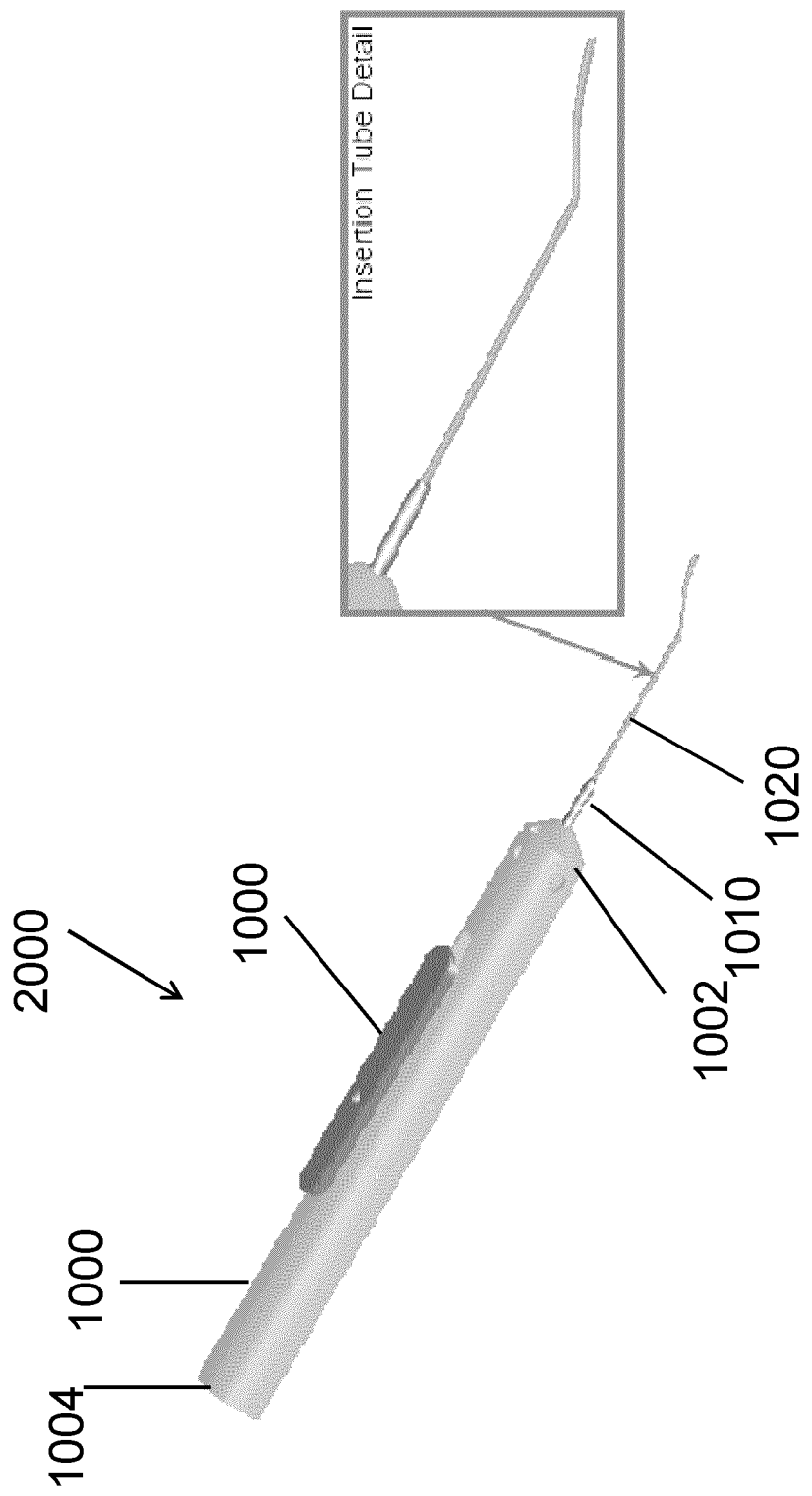
FIG. 20F illustrates one embodiment of a delivery device in accordance with embodiments disclosed herein.
Figure 20G:
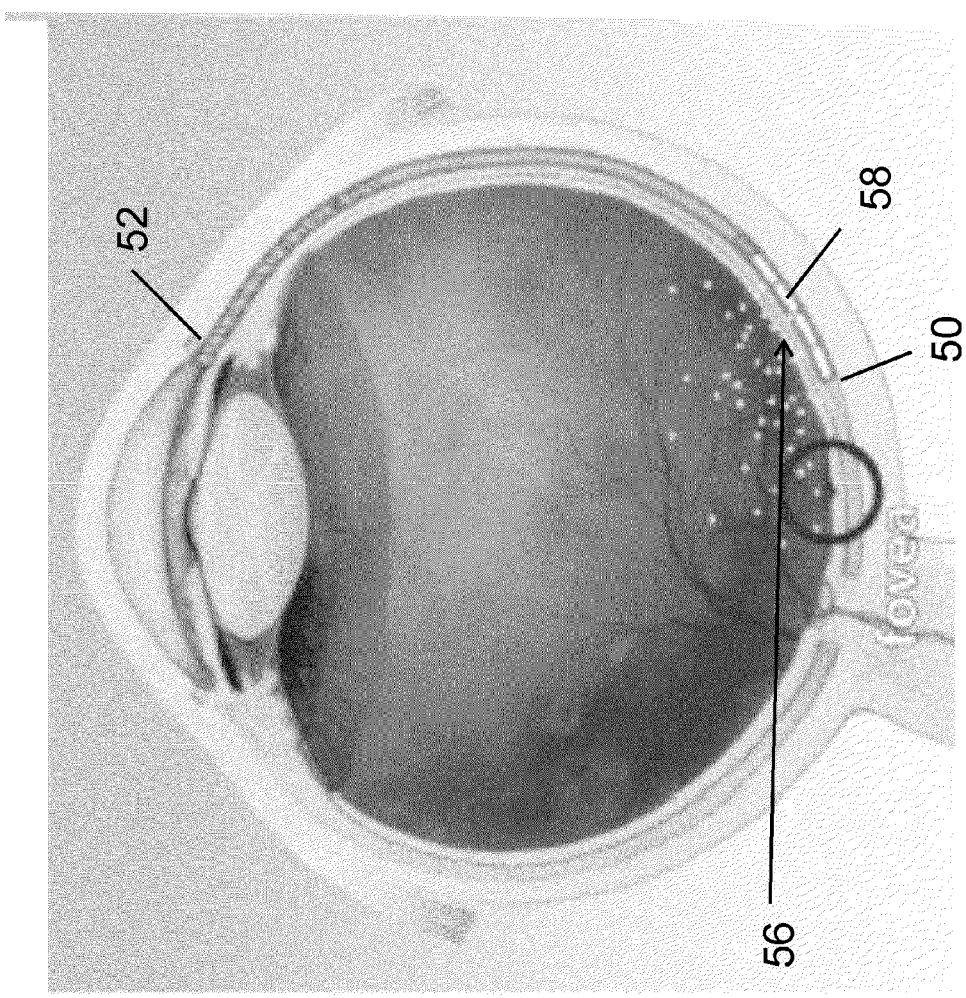
FIGS. 20G-20I illustrate various implantation configurations of drug delivery devices in accordance with embodiments disclosed herein.

FIG. 20G schematically depicts an eye with one embodiment of an elongate implant positioned in accordance with several embodiments disclosed herein. As shown the proximal end of the implant 52 resides near the anterior portion of the eye, while the distal end of the implant 50 resides in a more posterior position. The implant can be implanted in the suprachoroidal space, in one embodiment, and positioned such that the region of drug release 56 allows the therapeutic agent 58 to elute from the implant in a posterior region of the eye. While not expressly depicted here, it shall be appreciated that the implant may, optionally, include the fluid inflow and outflow pathway described herein.

Figure 20H:
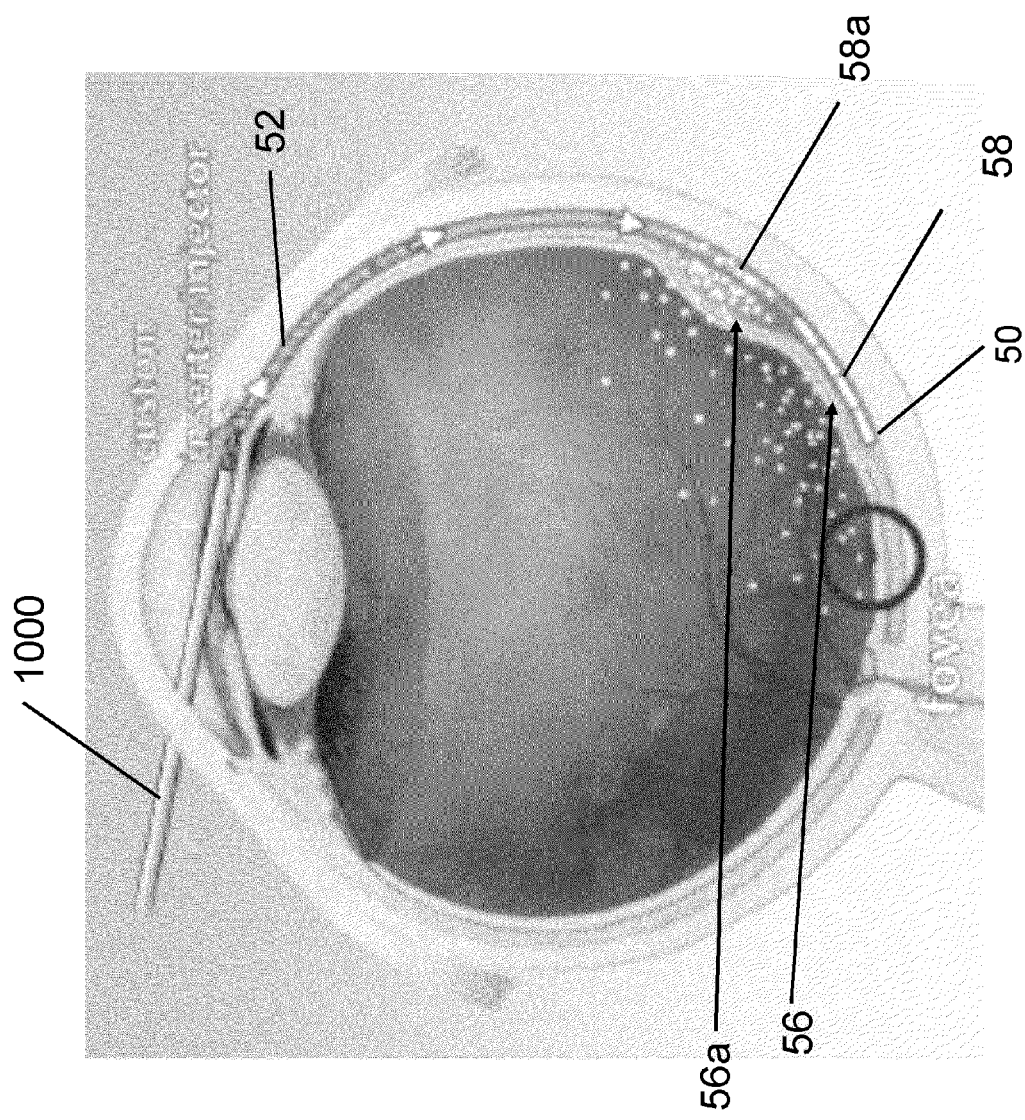
Figure 20L:
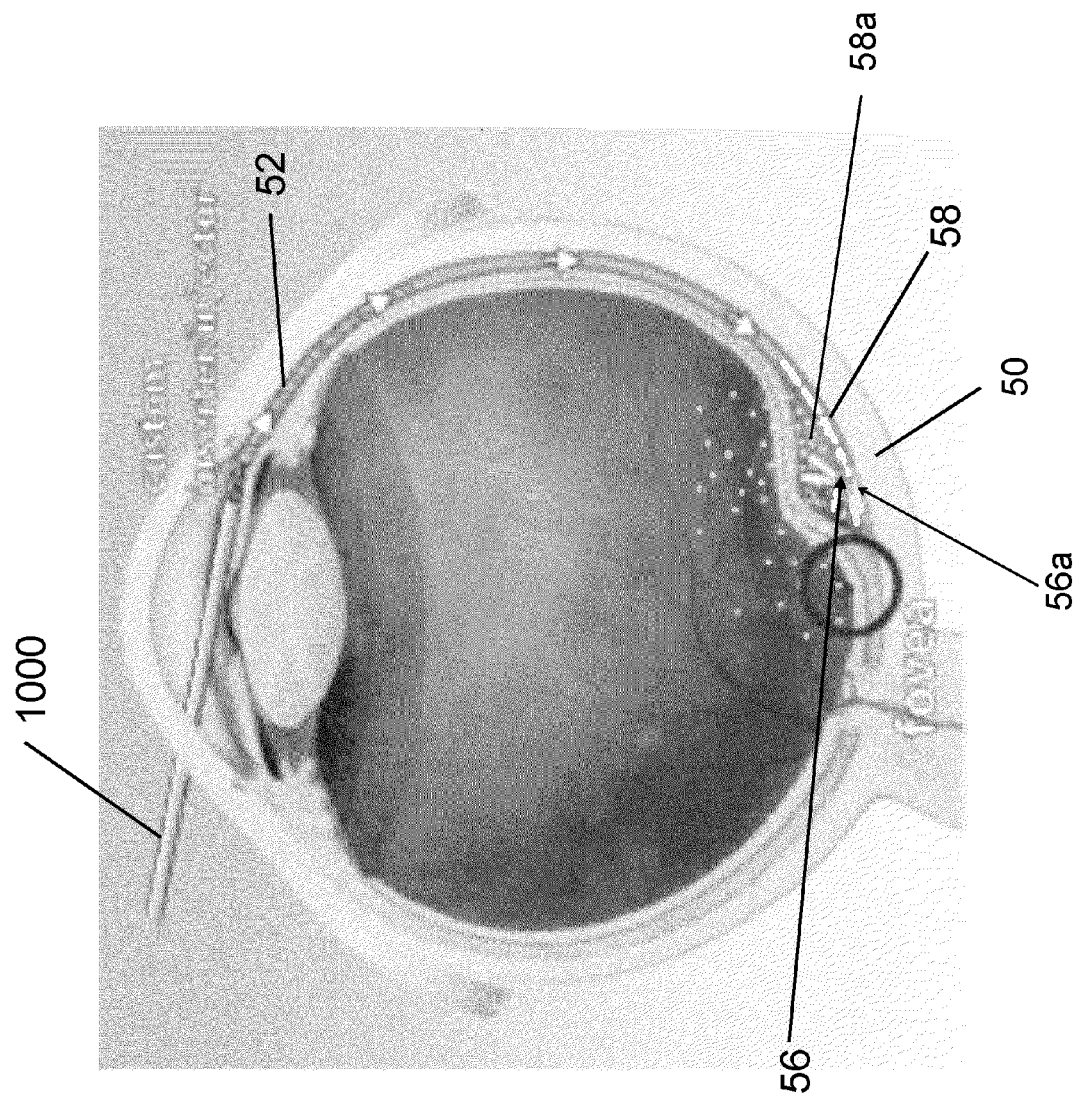
FIGS. 20D and 20E depict various features of elongate delivery devices in accordance with several embodiments disclosed herein.
FIG. 20J illustrates an additional feature of the distal portion of certain drug delivery devices in accordance with embodiments disclosed herein.

FIG. 20H depicts an additional configuration that is used in several embodiments. For example, in one embodiment the implant is positioned (e.g., via use of a custom inserter 1000) in the eye with the distal end 50 in a posterior portion of the eye and the proximal end 52 in a more anterior region. The implant depicted, and described in more detail elsewhere herein, comprises a plurality of regions of drug release, indicated as 56 and 56$a$, and a plurality of types of therapeutic agent, namely 58 and 58$a$ in FIG. 20H. Several embodiments of such an implant are used when, for example, it is beneficial to provide a loading or bolus dose of a therapeutic agent (58$a$) for acute or relatively short term effects (perhaps, for example to reduce inflammation or risk of infection). Thereafter, a more long term formulation of the therapeutic agent (e.g., a pellet; 58) provides controlled drug release for a period of time beyond the acute effect. In several embodiments, such a configuration reduces complications with insertion of the device and reduces the time from insertion to reduction in one or more symptoms associated with the disease or disorder being treated.

Figure 20J:
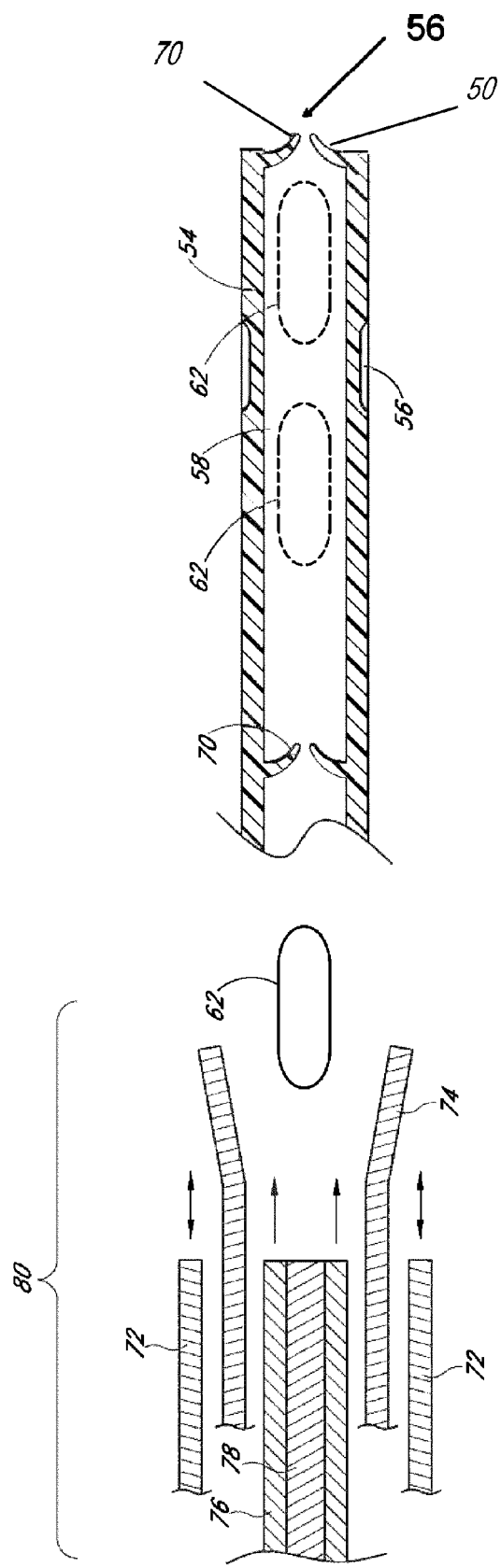

FIG. 20I depicts yet another embodiment of an elongate device with an alternative drug elution strategy. Again the implant is positioned with the distal portion 50 in the posterior region of the eye. In the depicted embodiment, the regions of drug release 56 and 56$a$ are positioned at or near the very distal end of the implant. The distal end is configured such that pellets of therapeutic agent 58, and or therapeutic agent in a different form (e.g., micropellets, vesicles, gel) or a different therapeutic agent (e.g., one that reduces or prevents a side effect due to the first therapeutic agent) are capable of being flushed out of the distal end of the implant. One schematic of such an implant is shown in FIG. 20J, wherein the distal end of the implant 50 comprises a region of drug release 56 that is generated by virtue of a one-way valve 70. In several embodiments, the valve comprises two or more flaps 70, open at the proximal end and reversibly closed at the distal end. The pressure provided on the proximal portion of the flaps induces the flaps to open and the drugs 58 and 58a are expelled (partially or completely) from the implant. In several embodiments, the flaps return to their closed (or substantially closed) position such that a seal is created to prevent backflow of ocular fluid (which may include expelled therapeutic agent) into the implant. In other embodiments, however, a fluid-tight seal is not formed. Other flap or sealing mechanisms are used, depending on the embodiment.

Such embodiments, are used, in several embodiments, during an initial implantation surgery. In such cases, flushing out the therapeutic agents 58 allows the agent 58 to be to fully exposed to the intraocular environment, which may hasten the therapeutic effects of the agent. Additionally, with the initial therapeutic agent 58 flushed out of the implant, the distal portion of the implant is open (e.g., not blocked with agent) for the delivery of a second therapeutic agent 58a. The flushing of the initial agent 58 from the device helps to ensure that the second agent (which, again, may reduce or prevent a side effect of the first agent) reaches the desired anatomical target tissue. If the device were not flushed and still contained the therapeutic agent 58, the second agent 58a would either have to move around the first agent within the implant or be eluted/flushed from the implant through side ports (which are more proximal, and thus farther from the posterior target tissue). Either approach may result in the second agent 58a failing to reach (at least in therapeutically effective concentrations) the desired target in the posterior region of the eye.

In additional embodiments, devices that are configured to allow flushing of their therapeutic drug contents out the distal end of the device are useful when assessing the efficacy and/or functionality of the device post-implantation. At such a time, it may be advantageous to be able to deliver a second agent (perhaps to ameliorate side effects) or a different concentration of an agent. This can thus be accomplished by flushing the implant with the second agent or a new concentration of a first agent.

In several embodiments, the agents 58a that are delivered secondarily and/or in conjunction with a flush of the first therapeutic agent 58 are in a fluid, semi-fluid, or fluid-like form. In several embodiments, microparticles that behave like a fluid (e.g., they have liquid-like flow properties) are used. In some embodiments, the secondary agent 58a is configured to have its own desired elution profile. In such cases, the secondary agent 58a is optionally housed or contained within a structure that allows for controlled release. In several embodiments, this comprises admixing the therapeutic agent with one or more polymers (e.g., creating a "matrix) that allows release of the therapeutic agent from the admixture with a known rate of elution. In several embodiments, the one or more polymers are selected such that they are readily interconvertible between a liquid or semi-liquid state and a solid or semi-solid state. In several embodiments, the interconversion is due to externally applied stimuli (e.g., radio frequency, light, etc.). In several embodiments, the interconversion is temperature or pressure induced. For example, in several embodiments, the polymers are liquid or semi-liquid at room temperature, but upon exposure to increased temperatures (e.g., physiological temperatures) become solid or semi-solid. In such a manner, the polymer matrix can be used to hold the therapeutic agent at a desired target site, thereby improving the accuracy of delivery and reduction of wash-out due to ocular fluid flow. In several embodiments, optionally, the polymers are biodegradable (such that repeated administration does not result in build-up of polymer at the delivery site). In several embodiments, the polymers are mixtures of polymers that are configured to mimic a membrane bound structure (e.g., a micelle or vesicle). In several such embodiments, the drug is intermixed with those polymers such that it is incorporated into the micelle or vesicle, and (based on the known characteristics of the polymers) elutes at a certain rate. Similarly, such micelles or vesicles are optionally mixed with a polymeric matrix that is readily interconvertible between a liquid or semi-liquid state and a solid or semi-solid state It will be appreciated that the elements discussed above are not to be read as limiting the implants to the specific combinations or embodiments described. Rather, the features discussed are freely interchangeable to allow flexibility in the construction of a drug delivery implant in accordance with this disclosure.

Delivery Instruments

Another aspect of the systems and methods described herein relates to delivery instruments for implanting an implant for delivering a drug to the eye and optionally for draining fluid from the anterior chamber into a physiologic outflow space. In some embodiments, the implant is inserted into the eye from a site transocularly situated from the implantation site. The delivery instrument is sufficiently long to advance the implant transocularly from the insertion site across the anterior chamber to the implantation site. At least a portion of the instrument may be flexible. The instrument may comprise a plurality of members longitudinally moveable relative to each other. In some embodiments, the plurality of members comprises one or more slideable guide tubes. In some embodiments, at least a portion of the delivery instrument is curved. In some embodiments, a portion of the delivery instrument is rigid and another portion of the instrument is flexible.

In some embodiments, the delivery instrument has a distal curvature. The distal curvature of the delivery instrument may be characterized in some embodiments as a radius of approximately 10 to 30 mm. In some embodiments the distal curvature has a radius of about 20 mm.

Figure 21:
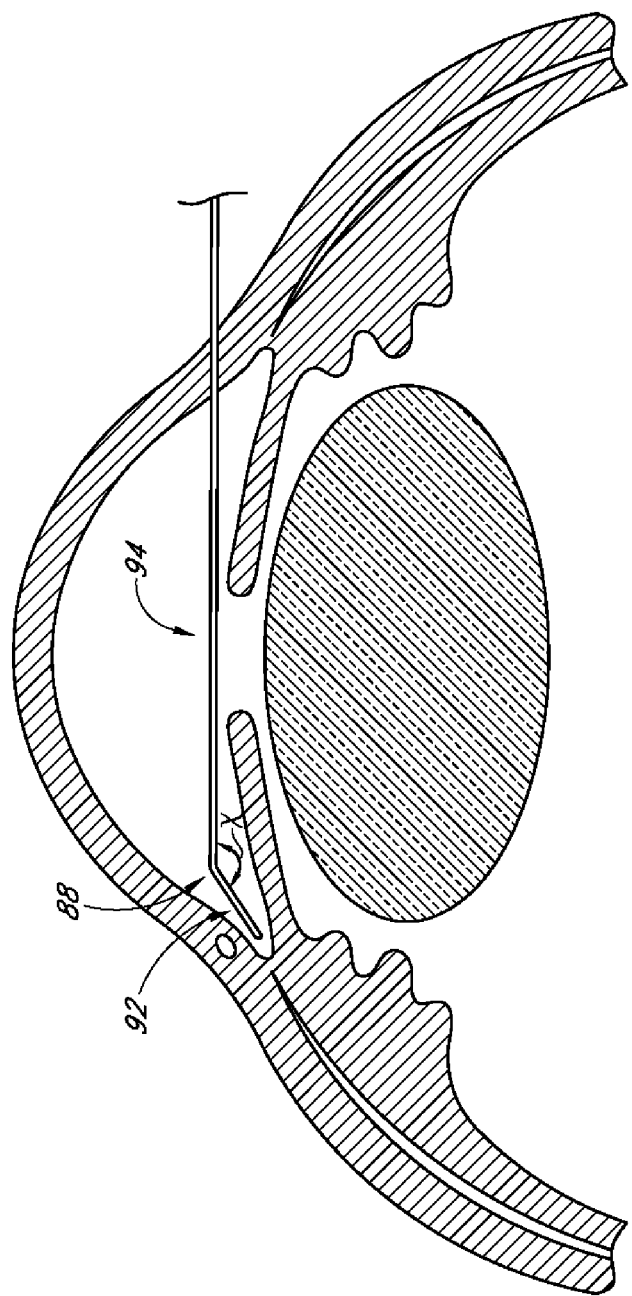
FIG. 21 illustrates an apparatus for implanting a drug delivery device in accordance with embodiments disclosed herein.

In some embodiments, the delivery instrument has a distal angle 88 (with a measure denoted by $\chi$ in FIG. 21). The angle measure $\chi$ may be characterized as approximately 90 to 180 degrees relative to the proximal segment 94 of the delivery instrument. In some embodiments, the angle measure $\chi$ may be characterized as between about 145 and about 170 degrees. In some embodiments the angle measure is between about 150 and about 170 degrees, or between about 155 and about 165 degrees. The angle can incorporate a small radius of curvature at the "elbow" so as to make a smooth transition from the proximal segment of the delivery instrument to the distal segment. The length of the distal segment may be approximately 0.5 to 7 mm in some embodiments, while in some other embodiments, the length of the distal segment is about 2 to 3 mm.

In other embodiments, a curved distal end is preferred. In such embodiments, the height of the delivery instrument/shunt assembly (dimension 90 in FIG. 22) is less than about 3 mm in some embodiments, and less than 2 mm in other embodiments.

In some embodiments, the instruments have a sharpened feature at the forward end and are self-trephinating, i.e., self-penetrating, so as to pass through tissue without preforming an incision, hole or aperture. In some embodiments, instruments that are self-trephinating are configured to penetrate the tissues of the cornea and/or limbus only. In other embodiments, instruments that are self-trephinating are configured to penetrate internal eye tissues, such as those in the anterior chamber angle, in order to deliver an implant. Alternatively, a separate trocar, scalpel, spatula, or similar instrument can be used to pre-form an incision in the eye tissue (either the cornea/sclera or more internal tissues) before passing the implant into such tissue. In some embodiments, the implant is blunt at the distal end, to aid in blunt dissection (and hence reduce risk of tissue trauma) of the ocular tissue. In other embodiments, however, the implant is also sharpened, tapered or otherwise configured to penetrate ocular tissues to aid in implantation.

For delivery of some embodiments of the drug eluting ocular implant, the instrument has a sufficiently small cross section such that the insertion site self seals without suturing upon withdrawal of the instrument from the eye. An outer dimension of the delivery instrument is preferably no greater than about 18 gauge and is not smaller than about 27 or 30 gauge.

For delivery of some embodiments of the drug eluting ocular implant, an incision in the corneal tissue is made with a hollow needle through which the implant is passed. The needle has a small diameter size (e.g., 18 or 19 or 20 or 21 or 22 or 23 or 24 or 25 or 26 or 27 gauge) so that the incision is self sealing and the implantation occurs in a closed chamber with or without viscoelastic. A self-sealing incision may also be formed using a conventional "tunneling" procedure in which a spatula-shaped scalpel is used to create a generally inverted V-shaped incision through the cornea. In a preferred mode, the instrument used to form the incision through the cornea remains in place (that is, extends through the corneal incision) during the procedure and is not removed until after implantation. Such incision-forming instrument either may be used to place the ocular implant or may cooperate with a delivery instrument to allow implantation through the same incision without withdrawing the incision-forming instrument. Of course, in other modes, various surgical instruments may be passed through one or more corneal incisions multiple times.

Some embodiments include a spring-loaded pusher system. In some embodiments, the spring-loaded pusher includes a button operably connected to a hinged rod device. The rod of the hinged rod device engages a depression in the surface of the pusher, keeping the spring of the pusher in a compressed conformation. When the user pushes the button, the rod is disengaged from the depression, thereby allowing the spring to decompress, thereby advancing the pusher forward.

In some embodiments, an over-the wire system is used to deliver the implant. The implant may be delivered over a wire. In some embodiments, the wire is self-trephinating. The wire may also function as a trocar. The wire may be superelastic, flexible, or relatively inflexible with respect to the implant. The wire may be pre-formed to have a certain shape. The wire may be curved. The wire may have shape memory, or be elastic. In some embodiments, the wire is a pull wire. The wire may also be a steerable catheter.

In some embodiments, the wire is positioned within a lumen in the implant. The wire may be axially movable within the lumen. The lumen may or may not include valves or other flow regulatory devices.

In some embodiments, the delivery instrument is a trocar. The trocar may be angled or curved. In some embodiments, the trocar is flexible. In other embodiments the trocar is relatively rigid. In other embodiments, the trocar is stiff. In embodiments where the trocar is stiff, the implant is relatively flexible. The diameter of the trocar is about 0.001 inches to about 0.01 inches. In some embodiments, the diameter of the trocar is 0.001, 0.002, 0.003, 0.004, 0.005, 0.006, 0.007, 0.008, 0.009, or 0.01 inches.

In some embodiments, delivery of the implant is achieved by applying a driving force at or near the proximal end of the implant. The driving force may be a pulling or a pushing applied to the end of the implant.

The instrument may include a seal or coating to prevent aqueous humor from passing through the delivery instrument and/or between the members of the instrument when the instrument is in the eye. The seal aids in preventing backflow. In some embodiments, the instrument is coated with the coating and a hydrophilic or hydrophobic agent. In some embodiments, one region of the instrument is coated with the coating plus the hydrophilic agent, and another region of the instrument is coated with the coating plus the hydrophobic agent. The delivery instrument may additionally comprise a seal between various members comprising the instrument. The seal may comprise a hydrophobic or hydrophilic coating between slip-fit surfaces of the members of the instrument. The seal may be disposed proximate of the implant when carried by the delivery instrument. In some embodiments, the seal is present on at least a section of each of two devices that are machined to closely fit with one another.

The delivery instrument may include a distal end having a beveled shape. The delivery instrument may include a distal end having a spatula shape. The beveled or spatula shape may or may not include a recess to contain the implant. The recess can include a pusher or other suitable means to push out or eject the implant.

The delivery instrument may be configured to deliver multiple implants. In some such embodiments, the implants may be arranged in tandem (or serially for implant numbers greater than two) within the device.

Procedures

For delivery of some embodiments of the ocular implant, the implantation occurs in a closed chamber with or without viscoelastic.

The implants may be placed using an applicator, such as a pusher, or they may be placed using a delivery instrument having energy stored in the instrument, such as disclosed in U.S. Patent Publication 2004/0050392, filed Aug. 28, 2002, now U.S. Pat. No. 7,331,984, issued Feb. 19, 2008, the entirety of which is incorporated herein by reference and made a part of this specification and disclosure. In some embodiments, fluid may be infused through an applicator to create an elevated fluid pressure at the forward end of the implant to ease implantation.

In one embodiment of the invention, a delivery apparatus (or "applicator") similar to that used for placing a trabecular stent through a trabecular meshwork of an eye is used. Certain embodiments of such a delivery apparatus are disclosed in U.S. Patent Publication 2004/0050392, filed Aug. 28, 2002, now U.S. Pat. No. 7,331,984, issued Feb. 19, 2008; U.S. Publication No.: 2002/0133168, entitled APPLICATOR AND METHODS FOR PLACING A TRABECULAR SHUNT FOR GLAUCOMA TREATMENT, now abandoned; and U.S. Provisional Application No. 60/276,609, filed Mar. 16, 2001, entitled APPLICATOR AND METHODS FOR PLACING A TRABECULAR SHUNT FOR GLAUCOMA TREATMENT, now expired, each of which is incorporated by reference and made a part of this specification and disclosure.

In one embodiment, the delivery apparatus 2000 includes a handpiece, an elongate tip, a holder and an actuator, which are schematically depicted in FIG. 20F. The handpiece 1000 has a distal end 1002 and a proximal end 1004. The elongate tip 1010 is connected to the distal end of the handpiece. The elongate tip has a distal portion and is configured to be placed through a corneal incision and into an anterior chamber of the eye. The holder 1020 (e.g., an insertion tube) is attached to the distal portion of the elongate tip. The holder is configured to hold and release the drug delivery implant. The actuator 1040 is on the handpiece and actuates the holder to release the drug delivery implant from the holder. In one embodiment, a deployment mechanism within the delivery apparatus includes a push-pull type plunger.

In some embodiments, the holder comprises a clamp. In some embodiments, the apparatus further comprises a spring within the handpiece that is configured to be loaded when the drug delivery implant is being held by the holder, the spring being at least partially unloaded upon actuating the actuator, allowing for release of the drug delivery implant from the holder.

In various embodiments, the clamp comprises a plurality of claws configured to exert a clamping force onto at least the proximal portion of the drug delivery implant. The holder may also comprise a plurality of flanges.

In some embodiments, the distal portion of the elongate tip is made of a flexible material. This can be a flexible wire. The distal portion can have a deflection range, preferably of about 45 degrees from the long axis of the handpiece. The delivery apparatus can further comprise an irrigation port in the elongate tip.

In some embodiments, the method includes using a delivery apparatus that comprises a handpiece having a distal end and a proximal end and an elongate tip connected to the distal end of the handpiece. The elongate tip has a distal portion and being configured to be placed through a corneal incision and into an anterior chamber of the eye. The apparatus further has a holder attached to the distal portion of the elongate tip, the holder being configured to hold and release the drug delivery implant, and an actuator on the handpiece that actuates the holder to release the drug delivery implant from the holder.

The delivery instrument may be advanced through an insertion site in the cornea and advanced either transocularly or posteriorly into the anterior chamber angle and positioned at base of the anterior chamber angle. Using the anterior chamber angle as a reference point, the delivery instrument can be advanced further in a generally posterior direction to drive the implant into the iris, inward of the anterior chamber angle.

Optionally, based on the implant structure, the implant may be laid within the anterior chamber angle, taking on a curved shape to match the annular shape of the anterior chamber angle.

In some embodiments, the implant may be brought into position adjacent the tissue in the anterior chamber angle or the iris tissue, and the pusher tube advanced axially toward the distal end of the delivery instrument. As the pusher tube is advanced, the implant is also advanced. When the implant is advanced through the tissue and such that it is no longer in the lumen of the delivery instrument, the delivery instrument is retracted, leaving the implant in the eye tissue.

The placement and implantation of the implant may be performed using a gonioscope or other conventional imaging equipment. In some embodiments, the delivery instrument is used to force the implant into a desired position by application of a continual implantation force, by tapping the implant into place using a distal portion of the delivery instrument, or by a combination of these methods. Once the implant is in the desired position, it may be further seated by tapping using a distal portion of the delivery instrument.

In one embodiment, the drug delivery implant is affixed to an additional portion of the iris or other intraocular tissue, to aid in fixating the implant. In one embodiment, this additional affixation may be performed with a biocompatible adhesive. In other embodiments, one or more sutures may be used. In another embodiment, the drug delivery implant is held substantially in place via the interaction of the implant body's outer surface and the surrounding tissue of the anterior chamber angle.

Figure 23:
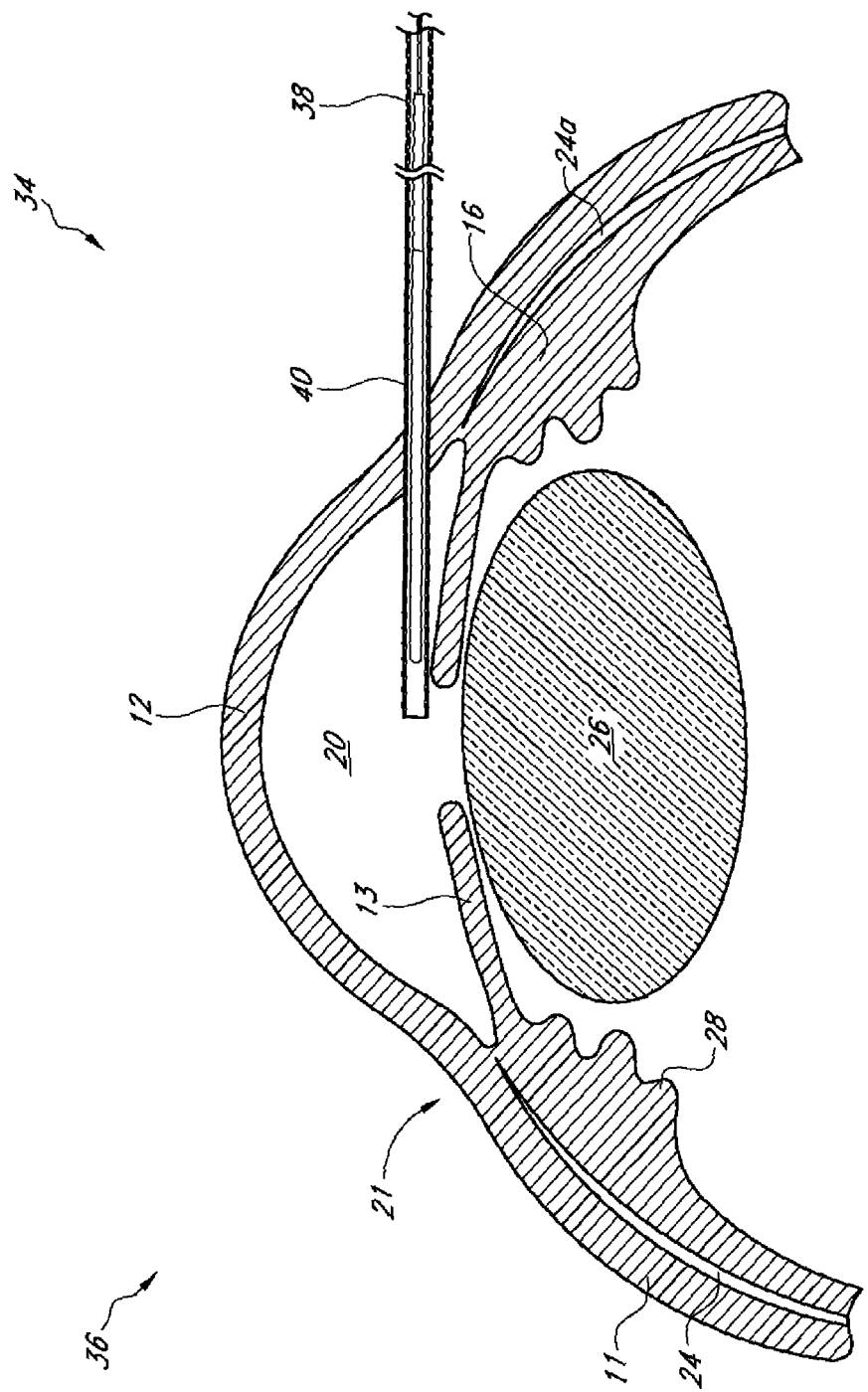
FIG. 23 illustrates a schematic cross-sectional view of an eye with a delivery device containing an implant being advanced across the anterior chamber. The size of the implant is exaggerated for illustration purposes.

FIG. 23 illustrates one embodiment of a surgical method for implanting the drug delivery implant into an eye, as described in the embodiments herein. A first incision or slit is made through the conjunctiva and the sclera 11 at a location rearward of the limbus 21, that is, posterior to the region of the sclera 11 at which the opaque white sclera 11 starts to become clear cornea 12. In some embodiments, the first incision is posterior to the limbus 21, including about 3 mm posterior to the limbus. In some embodiments, the incision is made such that a surgical tool may be inserted into the anterior chamber at a shallow angle (relative to the anteroposterior axis), as shown in FIG. 23. In other embodiments, the first incision may be made to allow a larger angle of instrument insertion (see, e.g. FIGS. 24-26). Also, the first incision is made slightly larger than the width of the drug delivery implant. In one embodiment, a conventional cyclodialysis spatula may be inserted through the first incision into the supraciliary space to confirm correct anatomic position.

A portion of the upper and lower surfaces of the drug delivery implant can be grasped securely by the surgical tool, for example, a forceps, so that the forward end of the implant is oriented properly. The implant may also be secured by viscoelastic or mechanical interlock with the pusher tube or wall of the implant delivery device. In one embodiment, the implant is oriented with a longitudinal axis of the implant being substantially co-axial to a longitudinal axis of the grasping end of the surgical tool. The drug delivery implant is disposed through the first incision.

The delivery instrument may be advanced from the insertion site transocularly into the anterior chamber angle and positioned at a location near the scleral spur. Using the scleral spur as a reference point, the delivery instrument can be advanced further in a generally posterior direction to drive the implant into eye tissue at a location just inward of the scleral spur toward the iris.

Optionally, based on the implant structure, the shearing edge of the insertion head of the implant can pass between the scleral spur and the ciliary body 16 posterior to the trabecular meshwork.

The drug delivery implant may be continually advanced posteriorly until a portion of its insertion head and the first end of the conduit is disposed within the anterior chamber 20 of the eye. Thus, the first end of the conduit is placed into fluid communication with the anterior chamber 20 of the eye. The distal end of the elongate body of the drug delivery implant can be disposed into the suprachoroidal space of the eye so that the second end of the conduit is placed into fluid communication with the suprachoroidal space. Alternatively, the implant may be brought into position adjacent the tissue in the anterior chamber angle, and the pusher tube advanced axially toward the distal end of the delivery instrument. As the pusher tube is advanced, the implant is also advanced. When the implant is advanced through the tissue and such that it is no longer in the lumen of the delivery instrument, the delivery instrument is retracted, leaving the implant in the eye tissue.

The placement and implantation of the implant may be performed using a gonioscope or other conventional imaging equipment. In some embodiments, the delivery instrument is used to force the implant into a desired position by application of a continual implantation force, by tapping the implant into place using a distal portion of the delivery instrument, or by a combination of these methods. Once the implant is in the desired position, it may be further seated by tapping using a distal portion of the delivery instrument.

In one embodiment, the drug delivery implant is sutured to a portion of the sclera 11 to aid in fixating the implant. In one embodiment, the first incision is subsequently sutured closed. As one will appreciate, the suture used to fixate the drug delivery implant may also be used to close the first incision. In another embodiment, the drug delivery implant is held substantially in place via the interaction of the implant body's outer surface and the tissue of the sclera 11 and ciliary body 16 and/or choroid 12 without suturing the implant to the sclera 11. Additionally, in one embodiment, the first incision is sufficiently small so that the incision self-seals upon withdrawal of the surgical tool following implantation of the drug delivery implant without suturing the incision.

As discussed herein, in some embodiments the drug delivery implant additionally includes a shunt comprising a lumen configured provide a drainage device between the anterior chamber 20 and the suprachoroidal space. Upon implantation, the drainage device may form a cyclodialysis with the implant providing a permanent, patent communication of aqueous humor through the shunt along its length. Aqueous humor is thus delivered to the suprachoroidal space where it can be absorbed, and additional reduction in pressure within the eye can be achieved.

Figure 24:
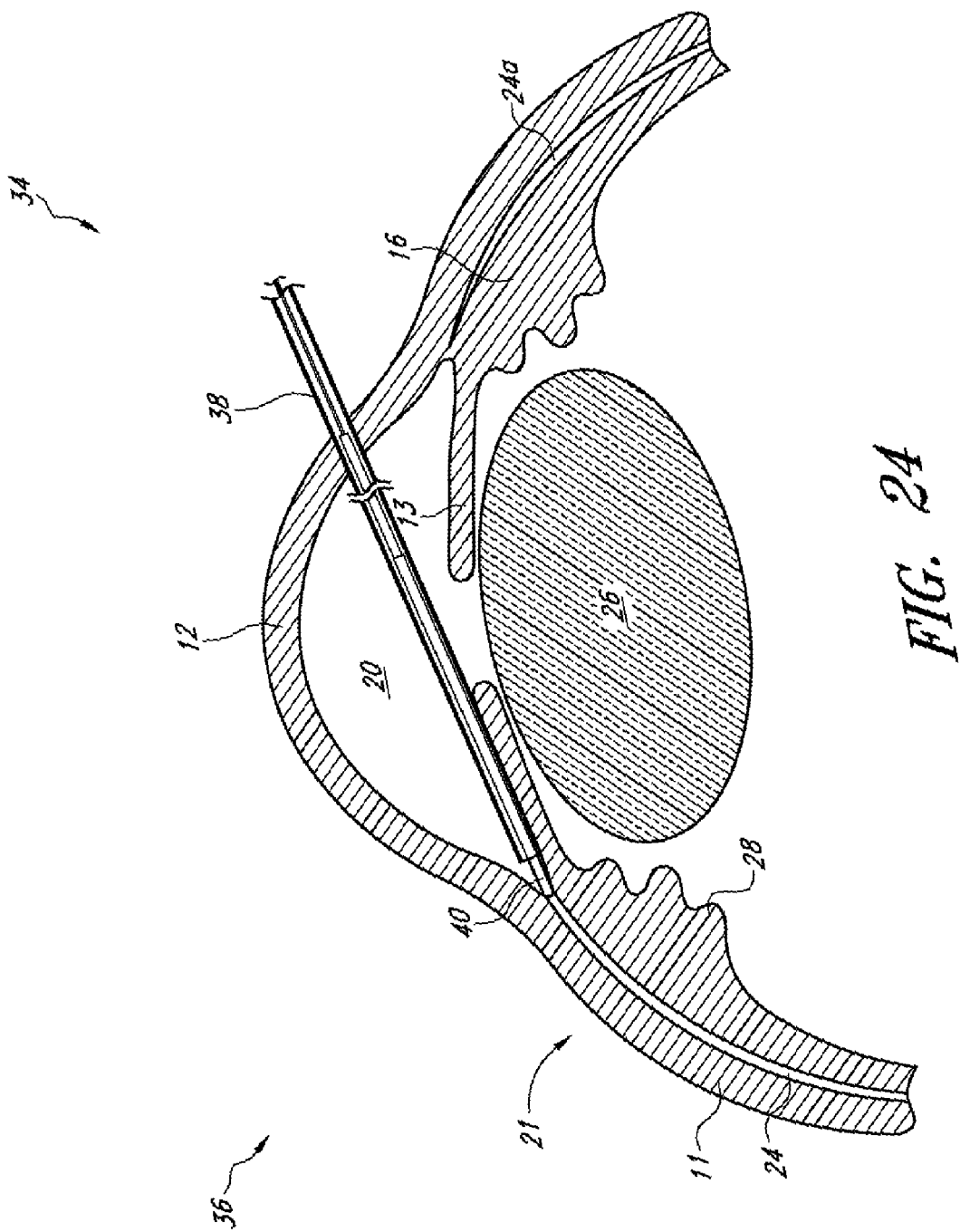
FIG. 24 illustrates an additional implantation procedure according to several embodiments disclosed herein. The size of the implant is exaggerated for illustration purposes.
Figure 25:
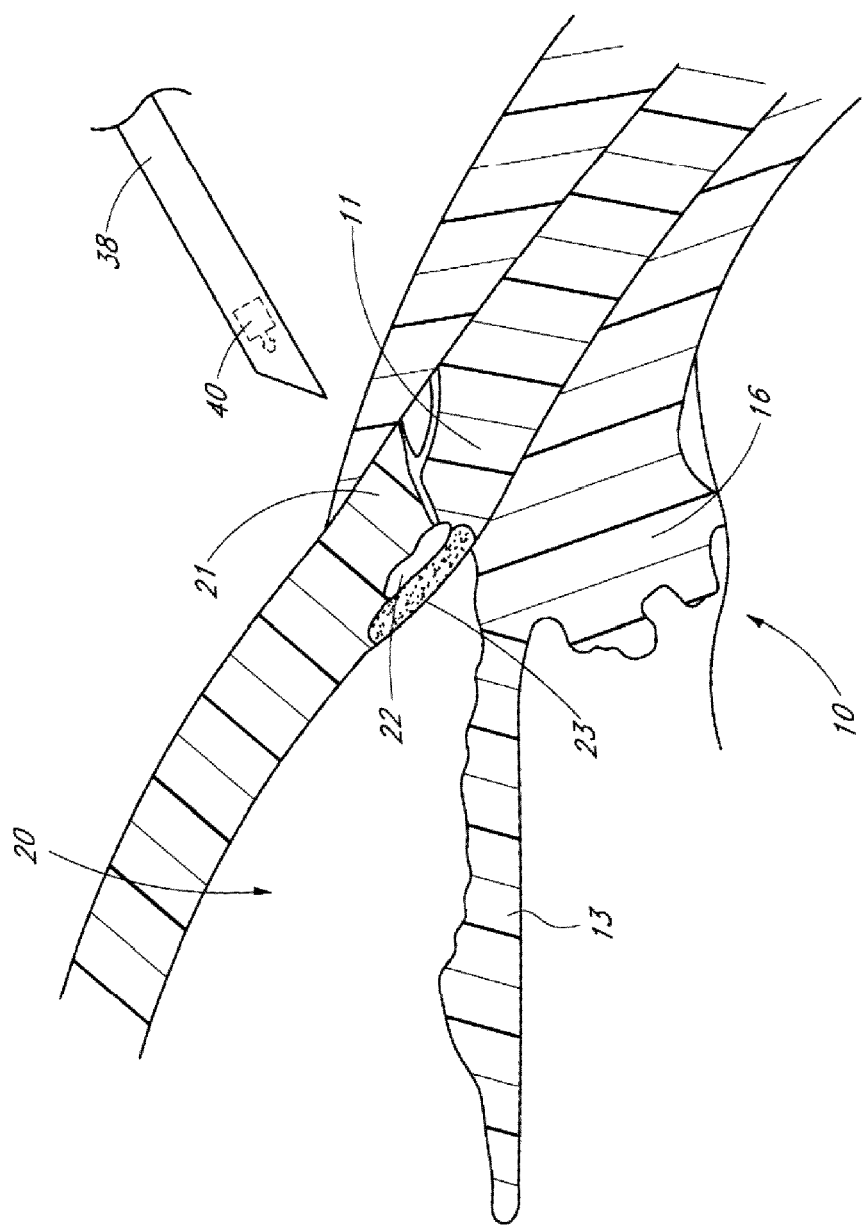
FIG. 25 illustrates a schematic cross-sectional view of an eye with a delivery device being advanced adjacent the anterior chamber angle. The size of the implant is exaggerated for illustration purposes.

In some embodiments it is desirable to deliver the drug delivery implant ab interno across the eye, through a small incision at or near the limbus (FIG. 24). The overall geometry of the system makes it advantageous that the delivery instrument incorporates a distal curvature, or a distal angle. In the former case, the drug delivery implant may be flexible to facilitate delivery along the curvature or may be more loosely held to move easily along an accurate path. In the latter case, the implant may be relatively rigid. The delivery instrument may incorporate an implant advancement element (e.g. pusher) that is flexible enough to pass through the distal angle.

In some embodiments, the implant and delivery instrument are advanced together through the anterior chamber 20 from an incision at or near the limbus 21, across the iris 13, and through the ciliary muscle attachment until the drug delivery implant outlet portion is located in the uveoscleral outflow pathway (e.g. exposed to the suprachoroidal space defined between the sclera 11 and the choroid 12). FIG. 24 illustrates a transocular implantation approach that may be used with the delivery instrument inserted well above the limbus 21. In other embodiments (see, e.g., FIG. 25), the incision may be made more posterior and closer to the limbus 21. In one embodiment, the incision will be placed on the nasal side of the eye with the implanted location of the drug delivery implant 40 on the temporal side of the eye. In another embodiment, the incision may be made temporally such that the implanted location of the drug delivery implant is on the nasal side of the eye. In some embodiments, the operator simultaneously pushes on a pusher device while pulling back on the delivery instrument, such that the drug delivery implant outlet portion maintains its location in the posterior region of the suprachoroidal space near the macula 34, as illustrated in FIG. 26. The implant is released from the delivery instrument, and the delivery instrument retracted proximally. The delivery instrument is withdrawn from the anterior chamber through the incision.

In some embodiments, it is desirable to implant a drug delivery implant with continuous aqueous outflow through the fibrous attachment zone, thus connecting the anterior chamber 20 to the uveoscleral outflow pathway, in order to reduce the intraocular pressure in glaucomatous patients. In some embodiments, it is desirable to deliver the drug delivery implant with a device that traverses the eye internally (ab interno), through a small incision in the limbus 21.

In several embodiments, microinvasive methods of implanting a drug delivery implant are provided. In several such embodiments, an ab externo technique is utilized. In some embodiments, the technique is non-penetrating, thereby limiting the invasiveness of the implantation method. As discussed herein, in some embodiments, the drug delivery device that is implanted comprises a shunt. In some embodiments, such implants facilitate removal of fluid from a first location, while simultaneously providing drug delivery. In some embodiments, the implants communicate fluid from the anterior chamber to the suprachoroidal space, which assists in removing fluid (e.g., aqueous humor) from and reducing pressure increases in the anterior chamber.

In some embodiments (see e.g., FIG. 27), a window (e.g. a slit or other small incision) is surgically made through the conjunctiva and the sclera 11 to the surface of the choroid 28 (without penetration). In some embodiments, the slit is made perpendicular to the optical axis of the eye. In some embodiments, a depth stop is used in conjunction with an incising device. In certain embodiments, the incising device is one of a diamond or metal blade, a laser, or the like. In some embodiments, an initial incision is made with a sharp device, while the final portion of the incision to the choroid surface is made with a less sharp instrument, thereby reducing risk of injury to the highly vascular choroid. In some embodiments, the slit is created at or nearly at a tangent to the sclera, in order to facilitate entry and manipulation of an implant.

In some embodiments, a small core of sclera is removed at or near the pars plana, again, without penetration of the choroid. In order to avoid penetration of the choroid, scleral thickness can optionally be measured using optical coherence tomography (OCT), ultrasound, or visual fixtures on the eye during the surgical process. In such embodiments, the scleral core is removed by a trephining instrument (e.g., a rotary or static trephintor) that optionally includes a depth stop gauge to ensure an incision to the proper depth. In other embodiments, a laser, diamond blade, metal blade, or other similar incising device is used.

Figure 27D:
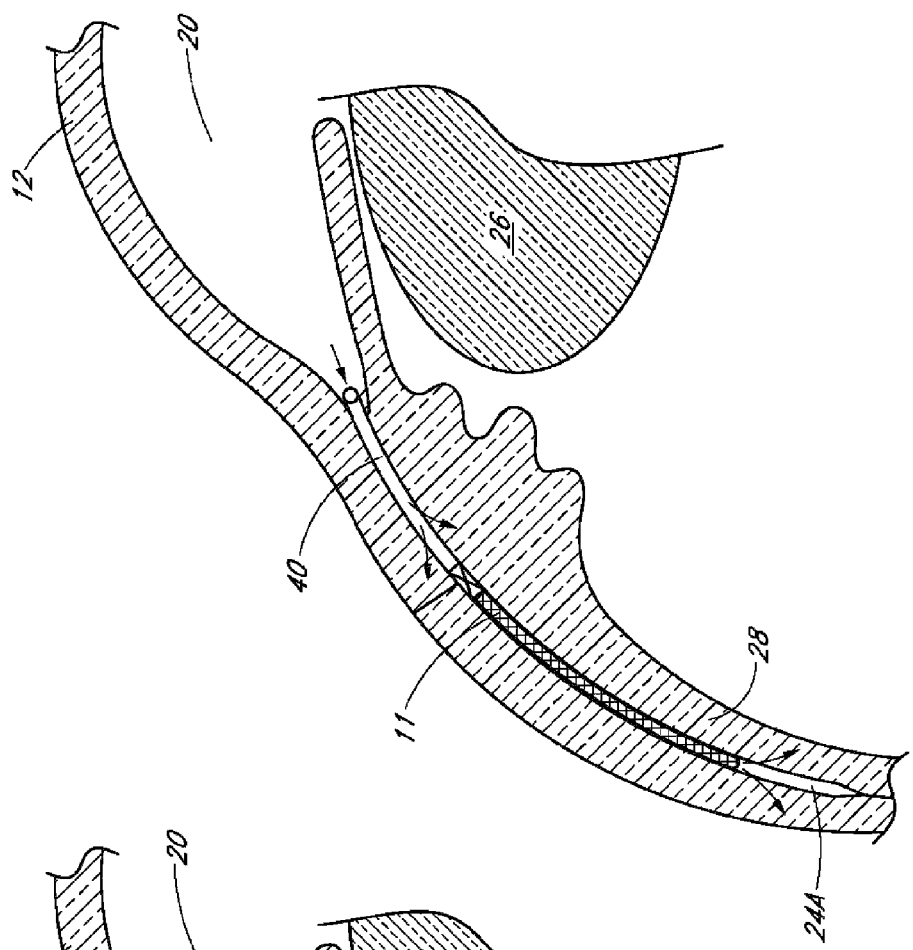
Figure 27C:
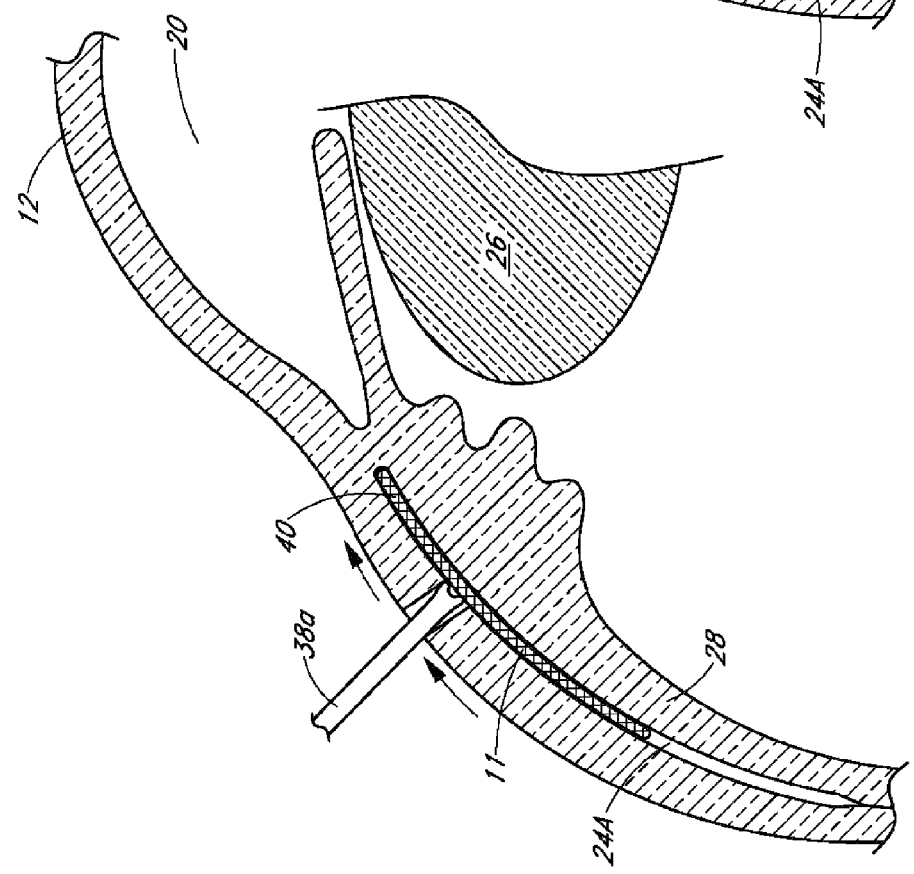

After a window or slit is made in the sclera and the suprachoroidal space is exposed, an implant 40 can be introduced into the window or slit and advanced in multiple directions through the use of an instrument 38a (see e.g., FIG. 27B-27C). Through the use of the instrument 38a, the implant 40 can be maneuvered in a posterior, anterior, superior, or inferior direction. The instrument 38a is specifically designed to advance the implant to the appropriate location without harming the choroid or other structures. The instrument 38a can then be removed and the implant 40 left behind. In some embodiments, the window in the conjunctiva and sclera is small enough to be a self sealing incision. In some embodiments, it can be a larger window or slit which can be sealed by means of a suture, staple, tissue common wound adhesive, or the like. A slit or window according to these embodiments can be 1 mm or less in length or diameter, for example. In some embodiments, the length of the incision ranges from about 0.2 to about 0.4 mm, about 0.4 to about 0.6 mm, about 0.6 mm to about 0.8 mm, about 0.8 mm to about 1.0 mm, about 1.0 to about 1.5 mm, and overlapping ranges thereof. In some embodiments larger incision (slit or window) dimensions are used.

In several embodiments, the implant 40 is tubular or oval tubular in shape. In some embodiments, such a shape facilitates passage of the implant through the small opening. In some embodiments, the implant 40 has a rounded closed distal end, while in other embodiments, the distal end is open. In several embodiments wherein open ended implants are used, the open end is filled (e.g., blocked temporarily) by a portion of the insertion instrument in order to prevent tissue plugging during advancement of the implant (e.g., into the suprachoroidal space). In several embodiments, the implant is an implant as described herein and comprises a lumen that contains a drug which elutes through holes, pores, or regions of drug release in the implant. As discussed herein, drug elution, in some embodiments, is targeted towards the posterior of the eye (e.g., the macula or optic nerve), and delivers therapeutic agents (e.g., steroids or anti VEGFs) to treat retinal or optic nerve disease.

In several embodiments, the implant 40 and implantation instrument 38a is designed with an appropriate tip to allow the implant to be advanced in an anterior direction and penetrate into the anterior chamber without a scleral cutdown. In some embodiments, the tip that penetrates into the anterior chamber is a part of the implant while in some embodiments, it is part of the insertion instrument. In such embodiments, the implant functions as a conduit for aqueous humor to pass from the anterior chamber to the suprachoroidal space to treat glaucoma or ocular hypertension (e.g., a shunt). In several embodiments, the implant is configured to deliver a drug to the anterior chamber to treat glaucoma. In some embodiments, the drug is configured (e.g., produced) to elute over a relatively long period of time (e.g., weeks to months or even years). Non-liming examples of such agents are beta blockers or prostaglandins. In some embodiments, a single implant is inserted, while in other embodiments, two or more implants are implanted in this way, at the same or different locations and in any combination of aqueous humor conduit or drug delivery mechanisms.

Figure 28:
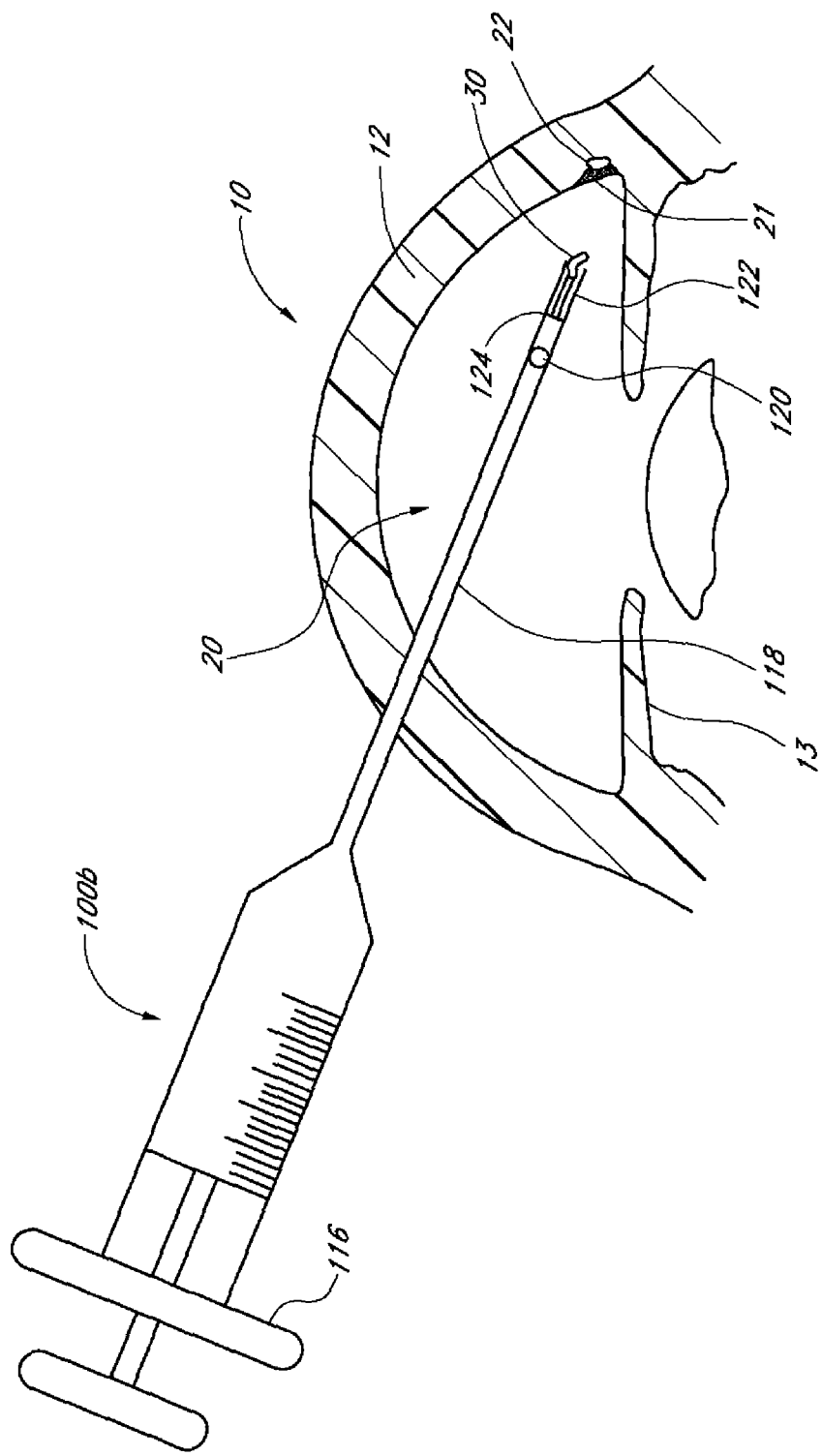
FIG. 28 illustrates a schematic cross-sectional view of an eye with a delivery device being advanced across the eye targeting the iris adjacent to the anterior chamber angle. The size of the shunt is exaggerated for illustration purposes.

FIG. 28 shows an illustrative transocular method for placing any of the various implant embodiments taught or suggested herein at the implant site within the eye 10. A delivery apparatus 100b generally comprises a syringe portion 116 and a cannula portion 118. The distal section of the cannula 118 optionally has at least one irrigating hole 120 and a distal space 122 for holding the drug delivery implant 30. The proximal end 124 of the lumen of the distal space 122 is sealed from the remaining lumen of the cannula portion 118. The delivery apparatus of FIG. 28 may be employed with the any of the various drug delivery implant embodiments taught or suggested herein. In some embodiments, the target implant site is the inferior portion of the iris. It should be understood that the angle of the delivery apparatus shown in FIG. 28 is illustrative, and angles more or less shallow than that shown may be preferable in some embodiments.

Figure 29:
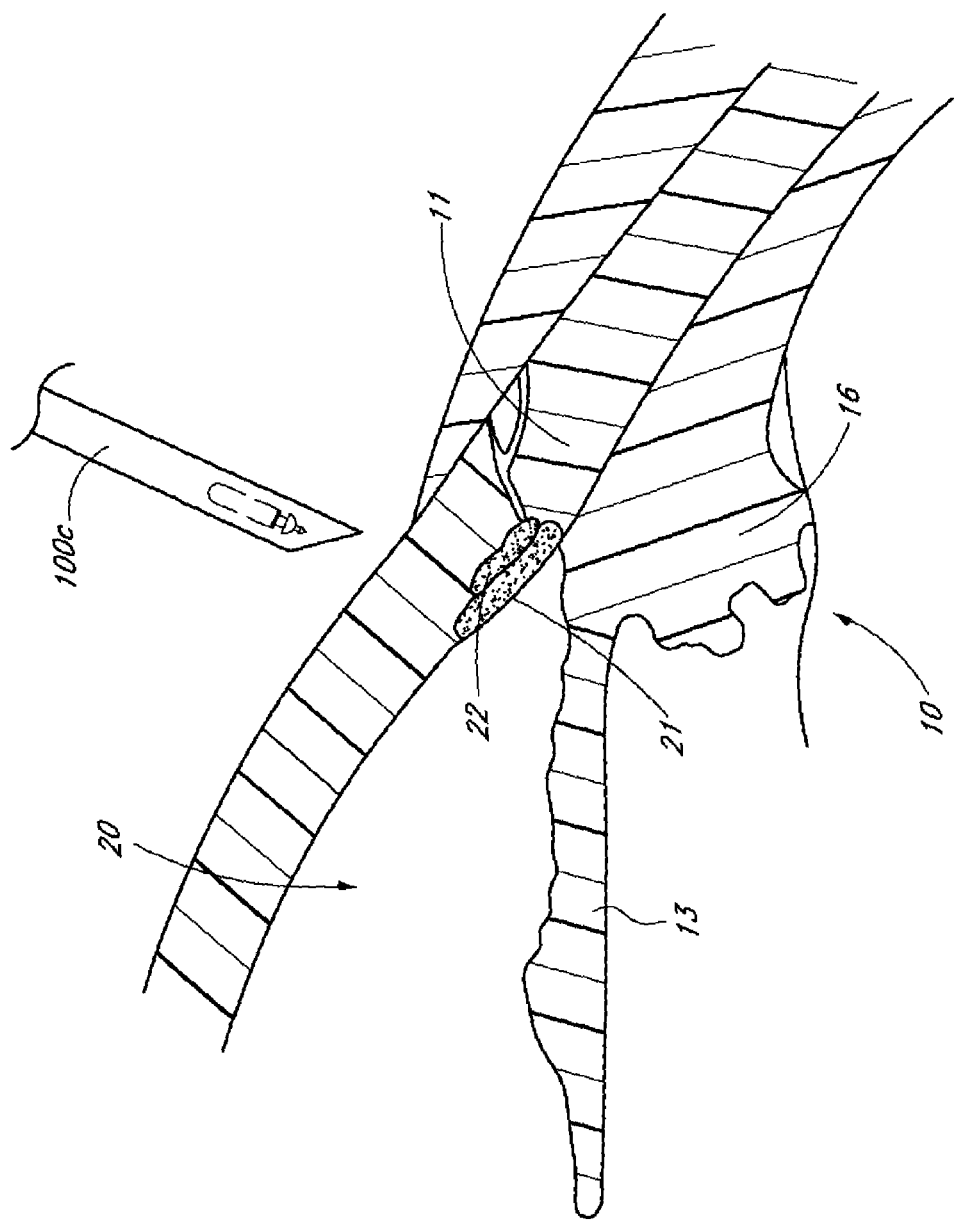
FIG. 29 illustrates a schematic cross-sectional view of an eye with another embodiment of a delivery device targeting the iris adjacent to the anterior chamber angle. The size of the shunt is exaggerated for illustration purposes.

FIG. 29 shows an illustrative method for placing any of the various implant embodiments taught or suggested herein at implant site on the same side of the eye. In one embodiment, the drug delivery implant is inserted into the anterior chamber 20 of the eye 10 to the iris with the aid of an applicator or delivery apparatus 100c that creates a small puncture in the eye from the outside. In some embodiments, the target implant site is the inferior portion of the iris.

Figure 30:
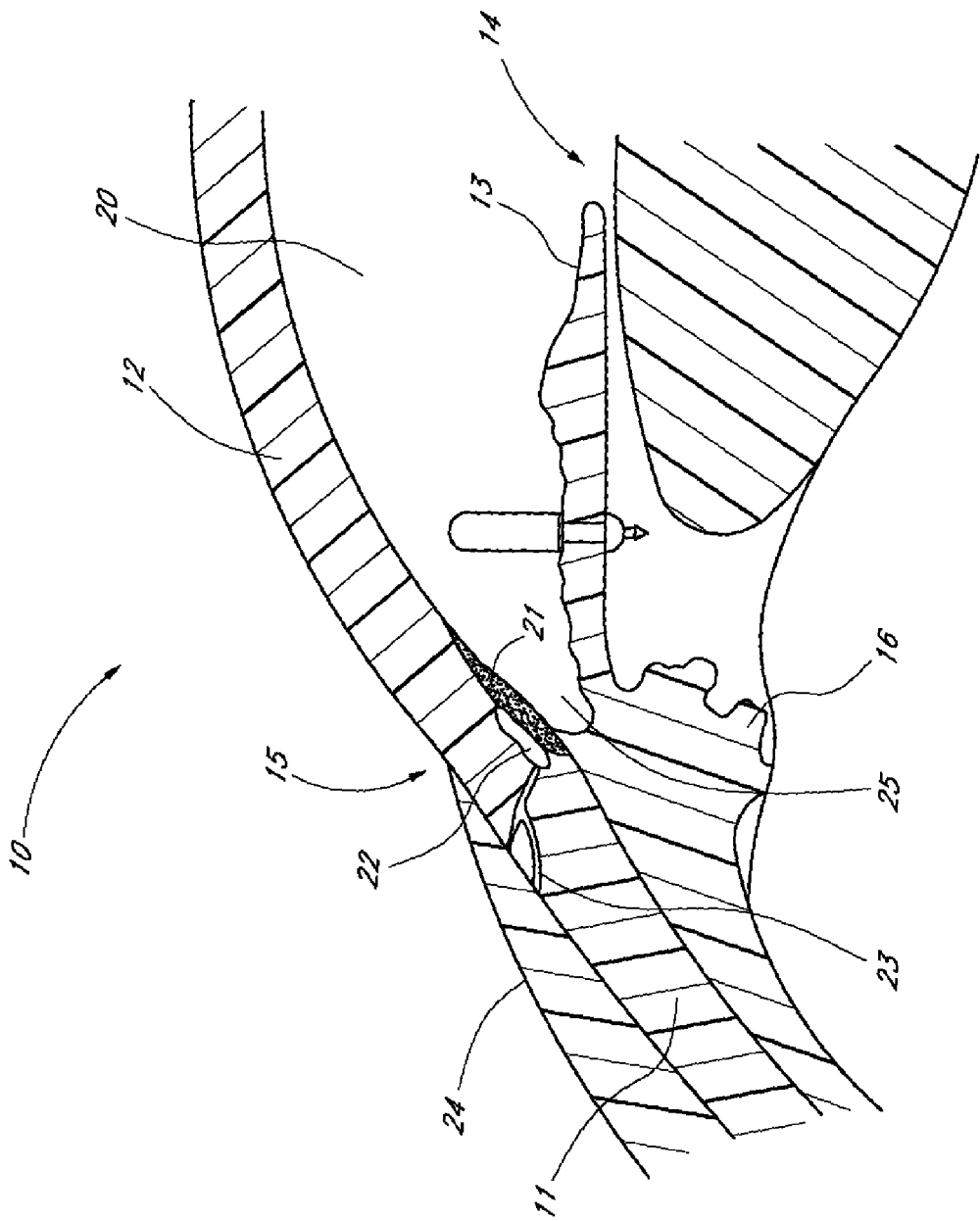
FIG. 30 illustrates a schematic cross-section view of an eye with an implant anchored to the iris.

FIG. 30 illustrates a drug delivery implant consistent with several embodiments disclosed herein affixed to the iris 13 of the eye 10 consistent with several implantation methods disclosed herein. It shall be appreciated that the iris is but one of many tissues that an implant as described here may be anchored to.

Figure 31:
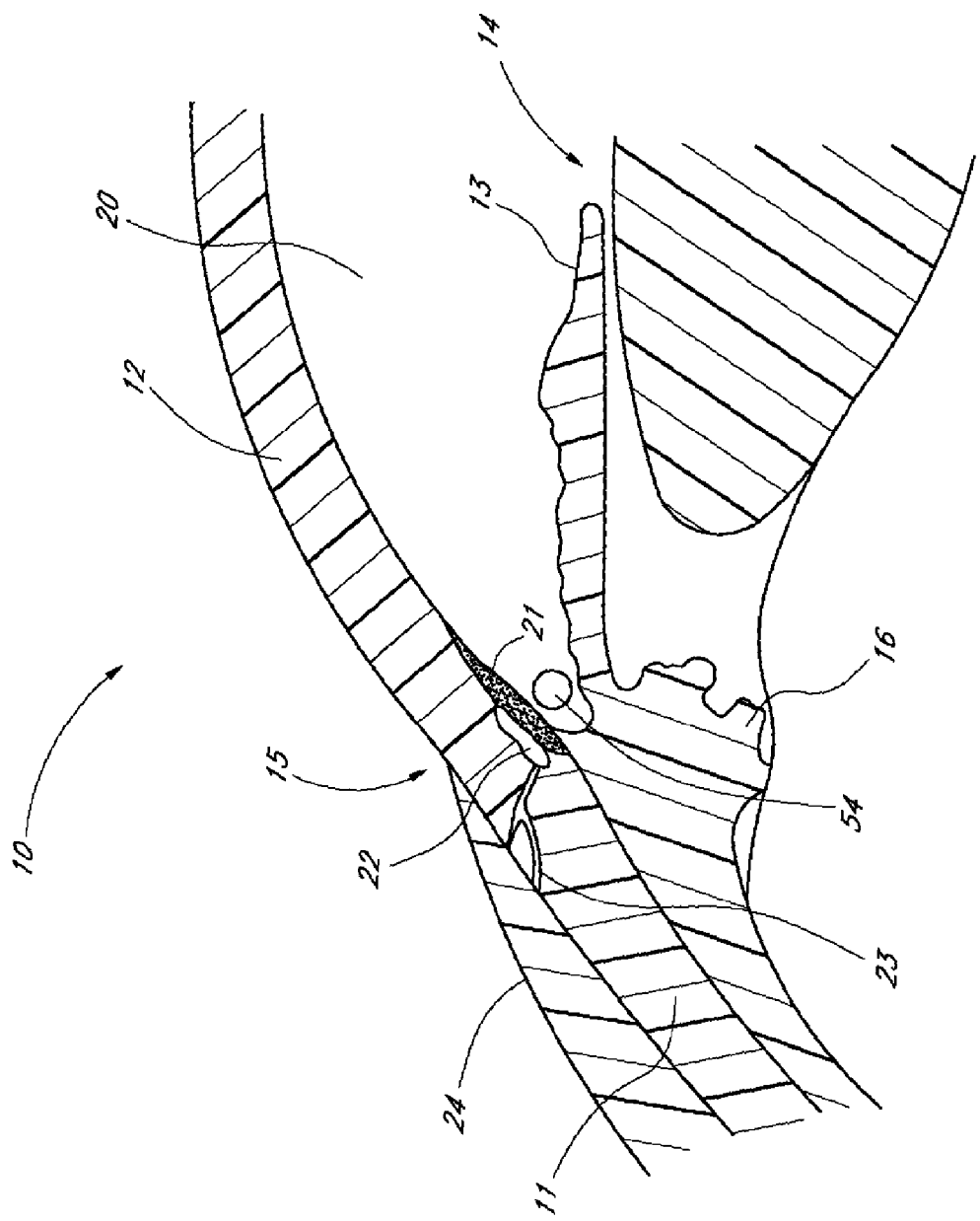
FIG. 31 illustrates a schematic cross-section view of an eye with an implant implanted in the anterior chamber angle.

FIG. 31 illustrates another possible embodiment of placement of a drug delivery implant consistent with several embodiments disclosed herein. In one embodiment, the outer shell 54 of an implant consistent with several embodiments disclosed herein is shown (in cross section) positioned in the anterior chamber angle. In one embodiment, the transocular delivery method and apparatus may be used to position the drug delivery implant wholly within the anterior chamber angle, wherein the drug delivery implant substantially tracks the curvature of the anterior angle. In some embodiments, the implant is positioned substantially within the anterior chamber angle along the inferior portion of the iris.

In some embodiments, the placement of the implant may result in the drug target being upstream of the natural flow of aqueous humor in the eye. For example, aqueous humor flows from the ciliary processes to the anterior chamber angle, which, based on the site of implantation in certain embodiments, may create a flow of fluid against which a drug released from an implant may have to travel in order to make contact with a target tissue. Thus, in certain embodiments, for example when the target tissue is the ciliary processes, eluted drug must diffuse through iris tissue to get from the anterior chamber to target receptors in the ciliary processes in the posterior chamber. The requirement for diffusion of drug through the iris, and the flow of the aqueous humor, in certain instances, may limit the amount of eluted drug reaching the ciliary body.

To overcome these issues, certain embodiments involve placement of a peripheral iridotomy (PI), or device-stented PI, at a location adjacent to a drug eluting implant to facilitate delivery of a drug directly to the intended site of action (i.e., the target tissue). The creation of a PI opens a relatively large communication passage between the posterior and anterior chambers. While a net flow of aqueous humor from the posterior chamber to the anterior chamber still exists, the relatively large diameter of the PI substantially reduces the linear flow velocity. Thus, eluted drug is able to diffuse through the PI without significant opposition from flow of aqueous humor. In certain such embodiments, a portion of the implant is structured to penetrate the iris and elute the drug directly into the posterior chamber at the ciliary body. In other embodiments, the implant is implanted and/or anchored in the iris and elutes drug directly to the posterior chamber and adjacent ciliary body.

Figure 22:
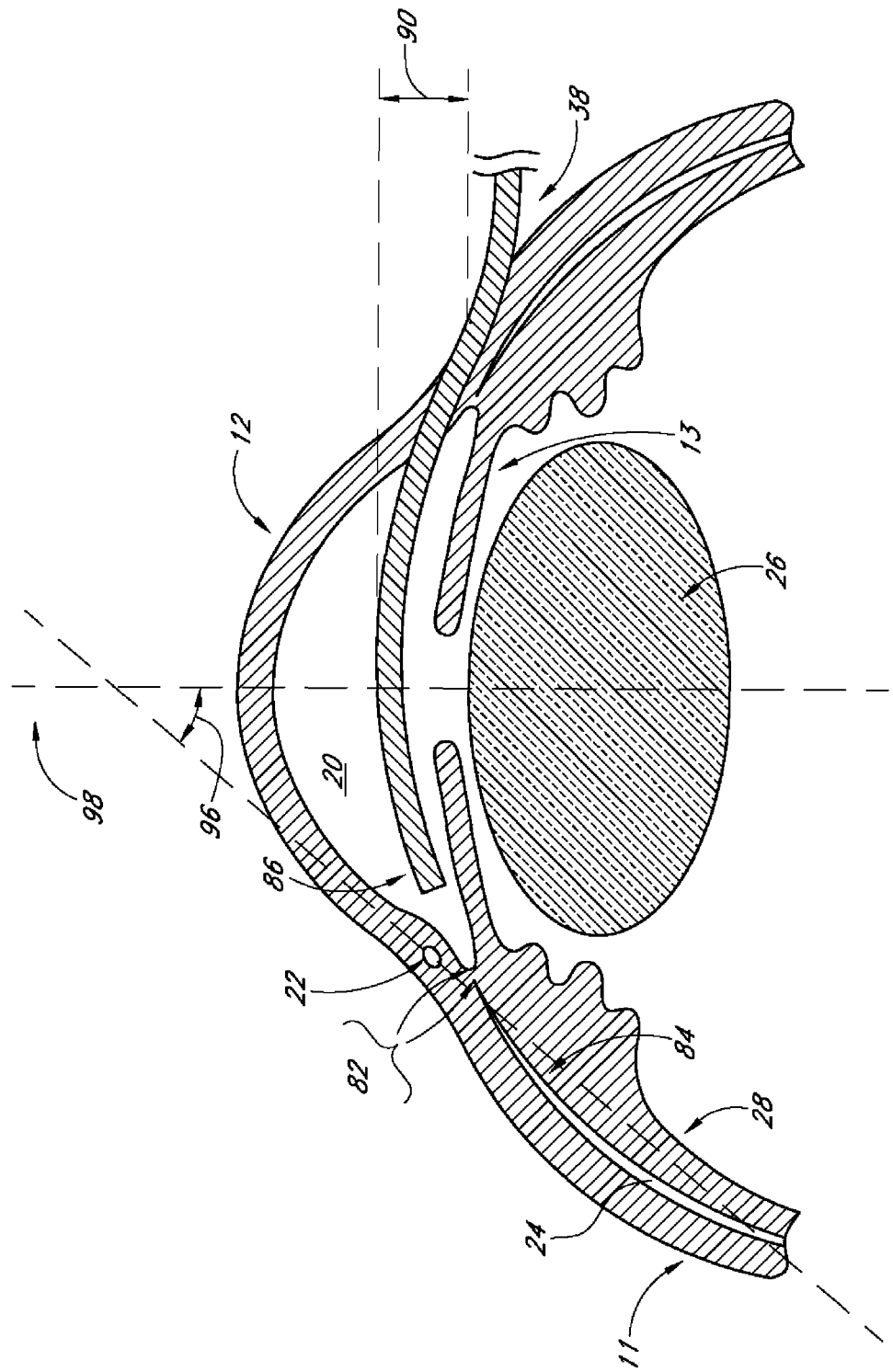
FIG. 22 illustrates another apparatus for implanting a drug delivery device in accordance with embodiments disclosed herein.

FIG. 22 shows a meridional section of the anterior segment of the human eye and schematically illustrates another embodiment of a delivery instrument 38 that may be used with embodiments of drug delivery implants described herein. In FIG. 22, arrows 82 show the fibrous attachment zone of the ciliary muscle 84 to the sclera 11. The ciliary muscle 84 is coextensive with the choroid 28. The suprachoroidal space is the interface between the choroid 28 and the sclera 11. Other structures in the eye include the lens 26, the cornea 12, the anterior chamber 20, the iris 13, and Schlemm's canal 22.

The delivery instrument/implant assembly can be passed between the iris 13 and the cornea 12 to reach the iridocorneal angle. Therefore, the height of the delivery instrument/shunt assembly (dimension 90 in FIG. 22) is less than about 3 mm in some embodiments, and less than 2 mm in other embodiments.

The suprachoroidal space between the choroid 28 and the sclera 11 generally forms an angle 96 of about 55° with the optical axis 98 of the eye. This angle, in addition to the height requirement described in the preceding paragraph, are features to consider in the geometrical design of the delivery instrument/implant assembly.

The overall geometry of the drug delivery implant system makes it advantageous that the delivery instrument 38 incorporates a distal curvature 86, as shown in FIG. 22, a distal angle 88, as shown in FIG. 21, or a combination thereof. The distal curvature (FIG. 23) is expected to pass more smoothly through the corneal or scleral incision at the limbus. In this embodiment, the drug delivery implant may be curved or flexible. Alternatively, in the design of FIG. 21, the drug delivery implant may be mounted on the straight segment of the delivery instrument, distal of the "elbow" or angle 88. In this case, the drug delivery implant may be straight and relatively inflexible, and the delivery instrument may incorporate a delivery mechanism that is flexible enough to advance through the angle. In some embodiments, the drug delivery implant may be a rigid tube, provided that the implant is no longer than the length of the distal segment 92.

The distal curvature 86 of delivery instrument 38 may be characterized as a radius of between about 10 to 30 mm in some embodiments, and about 20 mm in certain embodiments. The distal angle of the delivery instrument in an embodiment as depicted in FIG. 21 may be characterized as between about 90 to 170 degrees relative to an axis of the proximal segment 94 of the delivery instrument. In other embodiments, the angle may be between about 145 and about 170 degrees. The angle incorporates a small radius of curvature at the "elbow" so as to make a smooth transition from the proximal segment 94 of the delivery instrument to the distal segment 92. The length of the distal segment 92 may be approximately 0.5 to 7 mm in some embodiments, and about 2 to 3 mm in certain embodiments.

In some embodiments, a viscoelastic, or other fluid is injected into the suprachoroidal space to create a chamber or pocket between the choroid and sclera which can be accessed by a drug delivery implant. Such a pocket exposes more of the choroidal and scleral tissue area, provides lubrication and protection for tissues during implantation, and increases uveoscleral outflow in embodiments where the drug delivery implant includes a shunt, causing a lower intraocular pressure (IOP). In some embodiments, the viscoelastic material is injected with a 25 or 27G cannula, for example, through an incision in the ciliary muscle attachment or through the sclera (e.g. from outside the eye). The viscoelastic material may also be injected through the implant itself either before, during or after implantation is completed.

In some embodiments, a hyperosmotic agent is injected into the suprachoroidal space. Such an injection can delay IOP reduction. Thus, hypotony may be avoided in the acute postoperative period by temporarily reducing choroidal absorption. The hyperosmotic agent may be, for example glucose, albumin, HYPAQUE™ medium, glycerol, or poly (ethylene glycol). The hyperosmotic agent can breakdown or wash out as the patient heals, resulting in a stable, acceptably low IOP, and avoiding transient hypotony.

Controlled Drug Release

The drug delivery implants as described herein, function to house a drug and provide drug elution from the implant in a controlled fashion, based on the design of the various components of the implant, for an extended period of time. Various elements of the implant composition, implant physical characteristics, implant location in the eye, and the composition of the drug work in combination to produce the desired drug release profile.

As described above the drug delivery implant may be made from any biological inert and biocompatible materials having desired characteristics. Desirable characteristics, in some embodiments, include permeability to liquid water or water vapor, allowing for an implant to be manufactured, loaded with drug, and sterilized in a dry state, with subsequent rehydration of the drug upon implantation. Also desirable is an implant constructed of a material comprising microscopic porosities between polymer chains. These porosities may interconnect, which forms channels of water through the implant material. In several embodiments, the resultant channels are convoluted and thereby form a tortuous path which solubilzed drug travels during the elution process. Implant materials advantageously also possess sufficient permeability to a drug such that the implant may be a practical size for implantation. Thus, in several embodiments, the implant material is sufficiently permeable to the drug to be delivered that the implant is dimensioned to reside wholly contained within the eye of a subject. Implant material also ideally possesses sufficient elasticity, flexibility and potential elongation to not only conform to the target anatomy during and after implantation, but also remain unkinked, untorn, unpunctured, and with a patent lumen during and after implantation. In several embodiments, implant material would advantageously processable in a practical manner, such as, for example, by molding, extrusion, thermoforming, and the like.

Illustrative, examples of suitable materials for the outer shell include polypropylene, polyimide, glass, nitinol, polyvinyl alcohol, polyvinyl pyrolidone, collagen, chemically-treated collagen, polyethersulfone (PES), poly(styrene-isobutyl-styrene), polyurethane, ethyl vinyl acetate (EVA), polyetherether ketone (PEEK), Kynar (Polyvinylidene Fluoride; PVDF), Polytetrafluoroethylene (PTFE), Polymethylmethacrylate (PMMA), Pebax, acrylic, polyolefin, polydimethylsiloxane and other silicone elastomers, polypropylene, hydroxyapetite, titanium, gold, silver, platinum, other metals and alloys, ceramics, plastics and mixtures or combinations thereof. Additional suitable materials used to construct certain embodiments of the implant include, but are not limited to, poly(lactic acid), poly(tyrosine carbonate), polyethylene-vinyl acetate, poly(L-lactic acid), poly(D,L-lactic-co-glycolic acid), poly(D,L-lactide), poly(D,L-lactide-co-trimethylene carbonate), collagen, heparinized collagen, poly (caprolactone), poly(glycolic acid), and/or other polymer, copolymers, or block co-polymers, polyester urethanes, polyester amides, polyester ureas, polythioesters, thermoplastic polyurethanes, silicone-modified polyether urethanes, poly(carbonate urethane), or polyimide. Thermoplastic polyurethanes are polymers or copolymers which may comprise aliphatic polyurethanes, aromatic polyurethanes, polyurethane hydrogel-forming materials, hydrophilic polyurethanes (such as those described in U.S. Pat. No. 5,428,123, which is incorporated in its entirety by reference herein), or combinations thereof. Non-limiting examples include elasthane (poly(ether urethane)) such as Elasthane™ 80A, Lubrizol, Tecophilic™, Pellethane™, Carbothane™, Tecothane™, Tecoplast™, and Estane™. In some embodiments, polysiloxane-containing polyurethane elastomers are used, which include Carbosil™ 20 or Pursil™ 20 80A, Elast-Eon™, and the like. Hydrophilic and/or hydrophobic materials may be used. Non-limiting examples of such elastomers are provided in U.S. Pat. No. 6,627,724, which is incorporated in its entirety by reference herein. Poly(carbonate urethane) may include Bionate™ 80A or similar polymers. In several embodiments, such silicone modified polyether urethanes are particularly advantageous based on improved biostability of the polymer imparted by the inclusion of silicone. In addition, in some embodiments, oxidative stability and thrombo-resistance is also improved as compared to non-modified polyurethanes. In some embodiments, there is a reduction in angiogenesis, cellular adhesion, inflammation, and/or protein adsorption with silicone-modified polyether urethanes. In other embodiments, should angiogenesis, cellular adhesion or protein adsorption (e.g., for assistance in anchoring an implant) is preferable, the degree of silicone (or other modifier) may be adjusted accordingly. Moreover, in some embodiments, silicone modification reduces the coefficient of friction of the polymer, which reduces trauma during implantation of devices described herein. In some embodiments, silicone modification, in addition to the other mechanisms described herein, is another variable that can be used to tailor the permeability of the polymer. Further, in some embodiments, silicone modification of a polymer is accomplished through the addition of silicone-containing surface modifying endgroups to the base polymer. In other embodiments, fluorocarbon or polyethylene oxide surface modifying endgroups are added to a based polymer. In several embodiments, one or more biodegradable materials are used to construct all or a portion of the implant, or any other device disclosed herein. Such materials include any suitable material that degrades or erodes over time when placed in the human or animal body, whether due to a particular chemical reaction or enzymatic process or in the absence of such a reaction or process. Accordingly, as the term is used herein, biodegradable material includes bioerodible materials. In such biodegradable embodiments, the degradation rate of the biodegradable outer shell is another variable (of many) that may be used to tailor the drug elution rate from an implant.

In some embodiments, such as where the drug is sensitive to moisture (e.g. liquid water, water vapor, humidity) or where the drug's long term stability may be adversely affected by exposure to moisture, it may be desirable to utilize a material for the implant or at least a portion of the implant, which is water resistant, water impermeable or waterproof such that it presents a significant barrier to the intrusion of liquid water and/or water vapor, especially at or around human body temperature (e.g. about 35-40° C. or 37° C.). This may be accomplished by using a material that is, itself, water resistant, water impermeable or waterproof.

In some circumstances, however, even materials that are generally considered water impermeable may still allow in enough water to adversely affect the drug within an implant. For example, it may be desirable to have 5% by weight of the drug or less water intrusion over the course of a year. In one embodiment of implant, this would equate to a water vapor transmission rate for a material of about $1 \times 10^{-3}$ g/m²/day or less. This may be as much as one-tenth of the water transmission rate of some polymers generally considered to be water resistant or water impermeable. Therefore, it may be desirable to increase the water resistance or water impermeability of a material.

The water resistance or water impermeability of a material may be increased by any suitable method. Such methods of treatment include providing a coating for a material (including by lamination) or by compounding a material with a component that adds water resistance or increases impermeability. For example, such treatment may be performed on the implant (or portion of the implant) itself, it may be done on the material prior to fabrication (e.g. coating a polymeric tube), or it may be done in the formation of the material itself (e.g. by compounding a resin with a material prior to forming the resin into a tube or sheet). Such treatment may include, without limitation, one or more of the following: coating or laminating the material with a hydrophobic polymer or other material to increase water resistance or impermeability; compounding the material with hydrophobic or other material to increase water resistance or impermeability; compounding or treating the material with a substance that fills microscopic gaps or pores within the material that allow for ingress of water or water vapor; coating and/or compounding the material with a water scavenger or hygroscopic material that can absorb, adsorb or react with water so as to increase the water resistance or impermeability of the material.

One type of material that may be employed as a coating to increase water resistance and/or water impermeability is an inorganic material. Inorganic materials include, but are not limited to, metals, metal oxides and other metal compounds (e.g. metal sulfides, metal hydrides), ceramics, and main group materials and their compounds (e.g. carbon (e.g. carbon nanotubes), silicon, silicon oxides). Examples of suitable materials include aluminum oxides (e.g. $Al_2O_3$) and silicon oxides (e.g. $SiO_2$). Inorganic materials may be advantageously coated onto a material (at any stage of manufacture of the material or implant) using techniques such as are known in the art to create extremely thin coatings on a substrate, including by vapor deposition, atomic layer deposition, plasma deposition, and the like. Such techniques can provide for the deposition of very thin coatings (e.g. about 20 nm-40 nm thick, including about 25 nm thick, about 30 nm thick, and about 35 nm thick) on substrates, including polymeric substrates, and can provide a coating on the exterior and/or interior luminal surfaces of small tubing, including that of the size suitable for use in implants disclosed herein. Such coatings can provide excellent resistance to the permeation of water or water vapor while still being at least moderately flexible so as not to undesirably compromise the performance of an implant in which flexibility is desired.

In order to control the dose or duration of treatment, in embodiments wherein the therapeutic agents are delivered via flexible tethered implants (see, e.g., FIGS. 16-17), one or more flexible sheets or discs may be simultaneously used. Similarly the material used to construct the sheets or discs and/or the coatings covering them may be prepared to control the rate of release of the drug, similar to as discussed below.

The drugs carried by the drug delivery implant may be in any form that can be reasonably retained within the device and results in controlled elution of the resident drug or drugs over a period of time lasting at least several days and in some embodiments up to several weeks, and in certain preferred embodiments, up to several years. Certain embodiments utilize drugs that are readily soluble in ocular fluid, while other embodiments utilize drugs that are partially soluble in ocular fluid.

For example, the therapeutic agent may be in any form, including but not limited to a compressed pellet, a solid, a capsule, multiple particles, a liquid, a gel, a suspension, slurry, emulsion, and the like. In certain embodiments, drug particles are in the form of micro-pellets (e.g., micro-tablets), fine powders, or slurries, each of which has fluid-like properties, allowing for recharging by injection into the inner lumen(s). As discussed above, in some embodiments, the loading and/or recharging of a device is accomplished with a syringe/needle, through which the therapeutic agent is delivered. In some embodiments, micro-tablets are delivered through a needle of about 23 gauge to about 32 gauge, including 23-25 gauge, 25 to 27 gauge, 27-29 gauge, 29-30 gauge, 30-32 gauge, and overlapping ranges thereof. In some embodiments, the needle is 23, 24, 25, 26, 27, 28, 29, 30, 31, or 32 gauge.

When more than one drug is desired for treatment of a particular pathology or when a second drug is administered such as to counteract a side effect of the first drug, some embodiments may utilize two agents of the same form. In other embodiments, agents in different form may be used. Likewise, should one or more drugs utilize an adjuvant, excipient, or auxiliary compound, for example to enhance stability or tailor the elution profile, that compound or compounds may also be in any form that is compatible with the drug and can be reasonably retained with the implant.

In some embodiments, treatment of particular pathology with a drug released from the implant may not only treat the pathology, but also induce certain undesirable side effects. In some cases, delivery of certain drugs may treat a pathological condition, but indirectly increase intraocular pressure. Steroids, for example, may have such an effect. In certain embodiments, a drug delivery shunt delivers a steroid to an ocular target tissue, such as the retina or other target tissue as described herein, thereby treating a retinal pathology but also possibly inducing increased intraocular pressure which may be due to local inflammation or fluid accumulation. In such embodiments, the shunt feature reduces undesirable increased intraocular pressure by transporting away the accumulated fluid. Thus, in some embodiments, implants functioning both as drug delivery devices and shunts can not only serve to deliver a therapeutic agent, but simultaneously drain away accumulated fluid, thereby alleviating the side effect of the drug. Such embodiments can be deployed in an ocular setting, or in any other physiological setting where delivery of a drug coordinately causes fluid accumulation which needs to be reduced by the shunt feature of the implant. In some such embodiments, drainage of the accumulated fluid is necessary to avoid tissue damage or loss of function, in particular when the target tissue is pressure sensitive or has a limited space or capacity to expand in response to the accumulated fluid. The eye and the brain are two non-limiting examples of such tissues.

It will be understood that embodiments as described herein may include a drug mixed or compounded with a biodegradable material, excipient, or other agent modifying the release characteristics of the drug. Preferred biodegradable materials include copolymers of lactic acid and glycolic acid, also known as poly (lactic-co-glycolic acid) or PLGA. It will be understood by one skilled in the art that although some disclosure herein specifically describes use of PLGA, other suitable biodegradable materials may be substituted for PLGA or used in combination with PLGA in such embodiments. It will also be understood that in certain embodiments as described herein, the drug positioned within the lumen of the implant is not compounded or mixed with any other compound or material, thereby maximizing the volume of drug that is positioned within the lumen.

It may be desirable, in some embodiments, to provide for a particular rate of release of drug from a PLGA copolymer or other polymeric material. As the release rate of a drug from a polymer correlates with the degradation rate of that polymer, control of the degradation rate provides a means for control of the delivery rate of the drug contained within the therapeutic agent. Variation of the average molecular weight of the polymer or copolymer chains which make up the PLGA copolymer or other polymer may be used to control the degradation rate of the copolymer, thereby achieving a desired duration or other release profile of therapeutic agent delivery to the eye.

In certain other embodiments employing PLGA copolymers, rate of biodegradation of the PLGA copolymer may be controlled by varying the ratio of lactic acid to glycolic acid units in a copolymer.

Still other embodiments may utilize combinations of varying the average molecular weights of the constituents of the copolymer and varying the ratio of lactic acid to glycolic acid in the copolymer to achieve a desired biodegradation rate.

As described above, the outer shell of the implant comprises a polymer in some embodiments. Additionally, the shell may further comprise one or more polymeric coatings in various locations on or within the implant. The outer shell and any polymeric coatings are optionally biodegradable. The biodegradable outer shell and biodegradable polymer coating may be any suitable material including, but not limited to, poly(lactic acid), polyethylene-vinyl acetate, poly (lactic-co-glycolic acid), poly(D,L-lactide), poly(D,L-lactide-co-trimethylene carbonate), collagen, heparinized collagen, poly(caprolactone), poly(glycolic acid), and/or other polymer or copolymer.

As described above, some embodiments of the implants comprise a polymeric outer shell that is permeable to ocular fluids in a controlled fashion depending on the constituents used in forming the shell. For example, the concentration of the polymeric subunits dictates the permeability of the resulting shell. Therefore, the composition of the polymers making up the polymeric shell determines the rate of ocular fluid passage through the polymer and if biodegradable, the rate of biodegradation in ocular fluid. The permeability of the shell will also impact the release of the drug from the shell. Also as described above, the regions of drug release created on the shell will alter the release profile of a drug from the implant. Control of the release of the drug can further be controlled by coatings in or on the shell that either form the regions of drug release, or alter the characteristics of the regions of drug release (e.g., a coating over the region of drug release makes the region thicker, and therefore slows the rate of release of a drug).

For example, a given combination of drug and polymer will yield a characteristic diffusion coefficient D, such that:

$$\text{Elution rate} = \frac{[D \times A \times (C_i - C_o)]}{d}$$

where D=diffusion coefficient (cm²/sec)
A=area of the region of drug release
(Ci−Co)=difference in drug concentration between the inside and outside of the device.
d=thickness of the region of drug release Thus, the area and thickness of the region of drug release are variables that determine, in part, the rate of elution of the drug from the implant, and are also variable that can be controlled during the process of manufacturing the implant. In some embodiments using a highly insoluble drug, the region of drug release could be manufactured to be thin (d is small) or with a large overall area (A is large) or a combination of the two (as dictated by the structural sufficiency of the outer shell). In either case, the end result is that the elution rate of the drug can be increased to compensate for the low solubility of the drug based on the structure and design of the implant.

In contrast, in some embodiments using a highly soluble drug, the regions of drug release are made of substantially the same thickness as the remainder of the outer shell, made of small area, or combinations thereof.

Additionally, certain embodiments use additional polymer coatings to either (i) increase the effective thickness (d) of the region of drug release or (ii) decrease the overall permeability of the of that portion of the implant (region of drug release plus the coating), resulting in a reduction in drug elution. In still other embodiments, multiple additional polymer coatings are used. By covering either distinct or overlapping portions of the implant and the associated regions of drug release on the outer shell, drug release from various regions of the implant are controlled and result in a controlled pattern of drug release from the implant overall. For example, an implant with at least two regions of drug release may be coated with two additional polymers, wherein the additional polymers both cover over region of release and only a single polymer covers the other region. Thus the elution rate of drug from the two regions of drug release differ, and are controllable such that, for example, drug is released sequentially from the two regions. In other embodiments, the two regions may release at different rates. In those embodiments with multiple interior lumens, different concentrations or different drugs may also be released. It will be appreciated that these variables are controllable to alter to rate or duration of drug release from the implant such that a desired elution profile or treatment regimen can be created.

In several embodiments as described herein, there are no direct through holes or penetrating apertures needed or utilized to specifically facilitate or control drug elution. As such, in those embodiments, there is no direct contact between the drug core (which may be of very high concentration) and the ocular tissue where adjacent to the site where the implant is positioned. In some cases, direct contact of ocular tissue with high concentrations of drug residing within the implant could lead to local cell toxicity and possible local cell death.

It shall however, be appreciated that, in several other embodiments, disclosed herein, that the number, size, and placement of one or more orifices through the outer shell of the implant may be altered in order to produce a desired drug elution profile. As the number, size, or both, of the orifices increases relative to surface area of the implant, increasing amounts of ocular fluid pass across the outer shell and contact the therapeutic agent on the interior of the implant. Likewise, decreasing the ratio of orifice:outer shell area, less ocular fluid will enter the implant, thereby providing a decreased rate of release of drug from the implant. Additionally, multiple orifices provides a redundant communication means between the ocular environment that the implant is implanted in and the interior of the implant, should one or more orifices become blocked during implantation or after residing in the eye. In other embodiments, the outer shell may contain one (or more) orifice(s) in the distal tip of the implant. As described above, the shape and size of this orifice is selected based on the desired elution profile. In some embodiments, a biodegradable polymer plug is positioned within the distal orifice, thereby acting as a synthetic cork. Tissue trauma or coring of the ocular tissue during the process of implantation is also reduced, which may prevent plugging or partial occlusion of the distal orifice. Additionally, because the polymer plug may be tailored to biodegrade in a known time period, the plug ensures that the implant can be fully positioned before any elution of the drug takes place. Still other embodiments comprise a combination of a distal orifice and multiple orifices placed more proximally on the outer shell, as described above.

Moreover, the addition of one or more permeable or semi-permeable coatings on an implant (either with orifices or regions of drug release) may also be used to tailor the elution profile. Additionally, combinations of these various elements may be used in some embodiments to provide multiple methods of controlling the drug release profile.

Further benefiting the embodiments described herein is the expanded possible range of uses for some ocular therapy drugs. For example, a drug that is highly soluble in ocular fluid may have narrow applicability in treatment regimes, as its efficacy is limited to those pathologies treatable with acute drug administration. However, when coupled with the implants as disclosed herein, such a drug could be utilized in a long term therapeutic regime. A highly soluble drug positioned within the distal portion of the implant containing one or more regions of drug release may be made to yield a particular, long-term controlled release profile.

Alternatively, or in addition to one or more regions of drug release, one or more polymeric coatings may be located outside the implant shell, or within the interior lumen, enveloping or partially enveloping the drug. In some embodiments comprising one or more orifices, the polymeric coating is the first portion of the implant in contact with ocular fluid, and thus, is a primary controller of the rate of entry of ocular fluid into the drug containing interior lumen of the implant. By altering the composition of the polymer coating, the biodegradation rate (if biodegradable), and porosity of the polymer coating the rate at which the drug is exposed to and solubilzed in the ocular fluid may be controlled. Thus, there is a high degree of control over the rate at which the drug is released from such an embodiment of an implant to the target tissue of the eye. Similarly, a drug with a low ocular fluid solubility may be positioned within an implant coated with a rapidly biodegradable or highly porous polymer coating, allowing increased flow of ocular fluid over the drug within the implant.

In certain embodiments described herein, the polymer coating envelopes the therapeutic agent within the lumen of the implant. In some such embodiments, the ocular fluid passes through the outer shell of the implant and contacts the polymer layer. Such embodiments may be particularly useful when the implant comprises one or more orifices and/or the drug to be delivered is a liquid, slurry, emulsion, or particles, as the polymer layer would not only provide control of the elution of the drug, but would assist in providing a structural barrier to prevent uncontrolled leakage or loss of the drug outwardly through the orifices. The interior positioning of the polymer layer could, however, also be used in implants where the drug is in any form.

In some ocular disorders, therapy may require a defined kinetic profile of administration of drug to the eye. It will be appreciated from the above discussion of various embodiments that the ability to tailor the release rate of a drug from the implant can similarly be used to accomplish achieve a desired kinetic profile. For example the composition of the outer shell and any polymer coatings can be manipulated to provide a particular kinetic profile of release of the drug. Additionally, the design of the implant itself, including the thickness of the shell material, the thickness of the shell in the regions of drug release, the area of the regions of drug release, and the area and/or number of any orifices in the shell provide a means to create a particular drug release profile. Likewise, the use of PLGA copolymers and/or other controlled release materials and excipients, may provide particular kinetic profiles of release of the compounded drug. By tailoring the ratio of lactic to glycolic acid in a copolymer and/or average molecular weight of polymers or copolymers having the drug therein (optionally with one or more other excipients), sustained release of a drug, or other desirable release profile, may be achieved.

In certain embodiments, zero-order release of a drug may be achieved by manipulating any of the features and/or variables discussed above alone or in combination so that the characteristics of the implant are the principal factor controlling drug release from the implant. Similarly, in those embodiments employing PLGA compounded with the drug, tailoring the ratio of lactic to glycolic acid and/or average molecular weights in the copolymer-drug composition can adjust the release kinetics based on the combination of the implant structure and the biodegradation of the PLGA copolymer.

In other embodiments, pseudo zero-order release (or other desired release profile) may be achieved through the adjustment of the composition of the implant shell, the structure and dimension of the regions of drug release, the composition any polymer coatings, and use of certain excipients or compounded formulations (PLGA copolymers), the additive effect over time replicating true zero-order kinetics.

For example, in one embodiment, an implant with a polymer coating allowing entry of ocular fluid into the implant at a known rate may contain a series of pellets that compound PLGA with one or more drugs, wherein the pellets incorporate at least two different PLGA copolymer formulations. Based on the formulation of the first therapeutic agent, each subsequent agent may be compounded with PLGA in a manner as to allow a known quantity of drug to be released in a given unit of time. As each copolymer biodegrades or erodes at its individual and desired rate, the sum total of drug released to the eye over time is in effect released with zero-order kinetics. It will be appreciated that embodiments additionally employing the drug partitions as described herein, operating in conjunction with pellets having multiple PLGA formulations would add an additional level of control over the resulting rate of release and kinetic profile of the drug.

Non-continuous or pulsatile release may also be desirable. This may be achieved, for example, by manufacturing an implant with multiple sub-lumens, each associated with one or more regions of drug release. In some embodiments, additional polymer coatings are used to prevent drug release from certain regions of drug release at a given time, while drug is eluted from other regions of drug release at that time. Other embodiments additionally employ one or more biodegradable partitions as described above to provide permanent or temporary physical barriers within an implant to further tune the amplitude or duration of period of lowered or non-release of drug from the implant. Additionally, by controlling the biodegradation rate of the partition, the length of a drug holiday may be controlled. In some embodiments the biodegradation of the partition may be initiated or enhanced by an external stimulus. In some embodiments, the intraocular injection of a fluid stimulates or enhances biodegradation of the barrier. In some embodiments, the externally originating stimulus is one or more of application of heat, ultrasound, and radio frequency, or laser energy.

Certain embodiments are particularly advantageous as the regions of drug release minimize tissue trauma or coring of the ocular tissue during the process of implantation, as they are not open orifices. Additionally, because the regions are of a known thickness and area (and therefore of a known drug release profile) they can optionally be manufactured to ensure that the implant can be fully positioned before any elution of the drug takes place.

Placement of the drug within the interior of the outer shell may also be used as a mechanism to control drug release. In some embodiments, the lumen may be in a distal position, while in others it may be in a more proximal position, depending on the pathology to be treated. In those embodiments employing a nested or concentric tube device, the agent or agents may be placed within any of the lumens formed between the nested or concentric polymeric shells Further control over drug release is obtained by the placement location of drug in particular embodiments with multiple lumens. For example, when release of the drug is desired soon after implantation, the drug is placed within the implant in a first releasing lumen having a short time period between implantation and exposure of the therapeutic agent to ocular fluid. This is accomplished, for example by juxtaposing the first releasing lumen with a region of drug release having a thin outer shell thickness (or a large area, or both). A second agent, placed in a second releasing lumen with a longer time to ocular fluid exposure elutes drug into the eye after initiation of release of the first drug. This can be accomplished by juxtaposing the second releasing lumen with a region of drug release having a thicker shell or a smaller area (or both). Optionally, this second drug treats side effects caused by the release and activity of the first drug.

It will also be appreciated that the multiple lumens as described above are also useful in achieving a particular concentration profile of released drug. For example, in some embodiments, a first releasing lumen may contain a drug with a first concentration of drug and a second releasing lumen containing the same drug with a different concentration. The desired concentration profile may be tailored by the utilizing drugs having different drug concentration and placing them within the implant in such a way that the time to inception of drug elution, and thus concentration in ocular tissues, is controlled.

Further, placement location of the drug may be used to achieve periods of drug release followed by periods of no drug release. By way of example, a drug may be placed in a first releasing lumen such that the drug is released into the eye soon after implantation. A second releasing lumen may remain free of drug, or contain an inert bioerodible substance, yielding a period of time wherein no drug is released. A third releasing lumen containing drug could then be exposed to ocular fluids, thus starting a second period of drug release.

It will be appreciated that the ability to alter any one of or combination of the shell characteristics, the characteristics of any polymer coatings, any polymer-drug admixtures, the dimension and number of regions of drug release, the dimension and number of orifices, and the position of drugs within the implant provides a vast degree of flexibility in controlling the rate of drug delivery by the implant.

The drug elution profile may also be controlled by the utilization of multiple drugs contained within the same interior lumen of the implant that are separated by one or more plugs. By way of example, in an implant comprising a single region of drug release in the distal tip of the implant, ocular fluid entering the implant primarily contacts the distal-most drug until a point in time when the distal-most drug is substantially eroded and eluted. During that time, ocular fluid passes through a first semi-permeable partition and begins to erode a second drug, located proximal to the plug. As discussed below, the composition of these first two drugs, and the first plug, as well as the characteristics of the region of drug release may each be controlled to yield an overall desired elution profile, such as an increasing concentration over time or time-dependent delivery of two different doses of drug. Different drugs may also be deployed sequentially with a similar implant embodiment.

Partitions may be used if separation of two drugs is desirable. A partition is optionally biodegradable at a rate equal to or slower than that of the drugs to be delivered by the implant. The partitions are designed for the interior dimensions of a given implant embodiment such that the partition, when in place within the interior lumen of the implant, will seal off the more proximal portion of the lumen from the distal portion of the lumen. The partitions thus create individual compartments within the interior lumen. A first drug may be placed in the more proximal compartment, while a second drug, or a second concentration of the first drug, or an adjuvant agent may be placed in the more distal compartment. As described above, the entry of ocular fluid and rate of drug release is thus controllable and drugs can be released in tandem, in sequence or in a staggered fashion over time.

Partitions may also be used to create separate compartments for therapeutic agents or compounds that may react with one another, but whose reaction is desired at or near ocular tissue, not simply within the implant lumen. As a practical example, if each of two compounds was inactive until in the presence of the other (e.g. a prodrug and a modifier), these two compounds may still be delivered in a single implant having at least one region of drug release associated only with one drug-containing lumen. After the elution of the compounds from the implant to the ocular space the compounds would comingle, becoming active in close proximity to the target tissue. As can be determined from the above description, if more than two drugs are to be delivered in this manner, utilizing an appropriately increased number of partitions to segregate the drugs would be desirable.

In certain embodiments, a proximal barrier serves to seal the therapeutic agent within a distally located interior lumen of the implant. The purpose of such a barrier is to ensure that the ocular fluid from any more distally located points of ocular fluid entry is the primary source of ocular fluid contacting the therapeutic agent. Likewise, a drug impermeable seal is formed that prevents the elution of drug in an anterior direction. Prevention of anterior elution not only prevents dilution of the drug by ocular fluid originating from an anterior portion of the eye, but also reduces potential side of effects of drugs delivered by the device. Limiting the elution of the drug to sites originating in the distal region of the implant will enhance the delivery of the drug to the target sites in more posterior regions of the eye. In embodiments that are fully biodegradable, the proximal cap or barrier may comprise a biocompatible biodegradable polymer, characterized by a biodegradation rate slower than all the drugs to be delivered by that implant. It will be appreciated that the proximal cap is useful in those embodiments having a single central lumen running the length of the implant to allow recharging the implant after the first dose of drug has fully eluted. In those embodiments, the single central lumen is present to allow a new drug to be placed within the distal portion of the device, but is preferably sealed off at or near the proximal end to avoid anteriorly directed drug dilution or elution.

Similar to the multiple longitudinally located compartments that may be formed in an implant, drugs may also be positioned within one or more lumens nested within one another. By ordering particularly desirable drugs or concentrations of drugs in nested lumens, one may achieve similarly controlled release or kinetic profiles as described above.

Wicks, as described above, may also be employed to control the release characteristics of different drugs within the implant. One or more wicks leading into separate interior lumens of an implant assist in moving ocular fluid rapidly into the lumen where it may interact with the drug. Drugs requiring more ocular fluid for their release may optionally be positioned in a lumen where a wick brings in more ocular fluid than an orifice alone would allow. One or more wicks may be used in some embodiments.

In some embodiments, drugs are variably dimensioned to further tailor the release profile by increasing or limiting ocular fluid flow into the space in between the drug and walls of the interior lumen. For example, if it was optimal to have a first solid or semi solid drug elute more quickly than another solid or semi-solid drug, formation of the first drug to a dimension allowing substantial clearance between the drug and the walls of the interior lumen may be desirable, as ocular fluid entering the implant contacts the drug over a greater surface area. Such drug dimensions are easily variable based on the elution and solubility characteristics of a given drug. Conversely, initial drug elution may be slowed in embodiments with drugs dimensioned so that a minimal amount of residual space remains between the therapeutic agent and the walls of the interior lumen. In still other embodiments, the entirety of the implant lumen is filled with a drug, to maximize either the duration of drug release or limit the need to recharge an implant.

Certain embodiments may comprise a shunt in addition to the drug delivery portion of the implant. For example, once the implant is positioned in the desired intraocular space (in an anterior-posterior direction), a shunt portion of the implant comprising at least one outflow channel can be inserted into a physiological outflow space (for example anchored to the trabecular meshwork and releasing fluid to Schlemm's canal). In some embodiments, a plurality of apertures thus assists in maintaining patency and operability of the drainage shunt portion of the implant. Moreover, as described above, a plurality of apertures can assist in ameliorating any unwanted side effects involving excess fluid production or accumulation that may result from the actions of the therapeutic agent delivered by the implant.

As described above, duration of drug release is desired over an extended period of time. In some embodiments, an implant in accordance with embodiments described herein is capable of delivering a drug at a controlled rate to a target tissue for a period of several (i.e. at least three) months. In certain embodiments, implants can deliver drugs at a controlled rate to target tissues for about 6 months or longer, including 3, 4, 5, 6, 7, 8, 9, 12, 15, 18, and 24 months, without requiring recharging. In still other embodiments, the duration of controlled drug release (without recharging of the implant) exceeds 2 years (e.g., 3, 4, 5, or more years). It shall be appreciated that additional time frames including ranges bordering, overlapping or inclusive of two or more of the values listed above are also used in certain embodiments.

In conjunction with the controlled release of a drug to a target tissue, certain doses of a drug (or drugs) are desirable over time, in certain embodiments. As such, in some embodiments, the total drug load, for example the total load of a steroid, delivered to a target tissue over the lifetime of an implant ranges from about 10 to about 1000 µg. In certain embodiments the total drug load ranges from about 100 to about 900 µg, from about 200 to about 800 µg, from about 300 to about 700 µg, or from about 400 to about 600 µg. In some embodiments, the total drug load ranges from about 10 to about 300 µg, from about 10 to about 500 µg, or about 10 to about 700 µg. In other embodiments, total drug load ranges from about 200 to about 500 µg, from 400 to about 700 µg or from about 600 to about 1000 µg. In still other embodiments, total drug load ranges from about 200 to about 1000 µg, from about 400 to about 1000 µg, or from about 700 to about 1000 µg. In some embodiments total drug load ranges from about 500 to about 700 µg, about 550 to about 700 µg, or about 550 to about 650 µg, including 575, 590, 600, 610, and 625 µg. It shall be appreciated that additional ranges of drugs bordering, overlapping or inclusive of the ranges listed above are also used in certain embodiments.

Similarly, in other embodiments, controlled drug delivery is calculated based on the elution rate of the drug from the implant. In certain such embodiments, an elution rate of a drug, for example, a steroid, is about 0.05 µg/day to about 10 µg/day is achieved. In other embodiments an elution rate of about 0.05 µg/day to about 5 µg/day, about 0.05 µg/day to about 3 µg/day, or about 0.05 µg/day to about 2 µg/day is achieved. In other embodiment, an elution rate of about 2 µg/day to about 5 µg/day, about 4 µg/day to about 7 µg/day, or about 6 µg/day to about 10 µg/day is achieved. In other embodiments, an elution rate of about 1 µg/day to about 4 µg/day, about 3 µg/day to about 6 µg/day, or about 7 µg/day to about 10 µg/day is achieved. In still other embodiments, an elution rate of about 0.05 µg/day to about 1 µg/day, including 0.06, 0.07, 0.08, 0.09, 0.1, 0.2, 0.3, 0.4, 0.5, 0.6, 0.7, 0.8, or 0.9 µg/day is achieved. It shall be appreciated that additional ranges of drugs bordering, overlapping or inclusive of the ranges listed above are also used in certain embodiments.

Alternatively, or in addition to one or more of the parameters above, the release of drug from an implant may be controlled based on the desired concentration of the drug at target tissues. In some embodiments, the desired concentration of a drug, for example, a steroid, at the target tissue, ranges from about 1 nM to about 100 nM. In other embodiments the desired concentration of a drug at the site of action ranges from about 10 nM to about 90 nM, from about 20 nM to about 80 nM, from about 30 nM to about 70 nM, or from about 40 nM to about 60 nM. In still other embodiments the desired concentration of a drug at the site of action ranges from about 1 nM to about 40 nM, from about 20 nM to about 60 nM, from about 50 nM to about 70 nM, or from about 60 nM to about 90 nM. In yet other embodiments the desired concentration of a drug at the site of action ranges from about 1 nM to about 30 nM, from about 10 nM to about 50 nM, from about 30 nM to about 70 nM, or from about 60 nM to about 100 nM. In some embodiments, the desired concentration of a drug at the site of action ranges from about 45 nM to about 55 nM, including 46, 47, 48, 49, 50, 51, 52, 53, and 54 nM. It shall be appreciated that additional ranges of drugs bordering, overlapping or inclusive of the ranges listed above are also used in certain embodiments.

Certain embodiments described above are rechargeable. In some such embodiments, recharging is accomplished by injecting new drug into the lumen(s). In some embodiments, refilling the implanted drug delivery implant entails advancing a recharging device through the anterior chamber to the proximal end of the implant where the clamping sleeve may slide over the proximal end of the implant. See, e.g., FIG. 20A. An operator may then grasp the proximal end of the implant with the flexible clamping grippers to hold it securely. A new dose of drug in a therapeutic agent or a new drug is then pushed to its position within the implant by a flexible pusher tube which may be spring loaded. In some embodiments, the pusher tube includes a small internal recess to securely hold the therapeutic agent while in preparation for delivery to the implant. In other embodiments a flat surface propels the therapeutic agent into position within the implant.

The spring travel of the pusher is optionally pre-defined to push the therapeutic agent a known distance to the distal-most portion of the interior lumen of the implant. Alternatively, the spring travel can be set manually, for example if a new therapeutic agent is being placed prior to the time the resident therapeutic agent is fully eluted from the implant, thereby reducing the distance by which the new therapeutic agent needs to be advanced. In cooperation with optional anchor elements, the recharging process may be accomplished without significant displacement of the implant from its original position.

Optionally, seals for preventing leakage during recharging may be included in the recharging device. Such seals may desirable if, for example, the form of the drug to be refilled is a liquid. Suitable seals for preventing leakage include, for example, an o-ring, a coating, a hydrophilic agent, a hydrophobic agent, and combinations thereof. The coating can be, for example, a silicone coat such as MDX™ silicone fluid.

In other embodiments, recharging entails the advancement of a recharging device through the anterior chamber by way of a one-way valve. See FIGS. 20B and 20C. The valve comprises two or more flaps 70, open at the proximal end and reversibly closed at the distal end. The advancement of the recharging device opens the flaps at the posterior end, which allows for the deposition of drug into the posterior chamber. Upon removal of the recharging device, the flaps return to their closed position (at the distal end), thereby retaining the deposited drug within the lumen. In some embodiments, the one way valve is formed such that a seal is created to prevent backflow of liquid (including powders or micropellets with liquid-like flow properties) drug from the lumen. In other embodiments, a fluid-tight seal is not formed.

Other suitable retention methods may be used to hold the newly placed drug pellet in place. For example, in some embodiments, a deformable O-ring with an inner diameter smaller than the newly placed pellet is used. In such embodiments, the recharging device displaces the O-ring sufficiently to allow passage of the drug pellet through the O-ring. Upon removal of the device, however, the O-ring returns to its original diameter, thereby retaining the pellet within the lumen.

In yet other embodiments a plug made of a "self-healing" material that is penetrable by the recharging device is used. In such embodiments, pressure from the recharging device allows the device to penetrate the plug and deposit a new drug into the interior lumen. Upon withdrawal of the recharging device, the plug re-seals, and retains the drug within the lumen.

The one-way valve may be created of any material sufficiently flexible to allow the insertion and retention of a new drug into the lumen. Such materials include, but are not limited to, silicone, Teflon®, flexible graphite, sponge, silicone rubber, silicone rubber with fiberglass reinforcement, Neoprene®, red rubber, wire inserted red rubber, cork & Neoprene®, vegetable fiber, cork & rubber, cork & nitrile, fiberglass, cloth inserted rubber, vinyl, nitrile, butyl, natural gum rubber, urethane, carbon fiber, fluoroelastomer, and the like.

Drugs

The therapeutic agents utilized with the drug delivery implant, may include one or more drugs provided below, either alone or in combination. The drugs utilized may also be the equivalent of, derivatives of, or analogs of one or more of the drugs provided below. The drugs may include but are not limited to pharmaceutical agents including anti-glaucoma medications, ocular agents, antimicrobial agents (e.g., antibiotic, antiviral, antiparasitic, antifungal agents), anti-inflammatory agents (including steroids or non-steroidal anti-inflammatory), biological agents including hormones, enzymes or enzyme-related components, antibodies or antibody-related components, oligonucleotides (including DNA, RNA, short-interfering RNA, antisense oligonucleotides, and the like), DNA/RNA vectors, viruses (either wild type or genetically modified) or viral vectors, peptides, proteins, enzymes, extracellular matrix components, and live cells configured to produce one or more biological components. The use of any particular drug is not limited to its primary effect or regulatory body-approved treatment indication or manner of use. Drugs also include compounds or other materials that reduce or treat one or more side effects of another drug or therapeutic agent. As many drugs have more than a single mode of action, the listing of any particular drug within any one therapeutic class below is only representative of one possible use of the drug and is not intended to limit the scope of its use with the ophthalmic implant system.

As discussed above, the therapeutic agents may be combined with any number of excipients as is known in the art. In addition to the biodegradable polymeric excipients discussed above, other excipients may be used, including, but not limited to, benzyl alcohol, ethylcellulose, methylcellulose, hydroxymethylcellulose, cetyl alcohol, croscarmellose sodium, dextrans, dextrose, fructose, gelatin, glycerin, monoglycerides, diglycerides, kaolin, calcium chloride, lactose, lactose monohydrate, maltodextrins, polysorbates, pregelatinized starch, calcium stearate, magnesium stearate, silicon dioxide, cornstarch, talc, and the like. The one or more excipients may be included in total amounts as low as about 1%, 5%, or 10% and in other embodiments may be included in total amounts as high as 50%, 70% or 90%.

Examples of drugs may include various anti-secretory agents; antimitotics and other anti-proliferative agents, including among others, anti-angiogenesis agents such as angiostatin, anecortave acetate, thrombospondin, VEGF receptor tyrosine kinase inhibitors and anti-vascular endothelial growth factor (anti-VEGF) drugs such as ranibizumab (LUCENTIS®) and bevacizumab (AVASTIN®), pegaptanib (MACUGEN®), sunitinib and sorafenib and any of a variety of known small-molecule and transcription inhibitors having anti-angiogenesis effect; classes of known ophthalmic drugs, including: glaucoma agents, such as adrenergic antagonists, including for example, beta-blocker agents such as atenolol propranolol, metipranolol, betaxolol, carteolol, levobetaxolol, levobunolol and timolol; adrenergic agonists or sympathomimetic agents such as epinephrine, dipivefrin, clonidine, aparclonidine, and brimonidine; parasympathomimetics or cholingeric agonists such as pilocarpine, carbachol, phospholine iodine, and physostigmine, salicylate, acetylcholine chloride, eserine, diisopropyl fluorophosphate, demecarium bromide); muscarinics; carbonic anhydrase inhibitor agents, including topical and/or systemic agents, for example acetozolamide, brinzolamide, dorzolamide and methazolamide, ethoxzolamide, diamox, and dichlorphenamide; mydriatic-cycloplegic agents such as atropine, cyclopentolate, succinylcholine, homatropine, phenylephrine, scopolamine and tropicamide; prostaglandins such as prostaglandin F2 alpha, antiprostaglandins, prostaglandin precursors, or prostaglandin analog agents such as bimatoprost, latanoprost, travoprost and unoprostone.

Other examples of drugs may also include anti-inflammatory agents including for example glucocorticoids and corticosteroids such as betamethasone, cortisone, dexamethasone, dexamethasone 21-phosphate, methylprednisolone, prednisolone 21-phosphate, prednisolone acetate, prednisolone, fluoroometholone, loteprednol, medrysone, fluocinolone acetonide, triamcinolone acetonide, triamcinolone, triamcinolone acetonide, beclomethasone, budesonide, flunisolide, fluorometholone, fluticasone, hydrocortisone, hydrocortisone acetate, loteprednol, rimexolone and non-steroidal anti-inflammatory agents including, for example, diclofenac, flurbiprofen, ibuprofen, bromfenac, nepafenac, and ketorolac, salicylate, indomethacin, ibuprofen, naxopren, piroxicam and nabumetone; anti-infective or antimicrobial agents such as antibiotics including, for example, tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, aminoglycosides such as gentamicin and tobramycin; fluoroquinolones such as ciprofloxacin, gatifloxacin, levofloxacin, moxifloxacin, norfloxacin, ofloxacin; bacitracin, erythromycin, fusidic acid, neomycin, polymyxin B, gramicidin, trimethoprim and sulfacetamide; antifungals such as amphotericin B and miconazole; antivirals such as idoxuridine trifluorothymidine, acyclovir, gancyclovir, interferon; antimicotics; immune-modulating agents such as anti-allergenics, including, for example, sodium chromoglycate, antazoline, methapyriline, chlorpheniramine, cetrizine, pyrilamine, prophenpyridamine; anti-histamine agents such as azelastine, emedastine and levocabastine; immunological drugs (such as vaccines and immune stimulants); MAST cell stabilizer agents such as cromolyn sodium, ketotifen, lodoxamide, nedocrimil, olopatadine and pemirolastciliary body ablative agents, such as gentimicin and cidofovir; and other ophthalmic agents such as verteporfin, proparacaine, tetracaine, cyclosporine and pilocarpine; inhibitors of cell-surface glycoprotein receptors; decongestants such as phenylephrine, naphazoline, tetrahydrazoline; lipids or hypotensive lipids; dopaminergic agonists and/or antagonists such as quinpirole, fenoldopam, and ibopamine; vasospasm inhibitors; vasodilators; antihypertensive agents; angiotensin converting enzyme (ACE) inhibitors; angiotensin-1 receptor antagonists such as olmesartan; microtubule inhibitors; molecular motor (dynein and/or kinesin) inhibitors; actin cytoskeleton regulatory agents such as cyctchalasin, latrunculin, swinholide A, ethacrynic acid, H-7, and Rho-kinase (ROCK) inhibitors; remodeling inhibitors; modulators of the extracellular matrix such as tert-butylhydro-quinolone and AL-3037A; adenosine receptor agonists and/or antagonists such as N-6-cylclophexyladenosine and (R)-phenylisopropyladenosine; serotonin agonists; hormonal agents such as estrogens, estradiol, progestational hormones, progesterone, insulin, calcitonin, parathyroid hormone, peptide and vasopressin hypothalamus releasing factor; growth factor antagonists or growth factors, including, for example, epidermal growth factor, fibroblast growth factor, platelet derived growth factor or antagonists thereof (such as those disclosed in U.S. Pat. No. 7,759,472 or U.S. patent application Ser. Nos. 12/465,051, 12/564,863, or 12/641,270, each of which is incorporated in its entirety by reference herein), transforming growth factor beta, somatotrapin, fibronectin, connective tissue growth factor, bone morphogenic proteins (BMPs); cytokines such as interleukins, CD44, cochlin, and serum amyloids, such as serum amyloid A.

Other therapeutic agents may include neuroprotective agents such as lubezole, nimodipine and related compounds, and including blood flow enhancers such as dorzolamide or betaxolol; compounds that promote blood oxygenation such as erythropoietin; sodium channels blockers; calcium channel blockers such as nilvadipine or lomerizine; glutamate inhibitors such as memantine nitromemantine, riluzole, dextromethorphan or agmatine; acetylcholinsterase inhibitors such as galantamine; hydroxylamines or derivatives thereof, such as the water soluble hydroxylamine derivative OT-440; synaptic modulators such as hydrogen sulfide compounds containing flavonoid glycosides and/or terpenoids, such as ginkgo biloba; neurotrophic factors such as glial cell-line derived neutrophic factor, brain derived neurotrophic factor; cytokines of the IL-6 family of proteins such as ciliary neurotrophic factor or leukemia inhibitory factor; compounds or factors that affect nitric oxide levels, such as nitric oxide, nitroglycerin, or nitric oxide synthase inhibitors; cannabinoid receptor agonists such as WIN55-212-2; free radical scavengers such as methoxypolyethylene glycol thioester (MPDTE) or methoxypolyethlene glycol thiol coupled with EDTA methyl triester (MPSEDE); anti-oxidants such as astaxathin, dithiolethione, vitamin E, or metallocorroles (e.g., iron, manganese or gallium corroles); compounds or factors involved in oxygen homeostasis such as neuroglobin or cytoglobin; inhibitors or factors that impact mitochondrial division or fission, such as Mdivi-1 (a selective inhibitor of dynamin related protein 1 (Drp1)); kinase inhibitors or modulators such as the Rho-kinase inhibitor H-1152 or the tyrosine kinase inhibitor AG1478; compounds or factors that affect integrin function, such as the Beta 1-integrin activating antibody HUTS-21; N-acyl-ethanolamines and their precursors, N-acyl-ethanolamine phospholipids; stimulators of glucagon-like peptide 1 receptors (e.g., glucagon-like peptide 1); polyphenol containing compounds such as resveratrol; chelating compounds; apoptosis-related protease inhibitors; compounds that reduce new protein synthesis; radiotherapeutic agents; photodynamic therapy agents; gene therapy agents; genetic modulators; auto-immune modulators that prevent damage to nerves or portions of nerves (e.g., demyelination) such as glatimir; myelin inhibitors such as anti-NgR Blocking Protein, NgR (310)ecto-Fc; other immune modulators such as FK506 binding proteins (e.g., FKBP51); and dry eye medications such as cyclosporine A, delmulcents, and sodium hyaluronate.

Other therapeutic agents that may be used include: other beta-blocker agents such as acebutolol, atenolol, bisoprolol, carvedilol, asmolol, labetalol, nadolol, penbutolol, and pindolol; other corticosteroidal and non-steroidal anti-inflammatory agents such aspirin, betamethasone, cortisone, diflunisal, etodolac, fenoprofen, fludrocortisone, flurbiprofen, hydrocortisone, ibuprofen, indomethacine, ketoprofen, meclofenamate, mefenamic acid, meloxicam, methylprednisolone, nabumetone, naproxen, oxaprozin, prednisolone, prioxicam, salsalate, sulindac and tolmetin; COX-2 inhibitors like celecoxib, rofecoxib and Valdecoxib; other immune-modulating agents such as aldesleukin, adalimumab (HUMIRA®), azathioprine, basiliximab, daclizumab, etanercept (ENBREL®), hydroxychloroquine, infliximab (REMICADE®), leflunomide, methotrexate, mycophenolate mofetil, and sulfasalazine; other anti-histamine agents such as loratadine, desloratadine, cetirizine, diphenhydramine, chlorpheniramine, dexchlorpheniramine, clemastine, cyproheptadine, fexofenadine, hydroxyzine and promethazine; other anti-infective agents such as aminoglycosides such as amikacin and streptomycin; anti-fungal agents such as amphotericin B, caspofungin, clotrimazole, fluconazole, itraconazole, ketoconazole, voriconazole, terbinafine and nystatin; anti-malarial agents such as chloroquine, atovaquone, mefloquine, primaquine, quinidine and quinine; anti-mycobacterium agents such as ethambutol, isoniazid, pyrazinamide, rifampin and rifabutin; anti-parasitic agents such as albendazole, mebendazole, thiobendazole, metronidazole, pyrantel, atovaquone, iodoquinaol, ivermectin, paromycin, praziquantel, and trimatrexate; other anti-viral agents, including anti-CMV or anti-herpetic agents such as acyclovir, cidofovir, famciclovir, gangciclovir, valacyclovir, valganciclovir, vidarabine, trifluridine and foscarnet; protease inhibitors such as ritonavir, saquinavir, lopinavir, indinavir, atazanavir, amprenavir and nelfinavir; nucleotide/nucleoside/non-nucleoside reverse transcriptase inhibitors such as abacavir, ddI, 3TC, d4T, ddC, tenofovir and emtricitabine, delavirdine, efavirenz and nevirapine; other anti-viral agents such as interferons, ribavirin and trifluridiene; other anti-bacterial agents, including cabapenems like ertapenem, imipenem and meropenem; cephalosporins such as cefadroxil, cefazolin, cefdinir, cefditoren, cephalexin, cefaclor, cefepime, cefoperazone, cefotaxime, cefotetan, cefoxitin, cefpodoxime, cefprozil, ceftaxidime, ceftibuten, ceftizoxime, ceftriaxone, cefuroxime and loracarbef; other macrolides and ketolides such as azithromycin, clarithromycin, dirithromycin and telithromycin; penicillins (with and without clavulanate) including amoxicillin, ampicillin, pivampicillin, dicloxacillin, nafcillin, oxacillin, piperacillin, and ticarcillin; tetracyclines such as doxycycline, minocycline and tetracycline; other anti-bacterials such as aztreonam, chloramphenicol, clindamycin, linezolid, nitrofurantoin and vancomycin; alpha blocker agents such as doxazosin, prazosin and terazosin; calcium-channel blockers such as amlodipine, bepridil, diltiazem, felodipine, isradipine, nicardipine, nifedipine, nisoldipine and verapamil; other anti-hypertensive agents such as clonidine, diazoxide, fenoldopan, hydralazine, minoxidil, nitroprusside, phenoxybenzamine, epoprostenol, tolazoline, treprostinil and nitrate-based agents; anti-coagulant agents, including heparins and heparinoids such as heparin, dalteparin, enoxaparin, tinzaparin and fondaparinux; other anti-coagulant agents such as hirudin, aprotinin, argatroban, bivalirudin, desirudin, lepirudin, warfarin and ximelagatran; anti-platelet agents such as abciximab, clopidogrel, dipyridamole, optifibatide, ticlopidine and tirofiban; prostaglandin PDE-5 inhibitors and other prostaglandin agents such as alprostadil, carboprost, sildenafil, tadalafil and vardenafil; thrombin inhibitors; antithrombogenic agents; anti-platelet aggregating agents; thrombolytic agents and/or fibrinolytic agents such as alteplase, anistreplase, reteplase, streptokinase, tenecteplase and urokinase; anti-proliferative agents such as sirolimus, tacrolimus, everolimus, zotarolimus, paclitaxel and mycophenolic acid; hormonal-related agents including levothyroxine, fluoxymestrone, methyltestosterone, nandrolone, oxandrolone, testosterone, estradiol, estrone, estropipate, clomiphene, gonadotropins, hydroxyprogesterone, levonorgestrel, medroxyprogesterone, megestrol, mifepristone, norethindrone, oxytocin, progesterone, raloxifene and tamoxifen; anti-neoplastic agents, including alkylating agents such as carmustine lomustine, melphalan, cisplatin, fluorouracil3, and procarbazine antibiotic-like agents such as bleomycin, daunorubicin, doxorubicin, idarubicin, mitomycin and plicamycin; anti proliferative agents (such as 1,3-cis retinoic acid, 5-fluorouracil, taxol, rapamycin, mitomycin C and cisplatin); antimetabolite agents such as cytarabine, fludarabine, hydroxyurea, mercaptopurine and 5-fluorouracil (5-FU); immune modulating agents such as aldesleukin, imatinib, rituximab and tositumomab; mitotic inhibitors docetaxel, etoposide, vinblastine and vincristine; radioactive agents such as strontium-89; and other anti-neoplastic agents such as irinotecan, topotecan and mitotane.

While certain embodiments of the disclosure have been described, these embodiments have been presented by way of example only, and are not intended to limit the scope of the disclosure. Indeed, the novel methods, systems, and devices described herein may be embodied in a variety of other forms. For example, embodiments of one illustrated or described implant may be combined with embodiments of another illustrated or described shunt. Moreover, the implants described above may be utilized for other purposes. For example, the implants may be used to drain fluid from the anterior chamber to other locations of the eye or outside the eye. Furthermore, various omissions, substitutions and changes in the form of the methods, systems, and devices described herein may be made without departing from the spirit of the disclosure.

What is claimed is:

1. A drug delivery ocular implant comprising:
an outer shell having a proximal end, a distal end, said outer shell being shaped to define an interior space;
at least a first therapeutic agent disposed within said interior space;
a cap positioned on the proximal end of said outer shell, wherein said cap comprises at least one aperture; and
a permeable or semi-permeable material positioned between said cap and said proximal end of said outer shell,
wherein said permeable or semi-permeable material is permeable to said at least a first therapeutic agent,
wherein said permeable or semi-permeable material is dimensioned based on the permeability of said permeable or semi-permeable material to said at least a first therapeutic agent, and
wherein said permeable or semi-permeable material occludes said at least one aperture, thereby allowing elution of said at least a first therapeutic agent to occur only through said permeable or semi-permeable material;
wherein said proximal end of said outer shell is configured to be positioned in an anterior chamber of an eye.

2. The implant of claim 1, wherein said at least one first therapeutic agent comprises a prostaglandin, a prostaglandin analog, a prostaglandin inhibitor, and/or combinations thereof.

3. The implant of claim 1, further comprising at least one fluid inlet and one fluid outlet, wherein said at least one fluid inlet and one fluid outlet are configured to deliver ocular fluid to a physiological outflow pathway.

4. The implant of claim 3, wherein said physiological outflow pathway is Schlemm's Canal.

5. The implant of claim 3, wherein the at least one fluid outlet is positioned in closer proximity to the distal end of said outer shell, as compared to the at least one fluid inlet.

6. The implant of claim 1, wherein said permeable or semi-permeable material is a membrane.

7. The implant of claim 6, further comprising a retention protrusion on the distal end of said outer shell, wherein said retention protrusion is configured to anchor the ocular implant at a target tissue site.

8. The implant of claim 6, wherein upon positioning of the cap over the proximal end of the outer shell said cap extends towards said distal end of said outer shell and encloses only a portion of said outer shell.

9. The implant of claim 7, wherein said retention protrusion comprises a sharpened conical element configured to at least partially penetrate tissue at said target tissue site.

10. A drug delivery ocular implant comprising:
an outer shell having a proximal end, a distal end, said outer shell being shaped to define an interior space;
at least a first therapeutic agent disposed within said interior space;
a cap positioned on the proximal end of said outer shell, wherein said cap comprises at least one portion permeable or semi-permeable to said at least a first therapeutic agent,
wherein said at least one permeable or semi-permeable portion is dimensioned based on the permeability of said at least one permeable or semi-permeable portion to said at least a first therapeutic agent,
wherein upon placement of the cap over the proximal end of the outer shell, said cap extends towards said distal end of said outer shell and encloses a portion of said outer shell,
wherein elution of said at least a first therapeutic agent occurs only through said at least one permeable or semi-permeable portion; and
wherein said proximal end of said outer shell is configured to be positioned in an anterior chamber of an eye.

11. The implant of claim 10, wherein said at least a first therapeutic agent comprises a prostaglandin, a prostaglandin analog, a prostaglandin inhibitor, and/or combinations thereof.

12. The implant of claim 10, further comprising at least one fluid inlet and one fluid outlet, wherein said at least one fluid inlet and one fluid outlet are configured to deliver ocular fluid to a physiological outflow pathway.

13. The implant of claim 10, wherein the permeable or semi-permeable portion of the cap comprises an aperture.

14. The implant of claim 13, wherein said permeable or semi-permeable portion of the cap further comprises a material permeable or semi-permeable to said at least a first therapeutic agent.

15. The implant of claim 14, wherein said material permeable or semi-permeable to said at least a first therapeutic agent is a membrane.

16. The implant of claim 10, wherein said distal end of said outer shell further comprises a retention protrusion comprising a sharpened conical element configured to anchor said implant at a target tissue site.

17. A drug delivery ocular implant comprising:
an outer shell having a proximal end, a distal end, said outer shell being shaped to define an interior space;
at least a first therapeutic agent disposed within said interior space;
a cap comprising at least one aperture and dimensioned for positioning over the proximal end of the outer shell, wherein the cap extends towards said distal end of said outer shell and encloses a portion of said outer shell,
a first material through which the at least a therapeutic agent elutes positioned between said cap and said proximal end of said outer shell,
wherein said first material is permeable or semi-permeable to said at least a first therapeutic agent and occludes said at least one aperture, thereby allowing elution of said at least a first therapeutic agent to occur only through said first material; and a retention protrusion comprising a sharpened element on the distal end of said outer shell, wherein said proximal end of said outer shell is configured to be positioned in an anterior chamber of an eye.

18. The implant of claim 17, wherein said first material is a membrane.

19. The implant of claim 17, wherein said first therapeutic agent comprises a prostaglandin, a prostaglandin analog, a prostaglandin inhibitor, and/or combinations thereof.

20. The implant of claim 17, further comprising at least one fluid inlet and one fluid outlet, wherein said at least one fluid inlet and one fluid outlet are configured to deliver ocular fluid to a physiological outflow pathway.

21. The implant of claim 17, wherein said first material has a thickness of between about 50 and about 100 microns.

22. The implant of claim 17, wherein said at least a first therapeutic agent elutes from said ocular implant for a period of time ranging between about 12 to about 48 months.

23. The implant of claim 17, wherein the outer shell comprises a material selected from, polymers, metals, plastics, ceramics, and mixtures of said materials.

* * * * *